(12) United States Patent
Fire et al.

(10) Patent No.: US 9,068,224 B2
(45) Date of Patent: Jun. 30, 2015

(54) MEASUREMENT AND MONITORING OF CELL CLONALITY

(71) Applicant: The Board of Trustees of the Leland Stanford Junior University, Palo Alto, CA (US)

(72) Inventors: Andrew Fire, Stanford, CA (US); Scott D. Boyd, Stanford, CA (US); Jason Merker, Palo Alto, CA (US); Kyunga Seo, Daejon (KR); Eleanor M. Osborne, Washington, DC (US)

(73) Assignee: THE BOARD OF TRUSTEES OF THE LELAND STANFORD JUNIOR UNIVERSITY, Palo Alto, CA (US)

( * ) Notice: Subject to any disclaimer, the term of this patent is extended or adjusted under 35 U.S.C. 154(b) by 0 days.

(21) Appl. No.: 14/148,439

(22) Filed: Jan. 6, 2014

(65) Prior Publication Data

US 2014/0235477 A1    Aug. 21, 2014

Related U.S. Application Data

(62) Division of application No. 13/327,610, filed on Dec. 15, 2011.

(60) Provisional application No. 61/476,182, filed on Apr. 15, 2011, provisional application No. 61/459,666, filed on Dec. 15, 2010.

(51) Int. Cl.
    *C12P 19/34* (2006.01)
    *C12Q 1/68* (2006.01)

(52) U.S. Cl.
    CPC ............... *C12Q 1/6874* (2013.01); *C12P 19/34* (2013.01); *C12Q 1/6869* (2013.01); *C12Q 1/6881* (2013.01); *C12Q 2600/106* (2013.01)

(58) Field of Classification Search
    CPC ........................................................ C12P 19/34
    USPC ........................................................ 435/91.2
    See application file for complete search history.

(56) References Cited

U.S. PATENT DOCUMENTS

| 6,596,492 | B2 | 7/2003 | Avery et al. |
| 7,465,540 | B2 | 12/2008 | Jacobson et al. |
| 2004/0248172 | A1 | 12/2004 | Samoszuk et al. |
| 2007/0160994 | A1* | 7/2007 | Lim et al. ............... 435/6 |
| 2008/0166718 | A1 | 7/2008 | Lim et al. |
| 2010/0151471 | A1 | 6/2010 | Faham et al. |

OTHER PUBLICATIONS

Cleary; et al., "Immunoglobulin gene rearrangement as a diagnostic criterion of B-cell lymphoma", PNAS (Jan. 1984), 81:593-597.
Boyd; et al. "Measurement and Clinical Monitoring of Human Lymphocyte Clonality by Massively Parallel V-D-J Pyrosequecing", Sci Transl Med (Dec. 2009), 1(12):12ra23.
Weinstein; et al. "High-Throughput Sequencing of the Zebrafish Antibody Repertoire", Science (May 2009), 324 (5928):807-810.

* cited by examiner

*Primary Examiner* — Ardin Marschel
(74) *Attorney, Agent, or Firm* — Bozicevic, Field & Francis LLP; Pamela J. Sherwood

(57) ABSTRACT

Methods are provided for the detection and analysis of clonality in a cell population, where parallel sequencing is applied to a nucleic acid sample obtained from the cell population, optionally a population of lymphocytes. Replicate samples are amplified, and sequenced, where identification of coincident sequences in two or more replicates is indicative of clonal expansion.

4 Claims, 17 Drawing Sheets

SEQUENCE LISTING

<160> NUMBER OF SEQ ID NOS: 901

<210> SEQ ID NO 1
<211> LENGTH: 44
<212> TYPE: DNA
<213> ORGANISM: Homo Sapien

<400> SEQUENCE: 1
gcctccctcg cgccatcagc tgggtgcgac aggcccctgg acaa                44

<210> SEQ ID NO 2
<211> LENGTH: 44
<212> TYPE: DNA
<213> ORGANISM: Homo Sapien

<400> SEQUENCE: 2
gcctccctcg cgccatcagt ggatccgtca gcccccaggg aagg                44

<210> SEQ ID NO 3
<211> LENGTH: 40
<212> TYPE: DNA
<213> ORGANISM: Homo Sapien

<400> SEQUENCE: 3
gcctccctcg cgccatcagg gtccgccagg ctccagggaa                     40

<210> SEQ ID NO 4
<211> LENGTH: 44
<212> TYPE: DNA
<213> ORGANISM: Homo Sapien

<400> SEQUENCE: 4
gcctccctcg cgccatcagt ggatccgcca gcccccaggg aagg                44

<210> SEQ ID NO 5
<211> LENGTH: 44
<212> TYPE: DNA
<213> ORGANISM: Homo Sapien

<400> SEQUENCE: 5
gcctccctcg cgccatcagg ggtgcgccag atgcccggga aagg                44

<210> SEQ ID NO 6
<211> LENGTH: 44
<212> TYPE: DNA
<213> ORGANISM: Homo Sapien

<400> SEQUENCE: 6
gcctccctcg cgccatcagt ggatcaggca gtccccatcg agag                44

<210> SEQ ID NO 7
<211> LENGTH: 44
<212> TYPE: DNA
<213> ORGANISM: Homo Sapien

<400> SEQUENCE: 7
gcctccctcg cgccatcagt tgggtgcgac aggcccctgg acaa                    44

<210> SEQ ID NO 8
<211> LENGTH: 47
<212> TYPE: DNA
<213> ORGANISM: Homo Sapien

<400> SEQUENCE: 8
gccttgccag cccgctcagt tacctcttac ctgaggagac ggtgacc                 47

<210> SEQ ID NO 9
<211> LENGTH: 47
<212> TYPE: DNA
<213> ORGANISM: Homo Sapien

<400> SEQUENCE: 9
gccttgccag cccgctcagt taccgcttac ctgaggagac ggtgacc                 47

<210> SEQ ID NO 10
<211> LENGTH: 47
<212> TYPE: DNA
<213> ORGANISM: Homo Sapien

<400> SEQUENCE: 10
gccttgccag cccgctcagt taagtcttac ctgaggagac ggtgacc                 47

<210> SEQ ID NO 11
<211> LENGTH: 47
<212> TYPE: DNA
<213> ORGANISM: Homo Sapien

<400> SEQUENCE: 11
gccttgccag cccgctcagt tagttcttac ctgaggagac ggtgacc                 47

<210> SEQ ID NO 12
<211> LENGTH: 47
<212> TYPE: DNA
<213> ORGANISM: Homo Sapien

<400> SEQUENCE: 12
gccttgccag cccgctcagt taacccttac ctgaggagac ggtgacc                 47

<210> SEQ ID NO 13
<211> LENGTH: 47
<212> TYPE: DNA
<213> ORGANISM: Homo Sapien

<400> SEQUENCE: 13
gccttgccag cccgctcagt tccggcttac ctgaggagac ggtgacc                 47

<210> SEQ ID NO 14
<211> LENGTH: 47
<212> TYPE: DNA
<213> ORGANISM: Homo Sapien

<400> SEQUENCE: 14
gccttgccag cccgctcagt acgttcttac ctgaggagac ggtgacc                 47

<210> SEQ ID NO 15
<211> LENGTH: 47
<212> TYPE: DNA
<213> ORGANISM: Homo Sapien

<400> SEQUENCE: 15
gccttgccag cccgctcagt aacggcttac ctgaggagac ggtgacc                47

<210> SEQ ID NO 16
<211> LENGTH: 47
<212> TYPE: DNA
<213> ORGANISM: Homo Sapien

<400> SEQUENCE: 16
gccttgccag cccgctcagt aaggtcttac ctgaggagac ggtgacc                47

<210> SEQ ID NO 17
<211> LENGTH: 47
<212> TYPE: DNA
<213> ORGANISM: Homo Sapien

<400> SEQUENCE: 17
gccttgccag cccgctcagt aacttcttac ctgaggagac ggtgacc                47

<210> SEQ ID NO 18
<211> LENGTH: 47
<212> TYPE: DNA
<213> ORGANISM: Homo Sapien

<400> SEQUENCE: 18
gccttgccag cccgctcagt ccggtcttac ctgaggagac ggtgacc                47

<210> SEQ ID NO 19
<211> LENGTH: 47
<212> TYPE: DNA
<213> ORGANISM: Homo Sapien

<400> SEQUENCE: 19
gccttgccag cccgctcaga accttcttac ctgaggagac ggtgacc                47

<210> SEQ ID NO 20
<211> LENGTH: 48
<212> TYPE: DNA
<213> ORGANISM: Homo Sapien

<400> SEQUENCE: 20
gccttgccag cccgctcaga ttccagctta cctgaggaga cggtgacc               48

<210> SEQ ID NO 21
<211> LENGTH: 48
<212> TYPE: DNA
<213> ORGANISM: Homo Sapien

<400> SEQUENCE: 21
gccttgccag cccgctcaga tccaagctta cctgaggaga cggtgacc               48

<210> SEQ ID NO 22
<211> LENGTH: 48
<212> TYPE: DNA
<213> ORGANISM: Homo Sapien

<400> SEQUENCE: 22
gccttgccag cccgctcaga tcaaggctta cctgaggaga cggtgacc          48

<210> SEQ ID NO 23
<211> LENGTH: 48
<212> TYPE: DNA
<213> ORGANISM: Homo Sapien

<400> SEQUENCE: 23
gccttgccag cccgctcaga ttcaggctta cctgaggaga cggtgacc          48

<210> SEQ ID NO 24
<211> LENGTH: 48
<212> TYPE: DNA
<213> ORGANISM: Homo Sapien

<400> SEQUENCE: 24
gccttgccag cccgctcagc ttccagctta cctgaggaga cggtgacc          48

<210> SEQ ID NO 25
<211> LENGTH: 48
<212> TYPE: DNA
<213> ORGANISM: Homo Sapien

<400> SEQUENCE: 25
gccttgccag cccgctcagc tccaagctta cctgaggaga cggtgacc          48

<210> SEQ ID NO 26
<211> LENGTH: 48
<212> TYPE: DNA
<213> ORGANISM: Homo Sapien

<400> SEQUENCE: 26
gccttgccag cccgctcagc tcaaggctta cctgaggaga cggtgacc          48

<210> SEQ ID NO 27
<211> LENGTH: 47
<212> TYPE: DNA
<213> ORGANISM: Homo Sapien

<400> SEQUENCE: 27
gccttgccag cccgctcaga aggttcttac ctgaggagac ggtgacc           47

<210> SEQ ID NO 28
<211> LENGTH: 47
<212> TYPE: DNA
<213> ORGANISM: Homo Sapien

<400> SEQUENCE: 28
gccttgccag cccgctcaga acggtcttac ctgaggagac ggtgacc           47

<210> SEQ ID NO 29
<211> LENGTH: 47
<212> TYPE: DNA
<213> ORGANISM: Homo Sapien

<400> SEQUENCE: 29
gccttgccag cccgctcagc cggttcttac ctgaggagac ggtgacc           47

<210> SEQ ID NO 30
<211> LENGTH: 47
<212> TYPE: DNA
<213> ORGANISM: Homo Sapien

<400> SEQUENCE: 30
gccttgccag cccgctcagt aaacccttac ctgaggagac ggtgacc            47

<210> SEQ ID NO 31
<211> LENGTH: 48
<212> TYPE: DNA
<213> ORGANISM: Homo Sapien

<400> SEQUENCE: 31
gccttgccag cccgctcagc ttcaggctta cctgaggaga cggtgacc           48

<210> SEQ ID NO 32
<211> LENGTH: 48
<212> TYPE: DNA
<213> ORGANISM: Homo Sapien

<400> SEQUENCE: 32
gccttgccag cccgctcagt ttccagctta cctgaggaga cggtgacc           48

<210> SEQ ID NO 33
<211> LENGTH: 48
<212> TYPE: DNA
<213> ORGANISM: Homo Sapien

<400> SEQUENCE: 33
gccttgccag cccgctcagt tccaagctta cctgaggaga cggtgacc           48

<210> SEQ ID NO 34
<211> LENGTH: 48
<212> TYPE: DNA
<213> ORGANISM: Homo Sapien

<400> SEQUENCE: 34
gccttgccag cccgctcagt tcaaggctta cctgaggaga cggtgacc           48

<210> SEQ ID NO 35
<211> LENGTH: 48
<212> TYPE: DNA
<213> ORGANISM: Homo Sapien

<400> SEQUENCE: 35
gccttgccag cccgctcagt ttcaggctta cctgaggaga cggtgacc           48

<210> SEQ ID NO 36
<211> LENGTH: 60
<212> TYPE: DNA
<213> ORGANISM: Homo Sapien

<400> SEQUENCE: 36
gcctccctcg cgccatccga ctcagccttc ctaagctggg tgcgacaggc ccctggacaa   60

<210> SEQ ID NO 37
<211> LENGTH: 60
<212> TYPE: DNA
<213> ORGANISM: Homo Sapien

<400> SEQUENCE: 37
gcctccctcg cgccatccga ctcagccttc ctaagtggat ccgtcagccc ccagggaagg   60

<210> SEQ ID NO 38
<211> LENGTH: 56
<212> TYPE: DNA
<213> ORGANISM: Homo Sapien

```
<400> SEQUENCE: 38
gcctccctcg cgccatccga ctcagccttc ctaagggtcc gccaggctcc agggaa        56

<210> SEQ ID NO 39
<211> LENGTH: 60
<212> TYPE: DNA
<213> ORGANISM: Homo Sapien

<400> SEQUENCE: 39
gcctccctcg cgccatccga ctcagccttc ctaagtggat ccgccagccc ccagggaagg    60

<210> SEQ ID NO 40
<211> LENGTH: 60
<212> TYPE: DNA
<213> ORGANISM: Homo Sapien

<400> SEQUENCE: 40
gcctccctcg cgccatccga ctcagccttc ctaaggggtg cgccagatgc ccgggaaagg    60

<210> SEQ ID NO 41
<211> LENGTH: 60
<212> TYPE: DNA
<213> ORGANISM: Homo Sapien

<400> SEQUENCE: 41
gcctccctcg cgccatccga ctcagccttc ctaagtggat caggcagtcc ccatcgagag    60

<210> SEQ ID NO 42
<211> LENGTH: 60
<212> TYPE: DNA
<213> ORGANISM: Homo Sapien

<400> SEQUENCE: 42
gcctccctcg cgccatccga ctcagccttc ctaagttggg tgcgacaggc ccctggacaa    60

<210> SEQ ID NO 43
<211> LENGTH: 60
<212> TYPE: DNA
<213> ORGANISM: Homo Sapien

<400> SEQUENCE: 43
gcctccctcg cgccatccga ctcagagctc ctaagctggg tgcgacaggc ccctggacaa    60

<210> SEQ ID NO 44
<211> LENGTH: 60
<212> TYPE: DNA
<213> ORGANISM: Homo Sapien

<400> SEQUENCE: 44
gcctccctcg cgccatccga ctcagagctc ctaagtggat ccgtcagccc ccagggaagg    60

<210> SEQ ID NO 45
<211> LENGTH: 56
<212> TYPE: DNA
<213> ORGANISM: Homo Sapien

<400> SEQUENCE: 45
gcctccctcg cgccatccga ctcagagctc ctaagggtcc gccaggctcc agggaa        56

<210> SEQ ID NO 46
<211> LENGTH: 60
<212> TYPE: DNA
<213> ORGANISM: Homo Sapien
```

<400> SEQUENCE: 46
gcctccctcg cgccatccga ctcagagctc ctaagtggat ccgccagccc ccagggaagg    60

<210> SEQ ID NO 47
<211> LENGTH: 60
<212> TYPE: DNA
<213> ORGANISM: Homo Sapien

<400> SEQUENCE: 47
gcctccctcg cgccatccga ctcagagctc ctaaggggtg cgccagatgc ccgggaaagg    60

<210> SEQ ID NO 48
<211> LENGTH: 60
<212> TYPE: DNA
<213> ORGANISM: Homo Sapien

<400> SEQUENCE: 48
gcctccctcg cgccatccga ctcagagctc ctaagtggat caggcagtcc ccatcgagag    60

<210> SEQ ID NO 49
<211> LENGTH: 60
<212> TYPE: DNA
<213> ORGANISM: Homo Sapien

<400> SEQUENCE: 49
gcctccctcg cgccatccga ctcagagctc ctaagttggg tgcgacaggc ccctggacaa    60

<210> SEQ ID NO 50
<211> LENGTH: 60
<212> TYPE: DNA
<213> ORGANISM: Homo Sapien

<400> SEQUENCE: 50
gcctccctcg cgccatccga ctcagacgtc ctaagctggg tgcgacaggc ccctggacaa    60

<210> SEQ ID NO 51
<211> LENGTH: 60
<212> TYPE: DNA
<213> ORGANISM: Homo Sapien

<400> SEQUENCE: 51
gcctccctcg cgccatccga ctcagacgtc ctaagtggat ccgtcagccc ccagggaagg    60

<210> SEQ ID NO 52
<211> LENGTH: 56
<212> TYPE: DNA
<213> ORGANISM: Homo Sapien

<400> SEQUENCE: 52
gcctccctcg cgccatccga ctcagacgtc ctaagggtcc gccaggctcc agggaa    56

<210> SEQ ID NO 53
<211> LENGTH: 60
<212> TYPE: DNA
<213> ORGANISM: Homo Sapien

<400> SEQUENCE: 53
gcctccctcg cgccatccga ctcagacgtc ctaagtggat ccgccagccc ccagggaagg    60

<210> SEQ ID NO 54
<211> LENGTH: 60
<212> TYPE: DNA

<213> ORGANISM: Homo Sapien

<400> SEQUENCE: 54
gcctccctcg cgccatccga ctcagacgtc ctaaggggtg cgccagatgc ccgggaaagg    60

<210> SEQ ID NO 55
<211> LENGTH: 60
<212> TYPE: DNA
<213> ORGANISM: Homo Sapien

<400> SEQUENCE: 55
gcctccctcg cgccatccga ctcagacgtc ctaagtggat caggcagtcc ccatcgagag    60

<210> SEQ ID NO 56
<211> LENGTH: 60
<212> TYPE: DNA
<213> ORGANISM: Homo Sapien

<400> SEQUENCE: 56
gcctccctcg cgccatccga ctcagacgtc ctaagttggg tgcgacaggc ccctggacaa    60

<210> SEQ ID NO 57
<211> LENGTH: 57
<212> TYPE: DNA
<213> ORGANISM: Homo Sapien

<400> SEQUENCE: 57
gccttgccag cccgcgcagt ctcagtgtcc aataacttac ctgaggagac ggtgacc    57

<210> SEQ ID NO 58
<211> LENGTH: 57
<212> TYPE: DNA
<213> ORGANISM: Homo Sapien

<400> SEQUENCE: 58
gccttgccag cccgcgcagt ctcagcggcc aataacttac ctgaggagac ggtgacc    57

<210> SEQ ID NO 59
<211> LENGTH: 57
<212> TYPE: DNA
<213> ORGANISM: Homo Sapien

<400> SEQUENCE: 59
gccttgccag cccgcgcagt ctcagcaacc aataacttac ctgaggagac ggtgacc    57

<210> SEQ ID NO 60
<211> LENGTH: 57
<212> TYPE: DNA
<213> ORGANISM: Homo Sapien

<400> SEQUENCE: 60
gccttgccag cccgcgcagt ctcagcctcc aataacttac ctgaggagac ggtgacc    57

<210> SEQ ID NO 61
<211> LENGTH: 57
<212> TYPE: DNA
<213> ORGANISM: Homo Sapien

<400> SEQUENCE: 61
gccttgccag cccgcgcagt ctcagattcc aataacttac ctgaggagac ggtgacc    57

<210> SEQ ID NO 62
<211> LENGTH: 57

<212> TYPE: DNA
<213> ORGANISM: Homo Sapien

<400> SEQUENCE: 62
gccttgccag cccgcgcagt ctcagacgcc aataacttac ctgaggagac ggtgacc        57

<210> SEQ ID NO 63
<211> LENGTH: 57
<212> TYPE: DNA
<213> ORGANISM: Homo Sapien

<400> SEQUENCE: 63
gccttgccag cccgcgcagt ctcagtgtcc ggcaacttac ctgaggagac ggtgacc        57

<210> SEQ ID NO 64
<211> LENGTH: 57
<212> TYPE: DNA
<213> ORGANISM: Homo Sapien

<400> SEQUENCE: 64
gccttgccag cccgcgcagt ctcagcggcc ggcaacttac ctgaggagac ggtgacc        57

<210> SEQ ID NO 65
<211> LENGTH: 57
<212> TYPE: DNA
<213> ORGANISM: Homo Sapien

<400> SEQUENCE: 65
gccttgccag cccgcgcagt ctcagcaacc ggcaacttac ctgaggagac ggtgacc        57

<210> SEQ ID NO 66
<211> LENGTH: 57
<212> TYPE: DNA
<213> ORGANISM: Homo Sapien

<400> SEQUENCE: 66
gccttgccag cccgcgcagt ctcagcctcc ggcaacttac ctgaggagac ggtgacc        57

<210> SEQ ID NO 67
<211> LENGTH: 57
<212> TYPE: DNA
<213> ORGANISM: Homo Sapien

<400> SEQUENCE: 67
gccttgccag cccgcgcagt ctcagattcc ggcaacttac ctgaggagac ggtgacc        57

<210> SEQ ID NO 68
<211> LENGTH: 57
<212> TYPE: DNA
<213> ORGANISM: Homo Sapien

<400> SEQUENCE: 68
gccttgccag cccgcgcagt ctcagttacc ggcaacttac ctgaggagac ggtgacc        57

<210> SEQ ID NO 69
<211> LENGTH: 57
<212> TYPE: DNA
<213> ORGANISM: Homo Sapien

<400> SEQUENCE: 69
gccttgccag cccgcgcagt ctcagacgcc ggcaacttac ctgaggagac ggtgacc        57

<210> SEQ ID NO 70

```
<211> LENGTH: 60
<212> TYPE: DNA
<213> ORGANISM: Homo Sapien

<400> SEQUENCE: 70
gcctccctcg cgccatccga ctcagtagtg ccaggctggg tgcgacaggc ccctggacaa      60

<210> SEQ ID NO 71
<211> LENGTH: 60
<212> TYPE: DNA
<213> ORGANISM: Homo Sapien

<400> SEQUENCE: 71
gcctccctcg cgccatccga ctcagtagtg ccaggtggat ccgtcagccc ccagggaagg      60

<210> SEQ ID NO 72
<211> LENGTH: 56
<212> TYPE: DNA
<213> ORGANISM: Homo Sapien

<400> SEQUENCE: 72
gcctccctcg cgccatccga ctcagtagtg ccaggggtcc gccaggctcc agggaa          56

<210> SEQ ID NO 73
<211> LENGTH: 60
<212> TYPE: DNA
<213> ORGANISM: Homo Sapien

<400> SEQUENCE: 73
gcctccctcg cgccatccga ctcagtagtg ccaggtggat ccgccagccc ccagggaagg      60

<210> SEQ ID NO 74
<211> LENGTH: 60
<212> TYPE: DNA
<213> ORGANISM: Homo Sapien

<400> SEQUENCE: 74
gcctccctcg cgccatccga ctcagtagtg ccagggggtg cgccagatgc ccgggaaagg      60

<210> SEQ ID NO 75
<211> LENGTH: 60
<212> TYPE: DNA
<213> ORGANISM: Homo Sapien

<400> SEQUENCE: 75
gcctccctcg cgccatccga ctcagtagtg ccaggtggat caggcagtcc ccatcgagag      60

<210> SEQ ID NO 76
<211> LENGTH: 60
<212> TYPE: DNA
<213> ORGANISM: Homo Sapien

<400> SEQUENCE: 76
gcctccctcg cgccatccga ctcagtagtg ccaggttggg tgcgacaggc ccctggacaa      60

<210> SEQ ID NO 77
<211> LENGTH: 60
<212> TYPE: DNA
<213> ORGANISM: Homo Sapien

<400> SEQUENCE: 77
gcctccctcg cgccatccga ctcagtgttg ccaggctggg tgcgacaggc ccctggacaa      60
```

```
<210> SEQ ID NO 78
<211> LENGTH: 60
<212> TYPE: DNA
<213> ORGANISM: Homo Sapien

<400> SEQUENCE: 78
gcctccctcg cgccatccga ctcagtgttg ccaggtggat ccgtcagccc ccagggaagg      60

<210> SEQ ID NO 79
<211> LENGTH: 56
<212> TYPE: DNA
<213> ORGANISM: Homo Sapien

<400> SEQUENCE: 79
gcctccctcg cgccatccga ctcagtgttg ccaggggtcc gccaggctcc agggaa          56

<210> SEQ ID NO 80
<211> LENGTH: 60
<212> TYPE: DNA
<213> ORGANISM: Homo Sapien

<400> SEQUENCE: 80
gcctccctcg cgccatccga ctcagtgttg ccaggtggat ccgccagccc ccagggaagg      60

<210> SEQ ID NO 81
<211> LENGTH: 60
<212> TYPE: DNA
<213> ORGANISM: Homo Sapien

<400> SEQUENCE: 81
gcctccctcg cgccatccga ctcagtgttg ccaggggtg cgccagatgc ccgggaaagg       60

<210> SEQ ID NO 82
<211> LENGTH: 60
<212> TYPE: DNA
<213> ORGANISM: Homo Sapien

<400> SEQUENCE: 82
gcctccctcg cgccatccga ctcagtgttg ccaggtggat caggcagtcc ccatcgagag      60

<210> SEQ ID NO 83
<211> LENGTH: 60
<212> TYPE: DNA
<213> ORGANISM: Homo Sapien

<400> SEQUENCE: 83
gcctccctcg cgccatccga ctcagtgttg ccaggttggg tgcgacaggc ccctggacaa      60

<210> SEQ ID NO 84
<211> LENGTH: 60
<212> TYPE: DNA
<213> ORGANISM: Homo Sapien

<400> SEQUENCE: 84
gcctccctcg cgccatccga ctcagcggtg ccaggctggg tgcgacaggc ccctggacaa      60

<210> SEQ ID NO 85
<211> LENGTH: 60
<212> TYPE: DNA
<213> ORGANISM: Homo Sapien

<400> SEQUENCE: 85
gcctccctcg cgccatccga ctcagcggtg ccaggtggat ccgtcagccc ccagggaagg      60
```

<210> SEQ ID NO 86
<211> LENGTH: 56
<212> TYPE: DNA
<213> ORGANISM: Homo Sapien

<400> SEQUENCE: 86
gcctccctcg cgccatccga ctcagcggtg ccaggggtcc gccaggctcc agggaa        56

<210> SEQ ID NO 87
<211> LENGTH: 60
<212> TYPE: DNA
<213> ORGANISM: Homo Sapien

<400> SEQUENCE: 87
gcctccctcg cgccatccga ctcagcggtg ccaggtggat ccgccagccc ccagggaagg    60

<210> SEQ ID NO 88
<211> LENGTH: 60
<212> TYPE: DNA
<213> ORGANISM: Homo Sapien

<400> SEQUENCE: 88
gcctccctcg cgccatccga ctcagcggtg ccaggggtg cgccagatgc ccgggaaagg     60

<210> SEQ ID NO 89
<211> LENGTH: 60
<212> TYPE: DNA
<213> ORGANISM: Homo Sapien

<400> SEQUENCE: 89
gcctccctcg cgccatccga ctcagcggtg ccaggtggat caggcagtcc ccatcgagag    60

<210> SEQ ID NO 90
<211> LENGTH: 60
<212> TYPE: DNA
<213> ORGANISM: Homo Sapien

<400> SEQUENCE: 90
gcctccctcg cgccatccga ctcagcggtg ccaggttggg tgcgacaggc ccctggacaa    60

<210> SEQ ID NO 91
<211> LENGTH: 60
<212> TYPE: DNA
<213> ORGANISM: Homo Sapien

<400> SEQUENCE: 91
gcctccctcg cgccatccga ctcagcaatg ccaggctggg tgcgacaggc ccctggacaa    60

<210> SEQ ID NO 92
<211> LENGTH: 60
<212> TYPE: DNA
<213> ORGANISM: Homo Sapien

<400> SEQUENCE: 92
gcctccctcg cgccatccga ctcagcaatg ccaggtggat ccgtcagccc ccagggaagg    60

<210> SEQ ID NO 93
<211> LENGTH: 56
<212> TYPE: DNA
<213> ORGANISM: Homo Sapien

<400> SEQUENCE: 93
gcctccctcg cgccatccga ctcagcaatg ccaggggtcc gccaggctcc agggaa        56

<210> SEQ ID NO 94
<211> LENGTH: 60
<212> TYPE: DNA
<213> ORGANISM: Homo Sapien

<400> SEQUENCE: 94
gcctccctcg cgccatccga ctcagcaatg ccaggtggat ccgccagccc ccagggaagg    60

<210> SEQ ID NO 95
<211> LENGTH: 60
<212> TYPE: DNA
<213> ORGANISM: Homo Sapien

<400> SEQUENCE: 95
gcctccctcg cgccatccga ctcagcaatg ccaggggtg cgccagatgc ccgggaaagg     60

<210> SEQ ID NO 96
<211> LENGTH: 60
<212> TYPE: DNA
<213> ORGANISM: Homo Sapien

<400> SEQUENCE: 96
gcctccctcg cgccatccga ctcagcaatg ccaggtggat caggcagtcc ccatcgagag    60

<210> SEQ ID NO 97
<211> LENGTH: 60
<212> TYPE: DNA
<213> ORGANISM: Homo Sapien

<400> SEQUENCE: 97
gcctccctcg cgccatccga ctcagcaatg ccaggttggg tgcgacaggc ccctggacaa    60

<210> SEQ ID NO 98
<211> LENGTH: 60
<212> TYPE: DNA
<213> ORGANISM: Homo Sapien

<400> SEQUENCE: 98
gcctccctcg cgccatccga ctcagttatg ccaggggcct cagtgaaggt ctcctgcaag    60

<210> SEQ ID NO 99
<211> LENGTH: 60
<212> TYPE: DNA
<213> ORGANISM: Homo Sapien

<400> SEQUENCE: 99
gcctccctcg cgccatccga ctcagttatg ccagggtctg gtcctacgct ggtgaaaccc    60

<210> SEQ ID NO 100
<211> LENGTH: 60
<212> TYPE: DNA
<213> ORGANISM: Homo Sapien

<400> SEQUENCE: 100
gcctccctcg cgccatccga ctcagttatg ccaggctggg gggtccctga gactctcctg    60

<210> SEQ ID NO 101
<211> LENGTH: 60
<212> TYPE: DNA
<213> ORGANISM: Homo Sapien

<400> SEQUENCE: 101
gcctccctcg cgccatccga ctcagttatg ccaggcttcg agaccctgt ccctcacctg    60

<210> SEQ ID NO 102
<211> LENGTH: 60
<212> TYPE: DNA
<213> ORGANISM: Homo Sapien

<400> SEQUENCE: 102
gcctccctcg cgccatccga ctcagttatg ccaggcgggg agtctctgaa gatctcctgt    60

<210> SEQ ID NO 103
<211> LENGTH: 60
<212> TYPE: DNA
<213> ORGANISM: Homo Sapien

<400> SEQUENCE: 103
gcctccctcg cgccatccga ctcagttatg ccaggtcgca gaccctctca ctcacctgtg    60

<210> SEQ ID NO 104
<211> LENGTH: 60
<212> TYPE: DNA
<213> ORGANISM: Homo Sapien

<400> SEQUENCE: 104
gcctccctcg cgccatccga ctcagtcctg ccaggggcct cagtgaaggt ctcctgcaag    60

<210> SEQ ID NO 105
<211> LENGTH: 60
<212> TYPE: DNA
<213> ORGANISM: Homo Sapien

<400> SEQUENCE: 105
gcctccctcg cgccatccga ctcagtcctg ccagggtctg gtcctacgct ggtgaaaccc    60

<210> SEQ ID NO 106
<211> LENGTH: 60
<212> TYPE: DNA
<213> ORGANISM: Homo Sapien

<400> SEQUENCE: 106
gcctccctcg cgccatccga ctcagtcctg ccaggctggg gggtccctga gactctcctg    60

<210> SEQ ID NO 107
<211> LENGTH: 60
<212> TYPE: DNA
<213> ORGANISM: Homo Sapien

<400> SEQUENCE: 107
gcctccctcg cgccatccga ctcagtcctg ccaggcttcg agaccctgt ccctcacctg    60

<210> SEQ ID NO 108
<211> LENGTH: 60
<212> TYPE: DNA
<213> ORGANISM: Homo Sapien

<400> SEQUENCE: 108
gcctccctcg cgccatccga ctcagtcctg ccaggcgggg agtctctgaa gatctcctgt    60

<210> SEQ ID NO 109
<211> LENGTH: 60
<212> TYPE: DNA
<213> ORGANISM: Homo Sapien

<400> SEQUENCE: 109

```
gcctccctcg cgccatccga ctcagtcctg ccaggtcgca gaccctctca ctcacctgtg    60
```

<210> SEQ ID NO 110
<211> LENGTH: 57
<212> TYPE: DNA
<213> ORGANISM: Homo Sapien

<400> SEQUENCE: 110

```
gccttgccag cccgcgcagt ctcagattca ataagcttac ctgaggagac ggtgacc    57
```

<210> SEQ ID NO 111
<211> LENGTH: 57
<212> TYPE: DNA
<213> ORGANISM: Homo Sapien

<400> SEQUENCE: 111

```
gccttgccag cccgcgcagt ctcagtagca attcgcttac ctgaggagac ggtgacc    57
```

<210> SEQ ID NO 112
<211> LENGTH: 57
<212> TYPE: DNA
<213> ORGANISM: Homo Sapien

<400> SEQUENCE: 112

```
gccttgccag cccgcgcagt ctcagtgtca attcgcttac ctgaggagac ggtgacc    57
```

<210> SEQ ID NO 113
<211> LENGTH: 57
<212> TYPE: DNA
<213> ORGANISM: Homo Sapien

<400> SEQUENCE: 113

```
gccttgccag cccgcgcagt ctcagcggca attcgcttac ctgaggagac ggtgacc    57
```

<210> SEQ ID NO 114
<211> LENGTH: 57
<212> TYPE: DNA
<213> ORGANISM: Homo Sapien

<400> SEQUENCE: 114

```
gccttgccag cccgcgcagt ctcagcaaca attcgcttac ctgaggagac ggtgacc    57
```

<210> SEQ ID NO 115
<211> LENGTH: 57
<212> TYPE: DNA
<213> ORGANISM: Homo Sapien

<400> SEQUENCE: 115

```
gccttgccag cccgcgcagt ctcagcctca attcgcttac ctgaggagac ggtgacc    57
```

<210> SEQ ID NO 116
<211> LENGTH: 57
<212> TYPE: DNA
<213> ORGANISM: Homo Sapien

<400> SEQUENCE: 116

```
gccttgccag cccgcgcagt ctcagagcca attcgcttac ctgaggagac ggtgacc    57
```

<210> SEQ ID NO 117
<211> LENGTH: 57
<212> TYPE: DNA
<213> ORGANISM: Homo Sapien

<400> SEQUENCE: 117
gccttgccag cccgcgcagt ctcagattca attcgcttac ctgaggagac ggtgacc    57

<210> SEQ ID NO 118
<211> LENGTH: 57
<212> TYPE: DNA
<213> ORGANISM: Homo Sapien

<400> SEQUENCE: 118
gccttgccag cccgcgcagt ctcagacgca attcgcttac ctgaggagac ggtgacc    57

<210> SEQ ID NO 119
<211> LENGTH: 57
<212> TYPE: DNA
<213> ORGANISM: Homo Sapien

<400> SEQUENCE: 119
gccttgccag cccgcgcagt ctcagtagcc ataacttac ctgaggagac ggtgacc    57

<210> SEQ ID NO 120
<211> LENGTH: 57
<212> TYPE: DNA
<213> ORGANISM: Homo Sapien

<400> SEQUENCE: 120
gccttgccag cccgcgcagt ctcagttacc ataacttac ctgaggagac ggtgacc    57

<210> SEQ ID NO 121
<211> LENGTH: 57
<212> TYPE: DNA
<213> ORGANISM: Homo Sapien

<400> SEQUENCE: 121
gccttgccag cccgcgcagt ctcagtgtcc ataacttac ctgaggagac ggtgacc    57

<210> SEQ ID NO 122
<211> LENGTH: 57
<212> TYPE: DNA
<213> ORGANISM: Homo Sapien

<400> SEQUENCE: 122
gccttgccag cccgcgcagt ctcagcggcc ataacttac ctgaggagac ggtgacc    57

<210> SEQ ID NO 123
<211> LENGTH: 57
<212> TYPE: DNA
<213> ORGANISM: Homo Sapien

<400> SEQUENCE: 123
gccttgccag cccgcgcagt ctcagcctcc ataacttac ctgaggagac ggtgacc    57

<210> SEQ ID NO 124
<211> LENGTH: 57
<212> TYPE: DNA
<213> ORGANISM: Homo Sapien

<400> SEQUENCE: 124
gccttgccag cccgcgcagt ctcagacgcc ataacttac ctgaggagac ggtgacc    57

<210> SEQ ID NO 125
<211> LENGTH: 57
<212> TYPE: DNA
<213> ORGANISM: Homo Sapien

<400> SEQUENCE: 125
gccttgccag cccgcgcagt ctcagtagcc ggcaacttac ctgaggagac ggtgacc    57

<210> SEQ ID NO 126
<211> LENGTH: 57
<212> TYPE: DNA
<213> ORGANISM: Homo Sapien

<400> SEQUENCE: 126
gccttgccag cccgcgcagt ctcagttacc ggcaacttac ctgaggagac ggtgacc    57

<210> SEQ ID NO 127
<211> LENGTH: 57
<212> TYPE: DNA
<213> ORGANISM: Homo Sapien

<400> SEQUENCE: 127
gccttgccag cccgcgcagt ctcagtgtcc ggcaacttac ctgaggagac ggtgacc    57

<210> SEQ ID NO 128
<211> LENGTH: 57
<212> TYPE: DNA
<213> ORGANISM: Homo Sapien

<400> SEQUENCE: 128
gccttgccag cccgcgcagt ctcagcaacc ggcaacttac ctgaggagac ggtgacc    57

<210> SEQ ID NO 129
<211> LENGTH: 57
<212> TYPE: DNA
<213> ORGANISM: Homo Sapien

<400> SEQUENCE: 129
gccttgccag cccgcgcagt ctcagcctcc ggcaacttac ctgaggagac ggtgacc    57

<210> SEQ ID NO 130
<211> LENGTH: 57
<212> TYPE: DNA
<213> ORGANISM: Homo Sapien

<400> SEQUENCE: 130
gccttgccag cccgcgcagt ctcagattcc ggcaacttac ctgaggagac ggtgacc    57

<210> SEQ ID NO 131
<211> LENGTH: 57
<212> TYPE: DNA
<213> ORGANISM: Homo Sapien

<400> SEQUENCE: 131
gccttgccag cccgcgcagt ctcagacgcc ggcaacttac ctgaggagac ggtgacc    57

<210> SEQ ID NO 132
<211> LENGTH: 36
<212> TYPE: DNA
<213> ORGANISM: Homo Sapien

<400> SEQUENCE: 132
gccttgccag cccgcgcagt ctcagtagcc gcaggc    36

<210> SEQ ID NO 133
<211> LENGTH: 10
<212> TYPE: DNA

```
<213> ORGANISM: Homo Sapien

<400> SEQUENCE: 133
tagaagcaag                                                          10

<210> SEQ ID NO 134
<211> LENGTH: 10
<212> TYPE: DNA
<213> ORGANISM: Homo Sapien

<400> SEQUENCE: 134
tgtaagcaag                                                          10

<210> SEQ ID NO 135
<211> LENGTH: 10
<212> TYPE: DNA
<213> ORGANISM: Homo Sapien

<400> SEQUENCE: 135
cggaagcaag                                                          10

<210> SEQ ID NO 136
<211> LENGTH: 10
<212> TYPE: DNA
<213> ORGANISM: Homo Sapien

<400> SEQUENCE: 136
cctaagcaag                                                          10

<210> SEQ ID NO 137
<211> LENGTH: 10
<212> TYPE: DNA
<213> ORGANISM: Homo Sapien

<400> SEQUENCE: 137
agcaagcaag                                                          10

<210> SEQ ID NO 138
<211> LENGTH: 10
<212> TYPE: DNA
<213> ORGANISM: Homo Sapien

<400> SEQUENCE: 138
attaagcaag                                                          10

<210> SEQ ID NO 139
<211> LENGTH: 10
<212> TYPE: DNA
<213> ORGANISM: Homo Sapien

<400> SEQUENCE: 139
acgaagcaag                                                          10

<210> SEQ ID NO 140
<211> LENGTH: 10
<212> TYPE: DNA
<213> ORGANISM: Homo Sapien

<400> SEQUENCE: 140
tagaggcagg                                                          10

<210> SEQ ID NO 141
<211> LENGTH: 10
```

<212> TYPE: DNA
<213> ORGANISM: Homo Sapien

<400> SEQUENCE: 141
ttaaggcagg                                                          10

<210> SEQ ID NO 142
<211> LENGTH: 10
<212> TYPE: DNA
<213> ORGANISM: Homo Sapien

<400> SEQUENCE: 142
tgtaggcagg                                                          10

<210> SEQ ID NO 143
<211> LENGTH: 10
<212> TYPE: DNA
<213> ORGANISM: Homo Sapien

<400> SEQUENCE: 143
cggaggcagg                                                          10

<210> SEQ ID NO 144
<211> LENGTH: 10
<212> TYPE: DNA
<213> ORGANISM: Homo Sapien

<400> SEQUENCE: 144
cctaggcagg                                                          10

<210> SEQ ID NO 145
<211> LENGTH: 10
<212> TYPE: DNA
<213> ORGANISM: Homo Sapien

<400> SEQUENCE: 145
agcaggcagg                                                          10

<210> SEQ ID NO 146
<211> LENGTH: 10
<212> TYPE: DNA
<213> ORGANISM: Homo Sapien

<400> SEQUENCE: 146
attaggcagg                                                          10

<210> SEQ ID NO 147
<211> LENGTH: 10
<212> TYPE: DNA
<213> ORGANISM: Homo Sapien

<400> SEQUENCE: 147
acgaggcagg                                                          10

<210> SEQ ID NO 148
<211> LENGTH: 10
<212> TYPE: DNA
<213> ORGANISM: Homo Sapien

<400> SEQUENCE: 148
tagcattagg                                                          10

<210> SEQ ID NO 149

```
<211> LENGTH: 10
<212> TYPE: DNA
<213> ORGANISM: Homo Sapien

<400> SEQUENCE: 149
ttacattagg                                                              10

<210> SEQ ID NO 150
<211> LENGTH: 10
<212> TYPE: DNA
<213> ORGANISM: Homo Sapien

<400> SEQUENCE: 150
tgtcattagg                                                              10

<210> SEQ ID NO 151
<211> LENGTH: 10
<212> TYPE: DNA
<213> ORGANISM: Homo Sapien

<400> SEQUENCE: 151
cggcattagg                                                              10

<210> SEQ ID NO 152
<211> LENGTH: 10
<212> TYPE: DNA
<213> ORGANISM: Homo Sapien

<400> SEQUENCE: 152
caacattagg                                                              10

<210> SEQ ID NO 153
<211> LENGTH: 10
<212> TYPE: DNA
<213> ORGANISM: Homo Sapien

<400> SEQUENCE: 153
cctcattagg                                                              10

<210> SEQ ID NO 154
<211> LENGTH: 10
<212> TYPE: DNA
<213> ORGANISM: Homo Sapien

<400> SEQUENCE: 154
agccattagg                                                              10

<210> SEQ ID NO 155
<211> LENGTH: 10
<212> TYPE: DNA
<213> ORGANISM: Homo Sapien

<400> SEQUENCE: 155
attcattagg                                                              10

<210> SEQ ID NO 156
<211> LENGTH: 10
<212> TYPE: DNA
<213> ORGANISM: Homo Sapien

<400> SEQUENCE: 156
acgcattagg                                                              10
```

```
<210> SEQ ID NO 157
<211> LENGTH: 10
<212> TYPE: DNA
<213> ORGANISM: Homo Sapien

<400> SEQUENCE: 157
tagcattcca                                                          10

<210> SEQ ID NO 158
<211> LENGTH: 10
<212> TYPE: DNA
<213> ORGANISM: Homo Sapien

<400> SEQUENCE: 158
ttacattcca                                                          10

<210> SEQ ID NO 159
<211> LENGTH: 10
<212> TYPE: DNA
<213> ORGANISM: Homo Sapien

<400> SEQUENCE: 159
tgtcattcca                                                          10

<210> SEQ ID NO 160
<211> LENGTH: 10
<212> TYPE: DNA
<213> ORGANISM: Homo Sapien

<400> SEQUENCE: 160
cggcattcca                                                          10

<210> SEQ ID NO 161
<211> LENGTH: 10
<212> TYPE: DNA
<213> ORGANISM: Homo Sapien

<400> SEQUENCE: 161
caacattcca                                                          10

<210> SEQ ID NO 162
<211> LENGTH: 10
<212> TYPE: DNA
<213> ORGANISM: Homo Sapien

<400> SEQUENCE: 162
cctcattcca                                                          10

<210> SEQ ID NO 163
<211> LENGTH: 10
<212> TYPE: DNA
<213> ORGANISM: Homo Sapien

<400> SEQUENCE: 163
agccattcca                                                          10

<210> SEQ ID NO 164
<211> LENGTH: 10
<212> TYPE: DNA
<213> ORGANISM: Homo Sapien

<400> SEQUENCE: 164
attcattcca                                                          10
```

```
<210> SEQ ID NO 165
<211> LENGTH: 10
<212> TYPE: DNA
<213> ORGANISM: Homo Sapien

<400> SEQUENCE: 165
acgcattcca                                                              10

<210> SEQ ID NO 166
<211> LENGTH: 10
<212> TYPE: DNA
<213> ORGANISM: Homo Sapien

<400> SEQUENCE: 166
tagcaataag                                                              10

<210> SEQ ID NO 167
<211> LENGTH: 10
<212> TYPE: DNA
<213> ORGANISM: Homo Sapien

<400> SEQUENCE: 167
ttacaataag                                                              10

<210> SEQ ID NO 168
<211> LENGTH: 10
<212> TYPE: DNA
<213> ORGANISM: Homo Sapien

<400> SEQUENCE: 168
tgtcaataag                                                              10

<210> SEQ ID NO 169
<211> LENGTH: 10
<212> TYPE: DNA
<213> ORGANISM: Homo Sapien

<400> SEQUENCE: 169
cggcaataag                                                              10

<210> SEQ ID NO 170
<211> LENGTH: 10
<212> TYPE: DNA
<213> ORGANISM: Homo Sapien

<400> SEQUENCE: 170
caacaataag                                                              10

<210> SEQ ID NO 171
<211> LENGTH: 10
<212> TYPE: DNA
<213> ORGANISM: Homo Sapien

<400> SEQUENCE: 171
cctcaataag                                                              10

<210> SEQ ID NO 172
<211> LENGTH: 10
<212> TYPE: DNA
<213> ORGANISM: Homo Sapien

<400> SEQUENCE: 172
agccaataag                                                              10
```

```
<210> SEQ ID NO 173
<211> LENGTH: 10
<212> TYPE: DNA
<213> ORGANISM: Homo Sapien

<400> SEQUENCE: 173
attcaataag                                                          10

<210> SEQ ID NO 174
<211> LENGTH: 10
<212> TYPE: DNA
<213> ORGANISM: Homo Sapien

<400> SEQUENCE: 174
acgcaataag                                                          10

<210> SEQ ID NO 175
<211> LENGTH: 10
<212> TYPE: DNA
<213> ORGANISM: Homo Sapien

<400> SEQUENCE: 175
tagcaattcg                                                          10

<210> SEQ ID NO 176
<211> LENGTH: 10
<212> TYPE: DNA
<213> ORGANISM: Homo Sapien

<400> SEQUENCE: 176
ttacaattcg                                                          10

<210> SEQ ID NO 177
<211> LENGTH: 10
<212> TYPE: DNA
<213> ORGANISM: Homo Sapien

<400> SEQUENCE: 177
tgtcaattcg                                                          10

<210> SEQ ID NO 178
<211> LENGTH: 10
<212> TYPE: DNA
<213> ORGANISM: Homo Sapien

<400> SEQUENCE: 178
cggcaattcg                                                          10

<210> SEQ ID NO 179
<211> LENGTH: 10
<212> TYPE: DNA
<213> ORGANISM: Homo Sapien

<400> SEQUENCE: 179
caacaattcg                                                          10

<210> SEQ ID NO 180
<211> LENGTH: 10
<212> TYPE: DNA
<213> ORGANISM: Homo Sapien

<400> SEQUENCE: 180
```
cctcaattcg                                                              10

<210> SEQ ID NO 181
<211> LENGTH: 10
<212> TYPE: DNA
<213> ORGANISM: Homo Sapien

<400> SEQUENCE: 181
agccaattcg                                                              10

<210> SEQ ID NO 182
<211> LENGTH: 10
<212> TYPE: DNA
<213> ORGANISM: Homo Sapien

<400> SEQUENCE: 182
attcaattcg                                                              10

<210> SEQ ID NO 183
<211> LENGTH: 10
<212> TYPE: DNA
<213> ORGANISM: Homo Sapien

<400> SEQUENCE: 183
acgcaattcg                                                              10

<210> SEQ ID NO 184
<211> LENGTH: 10
<212> TYPE: DNA
<213> ORGANISM: Homo Sapien

<400> SEQUENCE: 184
tagccaataa                                                              10

<210> SEQ ID NO 185
<211> LENGTH: 10
<212> TYPE: DNA
<213> ORGANISM: Homo Sapien

<400> SEQUENCE: 185
ttaccaataa                                                              10

<210> SEQ ID NO 186
<211> LENGTH: 10
<212> TYPE: DNA
<213> ORGANISM: Homo Sapien

<400> SEQUENCE: 186
tgtccaataa                                                              10

<210> SEQ ID NO 187
<211> LENGTH: 10
<212> TYPE: DNA
<213> ORGANISM: Homo Sapien

<400> SEQUENCE: 187
cggccaataa                                                              10

<210> SEQ ID NO 188
<211> LENGTH: 10
<212> TYPE: DNA
<213> ORGANISM: Homo Sapien

<400> SEQUENCE: 188

```
caaccaataa                                                              10

<210> SEQ ID NO 189
<211> LENGTH: 10
<212> TYPE: DNA
<213> ORGANISM: Homo Sapien

<400> SEQUENCE: 189
cctccaataa                                                              10

<210> SEQ ID NO 190
<211> LENGTH: 10
<212> TYPE: DNA
<213> ORGANISM: Homo Sapien

<400> SEQUENCE: 190
attccaataa                                                              10

<210> SEQ ID NO 191
<211> LENGTH: 10
<212> TYPE: DNA
<213> ORGANISM: Homo Sapien

<400> SEQUENCE: 191
acgccaataa                                                              10

<210> SEQ ID NO 192
<211> LENGTH: 10
<212> TYPE: DNA
<213> ORGANISM: Homo Sapien

<400> SEQUENCE: 192
tagccggcaa                                                              10

<210> SEQ ID NO 193
<211> LENGTH: 10
<212> TYPE: DNA
<213> ORGANISM: Homo Sapien

<400> SEQUENCE: 193
ttaccggcaa                                                              10

<210> SEQ ID NO 194
<211> LENGTH: 10
<212> TYPE: DNA
<213> ORGANISM: Homo Sapien

<400> SEQUENCE: 194
tgtccggcaa                                                              10

<210> SEQ ID NO 195
<211> LENGTH: 10
<212> TYPE: DNA
<213> ORGANISM: Homo Sapien

<400> SEQUENCE: 195
cggccggcaa                                                              10

<210> SEQ ID NO 196
<211> LENGTH: 10
<212> TYPE: DNA
<213> ORGANISM: Homo Sapien
```

```
<400> SEQUENCE: 196
caaccggcaa                                                          10

<210> SEQ ID NO 197
<211> LENGTH: 10
<212> TYPE: DNA
<213> ORGANISM: Homo Sapien

<400> SEQUENCE: 197
cctccggcaa                                                          10

<210> SEQ ID NO 198
<211> LENGTH: 10
<212> TYPE: DNA
<213> ORGANISM: Homo Sapien

<400> SEQUENCE: 198
attccggcaa                                                          10

<210> SEQ ID NO 199
<211> LENGTH: 10
<212> TYPE: DNA
<213> ORGANISM: Homo Sapien

<400> SEQUENCE: 199
acgccggcaa                                                          10

<210> SEQ ID NO 200
<211> LENGTH: 10
<212> TYPE: DNA
<213> ORGANISM: Homo Sapien

<400> SEQUENCE: 200
tagccgcagg                                                          10

<210> SEQ ID NO 201
<211> LENGTH: 10
<212> TYPE: DNA
<213> ORGANISM: Homo Sapien

<400> SEQUENCE: 201
ttaccgcagg                                                          10

<210> SEQ ID NO 202
<211> LENGTH: 10
<212> TYPE: DNA
<213> ORGANISM: Homo Sapien

<400> SEQUENCE: 202
tgtccgcagg                                                          10

<210> SEQ ID NO 203
<211> LENGTH: 10
<212> TYPE: DNA
<213> ORGANISM: Homo Sapien

<400> SEQUENCE: 203
cggccgcagg                                                          10

<210> SEQ ID NO 204
<211> LENGTH: 10
<212> TYPE: DNA
<213> ORGANISM: Homo Sapien
```

```
<400> SEQUENCE: 204
caaccgcagg                                                          10

<210> SEQ ID NO 205
<211> LENGTH: 10
<212> TYPE: DNA
<213> ORGANISM: Homo Sapien

<400> SEQUENCE: 205
cctccgcagg                                                          10

<210> SEQ ID NO 206
<211> LENGTH: 10
<212> TYPE: DNA
<213> ORGANISM: Homo Sapien

<400> SEQUENCE: 206
attccgcagg                                                          10

<210> SEQ ID NO 207
<211> LENGTH: 10
<212> TYPE: DNA
<213> ORGANISM: Homo Sapien

<400> SEQUENCE: 207
acgccgcagg                                                          10

<210> SEQ ID NO 208
<211> LENGTH: 10
<212> TYPE: DNA
<213> ORGANISM: Homo Sapien

<400> SEQUENCE: 208
tagccgttag                                                          10

<210> SEQ ID NO 209
<211> LENGTH: 10
<212> TYPE: DNA
<213> ORGANISM: Homo Sapien

<400> SEQUENCE: 209
ttaccgttag                                                          10

<210> SEQ ID NO 210
<211> LENGTH: 10
<212> TYPE: DNA
<213> ORGANISM: Homo Sapien

<400> SEQUENCE: 210
tgtccgttag                                                          10

<210> SEQ ID NO 211
<211> LENGTH: 10
<212> TYPE: DNA
<213> ORGANISM: Homo Sapien

<400> SEQUENCE: 211
cggccgttag                                                          10

<210> SEQ ID NO 212
<211> LENGTH: 10
<212> TYPE: DNA
```

```
<213> ORGANISM: Homo Sapien

<400> SEQUENCE: 212
caaccgttag                                                          10

<210> SEQ ID NO 213
<211> LENGTH: 10
<212> TYPE: DNA
<213> ORGANISM: Homo Sapien

<400> SEQUENCE: 213
cctccgttag                                                          10

<210> SEQ ID NO 214
<211> LENGTH: 10
<212> TYPE: DNA
<213> ORGANISM: Homo Sapien

<400> SEQUENCE: 214
attccgttag                                                          10

<210> SEQ ID NO 215
<211> LENGTH: 10
<212> TYPE: DNA
<213> ORGANISM: Homo Sapien

<400> SEQUENCE: 215
acgccgttag                                                          10

<210> SEQ ID NO 216
<211> LENGTH: 10
<212> TYPE: DNA
<213> ORGANISM: Homo Sapien

<400> SEQUENCE: 216
tagcggtaag                                                          10

<210> SEQ ID NO 217
<211> LENGTH: 10
<212> TYPE: DNA
<213> ORGANISM: Homo Sapien

<400> SEQUENCE: 217
ttacggtaag                                                          10

<210> SEQ ID NO 218
<211> LENGTH: 10
<212> TYPE: DNA
<213> ORGANISM: Homo Sapien

<400> SEQUENCE: 218
tgtcggtaag                                                          10

<210> SEQ ID NO 219
<211> LENGTH: 10
<212> TYPE: DNA
<213> ORGANISM: Homo Sapien

<400> SEQUENCE: 219
cggcggtaag                                                          10

<210> SEQ ID NO 220
<211> LENGTH: 10
```

```
<212> TYPE: DNA
<213> ORGANISM: Homo Sapien

<400> SEQUENCE: 220
caacggtaag                                                              10

<210> SEQ ID NO 221
<211> LENGTH: 10
<212> TYPE: DNA
<213> ORGANISM: Homo Sapien

<400> SEQUENCE: 221
cctcggtaag                                                              10

<210> SEQ ID NO 222
<211> LENGTH: 10
<212> TYPE: DNA
<213> ORGANISM: Homo Sapien

<400> SEQUENCE: 222
agccggtaag                                                              10

<210> SEQ ID NO 223
<211> LENGTH: 10
<212> TYPE: DNA
<213> ORGANISM: Homo Sapien

<400> SEQUENCE: 223
attcggtaag                                                              10

<210> SEQ ID NO 224
<211> LENGTH: 10
<212> TYPE: DNA
<213> ORGANISM: Homo Sapien

<400> SEQUENCE: 224
acgcggtaag                                                              10

<210> SEQ ID NO 225
<211> LENGTH: 10
<212> TYPE: DNA
<213> ORGANISM: Homo Sapien

<400> SEQUENCE: 225
tagtaggcgg                                                              10

<210> SEQ ID NO 226
<211> LENGTH: 10
<212> TYPE: DNA
<213> ORGANISM: Homo Sapien

<400> SEQUENCE: 226
ttataggcgg                                                              10

<210> SEQ ID NO 227
<211> LENGTH: 10
<212> TYPE: DNA
<213> ORGANISM: Homo Sapien

<400> SEQUENCE: 227
tcctaggcgg                                                              10

<210> SEQ ID NO 228
```

```
<211> LENGTH: 10
<212> TYPE: DNA
<213> ORGANISM: Homo Sapien

<400> SEQUENCE: 228
tgttaggcgg                                                          10

<210> SEQ ID NO 229
<211> LENGTH: 10
<212> TYPE: DNA
<213> ORGANISM: Homo Sapien

<400> SEQUENCE: 229
cggtaggcgg                                                          10

<210> SEQ ID NO 230
<211> LENGTH: 10
<212> TYPE: DNA
<213> ORGANISM: Homo Sapien

<400> SEQUENCE: 230
caataggcgg                                                          10

<210> SEQ ID NO 231
<211> LENGTH: 10
<212> TYPE: DNA
<213> ORGANISM: Homo Sapien

<400> SEQUENCE: 231
ccttaggcgg                                                          10

<210> SEQ ID NO 232
<211> LENGTH: 10
<212> TYPE: DNA
<213> ORGANISM: Homo Sapien

<400> SEQUENCE: 232
agctaggcgg                                                          10

<210> SEQ ID NO 233
<211> LENGTH: 10
<212> TYPE: DNA
<213> ORGANISM: Homo Sapien

<400> SEQUENCE: 233
acgtaggcgg                                                          10

<210> SEQ ID NO 234
<211> LENGTH: 10
<212> TYPE: DNA
<213> ORGANISM: Homo Sapien

<400> SEQUENCE: 234
tagtaatagg                                                          10

<210> SEQ ID NO 235
<211> LENGTH: 10
<212> TYPE: DNA
<213> ORGANISM: Homo Sapien

<400> SEQUENCE: 235
ttataatagg                                                          10
```

```
<210> SEQ ID NO 236
<211> LENGTH: 10
<212> TYPE: DNA
<213> ORGANISM: Homo Sapien

<400> SEQUENCE: 236
tcctaatagg                                                          10

<210> SEQ ID NO 237
<211> LENGTH: 10
<212> TYPE: DNA
<213> ORGANISM: Homo Sapien

<400> SEQUENCE: 237
tgttaatagg                                                          10

<210> SEQ ID NO 238
<211> LENGTH: 10
<212> TYPE: DNA
<213> ORGANISM: Homo Sapien

<400> SEQUENCE: 238
cggtaatagg                                                          10

<210> SEQ ID NO 239
<211> LENGTH: 10
<212> TYPE: DNA
<213> ORGANISM: Homo Sapien

<400> SEQUENCE: 239
caataatagg                                                          10

<210> SEQ ID NO 240
<211> LENGTH: 10
<212> TYPE: DNA
<213> ORGANISM: Homo Sapien

<400> SEQUENCE: 240
ccttaatagg                                                          10

<210> SEQ ID NO 241
<211> LENGTH: 10
<212> TYPE: DNA
<213> ORGANISM: Homo Sapien

<400> SEQUENCE: 241
agctaatagg                                                          10

<210> SEQ ID NO 242
<211> LENGTH: 10
<212> TYPE: DNA
<213> ORGANISM: Homo Sapien

<400> SEQUENCE: 242
acgtaatagg                                                          10

<210> SEQ ID NO 243
<211> LENGTH: 10
<212> TYPE: DNA
<213> ORGANISM: Homo Sapien

<400> SEQUENCE: 243
tagtaaccaa                                                          10
```

```
<210> SEQ ID NO 244
<211> LENGTH: 10
<212> TYPE: DNA
<213> ORGANISM: Homo Sapien

<400> SEQUENCE: 244
ttataaccaa                                                          10

<210> SEQ ID NO 245
<211> LENGTH: 10
<212> TYPE: DNA
<213> ORGANISM: Homo Sapien

<400> SEQUENCE: 245
tcctaaccaa                                                          10

<210> SEQ ID NO 246
<211> LENGTH: 10
<212> TYPE: DNA
<213> ORGANISM: Homo Sapien

<400> SEQUENCE: 246
tgttaaccaa                                                          10

<210> SEQ ID NO 247
<211> LENGTH: 10
<212> TYPE: DNA
<213> ORGANISM: Homo Sapien

<400> SEQUENCE: 247
cggtaaccaa                                                          10

<210> SEQ ID NO 248
<211> LENGTH: 10
<212> TYPE: DNA
<213> ORGANISM: Homo Sapien

<400> SEQUENCE: 248
caataaccaa                                                          10

<210> SEQ ID NO 249
<211> LENGTH: 10
<212> TYPE: DNA
<213> ORGANISM: Homo Sapien

<400> SEQUENCE: 249
ccttaaccaa                                                          10

<210> SEQ ID NO 250
<211> LENGTH: 10
<212> TYPE: DNA
<213> ORGANISM: Homo Sapien

<400> SEQUENCE: 250
agctaaccaa                                                          10

<210> SEQ ID NO 251
<211> LENGTH: 10
<212> TYPE: DNA
<213> ORGANISM: Homo Sapien

<400> SEQUENCE: 251
acgtaaccaa                                                          10
```

```
<210> SEQ ID NO 252
<211> LENGTH: 10
<212> TYPE: DNA
<213> ORGANISM: Homo Sapien

<400> SEQUENCE: 252
tagtccgtaa                                                            10

<210> SEQ ID NO 253
<211> LENGTH: 10
<212> TYPE: DNA
<213> ORGANISM: Homo Sapien

<400> SEQUENCE: 253
ttatccgtaa                                                            10

<210> SEQ ID NO 254
<211> LENGTH: 10
<212> TYPE: DNA
<213> ORGANISM: Homo Sapien

<400> SEQUENCE: 254
tcctccgtaa                                                            10

<210> SEQ ID NO 255
<211> LENGTH: 10
<212> TYPE: DNA
<213> ORGANISM: Homo Sapien

<400> SEQUENCE: 255
tgttccgtaa                                                            10

<210> SEQ ID NO 256
<211> LENGTH: 10
<212> TYPE: DNA
<213> ORGANISM: Homo Sapien

<400> SEQUENCE: 256
cggtccgtaa                                                            10

<210> SEQ ID NO 257
<211> LENGTH: 10
<212> TYPE: DNA
<213> ORGANISM: Homo Sapien

<400> SEQUENCE: 257
caatccgtaa                                                            10

<210> SEQ ID NO 258
<211> LENGTH: 10
<212> TYPE: DNA
<213> ORGANISM: Homo Sapien

<400> SEQUENCE: 258
ccttccgtaa                                                            10

<210> SEQ ID NO 259
<211> LENGTH: 10
<212> TYPE: DNA
<213> ORGANISM: Homo Sapien

<400> SEQUENCE: 259
```

```
agctccgtaa                                                              10

<210> SEQ ID NO 260
<211> LENGTH: 10
<212> TYPE: DNA
<213> ORGANISM: Homo Sapien

<400> SEQUENCE: 260
acgtccgtaa                                                              10

<210> SEQ ID NO 261
<211> LENGTH: 10
<212> TYPE: DNA
<213> ORGANISM: Homo Sapien

<400> SEQUENCE: 261
tagtggcaag                                                              10

<210> SEQ ID NO 262
<211> LENGTH: 10
<212> TYPE: DNA
<213> ORGANISM: Homo Sapien

<400> SEQUENCE: 262
ttatggcaag                                                              10

<210> SEQ ID NO 263
<211> LENGTH: 10
<212> TYPE: DNA
<213> ORGANISM: Homo Sapien

<400> SEQUENCE: 263
tcctggcaag                                                              10

<210> SEQ ID NO 264
<211> LENGTH: 10
<212> TYPE: DNA
<213> ORGANISM: Homo Sapien

<400> SEQUENCE: 264
tgttggcaag                                                              10

<210> SEQ ID NO 265
<211> LENGTH: 10
<212> TYPE: DNA
<213> ORGANISM: Homo Sapien

<400> SEQUENCE: 265
cggtggcaag                                                              10

<210> SEQ ID NO 266
<211> LENGTH: 10
<212> TYPE: DNA
<213> ORGANISM: Homo Sapien

<400> SEQUENCE: 266
caatggcaag                                                              10

<210> SEQ ID NO 267
<211> LENGTH: 10
<212> TYPE: DNA
<213> ORGANISM: Homo Sapien

<400> SEQUENCE: 267
```
ccttggcaag                                                                10

<210> SEQ ID NO 268
<211> LENGTH: 10
<212> TYPE: DNA
<213> ORGANISM: Homo Sapien

<400> SEQUENCE: 268
agctggcaag                                                                10

<210> SEQ ID NO 269
<211> LENGTH: 10
<212> TYPE: DNA
<213> ORGANISM: Homo Sapien

<400> SEQUENCE: 269
acgtggcaag                                                                10

<210> SEQ ID NO 270
<211> LENGTH: 10
<212> TYPE: DNA
<213> ORGANISM: Homo Sapien

<400> SEQUENCE: 270
tagtccggtg                                                                10

<210> SEQ ID NO 271
<211> LENGTH: 10
<212> TYPE: DNA
<213> ORGANISM: Homo Sapien

<400> SEQUENCE: 271
ttatccggtg                                                                10

<210> SEQ ID NO 272
<211> LENGTH: 10
<212> TYPE: DNA
<213> ORGANISM: Homo Sapien

<400> SEQUENCE: 272
tcctccggtg                                                                10

<210> SEQ ID NO 273
<211> LENGTH: 10
<212> TYPE: DNA
<213> ORGANISM: Homo Sapien

<400> SEQUENCE: 273
tgttccggtg                                                                10

<210> SEQ ID NO 274
<211> LENGTH: 10
<212> TYPE: DNA
<213> ORGANISM: Homo Sapien

<400> SEQUENCE: 274
cggtccggtg                                                                10

<210> SEQ ID NO 275
<211> LENGTH: 10
<212> TYPE: DNA
<213> ORGANISM: Homo Sapien

```
<400> SEQUENCE: 275
caatccggtg                                                              10

<210> SEQ ID NO 276
<211> LENGTH: 10
<212> TYPE: DNA
<213> ORGANISM: Homo Sapien

<400> SEQUENCE: 276
ccttccggtg                                                              10

<210> SEQ ID NO 277
<211> LENGTH: 10
<212> TYPE: DNA
<213> ORGANISM: Homo Sapien

<400> SEQUENCE: 277
agctccggtg                                                              10

<210> SEQ ID NO 278
<211> LENGTH: 10
<212> TYPE: DNA
<213> ORGANISM: Homo Sapien

<400> SEQUENCE: 278
acgtccggtg                                                              10

<210> SEQ ID NO 279
<211> LENGTH: 10
<212> TYPE: DNA
<213> ORGANISM: Homo Sapien

<400> SEQUENCE: 279
tagtcctaag                                                              10

<210> SEQ ID NO 280
<211> LENGTH: 10
<212> TYPE: DNA
<213> ORGANISM: Homo Sapien

<400> SEQUENCE: 280
ttatcctaag                                                              10

<210> SEQ ID NO 281
<211> LENGTH: 10
<212> TYPE: DNA
<213> ORGANISM: Homo Sapien

<400> SEQUENCE: 281
tcctcctaag                                                              10

<210> SEQ ID NO 282
<211> LENGTH: 10
<212> TYPE: DNA
<213> ORGANISM: Homo Sapien

<400> SEQUENCE: 282
tgttcctaag                                                              10

<210> SEQ ID NO 283
<211> LENGTH: 10
<212> TYPE: DNA
<213> ORGANISM: Homo Sapien
```

-continued

```
<400> SEQUENCE: 283
cggtcctaag                                                            10

<210> SEQ ID NO 284
<211> LENGTH: 10
<212> TYPE: DNA
<213> ORGANISM: Homo Sapien

<400> SEQUENCE: 284
caatcctaag                                                            10

<210> SEQ ID NO 285
<211> LENGTH: 10
<212> TYPE: DNA
<213> ORGANISM: Homo Sapien

<400> SEQUENCE: 285
ccttcctaag                                                            10

<210> SEQ ID NO 286
<211> LENGTH: 10
<212> TYPE: DNA
<213> ORGANISM: Homo Sapien

<400> SEQUENCE: 286
agctcctaag                                                            10

<210> SEQ ID NO 287
<211> LENGTH: 10
<212> TYPE: DNA
<213> ORGANISM: Homo Sapien

<400> SEQUENCE: 287
acgtcctaag                                                            10

<210> SEQ ID NO 288
<211> LENGTH: 10
<212> TYPE: DNA
<213> ORGANISM: Homo Sapien

<400> SEQUENCE: 288
tagtgccagg                                                            10

<210> SEQ ID NO 289
<211> LENGTH: 10
<212> TYPE: DNA
<213> ORGANISM: Homo Sapien

<400> SEQUENCE: 289
ttatgccagg                                                            10

<210> SEQ ID NO 290
<211> LENGTH: 10
<212> TYPE: DNA
<213> ORGANISM: Homo Sapien

<400> SEQUENCE: 290
tcctgccagg                                                            10

<210> SEQ ID NO 291
<211> LENGTH: 10
<212> TYPE: DNA
```

```
<213> ORGANISM: Homo Sapien

<400> SEQUENCE: 291
tgttgccagg                                                              10

<210> SEQ ID NO 292
<211> LENGTH: 10
<212> TYPE: DNA
<213> ORGANISM: Homo Sapien

<400> SEQUENCE: 292
cggtgccagg                                                              10

<210> SEQ ID NO 293
<211> LENGTH: 10
<212> TYPE: DNA
<213> ORGANISM: Homo Sapien

<400> SEQUENCE: 293
caatgccagg                                                              10

<210> SEQ ID NO 294
<211> LENGTH: 10
<212> TYPE: DNA
<213> ORGANISM: Homo Sapien

<400> SEQUENCE: 294
ccttgccagg                                                              10

<210> SEQ ID NO 295
<211> LENGTH: 10
<212> TYPE: DNA
<213> ORGANISM: Homo Sapien

<400> SEQUENCE: 295
agctgccagg                                                              10

<210> SEQ ID NO 296
<211> LENGTH: 10
<212> TYPE: DNA
<213> ORGANISM: Homo Sapien

<400> SEQUENCE: 296
acgtgccagg                                                              10

<210> SEQ ID NO 297
<211> LENGTH: 10
<212> TYPE: DNA
<213> ORGANISM: Homo Sapien

<400> SEQUENCE: 297
tagttattcg                                                              10

<210> SEQ ID NO 298
<211> LENGTH: 10
<212> TYPE: DNA
<213> ORGANISM: Homo Sapien

<400> SEQUENCE: 298
ttattattcg                                                              10

<210> SEQ ID NO 299
<211> LENGTH: 10
```

```
<212> TYPE: DNA
<213> ORGANISM: Homo Sapien

<400> SEQUENCE: 299
tccttattcg                                                            10

<210> SEQ ID NO 300
<211> LENGTH: 10
<212> TYPE: DNA
<213> ORGANISM: Homo Sapien

<400> SEQUENCE: 300
cggttattcg                                                            10

<210> SEQ ID NO 301
<211> LENGTH: 10
<212> TYPE: DNA
<213> ORGANISM: Homo Sapien

<400> SEQUENCE: 301
caattattcg                                                            10

<210> SEQ ID NO 302
<211> LENGTH: 10
<212> TYPE: DNA
<213> ORGANISM: Homo Sapien

<400> SEQUENCE: 302
agcttattcg                                                            10

<210> SEQ ID NO 303
<211> LENGTH: 10
<212> TYPE: DNA
<213> ORGANISM: Homo Sapien

<400> SEQUENCE: 303
acgttattcg                                                            10

<210> SEQ ID NO 304
<211> LENGTH: 10
<212> TYPE: DNA
<213> ORGANISM: Homo Sapien

<400> SEQUENCE: 304
tagttaatcc                                                            10

<210> SEQ ID NO 305
<211> LENGTH: 10
<212> TYPE: DNA
<213> ORGANISM: Homo Sapien

<400> SEQUENCE: 305
ttattaatcc                                                            10

<210> SEQ ID NO 306
<211> LENGTH: 10
<212> TYPE: DNA
<213> ORGANISM: Homo Sapien

<400> SEQUENCE: 306
tccttaatcc                                                            10

<210> SEQ ID NO 307
```

```
<211> LENGTH: 10
<212> TYPE: DNA
<213> ORGANISM: Homo Sapien

<400> SEQUENCE: 307
cggttaatcc                                                            10

<210> SEQ ID NO 308
<211> LENGTH: 10
<212> TYPE: DNA
<213> ORGANISM: Homo Sapien

<400> SEQUENCE: 308
caattaatcc                                                            10

<210> SEQ ID NO 309
<211> LENGTH: 10
<212> TYPE: DNA
<213> ORGANISM: Homo Sapien

<400> SEQUENCE: 309
agcttaatcc                                                            10

<210> SEQ ID NO 310
<211> LENGTH: 10
<212> TYPE: DNA
<213> ORGANISM: Homo Sapien

<400> SEQUENCE: 310
acgttaatcc                                                            10

<210> SEQ ID NO 311
<211> LENGTH: 10
<212> TYPE: DNA
<213> ORGANISM: Homo Sapien

<400> SEQUENCE: 311
tagttcggaa                                                            10

<210> SEQ ID NO 312
<211> LENGTH: 10
<212> TYPE: DNA
<213> ORGANISM: Homo Sapien

<400> SEQUENCE: 312
ttattcggaa                                                            10

<210> SEQ ID NO 313
<211> LENGTH: 10
<212> TYPE: DNA
<213> ORGANISM: Homo Sapien

<400> SEQUENCE: 313
tccttcggaa                                                            10

<210> SEQ ID NO 314
<211> LENGTH: 10
<212> TYPE: DNA
<213> ORGANISM: Homo Sapien

<400> SEQUENCE: 314
cggttcggaa                                                            10
```

```
<210> SEQ ID NO 315
<211> LENGTH: 10
<212> TYPE: DNA
<213> ORGANISM: Homo Sapien

<400> SEQUENCE: 315
caattcggaa                                                          10

<210> SEQ ID NO 316
<211> LENGTH: 10
<212> TYPE: DNA
<213> ORGANISM: Homo Sapien

<400> SEQUENCE: 316
agcttcggaa                                                          10

<210> SEQ ID NO 317
<211> LENGTH: 10
<212> TYPE: DNA
<213> ORGANISM: Homo Sapien

<400> SEQUENCE: 317
acgttcggaa                                                          10

<210> SEQ ID NO 318
<211> LENGTH: 10
<212> TYPE: DNA
<213> ORGANISM: Homo Sapien

<400> SEQUENCE: 318
tagttgttaa                                                          10

<210> SEQ ID NO 319
<211> LENGTH: 10
<212> TYPE: DNA
<213> ORGANISM: Homo Sapien

<400> SEQUENCE: 319
ttattgttaa                                                          10

<210> SEQ ID NO 320
<211> LENGTH: 10
<212> TYPE: DNA
<213> ORGANISM: Homo Sapien

<400> SEQUENCE: 320
tccttgttaa                                                          10

<210> SEQ ID NO 321
<211> LENGTH: 10
<212> TYPE: DNA
<213> ORGANISM: Homo Sapien

<400> SEQUENCE: 321
cggttgttaa                                                          10

<210> SEQ ID NO 322
<211> LENGTH: 10
<212> TYPE: DNA
<213> ORGANISM: Homo Sapien

<400> SEQUENCE: 322
caattgttaa                                                          10
```

```
<210> SEQ ID NO 323
<211> LENGTH: 10
<212> TYPE: DNA
<213> ORGANISM: Homo Sapien

<400> SEQUENCE: 323
agcttgttaa                                                          10

<210> SEQ ID NO 324
<211> LENGTH: 10
<212> TYPE: DNA
<213> ORGANISM: Homo Sapien

<400> SEQUENCE: 324
acgttgttaa                                                          10

<210> SEQ ID NO 325
<211> LENGTH: 10
<212> TYPE: DNA
<213> ORGANISM: Homo Sapien

<400> SEQUENCE: 325
tagttaacag                                                          10

<210> SEQ ID NO 326
<211> LENGTH: 10
<212> TYPE: DNA
<213> ORGANISM: Homo Sapien

<400> SEQUENCE: 326
ttattaacag                                                          10

<210> SEQ ID NO 327
<211> LENGTH: 10
<212> TYPE: DNA
<213> ORGANISM: Homo Sapien

<400> SEQUENCE: 327
tccttaacag                                                          10

<210> SEQ ID NO 328
<211> LENGTH: 10
<212> TYPE: DNA
<213> ORGANISM: Homo Sapien

<400> SEQUENCE: 328
cggttaacag                                                          10

<210> SEQ ID NO 329
<211> LENGTH: 10
<212> TYPE: DNA
<213> ORGANISM: Homo Sapien

<400> SEQUENCE: 329
caattaacag                                                          10

<210> SEQ ID NO 330
<211> LENGTH: 10
<212> TYPE: DNA
<213> ORGANISM: Homo Sapien

<400> SEQUENCE: 330
agcttaacag                                                          10
```

```
<210> SEQ ID NO 331
<211> LENGTH: 10
<212> TYPE: DNA
<213> ORGANISM: Homo Sapien

<400> SEQUENCE: 331
acgttaacag                                                          10

<210> SEQ ID NO 332
<211> LENGTH: 10
<212> TYPE: DNA
<213> ORGANISM: Homo Sapien

<400> SEQUENCE: 332
ctccattagg                                                          10

<210> SEQ ID NO 333
<211> LENGTH: 10
<212> TYPE: DNA
<213> ORGANISM: Homo Sapien

<400> SEQUENCE: 333
ctccattcca                                                          10

<210> SEQ ID NO 334
<211> LENGTH: 10
<212> TYPE: DNA
<213> ORGANISM: Homo Sapien

<400> SEQUENCE: 334
ctccaataag                                                          10

<210> SEQ ID NO 335
<211> LENGTH: 10
<212> TYPE: DNA
<213> ORGANISM: Homo Sapien

<400> SEQUENCE: 335
ctccaattcg                                                          10

<210> SEQ ID NO 336
<211> LENGTH: 10
<212> TYPE: DNA
<213> ORGANISM: Homo Sapien

<400> SEQUENCE: 336
ctccggtaag                                                          10

<210> SEQ ID NO 337
<211> LENGTH: 25
<212> TYPE: DNA
<213> ORGANISM: Homo Sapien

<400> SEQUENCE: 337
cgtatcgcct ccctcgcgcc atcag                                         25

<210> SEQ ID NO 338
<211> LENGTH: 25
<212> TYPE: DNA
<213> ORGANISM: Homo Sapien

<400> SEQUENCE: 338
```
ctatgcgcct tgccagcccg ctcag                                         25

<210> SEQ ID NO 339
<211> LENGTH: 25
<212> TYPE: DNA
<213> ORGANISM: Homo Sapien

<400> SEQUENCE: 339
ctgggtgcga caggcccctg gacaa                                         25

<210> SEQ ID NO 340
<211> LENGTH: 25
<212> TYPE: DNA
<213> ORGANISM: Homo Sapien

<400> SEQUENCE: 340
tggatccgtc agcccccagg gaagg                                         25

<210> SEQ ID NO 341
<211> LENGTH: 21
<212> TYPE: DNA
<213> ORGANISM: Homo Sapien

<400> SEQUENCE: 341
ggtccgccag gctccaggga a                                             21

<210> SEQ ID NO 342
<211> LENGTH: 25
<212> TYPE: DNA
<213> ORGANISM: Homo Sapien

<400> SEQUENCE: 342
tggatccgcc agcccccagg gaagg                                         25

<210> SEQ ID NO 343
<211> LENGTH: 25
<212> TYPE: DNA
<213> ORGANISM: Homo Sapien

<400> SEQUENCE: 343
gggtgcgcca gatgcccggg aaagg                                         25

<210> SEQ ID NO 344
<211> LENGTH: 25
<212> TYPE: DNA
<213> ORGANISM: Homo Sapien

<400> SEQUENCE: 344
tggatcaggc agtccccatc gagag                                         25

<210> SEQ ID NO 345
<211> LENGTH: 25
<212> TYPE: DNA
<213> ORGANISM: Homo Sapien

<400> SEQUENCE: 345
ttgggtgcga caggcccctg gacaa                                         25

<210> SEQ ID NO 346
<211> LENGTH: 25
<212> TYPE: DNA
<213> ORGANISM: Homo Sapien

<400> SEQUENCE: 346
ggcctcagtg aaggtctcct gcaag                                         25

<210> SEQ ID NO 347
<211> LENGTH: 25
<212> TYPE: DNA
<213> ORGANISM: Homo Sapien

<400> SEQUENCE: 347
gtctggtcct acgctggtga aaccc                                         25

<210> SEQ ID NO 348
<211> LENGTH: 25
<212> TYPE: DNA
<213> ORGANISM: Homo Sapien

<400> SEQUENCE: 348 ctgggggtc cctgagactc tcctg                                          25

<210> SEQ ID NO 349
<211> LENGTH: 25
<212> TYPE: DNA
<213> ORGANISM: Homo Sapien

<400> SEQUENCE: 349
cttcggagac cctgtccctc acctg                                         25

<210> SEQ ID NO 350
<211> LENGTH: 25
<212> TYPE: DNA
<213> ORGANISM: Homo Sapien

<400> SEQUENCE: 350
cggggagtct ctgaagatct cctgt                                         25

<210> SEQ ID NO 351
<211> LENGTH: 25
<212> TYPE: DNA
<213> ORGANISM: Homo Sapien

<400> SEQUENCE: 351
tcgcagaccc tctcactcac ctgtg                                         25

<210> SEQ ID NO 352
<211> LENGTH: 22
<212> TYPE: DNA
<213> ORGANISM: Homo Sapien

<400> SEQUENCE: 352
cttacctgag gagacggtga cc                                            22

<210> SEQ ID NO 353
<211> LENGTH: 20
<212> TYPE: DNA
<213> ORGANISM: Homo Sapien

<400> SEQUENCE: 353
ttcggggaag tagtccttga                                               20

<210> SEQ ID NO 354
<211> LENGTH: 20
<212> TYPE: DNA
<213> ORGANISM: Homo Sapien

<400> SEQUENCE: 354
gggaattctc acaggagacg                                               20

<210> SEQ ID NO 355
<211> LENGTH: 20
<212> TYPE: DNA
<213> ORGANISM: Homo Sapien

<400> SEQUENCE: 355
ccctgatatg atggggaaca                                               20

<210> SEQ ID NO 356
<211> LENGTH: 18
<212> TYPE: DNA
<213> ORGANISM: Homo Sapien

<400> SEQUENCE: 356
gaagaccttg gggctggt                                                 18

<210> SEQ ID NO 357
<211> LENGTH: 19
<212> TYPE: DNA
<213> ORGANISM: Homo Sapien

<400> SEQUENCE: 357
gaagacggat gggctctgt                                                19

<210> SEQ ID NO 358
<211> LENGTH: 25
<212> TYPE: DNA
<213> ORGANISM: Homo Sapien

<400> SEQUENCE: 358
tctgcatctg taggagacag agtca                                         25

<210> SEQ ID NO 359
<211> LENGTH: 26
<212> TYPE: DNA
<213> ORGANISM: Homo Sapien

<400> SEQUENCE: 359
ggcctccatc tcctgcaggt ctagtc                                        26

<210> SEQ ID NO 360
<211> LENGTH: 24
<212> TYPE: DNA
<213> ORGANISM: Homo Sapien

<400> SEQUENCE: 360
accctctcct gcagggccag tcag                                          24

<210> SEQ ID NO 361
<211> LENGTH: 27
<212> TYPE: DNA
<213> ORGANISM: Homo Sapien

<400> SEQUENCE: 361
caactgcaag tccagccaga gtgtttt                                       27

<210> SEQ ID NO 362
<211> LENGTH: 26
<212> TYPE: DNA
<213> ORGANISM: Homo Sapien

```
<400> SEQUENCE: 362
cctgcaaagc cagccaagac attgat                                    26

<210> SEQ ID NO 363
<211> LENGTH: 24
<212> TYPE: DNA
<213> ORGANISM: Homo Sapien

<400> SEQUENCE: 363
aggagaaagt caccatcacc tgcc                                      24

<210> SEQ ID NO 364
<211> LENGTH: 25
<212> TYPE: DNA
<213> ORGANISM: Homo Sapien

<400> SEQUENCE: 364
gccaccatca cctgcagagc cagtg                                     25

<210> SEQ ID NO 365
<211> LENGTH: 25
<212> TYPE: DNA
<213> ORGANISM: Homo Sapien

<400> SEQUENCE: 365
tctgcatctg taggagacag agtca                                     25

<210> SEQ ID NO 366
<211> LENGTH: 26
<212> TYPE: DNA
<213> ORGANISM: Homo Sapien

<400> SEQUENCE: 366
ggcctccatc tcctgcaggt ctagtc                                    26

<210> SEQ ID NO 367
<211> LENGTH: 24
<212> TYPE: DNA
<213> ORGANISM: Homo Sapien

<400> SEQUENCE: 367
accctctcct gcagggccag tcag                                      24

<210> SEQ ID NO 368
<211> LENGTH: 27
<212> TYPE: DNA
<213> ORGANISM: Homo Sapien

<400> SEQUENCE: 368
caactgcaag tccagccaga gtgtttt                                   27

<210> SEQ ID NO 369
<211> LENGTH: 26
<212> TYPE: DNA
<213> ORGANISM: Homo Sapien

<400> SEQUENCE: 369
cctgcaaagc cagccaagac attgat                                    26

<210> SEQ ID NO 370
<211> LENGTH: 24
<212> TYPE: DNA
```

<213> ORGANISM: Homo Sapien

<400> SEQUENCE: 370
aggagaaagt caccatcacc tgcc                                    24

<210> SEQ ID NO 371
<211> LENGTH: 25
<212> TYPE: DNA
<213> ORGANISM: Homo Sapien

<400> SEQUENCE: 371
gccaccatca cctgcagagc cagtg                                   25

<210> SEQ ID NO 372
<211> LENGTH: 18
<212> TYPE: DNA
<213> ORGANISM: Homo Sapien

<400> SEQUENCE: 372
gatctccacc ttggtccc                                           18

<210> SEQ ID NO 373
<211> LENGTH: 18
<212> TYPE: DNA
<213> ORGANISM: Homo Sapien

<400> SEQUENCE: 373
aatctccagt cgtgtccc                                           18

<210> SEQ ID NO 374
<211> LENGTH: 18
<212> TYPE: DNA
<213> ORGANISM: Homo Sapien

<400> SEQUENCE: 374
gatctccacc ttggtccc                                           18

<210> SEQ ID NO 375
<211> LENGTH: 18
<212> TYPE: DNA
<213> ORGANISM: Homo Sapien

<400> SEQUENCE: 375
aatctccagt cgtgtccc                                           18

<210> SEQ ID NO 376
<211> LENGTH: 18
<212> TYPE: DNA
<213> ORGANISM: Homo Sapien

<400> SEQUENCE: 376
gatctccacc ttggtccc                                           18

<210> SEQ ID NO 377
<211> LENGTH: 18
<212> TYPE: DNA
<213> ORGANISM: Homo Sapien

<400> SEQUENCE: 377
aatctccagt cgtgtccc                                           18

<210> SEQ ID NO 378
<211> LENGTH: 18

<212> TYPE: DNA
<213> ORGANISM: Homo Sapien

<400> SEQUENCE: 378
gatctccacc ttggtccc                                                 18

<210> SEQ ID NO 379
<211> LENGTH: 18
<212> TYPE: DNA
<213> ORGANISM: Homo Sapien

<400> SEQUENCE: 379
aatctccagt cgtgtccc                                                 18

<210> SEQ ID NO 380
<211> LENGTH: 18
<212> TYPE: DNA
<213> ORGANISM: Homo Sapien

<400> SEQUENCE: 380
gatctccacc ttggtccc                                                 18

<210> SEQ ID NO 381
<211> LENGTH: 18
<212> TYPE: DNA
<213> ORGANISM: Homo Sapien

<400> SEQUENCE: 381
aatctccagt cgtgtccc                                                 18

<210> SEQ ID NO 382
<211> LENGTH: 22
<212> TYPE: DNA
<213> ORGANISM: Homo Sapien

<400> SEQUENCE: 382
cagggcagag ggtcaccatc tc                                            22

<210> SEQ ID NO 383
<211> LENGTH: 22
<212> TYPE: DNA
<213> ORGANISM: Homo Sapien

<400> SEQUENCE: 383
tcctgcactg gaaccagcag tg                                            22

<210> SEQ ID NO 384
<211> LENGTH: 22
<212> TYPE: DNA
<213> ORGANISM: Homo Sapien

<400> SEQUENCE: 384
gtaccagcag aagccaggcc ag                                            22

<210> SEQ ID NO 385
<211> LENGTH: 22
<212> TYPE: DNA
<213> ORGANISM: Homo Sapien

<400> SEQUENCE: 385
cctcggtcaa gctcacctgc ac                                            22

<210> SEQ ID NO 386

```
<211> LENGTH: 22
<212> TYPE: DNA
<213> ORGANISM: Homo Sapien

<400> SEQUENCE: 386
gcatcagcca gactcacctg ca                                          22

<210> SEQ ID NO 387
<211> LENGTH: 22
<212> TYPE: DNA
<213> ORGANISM: Homo Sapien

<400> SEQUENCE: 387
cggtaaccat ctcctgcacc cg                                          22

<210> SEQ ID NO 388
<211> LENGTH: 24
<212> TYPE: DNA
<213> ORGANISM: Homo Sapien

<400> SEQUENCE: 388
ccaggaggga cagtcactct cacc                                        24

<210> SEQ ID NO 389
<211> LENGTH: 24
<212> TYPE: DNA
<213> ORGANISM: Homo Sapien

<400> SEQUENCE: 389
cctggaggga cagtcacact cact                                        24

<210> SEQ ID NO 390
<211> LENGTH: 22
<212> TYPE: DNA
<213> ORGANISM: Homo Sapien

<400> SEQUENCE: 390
ccgccacact cacctgcact gg                                          22

<210> SEQ ID NO 391
<211> LENGTH: 22
<212> TYPE: DNA
<213> ORGANISM: Homo Sapien

<400> SEQUENCE: 391
ctaggacggt gagcttggtc cc                                          22

<210> SEQ ID NO 392
<211> LENGTH: 27
<212> TYPE: DNA
<213> ORGANISM: Homo Sapien

<400> SEQUENCE: 392
ctaaaatgat cagctgggtt cctccac                                     27

<210> SEQ ID NO 393
<211> LENGTH: 22
<212> TYPE: DNA
<213> ORGANISM: Homo Sapien

<400> SEQUENCE: 393
acggtcagct cggtcccctc ac                                          22
```

```
<210> SEQ ID NO 394
<211> LENGTH: 22
<212> TYPE: DNA
<213> ORGANISM: Homo Sapien

<400> SEQUENCE: 394
gacggtcacc ttggtgccac tg                                              22

<210> SEQ ID NO 395
<211> LENGTH: 22
<212> TYPE: DNA
<213> ORGANISM: Homo Sapien

<400> SEQUENCE: 395
aggacggtca gctgggtgcc tc                                              22

<210> SEQ ID NO 396
<211> LENGTH: 22
<212> TYPE: DNA
<213> ORGANISM: Homo Sapien

<400> SEQUENCE: 396
ctaggacggt gagcttggtc cc                                              22

<210> SEQ ID NO 397
<211> LENGTH: 27
<212> TYPE: DNA
<213> ORGANISM: Homo Sapien

<400> SEQUENCE: 397
ctaaaatgat cagctgggtt cctccac                                         27

<210> SEQ ID NO 398
<211> LENGTH: 22
<212> TYPE: DNA
<213> ORGANISM: Homo Sapien

<400> SEQUENCE: 398
acggtcagct cggtcccctc ac                                              22

<210> SEQ ID NO 399
<211> LENGTH: 22
<212> TYPE: DNA
<213> ORGANISM: Homo Sapien

<400> SEQUENCE: 399
gacggtcacc ttggtgccac tg                                              22

<210> SEQ ID NO 400
<211> LENGTH: 22
<212> TYPE: DNA
<213> ORGANISM: Homo Sapien

<400> SEQUENCE: 400
aggacggtca gctgggtgcc tc                                              22

<210> SEQ ID NO 401
<211> LENGTH: 22
<212> TYPE: DNA
<213> ORGANISM: Homo Sapien

<400> SEQUENCE: 401
ctaggacggt gagcttggtc cc                                              22
```

<210> SEQ ID NO 402
<211> LENGTH: 27
<212> TYPE: DNA
<213> ORGANISM: Homo Sapien

<400> SEQUENCE: 402
ctaaaatgat cagctgggtt cctccac                                          27

<210> SEQ ID NO 403
<211> LENGTH: 22
<212> TYPE: DNA
<213> ORGANISM: Homo Sapien

<400> SEQUENCE: 403
acggtcagct cggtcccctc ac                                               22

<210> SEQ ID NO 404
<211> LENGTH: 22
<212> TYPE: DNA
<213> ORGANISM: Homo Sapien

<400> SEQUENCE: 404
gacggtcacc ttggtgccac tg                                               22

<210> SEQ ID NO 405
<211> LENGTH: 22
<212> TYPE: DNA
<213> ORGANISM: Homo Sapien

<400> SEQUENCE: 405
aggacggtca gctgggtgcc tc                                               22

<210> SEQ ID NO 406
<211> LENGTH: 22
<212> TYPE: DNA
<213> ORGANISM: Homo Sapien

<400> SEQUENCE: 406
tggtaccagc agctcccagg aa                                               22

<210> SEQ ID NO 407
<211> LENGTH: 23
<212> TYPE: DNA
<213> ORGANISM: Homo Sapien

<400> SEQUENCE: 407
ggcggagcac ccacatttct ttc                                              23

<210> SEQ ID NO 408
<211> LENGTH: 22
<212> TYPE: DNA
<213> ORGANISM: Homo Sapien

<400> SEQUENCE: 408
gctggcgaag cacccacatt tc                                               22

<210> SEQ ID NO 409
<211> LENGTH: 21
<212> TYPE: DNA
<213> ORGANISM: Homo Sapien

<400> SEQUENCE: 409
ccgggatgtg caccaagact c                                                21

<210> SEQ ID NO 410
<211> LENGTH: 21
<212> TYPE: DNA
<213> ORGANISM: Homo Sapien

<400> SEQUENCE: 410 caataccccca accgaggcct c                                          21

<210> SEQ ID NO 411
<211> LENGTH: 21
<212> TYPE: DNA
<213> ORGANISM: Homo Sapien

<400> SEQUENCE: 411
gtttcccagc caaggaccac g                                           21

<210> SEQ ID NO 412
<211> LENGTH: 25
<212> TYPE: DNA
<213> ORGANISM: Homo Sapien

<400> SEQUENCE: 412
ggtataagca agaacctgga gcagg                                       25

<210> SEQ ID NO 413
<211> LENGTH: 23
<212> TYPE: DNA
<213> ORGANISM: Homo Sapien

<400> SEQUENCE: 413
cagtggtacc gacaagatcc agg                                         23

<210> SEQ ID NO 414
<211> LENGTH: 24
<212> TYPE: DNA
<213> ORGANISM: Homo Sapien

<400> SEQUENCE: 414
gcagtggtac aggcaaaata cagg                                        24

<210> SEQ ID NO 415
<211> LENGTH: 26
<212> TYPE: DNA
<213> ORGANISM: Homo Sapien

<400> SEQUENCE: 415
ccttatctct tctggtatgt ccagtc                                      26

<210> SEQ ID NO 416
<211> LENGTH: 26
<212> TYPE: DNA
<213> ORGANISM: Homo Sapien

<400> SEQUENCE: 416
ccttatctct tctggtatgt gcagtc                                      26

<210> SEQ ID NO 417
<211> LENGTH: 23
<212> TYPE: DNA
<213> ORGANISM: Homo Sapien

<400> SEQUENCE: 417
ggtctacagc tcctcctgaa agc                                                    23

<210> SEQ ID NO 418
<211> LENGTH: 26
<212> TYPE: DNA
<213> ORGANISM: Homo Sapien

<400> SEQUENCE: 418
gaggtcctgt ttccctgaca atcatg                                                 26

<210> SEQ ID NO 419
<211> LENGTH: 20
<212> TYPE: DNA
<213> ORGANISM: Homo Sapien

<400> SEQUENCE: 419
gcaggatccg gggagaagac                                                        20

<210> SEQ ID NO 420
<211> LENGTH: 29
<212> TYPE: DNA
<213> ORGANISM: Homo Sapien

<400> SEQUENCE: 420
gttgataatg trcatatact ccaatggtg                                              29

<210> SEQ ID NO 421
<211> LENGTH: 24
<212> TYPE: DNA
<213> ORGANISM: Homo Sapien

<400> SEQUENCE: 421
cctgagttgc tgatgtacac atac                                                   24

<210> SEQ ID NO 422
<211> LENGTH: 22
<212> TYPE: DNA
<213> ORGANISM: Homo Sapien

<400> SEQUENCE: 422
ctggtacaga caggattgca gg                                                     22

<210> SEQ ID NO 423
<211> LENGTH: 26
<212> TYPE: DNA
<213> ORGANISM: Homo Sapien

<400> SEQUENCE: 423
ctacttccct tggtataagc aagaac                                                 26

<210> SEQ ID NO 424
<211> LENGTH: 29
<212> TYPE: DNA
<213> ORGANISM: Homo Sapien

<400> SEQUENCE: 424
ggtcctcaat tcattataga cattcgttc                                              29

<210> SEQ ID NO 425
<211> LENGTH: 22
<212> TYPE: DNA
<213> ORGANISM: Homo Sapien

<400> SEQUENCE: 425

```
ggtacaagca gcccagcagt gg                                            22

<210> SEQ ID NO 426
<211> LENGTH: 22
<212> TYPE: DNA
<213> ORGANISM: Homo Sapien

<400> SEQUENCE: 426
cagtactcca gacaacgcct cc                                            22

<210> SEQ ID NO 427
<211> LENGTH: 21
<212> TYPE: DNA
<213> ORGANISM: Homo Sapien

<400> SEQUENCE: 427
caggtagagg ccttgtccac c                                             21

<210> SEQ ID NO 428
<211> LENGTH: 24
<212> TYPE: DNA
<213> ORGANISM: Homo Sapien

<400> SEQUENCE: 428
gcctgagctc ctcctgaaaa gttc                                          24

<210> SEQ ID NO 429
<211> LENGTH: 23
<212> TYPE: DNA
<213> ORGANISM: Homo Sapien

<400> SEQUENCE: 429
gtacaagcaa ccaccaagtg gag                                           23

<210> SEQ ID NO 430
<211> LENGTH: 26
<212> TYPE: DNA
<213> ORGANISM: Homo Sapien

<400> SEQUENCE: 430
ctggtatagg caagatcctg ggaaag                                        26

<210> SEQ ID NO 431
<211> LENGTH: 22
<212> TYPE: DNA
<213> ORGANISM: Homo Sapien

<400> SEQUENCE: 431
ctccagtggt ttaggcagga cc                                            22

<210> SEQ ID NO 432
<211> LENGTH: 22
<212> TYPE: DNA
<213> ORGANISM: Homo Sapien

<400> SEQUENCE: 432
ccttggggac agctcatcaa cc                                            22

<210> SEQ ID NO 433
<211> LENGTH: 26
<212> TYPE: DNA
<213> ORGANISM: Homo Sapien
```

```
<400> SEQUENCE: 433
gatagccata cgtccagatg tgagtg                                      26

<210> SEQ ID NO 434
<211> LENGTH: 22
<212> TYPE: DNA
<213> ORGANISM: Homo Sapien

<400> SEQUENCE: 434
cagcaccaat ttcacctgca gc                                          22

<210> SEQ ID NO 435
<211> LENGTH: 26
<212> TYPE: DNA
<213> ORGANISM: Homo Sapien

<400> SEQUENCE: 435
gtataagcaa aggcctggtg gacatc                                      26

<210> SEQ ID NO 436
<211> LENGTH: 27
<212> TYPE: DNA
<213> ORGANISM: Homo Sapien

<400> SEQUENCE: 436
attggtatcg acagattcac tcccagg                                     27

<210> SEQ ID NO 437
<211> LENGTH: 20
<212> TYPE: DNA
<213> ORGANISM: Homo Sapien

<400> SEQUENCE: 437
ggtatcgaca gcttccctcc                                             20

<210> SEQ ID NO 438
<211> LENGTH: 19
<212> TYPE: DNA
<213> ORGANISM: Homo Sapien

<400> SEQUENCE: 438
gagcctgggg aaggtcctg                                              19

<210> SEQ ID NO 439
<211> LENGTH: 29
<212> TYPE: DNA
<213> ORGANISM: Homo Sapien

<400> SEQUENCE: 439
gaaggtccta cattcctgat atctataag                                   29

<210> SEQ ID NO 440
<211> LENGTH: 22
<212> TYPE: DNA
<213> ORGANISM: Homo Sapien

<400> SEQUENCE: 440
ggcagaagca tggtgaagca cc                                          22

<210> SEQ ID NO 441
<211> LENGTH: 27
<212> TYPE: DNA
<213> ORGANISM: Homo Sapien
```

```
<400> SEQUENCE: 441
ctggtataag caaaagtatg gtgaagg                                          27

<210> SEQ ID NO 442
<211> LENGTH: 22
<212> TYPE: DNA
<213> ORGANISM: Homo Sapien

<400> SEQUENCE: 442
ggctggctat ggtacaagca gg                                               22

<210> SEQ ID NO 443
<211> LENGTH: 29
<212> TYPE: DNA
<213> ORGANISM: Homo Sapien

<400> SEQUENCE: 443
gctcccacat ttctatttat gctaacttc                                        29

<210> SEQ ID NO 444
<211> LENGTH: 21
<212> TYPE: DNA
<213> ORGANISM: Homo Sapien

<400> SEQUENCE: 444
ccagcaggca gatgattctc g                                                21

<210> SEQ ID NO 445
<211> LENGTH: 23
<212> TYPE: DNA
<213> ORGANISM: Homo Sapien

<400> SEQUENCE: 445
tattggtaca ggcaggatcc tgg                                              23

<210> SEQ ID NO 446
<211> LENGTH: 24
<212> TYPE: DNA
<213> ORGANISM: Homo Sapien

<400> SEQUENCE: 446 cctttttctgg tatgtggaat accc                                            24

<210> SEQ ID NO 447
<211> LENGTH: 23
<212> TYPE: DNA
<213> ORGANISM: Homo Sapien

<400> SEQUENCE: 447
gtgccttaca ctggctgcaa cag                                              23

<210> SEQ ID NO 448
<211> LENGTH: 25
<212> TYPE: DNA
<213> ORGANISM: Homo Sapien

<400> SEQUENCE: 448
aataggcaga cagacttgtc actgg                                            25

<210> SEQ ID NO 449
<211> LENGTH: 25
<212> TYPE: DNA
```

```
<213> ORGANISM: Homo Sapien

<400> SEQUENCE: 449
ttgagaatca aaatcggtga atagg                                    25

<210> SEQ ID NO 450
<211> LENGTH: 20
<212> TYPE: DNA
<213> ORGANISM: Homo Sapien

<400> SEQUENCE: 450
tcaaaatcgg tgaataggca                                          20

<210> SEQ ID NO 451
<211> LENGTH: 20
<212> TYPE: DNA
<213> ORGANISM: Homo Sapien

<400> SEQUENCE: 451
tctcagctgg tacacggcag                                          20

<210> SEQ ID NO 452
<211> LENGTH: 22
<212> TYPE: DNA
<213> ORGANISM: Homo Sapien

<400> SEQUENCE: 452
aatcacttca cacctgaatg cc                                       22

<210> SEQ ID NO 453
<211> LENGTH: 26
<212> TYPE: DNA
<213> ORGANISM: Homo Sapien

<400> SEQUENCE: 453
gctgaggctg atccattact catatg                                   26

<210> SEQ ID NO 454
<211> LENGTH: 23
<212> TYPE: DNA
<213> ORGANISM: Homo Sapien

<400> SEQUENCE: 454
ctgaggctga tctattactc agc                                      23

<210> SEQ ID NO 455
<211> LENGTH: 25
<212> TYPE: DNA
<213> ORGANISM: Homo Sapien

<400> SEQUENCE: 455
ctgaggctaa tccattactc atatg                                    25

<210> SEQ ID NO 456
<211> LENGTH: 18
<212> TYPE: DNA
<213> ORGANISM: Homo Sapien

<400> SEQUENCE: 456
cagatcctgg gacagggc                                            18

<210> SEQ ID NO 457
<211> LENGTH: 25
```

<212> TYPE: DNA
<213> ORGANISM: Homo Sapien

<400> SEQUENCE: 457
cctttactgg tacctgcaga acttg                                   25

<210> SEQ ID NO 458
<211> LENGTH: 22
<212> TYPE: DNA
<213> ORGANISM: Homo Sapien

<400> SEQUENCE: 458
cctttactgg taccggcaga ac                                      22

<210> SEQ ID NO 459
<211> LENGTH: 24
<212> TYPE: DNA
<213> ORGANISM: Homo Sapien

<400> SEQUENCE: 459
ctctggtaca gacagacctt tgtg                                    24

<210> SEQ ID NO 460
<211> LENGTH: 21
<212> TYPE: DNA
<213> ORGANISM: Homo Sapien

<400> SEQUENCE: 460
gagatacctt cgtgcaggga c                                       21

<210> SEQ ID NO 461
<211> LENGTH: 23
<212> TYPE: DNA
<213> ORGANISM: Homo Sapien

<400> SEQUENCE: 461
ctggtacaga cagaccatga tgc                                     23

<210> SEQ ID NO 462
<211> LENGTH: 24
<212> TYPE: DNA
<213> ORGANISM: Homo Sapien

<400> SEQUENCE: 462
gacactgtct actggtacca gcag                                    24

<210> SEQ ID NO 463
<211> LENGTH: 27
<212> TYPE: DNA
<213> ORGANISM: Homo Sapien

<400> SEQUENCE: 463
gataatcttt attggtatcg acgtgtt                                 27

<210> SEQ ID NO 464
<211> LENGTH: 24
<212> TYPE: DNA
<213> ORGANISM: Homo Sapien

<400> SEQUENCE: 464
aacgtcatgt actggtacca gcag                                    24

<210> SEQ ID NO 465

```
<211> LENGTH: 22
<212> TYPE: DNA
<213> ORGANISM: Homo Sapien

<400> SEQUENCE: 465
gatgaaacag gtatgcccaa gg                                    22

<210> SEQ ID NO 466
<211> LENGTH: 25
<212> TYPE: DNA
<213> ORGANISM: Homo Sapien

<400> SEQUENCE: 466
gttcactggt accgacagaa tctga                                 25

<210> SEQ ID NO 467
<211> LENGTH: 24
<212> TYPE: DNA
<213> ORGANISM: Homo Sapien

<400> SEQUENCE: 467
agtcatgttt actggtatcg gcag                                  24

<210> SEQ ID NO 468
<211> LENGTH: 22
<212> TYPE: DNA
<213> ORGANISM: Homo Sapien

<400> SEQUENCE: 468
gatgccatgt actggtaccg ac                                    22

<210> SEQ ID NO 469
<211> LENGTH: 29
<212> TYPE: DNA
<213> ORGANISM: Homo Sapien

<400> SEQUENCE: 469
ctcagagaag tctgaaatat tcgatgatc                             29

<210> SEQ ID NO 470
<211> LENGTH: 25
<212> TYPE: DNA
<213> ORGANISM: Homo Sapien

<400> SEQUENCE: 470
gccacaacta tgttttggta tcgtc                                 25

<210> SEQ ID NO 471
<211> LENGTH: 22
<212> TYPE: DNA
<213> ORGANISM: Homo Sapien

<400> SEQUENCE: 471
gctggaagaa gagctcaagt tt                                    22

<210> SEQ ID NO 472
<211> LENGTH: 22
<212> TYPE: DNA
<213> ORGANISM: Homo Sapien

<400> SEQUENCE: 472
gctggaagaa gagctcaagt tt                                    22
```

<210> SEQ ID NO 473
<211> LENGTH: 24
<212> TYPE: DNA
<213> ORGANISM: Homo Sapien

<400> SEQUENCE: 473
gaacaagttc ttcaagaaac ggag                                    24

<210> SEQ ID NO 474
<211> LENGTH: 24
<212> TYPE: DNA
<213> ORGANISM: Homo Sapien

<400> SEQUENCE: 474
gaacaagttc ttcaagaaat ggag                                    24

<210> SEQ ID NO 475
<211> LENGTH: 24
<212> TYPE: DNA
<213> ORGANISM: Homo Sapien

<400> SEQUENCE: 475
gaatgtactg gtatcgacaa gacc                                    24

<210> SEQ ID NO 476
<211> LENGTH: 24
<212> TYPE: DNA
<213> ORGANISM: Homo Sapien

<400> SEQUENCE: 476
caagatccag gaatggaact acac                                    24

<210> SEQ ID NO 477
<211> LENGTH: 26
<212> TYPE: DNA
<213> ORGANISM: Homo Sapien

<400> SEQUENCE: 477
gttacaatgt actggtatcg acagga                                  26

<210> SEQ ID NO 478
<211> LENGTH: 27
<212> TYPE: DNA
<213> ORGANISM: Homo Sapien

<400> SEQUENCE: 478
gttgcaatgt actggtatcg acagaac                                 27

<210> SEQ ID NO 479
<211> LENGTH: 25
<212> TYPE: DNA
<213> ORGANISM: Homo Sapien

<400> SEQUENCE: 479
gagtatatgt cctggtatcg acaag                                   25

<210> SEQ ID NO 480
<211> LENGTH: 22
<212> TYPE: DNA
<213> ORGANISM: Homo Sapien

<400> SEQUENCE: 480
gtatcgacaa gacccaggtc tg                                      22

<210> SEQ ID NO 481
<211> LENGTH: 19
<212> TYPE: DNA
<213> ORGANISM: Homo Sapien

<400> SEQUENCE: 481
gacagagcct gacactgat                                              19

<210> SEQ ID NO 482
<211> LENGTH: 22
<212> TYPE: DNA
<213> ORGANISM: Homo Sapien

<400> SEQUENCE: 482
ctggacagag cgtgacactg at                                          22

<210> SEQ ID NO 483
<211> LENGTH: 25
<212> TYPE: DNA
<213> ORGANISM: Homo Sapien

<400> SEQUENCE: 483
gatactatgt attggtataa acagg                                       25

<210> SEQ ID NO 484
<211> LENGTH: 28
<212> TYPE: DNA
<213> ORGANISM: Homo Sapien

<400> SEQUENCE: 484
ggagccaatt ttaaatgaaa cagttcca                                    28

<210> SEQ ID NO 485
<211> LENGTH: 20
<212> TYPE: DNA
<213> ORGANISM: Homo Sapien

<400> SEQUENCE: 485
gcctccagct gctcttctac                                             20

<210> SEQ ID NO 486
<211> LENGTH: 24
<212> TYPE: DNA
<213> ORGANISM: Homo Sapien

<400> SEQUENCE: 486
ggtacaagca gaaagctaag aagc                                        24

<210> SEQ ID NO 487
<211> LENGTH: 20
<212> TYPE: DNA
<213> ORGANISM: Homo Sapien

<400> SEQUENCE: 487
gtgtatcctg gtaccaacag                                             20

<210> SEQ ID NO 488
<211> LENGTH: 20
<212> TYPE: DNA
<213> ORGANISM: Homo Sapien

<400> SEQUENCE: 488
tgtgtcctgg taccaacagg                                             20

```
<210> SEQ ID NO 489
<211> LENGTH: 22
<212> TYPE: DNA
<213> ORGANISM: Homo Sapien

<400> SEQUENCE: 489
accagtgtgt cctcgtacca ac                                              22

<210> SEQ ID NO 490
<211> LENGTH: 18
<212> TYPE: DNA
<213> ORGANISM: Homo Sapien

<400> SEQUENCE: 490
ggtaccaaca ggccctgg                                                   18

<210> SEQ ID NO 491
<211> LENGTH: 20
<212> TYPE: DNA
<213> ORGANISM: Homo Sapien

<400> SEQUENCE: 491
gtatcgacaa gacccaggca                                                 20

<210> SEQ ID NO 492
<211> LENGTH: 25
<212> TYPE: DNA
<213> ORGANISM: Homo Sapien

<400> SEQUENCE: 492
ctggtataga caagatctag gactg                                           25

<210> SEQ ID NO 493
<211> LENGTH: 21
<212> TYPE: DNA
<213> ORGANISM: Homo Sapien

<400> SEQUENCE: 493
attggtaccg acagagcctg g                                               21

<210> SEQ ID NO 494
<211> LENGTH: 21
<212> TYPE: DNA
<213> ORGANISM: Homo Sapien

<400> SEQUENCE: 494
tgccctttac tggtaccgac a                                               21

<210> SEQ ID NO 495
<211> LENGTH: 25
<212> TYPE: DNA
<213> ORGANISM: Homo Sapien

<400> SEQUENCE: 495
gatgctcaac gagacaaatc agggc                                           25

<210> SEQ ID NO 496
<211> LENGTH: 25
<212> TYPE: DNA
<213> ORGANISM: Homo Sapien

<400> SEQUENCE: 496
```

```
gtatccctttattggtaccgacagg                                              25

<210> SEQ ID NO 497
<211> LENGTH: 18
<212> TYPE: DNA
<213> ORGANISM: Homo Sapien

<400> SEQUENCE: 497 ggtatcaacaggccctgg                                                     18

<210> SEQ ID NO 498
<211> LENGTH: 19
<212> TYPE: DNA
<213> ORGANISM: Homo Sapien

<400> SEQUENCE: 498 ggtaccaacaggccctcgg                                                    19

<210> SEQ ID NO 499
<211> LENGTH: 25
<212> TYPE: DNA
<213> ORGANISM: Homo Sapien

<400> SEQUENCE: 499 ccagagtttctgacttacttccaga                                              25

<210> SEQ ID NO 500
<211> LENGTH: 19
<212> TYPE: DNA
<213> ORGANISM: Homo Sapien

<400> SEQUENCE: 500 ctctctgtgtactggtacc                                                    19

<210> SEQ ID NO 501
<211> LENGTH: 21
<212> TYPE: DNA
<213> ORGANISM: Homo Sapien

<400> SEQUENCE: 501 caactgtgagtctggtgcctt                                                  21

<210> SEQ ID NO 502
<211> LENGTH: 21
<212> TYPE: DNA
<213> ORGANISM: Homo Sapien

<400> SEQUENCE: 502 ctacaacggtaacctggtcc                                                   21

<210> SEQ ID NO 503
<211> LENGTH: 21
<212> TYPE: DNA
<213> ORGANISM: Homo Sapien

<400> SEQUENCE: 503 cctacaacagtgagccaactt                                                  21

<210> SEQ ID NO 504
<211> LENGTH: 20
<212> TYPE: DNA
<213> ORGANISM: Homo Sapien

<400> SEQUENCE: 504
```

```
caagacagag agctgggttc                                          20

<210> SEQ ID NO 505
<211> LENGTH: 20
<212> TYPE: DNA
<213> ORGANISM: Homo Sapien

<400> SEQUENCE: 505
ctaggatgga gagtcgagtc                                          20

<210> SEQ ID NO 506
<211> LENGTH: 20
<212> TYPE: DNA
<213> ORGANISM: Homo Sapien

<400> SEQUENCE: 506
ctgtcacagt gagcctggtc                                          20

<210> SEQ ID NO 507
<211> LENGTH: 18
<212> TYPE: DNA
<213> ORGANISM: Homo Sapien

<400> SEQUENCE: 507
ctggcccgaa gaactgct                                            18

<210> SEQ ID NO 508
<211> LENGTH: 20
<212> TYPE: DNA
<213> ORGANISM: Homo Sapien

<400> SEQUENCE: 508
tcagcctaga gccttctcca                                          20

<210> SEQ ID NO 509
<211> LENGTH: 20
<212> TYPE: DNA
<213> ORGANISM: Homo Sapien

<400> SEQUENCE: 509
gtgcctgggc caaaatactg                                          20

<210> SEQ ID NO 510
<211> LENGTH: 21
<212> TYPE: DNA
<213> ORGANISM: Homo Sapien

<400> SEQUENCE: 510
ggcgccgaag tactgaatgt t                                        21

<210> SEQ ID NO 511
<211> LENGTH: 18
<212> TYPE: DNA
<213> ORGANISM: Homo Sapien

<400> SEQUENCE: 511
cctggcccga agtactgg                                            18

<210> SEQ ID NO 512
<211> LENGTH: 17
<212> TYPE: DNA
<213> ORGANISM: Homo Sapien
```

```
<400> SEQUENCE: 512
gtcagcctgc tgccggc                                                  17

<210> SEQ ID NO 513
<211> LENGTH: 17
<212> TYPE: DNA
<213> ORGANISM: Homo Sapien

<400> SEQUENCE: 513
gtgaccgtga gcctggt                                                  17

<210> SEQ ID NO 514
<211> LENGTH: 20
<212> TYPE: DNA
<213> ORGANISM: Homo Sapien

<400> SEQUENCE: 514
tctgatggct caaacacagc                                               20

<210> SEQ ID NO 515
<211> LENGTH: 20
<212> TYPE: DNA
<213> ORGANISM: Homo Sapien

<400> SEQUENCE: 515
ggaaggcccc acagcrtctt                                               20

<210> SEQ ID NO 516
<211> LENGTH: 20
<212> TYPE: DNA
<213> ORGANISM: Homo Sapien

<400> SEQUENCE: 516
agcatgggta agacaagcaa                                               20

<210> SEQ ID NO 517
<211> LENGTH: 21
<212> TYPE: DNA
<213> ORGANISM: Homo Sapien

<400> SEQUENCE: 517
cggcactgtc agaaggaat c                                              21

<210> SEQ ID NO 518
<211> LENGTH: 19
<212> TYPE: DNA
<213> ORGANISM: Homo Sapien

<400> SEQUENCE: 518
cttccacttc cactttgaa                                                19

<210> SEQ ID NO 519
<211> LENGTH: 24
<212> TYPE: DNA
<213> ORGANISM: Homo Sapien

<400> SEQUENCE: 519
ttaccaggcg aagttactat gagc                                          24

<210> SEQ ID NO 520
<211> LENGTH: 22
<212> TYPE: DNA
<213> ORGANISM: Homo Sapien
```

-continued

```
<400> SEQUENCE: 520
gtgttgttcc actgccaaag ag                                          22

<210> SEQ ID NO 521
<211> LENGTH: 10
<212> TYPE: DNA
<213> ORGANISM: Homo Sapien

<400> SEQUENCE: 521
aagggcggcg                                                        10

<210> SEQ ID NO 522
<211> LENGTH: 16
<212> TYPE: DNA
<213> ORGANISM: Homo Sapien

<400> SEQUENCE: 522 cccccccagta gggcgc                                                16

<210> SEQ ID NO 523
<211> LENGTH: 12
<212> TYPE: DNA
<213> ORGANISM: Homo Sapien

<400> SEQUENCE: 523
gggggtgccc ta                                                     12

<210> SEQ ID NO 524
<211> LENGTH: 13
<212> TYPE: DNA
<213> ORGANISM: Homo Sapien

<400> SEQUENCE: 524
cggacgtgcg ggg                                                    13

<210> SEQ ID NO 525
<211> LENGTH: 28
<212> TYPE: DNA
<213> ORGANISM: Homo Sapien

<400> SEQUENCE: 525
tggggatact gacactggag tccccccg                                    28

<210> SEQ ID NO 526
<211> LENGTH: 13
<212> TYPE: DNA
<213> ORGANISM: Homo Sapien

<400> SEQUENCE: 526
gttccgaccg ggg                                                    13

<210> SEQ ID NO 527
<211> LENGTH: 23
<212> TYPE: DNA
<213> ORGANISM: Homo Sapien

<400> SEQUENCE: 527
ggtcccctct gggaggggcc agg                                         23

<210> SEQ ID NO 528
<211> LENGTH: 15
<212> TYPE: DNA
```

<213> ORGANISM: Homo Sapien

<400> SEQUENCE: 528
gtttcctaat cgaat                                                    15

<210> SEQ ID NO 529
<211> LENGTH: 9
<212> TYPE: DNA
<213> ORGANISM: Homo Sapien

<400> SEQUENCE: 529 cggcgcgcg                                                            9

<210> SEQ ID NO 530
<211> LENGTH: 10
<212> TYPE: DNA
<213> ORGANISM: Homo Sapien

<400> SEQUENCE: 530
tctgtggccg                                                          10

<210> SEQ ID NO 531
<211> LENGTH: 12
<212> TYPE: DNA
<213> ORGANISM: Homo Sapien

<400> SEQUENCE: 531
cccgtatgcc tg                                                       12

<210> SEQ ID NO 532
<211> LENGTH: 26
<212> TYPE: DNA
<213> ORGANISM: Homo Sapien

<400> SEQUENCE: 532
tcgggtcccg tacggcccct tccgat                                        26

<210> SEQ ID NO 533
<211> LENGTH: 12
<212> TYPE: DNA
<213> ORGANISM: Homo Sapien

<400> SEQUENCE: 533
cttagaacga ca                                                       12

<210> SEQ ID NO 534
<211> LENGTH: 8
<212> TYPE: DNA
<213> ORGANISM: Homo Sapien

<400> SEQUENCE: 534 tgccagta                                                             8

<210> SEQ ID NO 535
<211> LENGTH: 9
<212> TYPE: DNA
<213> ORGANISM: Homo Sapien

<400> SEQUENCE: 535 ggccccacg                                                            9

<210> SEQ ID NO 536
<211> LENGTH: 10

```
<212> TYPE: DNA
<213> ORGANISM: Homo Sapien

<400> SEQUENCE: 536
cggcacttga                                                           10

<210> SEQ ID NO 537
<211> LENGTH: 5
<212> TYPE: DNA
<213> ORGANISM: Homo Sapien

<400> SEQUENCE: 537 tccgc                                                                 5

<210> SEQ ID NO 538
<211> LENGTH: 10
<212> TYPE: DNA
<213> ORGANISM: Homo Sapien

<400> SEQUENCE: 538
tgaggagccg                                                           10

<210> SEQ ID NO 539
<211> LENGTH: 7
<212> TYPE: DNA
<213> ORGANISM: Homo Sapien

<400> SEQUENCE: 539 aaggggc                                                               7

<210> SEQ ID NO 540
<211> LENGTH: 13
<212> TYPE: DNA
<213> ORGANISM: Homo Sapien

<400> SEQUENCE: 540
tgtgggcgaa ccc                                                       13

<210> SEQ ID NO 541
<211> LENGTH: 10
<212> TYPE: DNA
<213> ORGANISM: Homo Sapien

<400> SEQUENCE: 541
tgacatttag                                                           10

<210> SEQ ID NO 542
<211> LENGTH: 17
<212> TYPE: DNA
<213> ORGANISM: Homo Sapien

<400> SEQUENCE: 542
aggtctccat ccgggtc                                                   17

<210> SEQ ID NO 543
<211> LENGTH: 9
<212> TYPE: DNA
<213> ORGANISM: Homo Sapien

<400> SEQUENCE: 543 cccctgggg                                                             9

<210> SEQ ID NO 544
```

```
<211> LENGTH: 8
<212> TYPE: DNA
<213> ORGANISM: Homo Sapien

<400> SEQUENCE: 544 cagattac                                                                8

<210> SEQ ID NO 545
<211> LENGTH: 20
<212> TYPE: DNA
<213> ORGANISM: Homo Sapien

<400> SEQUENCE: 545
tctagagacc gtggcaccca                                                  20

<210> SEQ ID NO 546
<211> LENGTH: 14
<212> TYPE: DNA
<213> ORGANISM: Homo Sapien

<400> SEQUENCE: 546
tgttcgcaac tgtg                                                        14

<210> SEQ ID NO 547
<211> LENGTH: 8
<212> TYPE: DNA
<213> ORGANISM: Homo Sapien

<400> SEQUENCE: 547 tcgacccg                                                                8

<210> SEQ ID NO 548
<211> LENGTH: 31
<212> TYPE: DNA
<213> ORGANISM: Homo Sapien

<400> SEQUENCE: 548
gctccctgta gaatttcgtc ccgaaaccga t                                     31

<210> SEQ ID NO 549
<211> LENGTH: 7
<212> TYPE: DNA
<213> ORGANISM: Homo Sapien

<400> SEQUENCE: 549 tcaccct                                                                 7

<210> SEQ ID NO 550
<211> LENGTH: 26
<212> TYPE: DNA
<213> ORGANISM: Homo Sapien

<400> SEQUENCE: 550
tgatcgccgc cgatatttct ccggca                                           26

<210> SEQ ID NO 551
<211> LENGTH: 25
<212> TYPE: DNA
<213> ORGANISM: Homo Sapien

<400> SEQUENCE: 551
tcgggaggac ggacggggta taggt                                            25
```

```
<210> SEQ ID NO 552
<211> LENGTH: 18
<212> TYPE: DNA
<213> ORGANISM: Homo Sapien

<400> SEQUENCE: 552
tgttgaccgg gaccgtga                                                 18

<210> SEQ ID NO 553
<211> LENGTH: 10
<212> TYPE: DNA
<213> ORGANISM: Homo Sapien

<400> SEQUENCE: 553
ggcggtgggg                                                          10

<210> SEQ ID NO 554
<211> LENGTH: 9
<212> TYPE: DNA
<213> ORGANISM: Homo Sapien

<400> SEQUENCE: 554 tcgatcggg                                                            9

<210> SEQ ID NO 555
<211> LENGTH: 9
<212> TYPE: DNA
<213> ORGANISM: Homo Sapien

<400> SEQUENCE: 555 ggcgaggcc                                                            9

<210> SEQ ID NO 556
<211> LENGTH: 9
<212> TYPE: DNA
<213> ORGANISM: Homo Sapien

<400> SEQUENCE: 556 gagcacggc                                                            9

<210> SEQ ID NO 557
<211> LENGTH: 18
<212> TYPE: DNA
<213> ORGANISM: Homo Sapien

<400> SEQUENCE: 557
tgttacaacc ccattacc                                                 18

<210> SEQ ID NO 558
<211> LENGTH: 6
<212> TYPE: DNA
<213> ORGANISM: Homo Sapien

<400> SEQUENCE: 558 gagagg                                                               6

<210> SEQ ID NO 559
<211> LENGTH: 16
<212> TYPE: DNA
<213> ORGANISM: Homo Sapien

<400> SEQUENCE: 559
cagtacgggg gaccct                                                   16
```

<210> SEQ ID NO 560
<211> LENGTH: 10
<212> TYPE: DNA
<213> ORGANISM: Homo Sapien

<400> SEQUENCE: 560
cctctcacca                                                          10

<210> SEQ ID NO 561
<211> LENGTH: 6
<212> TYPE: DNA
<213> ORGANISM: Homo Sapien

<400> SEQUENCE: 561 cacgac                                                               6

<210> SEQ ID NO 562
<211> LENGTH: 14
<212> TYPE: DNA
<213> ORGANISM: Homo Sapien

<400> SEQUENCE: 562
ggccggtagt gtca                                                     14

<210> SEQ ID NO 563
<211> LENGTH: 12
<212> TYPE: DNA
<213> ORGANISM: Homo Sapien

<400> SEQUENCE: 563
ggacagcccg cc                                                       12

<210> SEQ ID NO 564
<211> LENGTH: 21
<212> TYPE: DNA
<213> ORGANISM: Homo Sapien

<400> SEQUENCE: 564
tcttccgttg tggctccatc a                                             21

<210> SEQ ID NO 565
<211> LENGTH: 11
<212> TYPE: DNA
<213> ORGANISM: Homo Sapien

<400> SEQUENCE: 565
cgttcgccca c                                                        11

<210> SEQ ID NO 566
<211> LENGTH: 12
<212> TYPE: DNA
<213> ORGANISM: Homo Sapien

<400> SEQUENCE: 566
tgagaagagg tc                                                       12

<210> SEQ ID NO 567
<211> LENGTH: 25
<212> TYPE: DNA
<213> ORGANISM: Homo Sapien

<400> SEQUENCE: 567
gatacctatt ggggtcgggg cgttc                                         25

<210> SEQ ID NO 568
<211> LENGTH: 13
<212> TYPE: DNA
<213> ORGANISM: Homo Sapien

<400> SEQUENCE: 568
ctagaatcct tgg                                                          13

<210> SEQ ID NO 569
<211> LENGTH: 22
<212> TYPE: DNA
<213> ORGANISM: Homo Sapien

<400> SEQUENCE: 569
tggggtaacc aggtacccgg gg                                                22

<210> SEQ ID NO 570
<211> LENGTH: 15
<212> TYPE: DNA
<213> ORGANISM: Homo Sapien

<400> SEQUENCE: 570
gggaatagcc ccccc                                                        15

<210> SEQ ID NO 571
<211> LENGTH: 17
<212> TYPE: DNA
<213> ORGANISM: Homo Sapien

<400> SEQUENCE: 571
tgtagcccgg ggtttcg                                                      17

<210> SEQ ID NO 572
<211> LENGTH: 16
<212> TYPE: DNA
<213> ORGANISM: Homo Sapien

<400> SEQUENCE: 572
gctcaggggg gttagg                                                       16

<210> SEQ ID NO 573
<211> LENGTH: 11
<212> TYPE: DNA
<213> ORGANISM: Homo Sapien

<400> SEQUENCE: 573
cgcccgggtg a                                                            11

<210> SEQ ID NO 574
<211> LENGTH: 13
<212> TYPE: DNA
<213> ORGANISM: Homo Sapien

<400> SEQUENCE: 574
ttaagtccga atc                                                          13

<210> SEQ ID NO 575
<211> LENGTH: 6
<212> TYPE: DNA
<213> ORGANISM: Homo Sapien

<400> SEQUENCE: 575

```
ggggcc                                                              6

<210> SEQ ID NO 576
<211> LENGTH: 14
<212> TYPE: DNA
<213> ORGANISM: Homo Sapien

<400> SEQUENCE: 576
tagtggggct gcac                                                    14

<210> SEQ ID NO 577
<211> LENGTH: 12
<212> TYPE: DNA
<213> ORGANISM: Homo Sapien

<400> SEQUENCE: 577 gtccccttg gg                                                       12

<210> SEQ ID NO 578
<211> LENGTH: 16
<212> TYPE: DNA
<213> ORGANISM: Homo Sapien

<400> SEQUENCE: 578
gtccccaacc ccgccc                                                  16

<210> SEQ ID NO 579
<211> LENGTH: 6
<212> TYPE: DNA
<213> ORGANISM: Homo Sapien

<400> SEQUENCE: 579 tcacca                                                              6

<210> SEQ ID NO 580
<211> LENGTH: 28
<212> TYPE: DNA
<213> ORGANISM: Homo Sapien

<400> SEQUENCE: 580
ctccccgcaa gagggcgcct tcaaggaa                                     28

<210> SEQ ID NO 581
<211> LENGTH: 19
<212> TYPE: DNA
<213> ORGANISM: Homo Sapien

<400> SEQUENCE: 581
cccaagcaaa tttctccga                                               19

<210> SEQ ID NO 582
<211> LENGTH: 7
<212> TYPE: DNA
<213> ORGANISM: Homo Sapien

<400> SEQUENCE: 582 tgtttct                                                             7

<210> SEQ ID NO 583
<211> LENGTH: 10
<212> TYPE: DNA
<213> ORGANISM: Homo Sapien

<400> SEQUENCE: 583
```
ccatagggcg                                                                  10

<210> SEQ ID NO 584
<211> LENGTH: 17
<212> TYPE: DNA
<213> ORGANISM: Homo Sapien

<400> SEQUENCE: 584
ttcgagtggt aaatggg                                                          17

<210> SEQ ID NO 585
<211> LENGTH: 10
<212> TYPE: DNA
<213> ORGANISM: Homo Sapien

<400> SEQUENCE: 585
gggttcctcg                                                                  10

<210> SEQ ID NO 586
<211> LENGTH: 1
<212> TYPE: DNA
<213> ORGANISM: Homo Sapien

<400> SEQUENCE: 586 c                                                                            1

<210> SEQ ID NO 587
<211> LENGTH: 16
<212> TYPE: DNA
<213> ORGANISM: Homo Sapien

<400> SEQUENCE: 587
gagcttcgta tctccc                                                           16

<210> SEQ ID NO 588
<211> LENGTH: 3
<212> TYPE: DNA
<213> ORGANISM: Homo Sapien

<400> SEQUENCE: 588 ctg                                                                          3

<210> SEQ ID NO 589
<211> LENGTH: 9
<212> TYPE: DNA
<213> ORGANISM: Homo Sapien

<400> SEQUENCE: 589 agggtcggg                                                                    9

<210> SEQ ID NO 590
<211> LENGTH: 6
<212> TYPE: DNA
<213> ORGANISM: Homo Sapien

<400> SEQUENCE: 590 gcccta                                                                       6

<210> SEQ ID NO 591
<211> LENGTH: 3
<212> TYPE: DNA
<213> ORGANISM: Homo Sapien

```
<400> SEQUENCE: 591 aac                                                                 3

<210> SEQ ID NO 592
<211> LENGTH: 5
<212> TYPE: DNA
<213> ORGANISM: Homo Sapien

<400> SEQUENCE: 592 tccct                                                               5

<210> SEQ ID NO 593
<211> LENGTH: 19
<212> TYPE: DNA
<213> ORGANISM: Homo Sapien

<400> SEQUENCE: 593
ctctcggttc aggggagg                                                19

<210> SEQ ID NO 594
<211> LENGTH: 8
<212> TYPE: DNA
<213> ORGANISM: Homo Sapien

<400> SEQUENCE: 594 gggcctac                                                            8

<210> SEQ ID NO 595
<211> LENGTH: 32
<212> TYPE: DNA
<213> ORGANISM: Homo Sapien

<400> SEQUENCE: 595
tagaagcaag cttacctgag gagacggtga cc                                32

<210> SEQ ID NO 596
<211> LENGTH: 32
<212> TYPE: DNA
<213> ORGANISM: Homo Sapien

<400> SEQUENCE: 596
tgtaagcaag cttacctgag gagacggtga cc                                32

<210> SEQ ID NO 597
<211> LENGTH: 32
<212> TYPE: DNA
<213> ORGANISM: Homo Sapien

<400> SEQUENCE: 597
cggaagcaag cttacctgag gagacggtga cc                                32

<210> SEQ ID NO 598
<211> LENGTH: 32
<212> TYPE: DNA
<213> ORGANISM: Homo Sapien

<400> SEQUENCE: 598
cctaagcaag cttacctgag gagacggtga cc                                32

<210> SEQ ID NO 599
<211> LENGTH: 32
<212> TYPE: DNA
<213> ORGANISM: Homo Sapien
```

```
<400> SEQUENCE: 599
agcaagcaag cttacctgag gagacggtga cc                                32

<210> SEQ ID NO 600
<211> LENGTH: 32
<212> TYPE: DNA
<213> ORGANISM: Homo Sapien

<400> SEQUENCE: 600
attaagcaag cttacctgag gagacggtga cc                                32

<210> SEQ ID NO 601
<211> LENGTH: 32
<212> TYPE: DNA
<213> ORGANISM: Homo Sapien

<400> SEQUENCE: 601
acgaagcaag cttacctgag gagacggtga cc                                32

<210> SEQ ID NO 602
<211> LENGTH: 32
<212> TYPE: DNA
<213> ORGANISM: Homo Sapien

<400> SEQUENCE: 602
tagaggcagg cttacctgag gagacggtga cc                                32

<210> SEQ ID NO 603
<211> LENGTH: 32
<212> TYPE: DNA
<213> ORGANISM: Homo Sapien

<400> SEQUENCE: 603
ttaaggcagg cttacctgag gagacggtga cc                                32

<210> SEQ ID NO 604
<211> LENGTH: 32
<212> TYPE: DNA
<213> ORGANISM: Homo Sapien

<400> SEQUENCE: 604
tgtaggcagg cttacctgag gagacggtga cc                                32

<210> SEQ ID NO 605
<211> LENGTH: 32
<212> TYPE: DNA
<213> ORGANISM: Homo Sapien

<400> SEQUENCE: 605
cggaggcagg cttacctgag gagacggtga cc                                32

<210> SEQ ID NO 606
<211> LENGTH: 32
<212> TYPE: DNA
<213> ORGANISM: Homo Sapien

<400> SEQUENCE: 606
cctaggcagg cttacctgag gagacggtga cc                                32

<210> SEQ ID NO 607
<211> LENGTH: 32
<212> TYPE: DNA
```

```
<213> ORGANISM: Homo Sapien

<400> SEQUENCE: 607
agcaggcagg cttacctgag gagacggtga cc                                32

<210> SEQ ID NO 608
<211> LENGTH: 32
<212> TYPE: DNA
<213> ORGANISM: Homo Sapien

<400> SEQUENCE: 608
attaggcagg cttacctgag gagacggtga cc                                32

<210> SEQ ID NO 609
<211> LENGTH: 32
<212> TYPE: DNA
<213> ORGANISM: Homo Sapien

<400> SEQUENCE: 609
acgaggcagg cttacctgag gagacggtga cc                                32

<210> SEQ ID NO 610
<211> LENGTH: 32
<212> TYPE: DNA
<213> ORGANISM: Homo Sapien

<400> SEQUENCE: 610
tagcattagg cttacctgag gagacggtga cc                                32

<210> SEQ ID NO 611
<211> LENGTH: 32
<212> TYPE: DNA
<213> ORGANISM: Homo Sapien

<400> SEQUENCE: 611
ttacattagg cttacctgag gagacggtga cc                                32

<210> SEQ ID NO 612
<211> LENGTH: 32
<212> TYPE: DNA
<213> ORGANISM: Homo Sapien

<400> SEQUENCE: 612
tgtcattagg cttacctgag gagacggtga cc                                32

<210> SEQ ID NO 613
<211> LENGTH: 32
<212> TYPE: DNA
<213> ORGANISM: Homo Sapien

<400> SEQUENCE: 613
cggcattagg cttacctgag gagacggtga cc                                32

<210> SEQ ID NO 614
<211> LENGTH: 32
<212> TYPE: DNA
<213> ORGANISM: Homo Sapien

<400> SEQUENCE: 614
caacattagg cttacctgag gagacggtga cc                                32

<210> SEQ ID NO 615
<211> LENGTH: 32
```

<212> TYPE: DNA
<213> ORGANISM: Homo Sapien

<400> SEQUENCE: 615
cctcattagg cttacctgag gagacggtga cc                                    32

<210> SEQ ID NO 616
<211> LENGTH: 32
<212> TYPE: DNA
<213> ORGANISM: Homo Sapien

<400> SEQUENCE: 616
agccattagg cttacctgag gagacggtga cc                                    32

<210> SEQ ID NO 617
<211> LENGTH: 32
<212> TYPE: DNA
<213> ORGANISM: Homo Sapien

<400> SEQUENCE: 617
attcattagg cttacctgag gagacggtga cc                                    32

<210> SEQ ID NO 618
<211> LENGTH: 32
<212> TYPE: DNA
<213> ORGANISM: Homo Sapien

<400> SEQUENCE: 618
acgcattagg cttacctgag gagacggtga cc                                    32

<210> SEQ ID NO 619
<211> LENGTH: 32
<212> TYPE: DNA
<213> ORGANISM: Homo Sapien

<400> SEQUENCE: 619
tagcattcca cttacctgag gagacggtga cc                                    32

<210> SEQ ID NO 620
<211> LENGTH: 32
<212> TYPE: DNA
<213> ORGANISM: Homo Sapien

<400> SEQUENCE: 620
ttacattcca cttacctgag gagacggtga cc                                    32

<210> SEQ ID NO 621
<211> LENGTH: 32
<212> TYPE: DNA
<213> ORGANISM: Homo Sapien

<400> SEQUENCE: 621
tgtcattcca cttacctgag gagacggtga cc                                    32

<210> SEQ ID NO 622
<211> LENGTH: 32
<212> TYPE: DNA
<213> ORGANISM: Homo Sapien

<400> SEQUENCE: 622
cggcattcca cttacctgag gagacggtga cc                                    32

<210> SEQ ID NO 623

```
<211> LENGTH: 32
<212> TYPE: DNA
<213> ORGANISM: Homo Sapien

<400> SEQUENCE: 623
caacattcca cttacctgag gagacggtga cc                                      32

<210> SEQ ID NO 624
<211> LENGTH: 32
<212> TYPE: DNA
<213> ORGANISM: Homo Sapien

<400> SEQUENCE: 624
cctcattcca cttacctgag gagacggtga cc                                      32

<210> SEQ ID NO 625
<211> LENGTH: 32
<212> TYPE: DNA
<213> ORGANISM: Homo Sapien

<400> SEQUENCE: 625
agccattcca cttacctgag gagacggtga cc                                      32

<210> SEQ ID NO 626
<211> LENGTH: 32
<212> TYPE: DNA
<213> ORGANISM: Homo Sapien

<400> SEQUENCE: 626
attcattcca cttacctgag gagacggtga cc                                      32

<210> SEQ ID NO 627
<211> LENGTH: 32
<212> TYPE: DNA
<213> ORGANISM: Homo Sapien

<400> SEQUENCE: 627
acgcattcca cttacctgag gagacggtga cc                                      32

<210> SEQ ID NO 628
<211> LENGTH: 32
<212> TYPE: DNA
<213> ORGANISM: Homo Sapien

<400> SEQUENCE: 628
tagcaataag cttacctgag gagacggtga cc                                      32

<210> SEQ ID NO 629
<211> LENGTH: 32
<212> TYPE: DNA
<213> ORGANISM: Homo Sapien

<400> SEQUENCE: 629
ttacaataag cttacctgag gagacggtga cc                                      32

<210> SEQ ID NO 630
<211> LENGTH: 32
<212> TYPE: DNA
<213> ORGANISM: Homo Sapien

<400> SEQUENCE: 630
tgtcaataag cttacctgag gagacggtga cc                                      32
```

```
<210> SEQ ID NO 631
<211> LENGTH: 32
<212> TYPE: DNA
<213> ORGANISM: Homo Sapien

<400> SEQUENCE: 631
cggcaataag cttacctgag gagacggtga cc                                    32

<210> SEQ ID NO 632
<211> LENGTH: 32
<212> TYPE: DNA
<213> ORGANISM: Homo Sapien

<400> SEQUENCE: 632
caacaataag cttacctgag gagacggtga cc                                    32

<210> SEQ ID NO 633
<211> LENGTH: 32
<212> TYPE: DNA
<213> ORGANISM: Homo Sapien

<400> SEQUENCE: 633
cctcaataag cttacctgag gagacggtga cc                                    32

<210> SEQ ID NO 634
<211> LENGTH: 32
<212> TYPE: DNA
<213> ORGANISM: Homo Sapien

<400> SEQUENCE: 634
agccaataag cttacctgag gagacggtga cc                                    32

<210> SEQ ID NO 635
<211> LENGTH: 32
<212> TYPE: DNA
<213> ORGANISM: Homo Sapien

<400> SEQUENCE: 635
attcaataag cttacctgag gagacggtga cc                                    32

<210> SEQ ID NO 636
<211> LENGTH: 32
<212> TYPE: DNA
<213> ORGANISM: Homo Sapien

<400> SEQUENCE: 636
acgcaataag cttacctgag gagacggtga cc                                    32

<210> SEQ ID NO 637
<211> LENGTH: 32
<212> TYPE: DNA
<213> ORGANISM: Homo Sapien

<400> SEQUENCE: 637
tagcaattcg cttacctgag gagacggtga cc                                    32

<210> SEQ ID NO 638
<211> LENGTH: 32
<212> TYPE: DNA
<213> ORGANISM: Homo Sapien

<400> SEQUENCE: 638
ttacaattcg cttacctgag gagacggtga cc                                    32
```

```
<210> SEQ ID NO 639
<211> LENGTH: 32
<212> TYPE: DNA
<213> ORGANISM: Homo Sapien

<400> SEQUENCE: 639
tgtcaattcg cttacctgag gagacggtga cc                              32

<210> SEQ ID NO 640
<211> LENGTH: 32
<212> TYPE: DNA
<213> ORGANISM: Homo Sapien

<400> SEQUENCE: 640
cggcaattcg cttacctgag gagacggtga cc                              32

<210> SEQ ID NO 641
<211> LENGTH: 32
<212> TYPE: DNA
<213> ORGANISM: Homo Sapien

<400> SEQUENCE: 641
caacaattcg cttacctgag gagacggtga cc                              32

<210> SEQ ID NO 642
<211> LENGTH: 32
<212> TYPE: DNA
<213> ORGANISM: Homo Sapien

<400> SEQUENCE: 642
cctcaattcg cttacctgag gagacggtga cc                              32

<210> SEQ ID NO 643
<211> LENGTH: 32
<212> TYPE: DNA
<213> ORGANISM: Homo Sapien

<400> SEQUENCE: 643
agccaattcg cttacctgag gagacggtga cc                              32

<210> SEQ ID NO 644
<211> LENGTH: 32
<212> TYPE: DNA
<213> ORGANISM: Homo Sapien

<400> SEQUENCE: 644
attcaattcg cttacctgag gagacggtga cc                              32

<210> SEQ ID NO 645
<211> LENGTH: 32
<212> TYPE: DNA
<213> ORGANISM: Homo Sapien

<400> SEQUENCE: 645
acgcaattcg cttacctgag gagacggtga cc                              32

<210> SEQ ID NO 646
<211> LENGTH: 32
<212> TYPE: DNA
<213> ORGANISM: Homo Sapien

<400> SEQUENCE: 646
tagccaataa cttacctgag gagacggtga cc                              32
```

<210> SEQ ID NO 647
<211> LENGTH: 32
<212> TYPE: DNA
<213> ORGANISM: Homo Sapien

<400> SEQUENCE: 647
ttaccaataa cttacctgag gagacggtga cc                                    32

<210> SEQ ID NO 648
<211> LENGTH: 32
<212> TYPE: DNA
<213> ORGANISM: Homo Sapien

<400> SEQUENCE: 648
tgtccaataa cttacctgag gagacggtga cc                                    32

<210> SEQ ID NO 649
<211> LENGTH: 32
<212> TYPE: DNA
<213> ORGANISM: Homo Sapien

<400> SEQUENCE: 649
cggccaataa cttacctgag gagacggtga cc                                    32

<210> SEQ ID NO 650
<211> LENGTH: 32
<212> TYPE: DNA
<213> ORGANISM: Homo Sapien

<400> SEQUENCE: 650
caaccaataa cttacctgag gagacggtga cc                                    32

<210> SEQ ID NO 651
<211> LENGTH: 32
<212> TYPE: DNA
<213> ORGANISM: Homo Sapien

<400> SEQUENCE: 651
cctccaataa cttacctgag gagacggtga cc                                    32

<210> SEQ ID NO 652
<211> LENGTH: 32
<212> TYPE: DNA
<213> ORGANISM: Homo Sapien

<400> SEQUENCE: 652
attccaataa cttacctgag gagacggtga cc                                    32

<210> SEQ ID NO 653
<211> LENGTH: 32
<212> TYPE: DNA
<213> ORGANISM: Homo Sapien

<400> SEQUENCE: 653
acgccaataa cttacctgag gagacggtga cc                                    32

<210> SEQ ID NO 654
<211> LENGTH: 32
<212> TYPE: DNA
<213> ORGANISM: Homo Sapien

<400> SEQUENCE: 654
tagccggcaa cttacctgag gagacggtga cc					32

<210> SEQ ID NO 655
<211> LENGTH: 32
<212> TYPE: DNA
<213> ORGANISM: Homo Sapien

<400> SEQUENCE: 655
ttaccggcaa cttacctgag gagacggtga cc					32

<210> SEQ ID NO 656
<211> LENGTH: 32
<212> TYPE: DNA
<213> ORGANISM: Homo Sapien

<400> SEQUENCE: 656
tgtccggcaa cttacctgag gagacggtga cc					32

<210> SEQ ID NO 657
<211> LENGTH: 32
<212> TYPE: DNA
<213> ORGANISM: Homo Sapien

<400> SEQUENCE: 657
cggccggcaa cttacctgag gagacggtga cc					32

<210> SEQ ID NO 658
<211> LENGTH: 32
<212> TYPE: DNA
<213> ORGANISM: Homo Sapien

<400> SEQUENCE: 658
caaccggcaa cttacctgag gagacggtga cc					32

<210> SEQ ID NO 659
<211> LENGTH: 32
<212> TYPE: DNA
<213> ORGANISM: Homo Sapien

<400> SEQUENCE: 659
cctccggcaa cttacctgag gagacggtga cc					32

<210> SEQ ID NO 660
<211> LENGTH: 32
<212> TYPE: DNA
<213> ORGANISM: Homo Sapien

<400> SEQUENCE: 660
attccggcaa cttacctgag gagacggtga cc					32

<210> SEQ ID NO 661
<211> LENGTH: 32
<212> TYPE: DNA
<213> ORGANISM: Homo Sapien

<400> SEQUENCE: 661
acgccggcaa cttacctgag gagacggtga cc					32

<210> SEQ ID NO 662
<211> LENGTH: 32
<212> TYPE: DNA
<213> ORGANISM: Homo Sapien

<400> SEQUENCE: 662
tagccgcagg cttacctgag gagacggtga cc                          32

<210> SEQ ID NO 663
<211> LENGTH: 32
<212> TYPE: DNA
<213> ORGANISM: Homo Sapien

<400> SEQUENCE: 663
ttaccgcagg cttacctgag gagacggtga cc                          32

<210> SEQ ID NO 664
<211> LENGTH: 32
<212> TYPE: DNA
<213> ORGANISM: Homo Sapien

<400> SEQUENCE: 664
tgtccgcagg cttacctgag gagacggtga cc                          32

<210> SEQ ID NO 665
<211> LENGTH: 32
<212> TYPE: DNA
<213> ORGANISM: Homo Sapien

<400> SEQUENCE: 665
cggccgcagg cttacctgag gagacggtga cc                          32

<210> SEQ ID NO 666
<211> LENGTH: 32
<212> TYPE: DNA
<213> ORGANISM: Homo Sapien

<400> SEQUENCE: 666
caaccgcagg cttacctgag gagacggtga cc                          32

<210> SEQ ID NO 667
<211> LENGTH: 32
<212> TYPE: DNA
<213> ORGANISM: Homo Sapien

<400> SEQUENCE: 667
cctccgcagg cttacctgag gagacggtga cc                          32

<210> SEQ ID NO 668
<211> LENGTH: 32
<212> TYPE: DNA
<213> ORGANISM: Homo Sapien

<400> SEQUENCE: 668
attccgcagg cttacctgag gagacggtga cc                          32

<210> SEQ ID NO 669
<211> LENGTH: 32
<212> TYPE: DNA
<213> ORGANISM: Homo Sapien

<400> SEQUENCE: 669
acgccgcagg cttacctgag gagacggtga cc                          32

<210> SEQ ID NO 670
<211> LENGTH: 32
<212> TYPE: DNA
<213> ORGANISM: Homo Sapien

```
<400> SEQUENCE: 670
tagccgttag cttacctgag gagacggtga cc                                    32

<210> SEQ ID NO 671
<211> LENGTH: 32
<212> TYPE: DNA
<213> ORGANISM: Homo Sapien

<400> SEQUENCE: 671
ttaccgttag cttacctgag gagacggtga cc                                    32

<210> SEQ ID NO 672
<211> LENGTH: 32
<212> TYPE: DNA
<213> ORGANISM: Homo Sapien

<400> SEQUENCE: 672
tgtccgttag cttacctgag gagacggtga cc                                    32

<210> SEQ ID NO 673
<211> LENGTH: 32
<212> TYPE: DNA
<213> ORGANISM: Homo Sapien

<400> SEQUENCE: 673
cggccgttag cttacctgag gagacggtga cc                                    32

<210> SEQ ID NO 674
<211> LENGTH: 32
<212> TYPE: DNA
<213> ORGANISM: Homo Sapien

<400> SEQUENCE: 674
caaccgttag cttacctgag gagacggtga cc                                    32

<210> SEQ ID NO 675
<211> LENGTH: 32
<212> TYPE: DNA
<213> ORGANISM: Homo Sapien

<400> SEQUENCE: 675
cctccgttag cttacctgag gagacggtga cc                                    32

<210> SEQ ID NO 676
<211> LENGTH: 32
<212> TYPE: DNA
<213> ORGANISM: Homo Sapien

<400> SEQUENCE: 676
attccgttag cttacctgag gagacggtga cc                                    32

<210> SEQ ID NO 677
<211> LENGTH: 32
<212> TYPE: DNA
<213> ORGANISM: Homo Sapien

<400> SEQUENCE: 677
acgccgttag cttacctgag gagacggtga cc                                    32

<210> SEQ ID NO 678
<211> LENGTH: 32
<212> TYPE: DNA
<213> ORGANISM: Homo Sapien
```

```
<400> SEQUENCE: 678
tagcggtaag cttacctgag gagacggtga cc                    32

<210> SEQ ID NO 679
<211> LENGTH: 32
<212> TYPE: DNA
<213> ORGANISM: Homo Sapien

<400> SEQUENCE: 679
ttacggtaag cttacctgag gagacggtga cc                    32

<210> SEQ ID NO 680
<211> LENGTH: 32
<212> TYPE: DNA
<213> ORGANISM: Homo Sapien

<400> SEQUENCE: 680
tgtcggtaag cttacctgag gagacggtga cc                    32

<210> SEQ ID NO 681
<211> LENGTH: 32
<212> TYPE: DNA
<213> ORGANISM: Homo Sapien

<400> SEQUENCE: 681
cggcggtaag cttacctgag gagacggtga cc                    32

<210> SEQ ID NO 682
<211> LENGTH: 32
<212> TYPE: DNA
<213> ORGANISM: Homo Sapien

<400> SEQUENCE: 682
caacggtaag cttacctgag gagacggtga cc                    32

<210> SEQ ID NO 683
<211> LENGTH: 32
<212> TYPE: DNA
<213> ORGANISM: Homo Sapien

<400> SEQUENCE: 683
cctcggtaag cttacctgag gagacggtga cc                    32

<210> SEQ ID NO 684
<211> LENGTH: 32
<212> TYPE: DNA
<213> ORGANISM: Homo Sapien

<400> SEQUENCE: 684
agccggtaag cttacctgag gagacggtga cc                    32

<210> SEQ ID NO 685
<211> LENGTH: 32
<212> TYPE: DNA
<213> ORGANISM: Homo Sapien

<400> SEQUENCE: 685
attcggtaag cttacctgag gagacggtga cc                    32

<210> SEQ ID NO 686
<211> LENGTH: 32
<212> TYPE: DNA
```

<213> ORGANISM: Homo Sapien

<400> SEQUENCE: 686
acgcggtaag cttacctgag gagacggtga cc                      32

<210> SEQ ID NO 687
<211> LENGTH: 32
<212> TYPE: DNA
<213> ORGANISM: Homo Sapien

<400> SEQUENCE: 687
tagtaggcgg cttacctgag gagacggtga cc                      32

<210> SEQ ID NO 688
<211> LENGTH: 32
<212> TYPE: DNA
<213> ORGANISM: Homo Sapien

<400> SEQUENCE: 688
ttataggcgg cttacctgag gagacggtga cc                      32

<210> SEQ ID NO 689
<211> LENGTH: 32
<212> TYPE: DNA
<213> ORGANISM: Homo Sapien

<400> SEQUENCE: 689
tcctaggcgg cttacctgag gagacggtga cc                      32

<210> SEQ ID NO 690
<211> LENGTH: 32
<212> TYPE: DNA
<213> ORGANISM: Homo Sapien

<400> SEQUENCE: 690
tgttaggcgg cttacctgag gagacggtga cc                      32

<210> SEQ ID NO 691
<211> LENGTH: 32
<212> TYPE: DNA
<213> ORGANISM: Homo Sapien

<400> SEQUENCE: 691
cggtaggcgg cttacctgag gagacggtga cc                      32

<210> SEQ ID NO 692
<211> LENGTH: 32
<212> TYPE: DNA
<213> ORGANISM: Homo Sapien

<400> SEQUENCE: 692
caataggcgg cttacctgag gagacggtga cc                      32

<210> SEQ ID NO 693
<211> LENGTH: 32
<212> TYPE: DNA
<213> ORGANISM: Homo Sapien

<400> SEQUENCE: 693
ccttaggcgg cttacctgag gagacggtga cc                      32

<210> SEQ ID NO 694
<211> LENGTH: 32

```
<212> TYPE: DNA
<213> ORGANISM: Homo Sapien

<400> SEQUENCE: 694
agctaggcgg cttacctgag gagacggtga cc                          32

<210> SEQ ID NO 695
<211> LENGTH: 32
<212> TYPE: DNA
<213> ORGANISM: Homo Sapien

<400> SEQUENCE: 695
acgtaggcgg cttacctgag gagacggtga cc                          32

<210> SEQ ID NO 696
<211> LENGTH: 32
<212> TYPE: DNA
<213> ORGANISM: Homo Sapien

<400> SEQUENCE: 696
tagtaatagg cttacctgag gagacggtga cc                          32

<210> SEQ ID NO 697
<211> LENGTH: 32
<212> TYPE: DNA
<213> ORGANISM: Homo Sapien

<400> SEQUENCE: 697
ttataatagg cttacctgag gagacggtga cc                          32

<210> SEQ ID NO 698
<211> LENGTH: 32
<212> TYPE: DNA
<213> ORGANISM: Homo Sapien

<400> SEQUENCE: 698
tcctaatagg cttacctgag gagacggtga cc                          32

<210> SEQ ID NO 699
<211> LENGTH: 32
<212> TYPE: DNA
<213> ORGANISM: Homo Sapien

<400> SEQUENCE: 699
tgttaatagg cttacctgag gagacggtga cc                          32

<210> SEQ ID NO 700
<211> LENGTH: 32
<212> TYPE: DNA
<213> ORGANISM: Homo Sapien

<400> SEQUENCE: 700
cggtaatagg cttacctgag gagacggtga cc                          32

<210> SEQ ID NO 701
<211> LENGTH: 32
<212> TYPE: DNA
<213> ORGANISM: Homo Sapien

<400> SEQUENCE: 701
caataatagg cttacctgag gagacggtga cc                          32

<210> SEQ ID NO 702
```

```
<211> LENGTH: 32
<212> TYPE: DNA
<213> ORGANISM: Homo Sapien

<400> SEQUENCE: 702
ccttaatagg cttacctgag gagacggtga cc                                    32

<210> SEQ ID NO 703
<211> LENGTH: 32
<212> TYPE: DNA
<213> ORGANISM: Homo Sapien

<400> SEQUENCE: 703
agctaatagg cttacctgag gagacggtga cc                                    32

<210> SEQ ID NO 704
<211> LENGTH: 32
<212> TYPE: DNA
<213> ORGANISM: Homo Sapien

<400> SEQUENCE: 704
acgtaatagg cttacctgag gagacggtga cc                                    32

<210> SEQ ID NO 705
<211> LENGTH: 32
<212> TYPE: DNA
<213> ORGANISM: Homo Sapien

<400> SEQUENCE: 705
tagtaaccaa cttacctgag gagacggtga cc                                    32

<210> SEQ ID NO 706
<211> LENGTH: 32
<212> TYPE: DNA
<213> ORGANISM: Homo Sapien

<400> SEQUENCE: 706
ttataaccaa cttacctgag gagacggtga cc                                    32

<210> SEQ ID NO 707
<211> LENGTH: 32
<212> TYPE: DNA
<213> ORGANISM: Homo Sapien

<400> SEQUENCE: 707
tcctaaccaa cttacctgag gagacggtga cc                                    32

<210> SEQ ID NO 708
<211> LENGTH: 32
<212> TYPE: DNA
<213> ORGANISM: Homo Sapien

<400> SEQUENCE: 708
tgttaaccaa cttacctgag gagacggtga cc                                    32

<210> SEQ ID NO 709
<211> LENGTH: 32
<212> TYPE: DNA
<213> ORGANISM: Homo Sapien

<400> SEQUENCE: 709
cggtaaccaa cttacctgag gagacggtga cc                                    32
```

```
<210> SEQ ID NO 710
<211> LENGTH: 32
<212> TYPE: DNA
<213> ORGANISM: Homo Sapien

<400> SEQUENCE: 710
caataaccaa cttacctgag gagacggtga cc                                    32

<210> SEQ ID NO 711
<211> LENGTH: 32
<212> TYPE: DNA
<213> ORGANISM: Homo Sapien

<400> SEQUENCE: 711
ccttaaccaa cttacctgag gagacggtga cc                                    32

<210> SEQ ID NO 712
<211> LENGTH: 32
<212> TYPE: DNA
<213> ORGANISM: Homo Sapien

<400> SEQUENCE: 712
agctaaccaa cttacctgag gagacggtga cc                                    32

<210> SEQ ID NO 713
<211> LENGTH: 32
<212> TYPE: DNA
<213> ORGANISM: Homo Sapien

<400> SEQUENCE: 713
acgtaaccaa cttacctgag gagacggtga cc                                    32

<210> SEQ ID NO 714
<211> LENGTH: 32
<212> TYPE: DNA
<213> ORGANISM: Homo Sapien

<400> SEQUENCE: 714
tagtccgtaa cttacctgag gagacggtga cc                                    32

<210> SEQ ID NO 715
<211> LENGTH: 32
<212> TYPE: DNA
<213> ORGANISM: Homo Sapien

<400> SEQUENCE: 715
ttatccgtaa cttacctgag gagacggtga cc                                    32

<210> SEQ ID NO 716
<211> LENGTH: 32
<212> TYPE: DNA
<213> ORGANISM: Homo Sapien

<400> SEQUENCE: 716
tcctccgtaa cttacctgag gagacggtga cc                                    32

<210> SEQ ID NO 717
<211> LENGTH: 32
<212> TYPE: DNA
<213> ORGANISM: Homo Sapien

<400> SEQUENCE: 717
tgttccgtaa cttacctgag gagacggtga cc                                    32
```

<210> SEQ ID NO 718
<211> LENGTH: 32
<212> TYPE: DNA
<213> ORGANISM: Homo Sapien

<400> SEQUENCE: 718
cggtccgtaa cttacctgag gagacggtga cc                                   32

<210> SEQ ID NO 719
<211> LENGTH: 32
<212> TYPE: DNA
<213> ORGANISM: Homo Sapien

<400> SEQUENCE: 719
caatccgtaa cttacctgag gagacggtga cc                                   32

<210> SEQ ID NO 720
<211> LENGTH: 32
<212> TYPE: DNA
<213> ORGANISM: Homo Sapien

<400> SEQUENCE: 720
ccttccgtaa cttacctgag gagacggtga cc                                   32

<210> SEQ ID NO 721
<211> LENGTH: 32
<212> TYPE: DNA
<213> ORGANISM: Homo Sapien

<400> SEQUENCE: 721
agctccgtaa cttacctgag gagacggtga cc                                   32

<210> SEQ ID NO 722
<211> LENGTH: 32
<212> TYPE: DNA
<213> ORGANISM: Homo Sapien

<400> SEQUENCE: 722
acgtccgtaa cttacctgag gagacggtga cc                                   32

<210> SEQ ID NO 723
<211> LENGTH: 32
<212> TYPE: DNA
<213> ORGANISM: Homo Sapien

<400> SEQUENCE: 723
tagtggcaag cttacctgag gagacggtga cc                                   32

<210> SEQ ID NO 724
<211> LENGTH: 32
<212> TYPE: DNA
<213> ORGANISM: Homo Sapien

<400> SEQUENCE: 724
ttatggcaag cttacctgag gagacggtga cc                                   32

<210> SEQ ID NO 725
<211> LENGTH: 32
<212> TYPE: DNA
<213> ORGANISM: Homo Sapien

<400> SEQUENCE: 725
tcctggcaag cttacctgag gagacggtga cc                                   32

<210> SEQ ID NO 726
<211> LENGTH: 32
<212> TYPE: DNA
<213> ORGANISM: Homo Sapien

<400> SEQUENCE: 726
tgttggcaag cttacctgag gagacggtga cc                                    32

<210> SEQ ID NO 727
<211> LENGTH: 32
<212> TYPE: DNA
<213> ORGANISM: Homo Sapien

<400> SEQUENCE: 727
cggtggcaag cttacctgag gagacggtga cc                                    32

<210> SEQ ID NO 728
<211> LENGTH: 32
<212> TYPE: DNA
<213> ORGANISM: Homo Sapien

<400> SEQUENCE: 728
caatggcaag cttacctgag gagacggtga cc                                    32

<210> SEQ ID NO 729
<211> LENGTH: 32
<212> TYPE: DNA
<213> ORGANISM: Homo Sapien

<400> SEQUENCE: 729
ccttggcaag cttacctgag gagacggtga cc                                    32

<210> SEQ ID NO 730
<211> LENGTH: 32
<212> TYPE: DNA
<213> ORGANISM: Homo Sapien

<400> SEQUENCE: 730
agctggcaag cttacctgag gagacggtga cc                                    32

<210> SEQ ID NO 731
<211> LENGTH: 32
<212> TYPE: DNA
<213> ORGANISM: Homo Sapien

<400> SEQUENCE: 731
acgtggcaag cttacctgag gagacggtga cc                                    32

<210> SEQ ID NO 732
<211> LENGTH: 32
<212> TYPE: DNA
<213> ORGANISM: Homo Sapien

<400> SEQUENCE: 732
tagtccggtg cttacctgag gagacggtga cc                                    32

<210> SEQ ID NO 733
<211> LENGTH: 32
<212> TYPE: DNA
<213> ORGANISM: Homo Sapien

<400> SEQUENCE: 733
ttatccggtg cttacctgag gagacggtga cc                                         32

<210> SEQ ID NO 734
<211> LENGTH: 32
<212> TYPE: DNA
<213> ORGANISM: Homo Sapien

<400> SEQUENCE: 734
tcctccggtg cttacctgag gagacggtga cc                                         32

<210> SEQ ID NO 735
<211> LENGTH: 32
<212> TYPE: DNA
<213> ORGANISM: Homo Sapien

<400> SEQUENCE: 735
tgttccggtg cttacctgag gagacggtga cc                                         32

<210> SEQ ID NO 736
<211> LENGTH: 32
<212> TYPE: DNA
<213> ORGANISM: Homo Sapien

<400> SEQUENCE: 736
cggtccggtg cttacctgag gagacggtga cc                                         32

<210> SEQ ID NO 737
<211> LENGTH: 32
<212> TYPE: DNA
<213> ORGANISM: Homo Sapien

<400> SEQUENCE: 737
caatccggtg cttacctgag gagacggtga cc                                         32

<210> SEQ ID NO 738
<211> LENGTH: 32
<212> TYPE: DNA
<213> ORGANISM: Homo Sapien

<400> SEQUENCE: 738
ccttccggtg cttacctgag gagacggtga cc                                         32

<210> SEQ ID NO 739
<211> LENGTH: 32
<212> TYPE: DNA
<213> ORGANISM: Homo Sapien

<400> SEQUENCE: 739
agctccggtg cttacctgag gagacggtga cc                                         32

<210> SEQ ID NO 740
<211> LENGTH: 32
<212> TYPE: DNA
<213> ORGANISM: Homo Sapien

<400> SEQUENCE: 740
acgtccggtg cttacctgag gagacggtga cc                                         32

<210> SEQ ID NO 741
<211> LENGTH: 32
<212> TYPE: DNA
<213> ORGANISM: Homo Sapien

<400> SEQUENCE: 741
tagtcctaag cttacctgag gagacggtga cc            32

<210> SEQ ID NO 742
<211> LENGTH: 32
<212> TYPE: DNA
<213> ORGANISM: Homo Sapien

<400> SEQUENCE: 742
ttatcctaag cttacctgag gagacggtga cc            32

<210> SEQ ID NO 743
<211> LENGTH: 32
<212> TYPE: DNA
<213> ORGANISM: Homo Sapien

<400> SEQUENCE: 743
tcctcctaag cttacctgag gagacggtga cc            32

<210> SEQ ID NO 744
<211> LENGTH: 32
<212> TYPE: DNA
<213> ORGANISM: Homo Sapien

<400> SEQUENCE: 744
tgttcctaag cttacctgag gagacggtga cc            32

<210> SEQ ID NO 745
<211> LENGTH: 32
<212> TYPE: DNA
<213> ORGANISM: Homo Sapien

<400> SEQUENCE: 745
cggtcctaag cttacctgag gagacggtga cc            32

<210> SEQ ID NO 746
<211> LENGTH: 32
<212> TYPE: DNA
<213> ORGANISM: Homo Sapien

<400> SEQUENCE: 746
caatcctaag cttacctgag gagacggtga cc            32

<210> SEQ ID NO 747
<211> LENGTH: 32
<212> TYPE: DNA
<213> ORGANISM: Homo Sapien

<400> SEQUENCE: 747
tagttattcg cttacctgag gagacggtga cc            32

<210> SEQ ID NO 748
<211> LENGTH: 32
<212> TYPE: DNA
<213> ORGANISM: Homo Sapien

<400> SEQUENCE: 748
ttattattcg cttacctgag gagacggtga cc            32

<210> SEQ ID NO 749
<211> LENGTH: 32
<212> TYPE: DNA
<213> ORGANISM: Homo Sapien

```
<400> SEQUENCE: 749
tccttattcg cttacctgag gagacggtga cc                                    32

<210> SEQ ID NO 750
<211> LENGTH: 32
<212> TYPE: DNA
<213> ORGANISM: Homo Sapien

<400> SEQUENCE: 750
cggttattcg cttacctgag gagacggtga cc                                    32

<210> SEQ ID NO 751
<211> LENGTH: 32
<212> TYPE: DNA
<213> ORGANISM: Homo Sapien

<400> SEQUENCE: 751
caattattcg cttacctgag gagacggtga cc                                    32

<210> SEQ ID NO 752
<211> LENGTH: 32
<212> TYPE: DNA
<213> ORGANISM: Homo Sapien

<400> SEQUENCE: 752
agcttattcg cttacctgag gagacggtga cc                                    32

<210> SEQ ID NO 753
<211> LENGTH: 32
<212> TYPE: DNA
<213> ORGANISM: Homo Sapien

<400> SEQUENCE: 753
acgttattcg cttacctgag gagacggtga cc                                    32

<210> SEQ ID NO 754
<211> LENGTH: 32
<212> TYPE: DNA
<213> ORGANISM: Homo Sapien

<400> SEQUENCE: 754
tagttaatcc cttacctgag gagacggtga cc                                    32

<210> SEQ ID NO 755
<211> LENGTH: 32
<212> TYPE: DNA
<213> ORGANISM: Homo Sapien

<400> SEQUENCE: 755
ttattaatcc cttacctgag gagacggtga cc                                    32

<210> SEQ ID NO 756
<211> LENGTH: 32
<212> TYPE: DNA
<213> ORGANISM: Homo Sapien

<400> SEQUENCE: 756
tccttaatcc cttacctgag gagacggtga cc                                    32

<210> SEQ ID NO 757
<211> LENGTH: 32
<212> TYPE: DNA
<213> ORGANISM: Homo Sapien
```

<400> SEQUENCE: 757
cggttaatcc cttacctgag gagacggtga cc                                    32

<210> SEQ ID NO 758
<211> LENGTH: 32
<212> TYPE: DNA
<213> ORGANISM: Homo Sapien

<400> SEQUENCE: 758
caattaatcc cttacctgag gagacggtga cc                                    32

<210> SEQ ID NO 759
<211> LENGTH: 35
<212> TYPE: DNA
<213> ORGANISM: Homo Sapien

<400> SEQUENCE: 759
ccttcctaag tggatccgtc agcccccagg gaagg                                 35

<210> SEQ ID NO 760
<211> LENGTH: 31
<212> TYPE: DNA
<213> ORGANISM: Homo Sapien

<400> SEQUENCE: 760
ccttcctaag ggtccgccag gctccaggga a                                     31

<210> SEQ ID NO 761
<211> LENGTH: 35
<212> TYPE: DNA
<213> ORGANISM: Homo Sapien

<400> SEQUENCE: 761
ccttcctaag tggatccgcc agcccccagg gaagg                                 35

<210> SEQ ID NO 762
<211> LENGTH: 35
<212> TYPE: DNA
<213> ORGANISM: Homo Sapien

<400> SEQUENCE: 762
ccttcctaag gggtgcgcca gatgcccggg aaagg                                 35

<210> SEQ ID NO 763
<211> LENGTH: 35
<212> TYPE: DNA
<213> ORGANISM: Homo Sapien

<400> SEQUENCE: 763
ccttcctaag tggatcaggc agtccccatc gagag                                 35

<210> SEQ ID NO 764
<211> LENGTH: 35
<212> TYPE: DNA
<213> ORGANISM: Homo Sapien

<400> SEQUENCE: 764
ccttcctaag ttgggtgcga caggcccctg gacaa                                 35

<210> SEQ ID NO 765
<211> LENGTH: 35
<212> TYPE: DNA

<213> ORGANISM: Homo Sapien

<400> SEQUENCE: 765
agctcctaag ctgggtgcga caggcccctg gacaa    35

<210> SEQ ID NO 766
<211> LENGTH: 35
<212> TYPE: DNA
<213> ORGANISM: Homo Sapien

<400> SEQUENCE: 766
agctcctaag tggatccgtc agcccccagg gaagg    35

<210> SEQ ID NO 767
<211> LENGTH: 31
<212> TYPE: DNA
<213> ORGANISM: Homo Sapien

<400> SEQUENCE: 767
agctcctaag ggtccgccag gctccaggga a    31

<210> SEQ ID NO 768
<211> LENGTH: 35
<212> TYPE: DNA
<213> ORGANISM: Homo Sapien

<400> SEQUENCE: 768
agctcctaag tggatccgcc agcccccagg gaagg    35

<210> SEQ ID NO 769
<211> LENGTH: 35
<212> TYPE: DNA
<213> ORGANISM: Homo Sapien

<400> SEQUENCE: 769
agctcctaag gggtgcgcca gatgcccggg aaagg    35

<210> SEQ ID NO 770
<211> LENGTH: 35
<212> TYPE: DNA
<213> ORGANISM: Homo Sapien

<400> SEQUENCE: 770
agctcctaag tggatcaggc agtccccatc gagag    35

<210> SEQ ID NO 771
<211> LENGTH: 35
<212> TYPE: DNA
<213> ORGANISM: Homo Sapien

<400> SEQUENCE: 771
agctcctaag ttgggtgcga caggcccctg gacaa    35

<210> SEQ ID NO 772
<211> LENGTH: 35
<212> TYPE: DNA
<213> ORGANISM: Homo Sapien

<400> SEQUENCE: 772
acgtcctaag ctgggtgcga caggcccctg gacaa    35

<210> SEQ ID NO 773
<211> LENGTH: 35

```
<212> TYPE: DNA
<213> ORGANISM: Homo Sapien

<400> SEQUENCE: 773
acgtcctaag tggatccgtc agcccccagg gaagg                              35

<210> SEQ ID NO 774
<211> LENGTH: 31
<212> TYPE: DNA
<213> ORGANISM: Homo Sapien

<400> SEQUENCE: 774
acgtcctaag ggtccgccag gctccaggga a                                  31

<210> SEQ ID NO 775
<211> LENGTH: 35
<212> TYPE: DNA
<213> ORGANISM: Homo Sapien

<400> SEQUENCE: 775
acgtcctaag tggatccgcc agcccccagg gaagg                              35

<210> SEQ ID NO 776
<211> LENGTH: 35
<212> TYPE: DNA
<213> ORGANISM: Homo Sapien

<400> SEQUENCE: 776
acgtcctaag gggtgcgcca gatgcccggg aaagg                              35

<210> SEQ ID NO 777
<211> LENGTH: 35
<212> TYPE: DNA
<213> ORGANISM: Homo Sapien

<400> SEQUENCE: 777
acgtcctaag tggatcaggc agtccccatc gagag                              35

<210> SEQ ID NO 778
<211> LENGTH: 35
<212> TYPE: DNA
<213> ORGANISM: Homo Sapien

<400> SEQUENCE: 778
acgtcctaag ttgggtgcga caggcccctg gacaa                              35

<210> SEQ ID NO 779
<211> LENGTH: 35
<212> TYPE: DNA
<213> ORGANISM: Homo Sapien

<400> SEQUENCE: 779
tagtgccagg ctgggtgcga caggcccctg gacaa                              35

<210> SEQ ID NO 780
<211> LENGTH: 35
<212> TYPE: DNA
<213> ORGANISM: Homo Sapien

<400> SEQUENCE: 780
tagtgccagg tggatccgtc agcccccagg gaagg                              35

<210> SEQ ID NO 781
```

```
<211> LENGTH: 31
<212> TYPE: DNA
<213> ORGANISM: Homo Sapien

<400> SEQUENCE: 781
tagtgccagg ggtccgccag gctccaggga a                              31

<210> SEQ ID NO 782
<211> LENGTH: 35
<212> TYPE: DNA
<213> ORGANISM: Homo Sapien

<400> SEQUENCE: 782
tagtgccagg tggatccgcc agcccccagg gaagg                          35

<210> SEQ ID NO 783
<211> LENGTH: 35
<212> TYPE: DNA
<213> ORGANISM: Homo Sapien

<400> SEQUENCE: 783
tagtgccagg gggtgcgcca gatgcccggg aaagg                          35

<210> SEQ ID NO 784
<211> LENGTH: 35
<212> TYPE: DNA
<213> ORGANISM: Homo Sapien

<400> SEQUENCE: 784
tagtgccagg tggatcaggc agtccccatc gagag                          35

<210> SEQ ID NO 785
<211> LENGTH: 35
<212> TYPE: DNA
<213> ORGANISM: Homo Sapien

<400> SEQUENCE: 785
tagtgccagg ttgggtgcga caggccctg gacaa                           35

<210> SEQ ID NO 786
<211> LENGTH: 35
<212> TYPE: DNA
<213> ORGANISM: Homo Sapien

<400> SEQUENCE: 786
tgttgccagg ctgggtgcga caggccctg gacaa                           35

<210> SEQ ID NO 787
<211> LENGTH: 35
<212> TYPE: DNA
<213> ORGANISM: Homo Sapien

<400> SEQUENCE: 787
tgttgccagg tggatccgtc agcccccagg gaagg                          35

<210> SEQ ID NO 788
<211> LENGTH: 31
<212> TYPE: DNA
<213> ORGANISM: Homo Sapien

<400> SEQUENCE: 788
tgttgccagg ggtccgccag gctccaggga a                              31
```

```
<210> SEQ ID NO 789
<211> LENGTH: 35
<212> TYPE: DNA
<213> ORGANISM: Homo Sapien

<400> SEQUENCE: 789
tgttgccagg tggatccgcc agcccccagg gaagg                    35

<210> SEQ ID NO 790
<211> LENGTH: 35
<212> TYPE: DNA
<213> ORGANISM: Homo Sapien

<400> SEQUENCE: 790
tgttgccagg gggtgcgcca gatgcccggg aaagg                    35

<210> SEQ ID NO 791
<211> LENGTH: 35
<212> TYPE: DNA
<213> ORGANISM: Homo Sapien

<400> SEQUENCE: 791
tgttgccagg tggatcaggc agtccccatc gagag                    35

<210> SEQ ID NO 792
<211> LENGTH: 35
<212> TYPE: DNA
<213> ORGANISM: Homo Sapien

<400> SEQUENCE: 792
tgttgccagg ttgggtgcga caggccctg gacaa                     35

<210> SEQ ID NO 793
<211> LENGTH: 35
<212> TYPE: DNA
<213> ORGANISM: Homo Sapien

<400> SEQUENCE: 793
cggtgccagg ctgggtgcga caggccctg gacaa                     35

<210> SEQ ID NO 794
<211> LENGTH: 35
<212> TYPE: DNA
<213> ORGANISM: Homo Sapien

<400> SEQUENCE: 794
cggtgccagg tggatccgtc agcccccagg gaagg                    35

<210> SEQ ID NO 795
<211> LENGTH: 31
<212> TYPE: DNA
<213> ORGANISM: Homo Sapien

<400> SEQUENCE: 795
cggtgccagg ggtccgccag gctccaggga a                        31

<210> SEQ ID NO 796
<211> LENGTH: 35
<212> TYPE: DNA
<213> ORGANISM: Homo Sapien

<400> SEQUENCE: 796
cggtgccagg tggatccgcc agcccccagg gaagg                    35
```

<210> SEQ ID NO 797
<211> LENGTH: 35
<212> TYPE: DNA
<213> ORGANISM: Homo Sapien

<400> SEQUENCE: 797
cggtgccagg gggtgcgcca gatgcccggg aaagg      35

<210> SEQ ID NO 798
<211> LENGTH: 35
<212> TYPE: DNA
<213> ORGANISM: Homo Sapien

<400> SEQUENCE: 798
cggtgccagg tggatcaggc agtccccatc gagag      35

<210> SEQ ID NO 799
<211> LENGTH: 35
<212> TYPE: DNA
<213> ORGANISM: Homo Sapien

<400> SEQUENCE: 799
cggtgccagg ttgggtgcga caggccctg gacaa       35

<210> SEQ ID NO 800
<211> LENGTH: 35
<212> TYPE: DNA
<213> ORGANISM: Homo Sapien

<400> SEQUENCE: 800
caatgccagg ctgggtgcga caggccctg gacaa       35

<210> SEQ ID NO 801
<211> LENGTH: 35
<212> TYPE: DNA
<213> ORGANISM: Homo Sapien

<400> SEQUENCE: 801
caatgccagg tggatccgtc agcccccagg gaagg      35

<210> SEQ ID NO 802
<211> LENGTH: 31
<212> TYPE: DNA
<213> ORGANISM: Homo Sapien

<400> SEQUENCE: 802
caatgccagg ggtccgccag gctccaggga a          31

<210> SEQ ID NO 803
<211> LENGTH: 35
<212> TYPE: DNA
<213> ORGANISM: Homo Sapien

<400> SEQUENCE: 803
caatgccagg tggatccgcc agcccccagg gaagg      35

<210> SEQ ID NO 804
<211> LENGTH: 35
<212> TYPE: DNA
<213> ORGANISM: Homo Sapien

<400> SEQUENCE: 804
caatgccagg gggtgcgcca gatgcccggg aaagg      35

<210> SEQ ID NO 805
<211> LENGTH: 35
<212> TYPE: DNA
<213> ORGANISM: Homo Sapien

<400> SEQUENCE: 805
caatgccagg tggatcaggc agtccccatc gagag           35

<210> SEQ ID NO 806
<211> LENGTH: 35
<212> TYPE: DNA
<213> ORGANISM: Homo Sapien

<400> SEQUENCE: 806
caatgccagg ttgggtgcga caggccctg gacaa            35

<210> SEQ ID NO 807
<211> LENGTH: 35
<212> TYPE: DNA
<213> ORGANISM: Homo Sapien

<400> SEQUENCE: 807
ctccggtaag ctgggtgcga caggccctg gacaa            35

<210> SEQ ID NO 808
<211> LENGTH: 35
<212> TYPE: DNA
<213> ORGANISM: Homo Sapien

<400> SEQUENCE: 808
ctccggtaag tggatccgtc agccccagg gaagg            35

<210> SEQ ID NO 809
<211> LENGTH: 31
<212> TYPE: DNA
<213> ORGANISM: Homo Sapien

<400> SEQUENCE: 809
ctccggtaag ggtccgccag gctccaggga a               31

<210> SEQ ID NO 810
<211> LENGTH: 35
<212> TYPE: DNA
<213> ORGANISM: Homo Sapien

<400> SEQUENCE: 810
ctccggtaag tggatccgcc agccccagg gaagg            35

<210> SEQ ID NO 811
<211> LENGTH: 35
<212> TYPE: DNA
<213> ORGANISM: Homo Sapien

<400> SEQUENCE: 811
ctccggtaag gggtgcgcca gatgcccggg aaagg           35

<210> SEQ ID NO 812
<211> LENGTH: 35
<212> TYPE: DNA
<213> ORGANISM: Homo Sapien

<400> SEQUENCE: 812

-continued ctccggtaag tggatcaggc agtccccatc gagag 35

<210> SEQ ID NO 813
<211> LENGTH: 35
<212> TYPE: DNA
<213> ORGANISM: Homo Sapien

<400> SEQUENCE: 813
ctccggtaag ttgggtgcga caggcccctg gacaa 35

<210> SEQ ID NO 814
<211> LENGTH: 35
<212> TYPE: DNA
<213> ORGANISM: Homo Sapien

<400> SEQUENCE: 814
caattcggaa ctgggtgcga caggcccctg gacaa 35

<210> SEQ ID NO 815
<211> LENGTH: 35
<212> TYPE: DNA
<213> ORGANISM: Homo Sapien

<400> SEQUENCE: 815
caattcggaa tggatccgtc agcccccagg gaagg 35

<210> SEQ ID NO 816
<211> LENGTH: 31
<212> TYPE: DNA
<213> ORGANISM: Homo Sapien

<400> SEQUENCE: 816
caattcggaa ggtccgccag gctccaggga a 31

<210> SEQ ID NO 817
<211> LENGTH: 35
<212> TYPE: DNA
<213> ORGANISM: Homo Sapien

<400> SEQUENCE: 817
caattcggaa tggatccgcc agcccccagg gaagg 35

<210> SEQ ID NO 818
<211> LENGTH: 35
<212> TYPE: DNA
<213> ORGANISM: Homo Sapien

<400> SEQUENCE: 818
caattcggaa gggtgcgcca gatgcccggg aaagg 35

<210> SEQ ID NO 819
<211> LENGTH: 35
<212> TYPE: DNA
<213> ORGANISM: Homo Sapien

<400> SEQUENCE: 819
caattcggaa tggatcaggc agtccccatc gagag 35

<210> SEQ ID NO 820
<211> LENGTH: 35
<212> TYPE: DNA
<213> ORGANISM: Homo Sapien

<400> SEQUENCE: 820

```
caattcggaa ttgggtgcga caggcccctg gacaa                                    35

<210> SEQ ID NO 821
<211> LENGTH: 35
<212> TYPE: DNA
<213> ORGANISM: Homo Sapien

<400> SEQUENCE: 821
acgttaatcc ctgggtgcga caggcccctg gacaa                                    35

<210> SEQ ID NO 822
<211> LENGTH: 35
<212> TYPE: DNA
<213> ORGANISM: Homo Sapien

<400> SEQUENCE: 822
acgttaatcc tggatccgtc agcccccagg gaagg                                    35

<210> SEQ ID NO 823
<211> LENGTH: 31
<212> TYPE: DNA
<213> ORGANISM: Homo Sapien

<400> SEQUENCE: 823
acgttaatcc ggtccgccag gctccaggga a                                        31

<210> SEQ ID NO 824
<211> LENGTH: 35
<212> TYPE: DNA
<213> ORGANISM: Homo Sapien

<400> SEQUENCE: 824
acgttaatcc tggatccgcc agcccccagg gaagg                                    35

<210> SEQ ID NO 825
<211> LENGTH: 35
<212> TYPE: DNA
<213> ORGANISM: Homo Sapien

<400> SEQUENCE: 825
acgttaatcc gggtgcgcca gatgcccggg aaagg                                    35

<210> SEQ ID NO 826
<211> LENGTH: 35
<212> TYPE: DNA
<213> ORGANISM: Homo Sapien

<400> SEQUENCE: 826
acgttaatcc tggatcaggc agtccccatc gagag                                    35

<210> SEQ ID NO 827
<211> LENGTH: 35
<212> TYPE: DNA
<213> ORGANISM: Homo Sapien

<400> SEQUENCE: 827
acgttaatcc ttgggtgcga caggcccctg gacaa                                    35

<210> SEQ ID NO 828
<211> LENGTH: 35
<212> TYPE: DNA
<213> ORGANISM: Homo Sapien
```

<400> SEQUENCE: 828
tagttcggaa ctgggtgcga caggcccctg gacaa                35

<210> SEQ ID NO 829
<211> LENGTH: 35
<212> TYPE: DNA
<213> ORGANISM: Homo Sapien

<400> SEQUENCE: 829
tagttcggaa tggatccgtc agcccccagg gaagg                35

<210> SEQ ID NO 830
<211> LENGTH: 31
<212> TYPE: DNA
<213> ORGANISM: Homo Sapien

<400> SEQUENCE: 830
tagttcggaa ggtccgccag gctccaggga a                    31

<210> SEQ ID NO 831
<211> LENGTH: 35
<212> TYPE: DNA
<213> ORGANISM: Homo Sapien

<400> SEQUENCE: 831
tagttcggaa tggatccgcc agcccccagg gaagg                35

<210> SEQ ID NO 832
<211> LENGTH: 35
<212> TYPE: DNA
<213> ORGANISM: Homo Sapien

<400> SEQUENCE: 832
tagttcggaa gggtgcgcca gatgcccggg aaagg                35

<210> SEQ ID NO 833
<211> LENGTH: 35
<212> TYPE: DNA
<213> ORGANISM: Homo Sapien

<400> SEQUENCE: 833
tagttcggaa tggatcaggc agtccccatc gagag                35

<210> SEQ ID NO 834
<211> LENGTH: 35
<212> TYPE: DNA
<213> ORGANISM: Homo Sapien

<400> SEQUENCE: 834
tagttcggaa ttgggtgcga caggcccctg gacaa                35

<210> SEQ ID NO 835
<211> LENGTH: 35
<212> TYPE: DNA
<213> ORGANISM: Homo Sapien

<400> SEQUENCE: 835
ttattcggaa ctgggtgcga caggcccctg gacaa                35

<210> SEQ ID NO 836
<211> LENGTH: 35
<212> TYPE: DNA
<213> ORGANISM: Homo Sapien

```
<400> SEQUENCE: 836
ttattcggaa tggatccgtc agcccccagg gaagg                              35

<210> SEQ ID NO 837
<211> LENGTH: 31
<212> TYPE: DNA
<213> ORGANISM: Homo Sapien

<400> SEQUENCE: 837
ttattcggaa ggtccgccag gctccaggga a                                  31

<210> SEQ ID NO 838
<211> LENGTH: 35
<212> TYPE: DNA
<213> ORGANISM: Homo Sapien

<400> SEQUENCE: 838
ttattcggaa tggatccgcc agcccccagg gaagg                              35

<210> SEQ ID NO 839
<211> LENGTH: 35
<212> TYPE: DNA
<213> ORGANISM: Homo Sapien

<400> SEQUENCE: 839
ttattcggaa gggtgcgcca gatgcccggg aaagg                              35

<210> SEQ ID NO 840
<211> LENGTH: 35
<212> TYPE: DNA
<213> ORGANISM: Homo Sapien

<400> SEQUENCE: 840
ttattcggaa tggatcaggc agtccccatc gagag                              35

<210> SEQ ID NO 841
<211> LENGTH: 35
<212> TYPE: DNA
<213> ORGANISM: Homo Sapien

<400> SEQUENCE: 841
ttattcggaa ttgggtgcga caggcccctg gacaa                              35

<210> SEQ ID NO 842
<211> LENGTH: 35
<212> TYPE: DNA
<213> ORGANISM: Homo Sapien

<400> SEQUENCE: 842
ttatgccagg ggcctcagtg aaggtctcct gcaag                              35

<210> SEQ ID NO 843
<211> LENGTH: 35
<212> TYPE: DNA
<213> ORGANISM: Homo Sapien

<400> SEQUENCE: 843
ttatgccagg gtctggtcct acgctggtga aaccc                              35

<210> SEQ ID NO 844
<211> LENGTH: 35
<212> TYPE: DNA
```

```
<213> ORGANISM: Homo Sapien

<400> SEQUENCE: 844
ttatgccagg ctgggggtc cctgagactc tcctg                          35

<210> SEQ ID NO 845
<211> LENGTH: 35
<212> TYPE: DNA
<213> ORGANISM: Homo Sapien

<400> SEQUENCE: 845
ttatgccagg cttcggagac cctgtccctc acctg                         35

<210> SEQ ID NO 846
<211> LENGTH: 35
<212> TYPE: DNA
<213> ORGANISM: Homo Sapien

<400> SEQUENCE: 846
ttatgccagg cggggagtct ctgaagatct cctgt                         35

<210> SEQ ID NO 847
<211> LENGTH: 35
<212> TYPE: DNA
<213> ORGANISM: Homo Sapien

<400> SEQUENCE: 847
ttatgccagg tcgcagaccc tctcactcac ctgtg                         35

<210> SEQ ID NO 848
<211> LENGTH: 35
<212> TYPE: DNA
<213> ORGANISM: Homo Sapien

<400> SEQUENCE: 848
tcctgccagg ggcctcagtg aaggtctcct gcaag                         35

<210> SEQ ID NO 849
<211> LENGTH: 35
<212> TYPE: DNA
<213> ORGANISM: Homo Sapien

<400> SEQUENCE: 849
tcctgccagg gtctggtcct acgctggtga aaccc                         35

<210> SEQ ID NO 850
<211> LENGTH: 35
<212> TYPE: DNA
<213> ORGANISM: Homo Sapien

<400> SEQUENCE: 850
tcctgccagg ctgggggtc cctgagactc tcctg                          35

<210> SEQ ID NO 851
<211> LENGTH: 35
<212> TYPE: DNA
<213> ORGANISM: Homo Sapien

<400> SEQUENCE: 851
tcctgccagg cttcggagac cctgtccctc acctg                         35

<210> SEQ ID NO 852
<211> LENGTH: 35
```

<212> TYPE: DNA
<213> ORGANISM: Homo Sapien

<400> SEQUENCE: 852
tcctgccagg cggggagtct ctgaagatct cctgt         35

<210> SEQ ID NO 853
<211> LENGTH: 35
<212> TYPE: DNA
<213> ORGANISM: Homo Sapien

<400> SEQUENCE: 853
tcctgccagg tcgcagaccc tctcactcac ctgtg         35

<210> SEQ ID NO 854
<211> LENGTH: 35
<212> TYPE: DNA
<213> ORGANISM: Homo Sapien

<400> SEQUENCE: 854
ccttgccagg ggcctcagtg aaggtctcct gcaag         35

<210> SEQ ID NO 855
<211> LENGTH: 35
<212> TYPE: DNA
<213> ORGANISM: Homo Sapien

<400> SEQUENCE: 855
ccttgccagg gtctggtcct acgctggtga accc          35

<210> SEQ ID NO 856
<211> LENGTH: 35
<212> TYPE: DNA
<213> ORGANISM: Homo Sapien

<400> SEQUENCE: 856
ccttgccagg ctgggggtc cctgagactc tcctg          35

<210> SEQ ID NO 857
<211> LENGTH: 35
<212> TYPE: DNA
<213> ORGANISM: Homo Sapien

<400> SEQUENCE: 857
ccttgccagg cttcggagac cctgtccctc acctg         35

<210> SEQ ID NO 858
<211> LENGTH: 35
<212> TYPE: DNA
<213> ORGANISM: Homo Sapien

<400> SEQUENCE: 858
ccttgccagg cggggagtct ctgaagatct cctgt         35

<210> SEQ ID NO 859
<211> LENGTH: 35
<212> TYPE: DNA
<213> ORGANISM: Homo Sapien

<400> SEQUENCE: 859
ccttgccagg tcgcagaccc tctcactcac ctgtg         35

<210> SEQ ID NO 860

```
<211> LENGTH: 35
<212> TYPE: DNA
<213> ORGANISM: Homo Sapien

<400> SEQUENCE: 860
agcttaatcc ggcctcagtg aaggtctcct gcaag                              35

<210> SEQ ID NO 861
<211> LENGTH: 35
<212> TYPE: DNA
<213> ORGANISM: Homo Sapien

<400> SEQUENCE: 861
agcttaatcc gtctggtcct acgctggtga acccc                              35

<210> SEQ ID NO 862
<211> LENGTH: 35
<212> TYPE: DNA
<213> ORGANISM: Homo Sapien

<400> SEQUENCE: 862
agcttaatcc ctgggggtc cctgagactc tcctg                               35

<210> SEQ ID NO 863
<211> LENGTH: 35
<212> TYPE: DNA
<213> ORGANISM: Homo Sapien

<400> SEQUENCE: 863
agcttaatcc cttcggagac cctgtccctc acctg                              35

<210> SEQ ID NO 864
<211> LENGTH: 35
<212> TYPE: DNA
<213> ORGANISM: Homo Sapien

<400> SEQUENCE: 864
agcttaatcc cggggagtct ctgaagatct cctgt                              35

<210> SEQ ID NO 865
<211> LENGTH: 35
<212> TYPE: DNA
<213> ORGANISM: Homo Sapien

<400> SEQUENCE: 865
agcttaatcc tcgcagaccc tctcactcac ctgtg                              35

<210> SEQ ID NO 866
<211> LENGTH: 35
<212> TYPE: DNA
<213> ORGANISM: Homo Sapien

<400> SEQUENCE: 866
ctccattagg ggcctcagtg aaggtctcct gcaag                              35

<210> SEQ ID NO 867
<211> LENGTH: 35
<212> TYPE: DNA
<213> ORGANISM: Homo Sapien

<400> SEQUENCE: 867
ctccattagg gtctggtcct acgctggtga acccc                              35
```

```
<210> SEQ ID NO 868
<211> LENGTH: 35
<212> TYPE: DNA
<213> ORGANISM: Homo Sapien

<400> SEQUENCE: 868
ctccattagg ctgggggtc cctgagactc tcctg                              35

<210> SEQ ID NO 869
<211> LENGTH: 35
<212> TYPE: DNA
<213> ORGANISM: Homo Sapien

<400> SEQUENCE: 869
ctccattagg cttcggagac cctgtccctc acctg                             35

<210> SEQ ID NO 870
<211> LENGTH: 35
<212> TYPE: DNA
<213> ORGANISM: Homo Sapien

<400> SEQUENCE: 870
ctccattagg cggggagtct ctgaagatct cctgt                             35

<210> SEQ ID NO 871
<211> LENGTH: 35
<212> TYPE: DNA
<213> ORGANISM: Homo Sapien

<400> SEQUENCE: 871
ctccattagg tcgcagaccc tctcactcac ctgtg                             35

<210> SEQ ID NO 872
<211> LENGTH: 35
<212> TYPE: DNA
<213> ORGANISM: Homo Sapien

<400> SEQUENCE: 872
ctccattcca ggcctcagtg aaggtctcct gcaag                             35

<210> SEQ ID NO 873
<211> LENGTH: 35
<212> TYPE: DNA
<213> ORGANISM: Homo Sapien

<400> SEQUENCE: 873
ctccattcca gtctggtcct acgctggtga aaccc                             35

<210> SEQ ID NO 874
<211> LENGTH: 35
<212> TYPE: DNA
<213> ORGANISM: Homo Sapien

<400> SEQUENCE: 874
ctccattcca ctgggggtc cctgagactc tcctg                              35

<210> SEQ ID NO 875
<211> LENGTH: 35
<212> TYPE: DNA
<213> ORGANISM: Homo Sapien

<400> SEQUENCE: 875
ctccattcca cttcggagac cctgtccctc acctg                             35
```

```
<210> SEQ ID NO 876
<211> LENGTH: 35
<212> TYPE: DNA
<213> ORGANISM: Homo Sapien

<400> SEQUENCE: 876
ctccattcca cggggagtct ctgaagatct cctgt                    35

<210> SEQ ID NO 877
<211> LENGTH: 35
<212> TYPE: DNA
<213> ORGANISM: Homo Sapien

<400> SEQUENCE: 877
ctccattcca tcgcagaccc tctcactcac ctgtg                    35

<210> SEQ ID NO 878
<211> LENGTH: 35
<212> TYPE: DNA
<213> ORGANISM: Homo Sapien

<400> SEQUENCE: 878
ctccaataag ggcctcagtg aaggtctcct gcaag                    35

<210> SEQ ID NO 879
<211> LENGTH: 35
<212> TYPE: DNA
<213> ORGANISM: Homo Sapien

<400> SEQUENCE: 879
ctccaataag gtctggtcct acgctggtga aaccc                    35

<210> SEQ ID NO 880
<211> LENGTH: 35
<212> TYPE: DNA
<213> ORGANISM: Homo Sapien

<400> SEQUENCE: 880
ctccaataag ctgggggtc cctgagactc tcctg                     35

<210> SEQ ID NO 881
<211> LENGTH: 35
<212> TYPE: DNA
<213> ORGANISM: Homo Sapien

<400> SEQUENCE: 881
ctccaataag cttcggagac cctgtccctc acctg                    35

<210> SEQ ID NO 882
<211> LENGTH: 35
<212> TYPE: DNA
<213> ORGANISM: Homo Sapien

<400> SEQUENCE: 882
ctccaataag cggggagtct ctgaagatct cctgt                    35

<210> SEQ ID NO 883
<211> LENGTH: 35
<212> TYPE: DNA
<213> ORGANISM: Homo Sapien

<400> SEQUENCE: 883
ctccaataag tcgcagaccc tctcactcac ctgtg                    35
```

<210> SEQ ID NO 884
<211> LENGTH: 35
<212> TYPE: DNA
<213> ORGANISM: Homo Sapien

<400> SEQUENCE: 884
ctccaattcg ggcctcagtg aaggtctcct gcaag         35

<210> SEQ ID NO 885
<211> LENGTH: 35
<212> TYPE: DNA
<213> ORGANISM: Homo Sapien

<400> SEQUENCE: 885
ctccaattcg gtctggtcct acgctggtga aaccc         35

<210> SEQ ID NO 886
<211> LENGTH: 35
<212> TYPE: DNA
<213> ORGANISM: Homo Sapien

<400> SEQUENCE: 886
ctccaattcg ctgggggtc cctgagactc tcctg          35

<210> SEQ ID NO 887
<211> LENGTH: 35
<212> TYPE: DNA
<213> ORGANISM: Homo Sapien

<400> SEQUENCE: 887
ctccaattcg cttcggagac cctgtccctc acctg         35

<210> SEQ ID NO 888
<211> LENGTH: 35
<212> TYPE: DNA
<213> ORGANISM: Homo Sapien

<400> SEQUENCE: 888
ctccaattcg cggggagtct ctgaagatct cctgt         35

<210> SEQ ID NO 889
<211> LENGTH: 35
<212> TYPE: DNA
<213> ORGANISM: Homo Sapien

<400> SEQUENCE: 889
ctccaattcg tcgcagaccc tctcactcac ctgtg         35

<210> SEQ ID NO 890
<211> LENGTH: 35
<212> TYPE: DNA
<213> ORGANISM: Homo Sapien

<400> SEQUENCE: 890
cggttcggaa ggcctcagtg aaggtctcct gcaag         35

<210> SEQ ID NO 891
<211> LENGTH: 35
<212> TYPE: DNA
<213> ORGANISM: Homo Sapien

<400> SEQUENCE: 891

```
cggttcggaa gtctggtcct acgctggtga aaccc          35

<210> SEQ ID NO 892
<211> LENGTH: 35
<212> TYPE: DNA
<213> ORGANISM: Homo Sapien

<400> SEQUENCE: 892
tccttcggaa ctgggggtc cctgagactc tcctg           35

<210> SEQ ID NO 893
<211> LENGTH: 35
<212> TYPE: DNA
<213> ORGANISM: Homo Sapien

<400> SEQUENCE: 893
tccttcggaa cttcggagac cctgtccctc acctg          35

<210> SEQ ID NO 894
<211> LENGTH: 35
<212> TYPE: DNA
<213> ORGANISM: Homo Sapien

<400> SEQUENCE: 894
tccttcggaa cggggagtct ctgaagatct cctgt          35

<210> SEQ ID NO 895
<211> LENGTH: 35
<212> TYPE: DNA
<213> ORGANISM: Homo Sapien

<400> SEQUENCE: 895
tccttcggaa tcgcagaccc tctcactcac ctgtg          35

<210> SEQ ID NO 896
<211> LENGTH: 35
<212> TYPE: DNA
<213> ORGANISM: Homo Sapien

<400> SEQUENCE: 896
tccttcggaa ggcctcagtg aaggtctcct gcaag          35

<210> SEQ ID NO 897
<211> LENGTH: 35
<212> TYPE: DNA
<213> ORGANISM: Homo Sapien

<400> SEQUENCE: 897
tccttcggaa gtctggtcct acgctggtga aaccc          35

<210> SEQ ID NO 898
<211> LENGTH: 35
<212> TYPE: DNA
<213> ORGANISM: Homo Sapien

<400> SEQUENCE: 898
tccttcggaa ctgggggtc cctgagactc tcctg           35

<210> SEQ ID NO 899
<211> LENGTH: 35
<212> TYPE: DNA
<213> ORGANISM: Homo Sapien

<400> SEQUENCE: 899
```

```
tccttcggaa cttcggagac cctgtccctc acctg                            35

<210> SEQ ID NO 900
<211> LENGTH: 35
<212> TYPE: DNA
<213> ORGANISM: Homo Sapien

<400> SEQUENCE: 900
tccttcggaa cggggagtct ctgaagatct cctgt                            35

<210> SEQ ID NO 901
<211> LENGTH: 35
<212> TYPE: DNA
<213> ORGANISM: Homo Sapien

<400> SEQUENCE: 901
tccttcggaa tcgcagaccc tctcactcac ctgtg                            35
```

MEASUREMENT AND MONITORING OF CELL CLONALITY

FEDERALLY SPONSORED RESEARCH AND DEVELOPMENT

This invention was made with Government support under contract AI090019 awarded by the National Institutes of Health. The Government has certain rights in this invention.

BACKGROUND OF THE INVENTION

Antigen receptors with diverse binding activities are the hallmark of B and T cells of the adaptive immune system in jawed vertebrates and are generated by genomic rearrangement of variable (V), diversity (D), and joining (J) gene segments separated by highly variable junction regions (Schatz (2004) Semin. Immunol. 16, 245-256). Initial calculations have been made of the combinatorial and junctional possibilities that contribute to the human immune receptor repertoire, and it is estimated that the number of possibilities may greatly exceed the total number of peripheral T or B cells in an individual (Davis and Bjorkman (1988) Nature 334, 395-402).

For example, one study in which small subsets of rearranged T cell receptor (TCR) subunit genes were extensively sequenced with a few segment-specific primers yielded extrapolations for the full TCR repertoire corresponding to $2.5 \times 10^7$ distinct TCRα-TCRβ pairs in the peripheral blood of an individual (Arstila et al. (1999) Science 286, 958-961). Extensive repertoire analyses for the human B cell compartment have been more limited, although small-scale studies and focused analysis of immunoglobulin (Ig) class subsets, such as IgE, have been performed (Brezinschek et al. (1995) J. Immunol. 155, 190-202, Lim et al. (2007) J. Allergy Clin. Immunol. 120, 696-706). Advanced sequencing methods have recently been used to analyze B cell receptor diversity in the relatively simple model immune system in zebrafish (Weinstein et al. (2009) Science 324, 807-810).

Against a background of continually generated novel DNA sequences, expanded clones of lymphocytes with useful antigen specificities persist over time to enable rapid responses to antigens previously detected by the immune system. Systematic means for detection of such expanded clones in human beings would provide significant opportunities for specific analysis and tracking, including measurement of clonal population sizes, anatomic distributions, and changes in response to immunological events.

In contrast to healthy immune systems, malignancies of B or T cell origin typically express a single dominant clonal Ig or TCR receptor. A variety of assays have been used to detect the presence of B cell clonality for diagnosis of lymphomas and leukemias, including analysis of Ig light chain gene restriction and Southern blotting or sizing of polymerase chain reaction (PCR) products from rearranged Ig or TCR loci (Rezuke et al. (1997) Clin. Chem. 43, 1814-1823; Arber (2000) J. Mol. Diagn. 2, 178-190). Although adequate for many applications, these strategies make limited use of the high information content inherent in rearranged immune receptor gene sequences and can give indeterminate results.

A recent study using deep sequencing of clonal IgH (Ig heavy chain) receptor genes in chronic lymphocytic leukemia revealed unexpected intraclonal heterogeneity in a subset of cases, showing that previous approaches have not captured the fundamental features of leukemic cell populations (Campbell et al. (2008) Proc. Natl. Acad. Sci. U.S.A. 105, 13081-13086). Detection of more subtle clonal populations (for example, to follow the response of lymphomas or leukemias to treatment) now relies on time- and labor-intensive multiparameter flow cytometry or custom-designed patient- and clone-specific realtime PCR assays (Sayala et al. (2007) Best Pract. Res. Clin. Haematol. 20, 499-512; Ladetto et al. (2000) Biol. Blood Marrow Transplant. 6, 241-253). Early diagnostic screening approaches may benefit from generalized and more efficient clonal detection. Indeed, a recent population-based epidemiological study showed that small amplified B cell populations can be seen in almost all individuals who go on to develop chronic lymphocytic leukemia, further underscoring the importance of assessing lymphocyte clonality in human specimens.

Detection and analysis of clonality is also of fundamental interest in characterizing and tracking normal and pathogenic immune reactions. For protective and healthy humoral immune responses, high-resolution analysis of immune receptor clonality and evolution offers the potential for definitive detection and monitoring of effective immune responses to vaccination and specific infections, whereas for some autoimmune disorders this type of analysis may facilitate diagnosis, long-term therapeutic monitoring strategies, and, eventually, specific interventions.

SUMMARY OF THE INVENTION

Methods are provided for the detection and analysis of clonality in a cell population, where the cells in the population are diverse with respect to genetic sequences at a locus of interest. Loci of interest are typically sites susceptible to somatic mutation and/or recombination, including without limitation, immune receptor genes, oncogenes, tumor suppressor genes, and the like. Cell populations for analysis are optionally complex populations having a high degree of sequence heterogeneity at the locus of interest.

Exemplary loci of interest are immunoglobulin and T cell antigen receptor genetic sequences, including without limitation each of IgH, IgLλ, IgLκ, TCRα, TCRβ, TCRγ, TCRδ, wherein genetic recombination events act to create an extensive repertoire of different sequences distinct from that of the germline. For purposes of the present invention, these loci may be referred to collectively as combinatorial antigen receptors. In biological samples, e.g. peripheral blood, lymph nodes, spleen, etc., it is rare for normal, naïve lymphocytes to share a combinatorial antigen receptor sequence. However, when stimulated by antigen, e.g. autoantigens, vaccines, infections, etc.; or when affected by hyperproliferative conditions such as cancer and other lymphoproliferative disorders; there can be a clonal expansion of cells having a single specificity. The result of such clonal expansion is the presence of multiple cells in the biological sample sharing a specific combinatorial antigen receptor sequence.

In some specific embodiments, the serological response to an antigenic stimulation, including vaccination, is determined by utilizing the methods of the invention. Following vaccination or other strong antigenic exposure, it has been found that within a defined period of time, e.g. at least about 5 days and not more than about 14 days, in some embodiments from about 6 to about 10 days, including about 7 days; there is a distinct increase in clonal B cell populations in sero-responsive individuals. The sequence of the clonal antibodies is not required for identification of the serologic responsiveness, although the methods of the invention provide for optional sequence determination if desired.

In some methods, including, without limitation, those datasets in which samples have been sequenced to different depths; which may include the determination of serologic response to vaccination, the counts of coincident sequences are normalized. Normalization can include dividing the total number of coincident sequences detected between replicates of a sample by the total number of possible pairwise comparisons between sequences in different replicates from that sample.

In the methods of the invention, parallel sequencing is applied to a DNA sample obtained from a population of cells, frequently a complex population of cells, e.g. a mammalian cell population, which may be a human lymphocyte population. The DNA sample may be genomic DNA, or cDNA obtained from cellular mRNA. Replicate samples, e.g. at least 2, 3, 4, 5, 6, 8, 10 or more replicate DNA samples are amplified, where the replicates may be derived from a single pool of cells or from multiple pools of cells.

Amplification utilizes one or more sets of amplification primers, which optionally comprise a bar-code for identification, and/or optionally a primer sequence for sequencing reactions. Where the locus of interest is a combinatorial antigen receptor, primers are often designed to amplify the hypervariable regions of the genetic loci of interest, which regions typically comprise combinatorial junctions. Other loci may be amplified with primers designed to span the locus of interest The amplified DNA is sequenced; preferably a significant portion of one or more variable or hypervariable region(s) of interest are contained within a single "read", e.g. at least about 32 nucleotides, at least about 50 nt., at least about 100 nt., at least about 200 nt., and may be about 500 nt. or more in length. The number of sequencing reads performed per replicate amplification reaction will vary with the specific analysis to be performed, but will generally comprise at least 10, at least $10^2$, at least $10^3$ or more reads per replicate. The sequences thus obtained are compared and a determination is made of coincident sequences across replicates, where coincident sequences are defined as those that share substantial sequence identity. Where the loci is a combinatorial antigen receptor, coincident sequences are those that share germline segments, e.g. V, D, J, as appropriate for the receptor being analyzed, and that share substantial identity in junctional nucleotide sequences. A variety of algorithms can be used to analyze the sequence data obtained using this method. The presence of coincident sequences across replicates is indicative of clonal expansion of a cell.

The methods of the invention provide a highly sensitive and consistent assay for determining the presence of clonal expansion even of rare cells, and further provide identification of the specific expanded sequence. The numbers and diversity of individual cells can be measured in a clinical sample in a manner that is not possible with other methods, using only very small amounts of cells. The identification of the clonal sequence provides information that can be associated with the biological relevance of the sequence, e.g. identification of antigens bound by a combinatorial antigen receptor, loss of tumor supressor activity, etc. While certain clonal expansions of lymphocytes are associated with expression of the combinatorial antigen receptor, it should be noted that other conditions that can be analyzed by the methods of the invention, such as hyperproliferative conditions, including without limitation carcinomas, leukemias and lymphomas, may not be associated with productive expression of an antigen receptor.

Conditions of interest for analysis of clonal expansion include numerous aspects of cellular proliferation and antigenic exposure, e.g. the presence of autoimmune disease; the status of transplantation; the presence of cancer, including without limitation cancers of the immune system, e.g. leukemias, lymphomas, myelomas, etc.; exposure to antigenic stimulus, e.g. exposure to cancer antigens; exposure to viral, bacterial, parasitic antigens; exposure to vaccines; exposure to allergens; exposure to foodstuffs, e.g. gluten proteins, and the like.

The information obtained from the clonality analysis may be used to monitor progression and/or treatment of hyperproliferative diseases, including detection of residual disease after treatment of patients; to monitor conditions of antigenic stimulation, including clonal expansion following vaccination, progression and/or treatment of autoimmune disease, transplantation monitoring and the like; to modify therapeutic regimens, and to further optimize the selection of therapeutic agents. With this approach, therapeutic and/or diagnostic regimens can be individualized and tailored according to the specificity data obtained at different times over the course of treatment, thereby providing a regimen that is individually appropriate. In addition, patient samples can be obtained at any point during the treatment process for analysis.

DEFINITIONS

Figure 1:
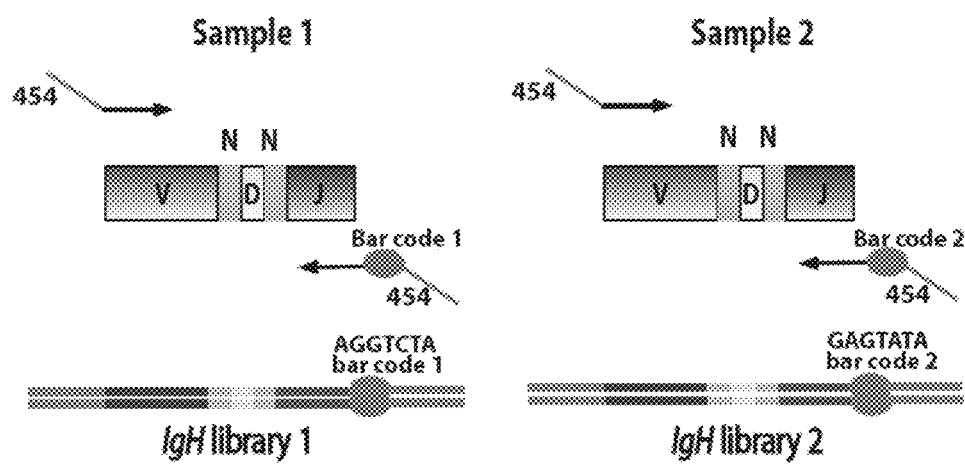
FIG. 1. Bar-coded PCR amplicons for multiplexed IgH sequencing. PCR primers used for preparing bar-coded amplicons for high-throughput sequencing were designed with the FR2 IgH V gene segment family primers and the common IgH J segment primer from the BIOMED-2 consortium (19). Additional sequences required for emulsion PCR and pyrosequencing were added (indicated in green) at the 5' end of the IgH-specific primers. In addition, a 6-, 7-, or 10-nucleotide sequence bar code was designed into the modified IgH J primer to identify the sample from which the PCR amplicons were derived. In the specimens analyzed with the 454 Titanium sequencer, an additional 10-nucleotide sample bar code was incorporated into the multiplexed IgH V gene segment primers used for amplification. Lines with arrowheads indicate PCR primers. Green segments, primer sequences needed for 454 sequencing protocol; red segments, V gene segment sequence; gray segments, nontemplated N base sequences; yellow segments, D gene segment sequence; blue segments, J gene segment sequence; green ellipse, sample-specific bar code enabling pooling of IgH libraries for multiplexed sequencing. Samples 1 and 2 could represent DNA template from any two clinical specimens or independent DNA template aliquots from the same specimen.

To facilitate an understanding of the invention, a number of terms are defined below.

The term "antibody," as used herein, is intended to refer to immunoglobulin molecules comprised of four polypeptide chains, two heavy (H) chains and two light (L) chains (lambda or kappa) inter-connected by disulfide bonds. An antibody has a known specific antigen with which it binds. Each heavy chain of an antibody is comprised of a heavy chain variable region (abbreviated herein as HCVR, HV or VH) and a heavy chain constant region. The heavy chain constant region is comprised of three domains, CH1, CH2 and CH3. Each light chain is comprised of a light chain variable region (abbreviated herein as LCVR or VL or KV or LV to designate kappa or lambda light chains) and a light chain constant region. The light chain constant region is comprised of one domain, CL. The VH and VL regions can be further subdivided into regions of hypervariability, termed complementarity determining regions (CDRs), interspersed with regions that are more conserved, termed framework regions (FR). Each variable region (VH or VL) contains 3 CDRs, designated CDR1, CDR2 and CDR3. Each variable region also contains 4 framework sub-regions, designated FR1, FR2, FR3 and FR4.

As used herein, the terms "complementarity determining region" and "CDR" made with respect to the immunoglobulin loci refer to the regions that are primarily responsible for antigen-binding. There are three CDRs in a light chain variable region (CDRL1, CDRL2, and CDRL3), and three CDRs in a heavy chain variable region (CDRH1, CDRH2, and CDRH3). The particular designation in the art for the exact location of the CDRs varies depending on what definition is employed. Preferably, the IMGT designations are used (see Brochet et al. (2008) Nucleic Acids Res. 36:W503-8, herein specifically incorporated by reference), which uses the following designations for both light and heavy chains: residues 27-38 (CDR1), residues 56-65 (CDR2), and residues 105-116 (CDR3); see also Lefranc, M P, The Immunologist, 7:132-136, 1999, herein incorporated by reference.

As one example of CDR designations, the residues that make up the six CDRs have been characterized by Kabat and Chothia as follows: residues 24-34 (CDRL1), 50-56 (CDRL2) and 89-97 (CDRL3) in the light chain variable region and 31-35 (CDRH1), 50-65 (CDRH2) and 95-102 (CDRH3) in the heavy chain variable region; Kabat et al., (1991) Sequences of Proteins of Immunological Interest, 5th Ed. Public Health Service, National Institutes of Health, Bethesda, Md., herein incorporated by reference; and residues 26-32 (CDRL1), 50-52 (CDRL2) and 91-96 (CDRL3) in the light chain variable region and 26-32 (CDRH1), 53-55 (CDRH2) and 96-101 (CDRH3) in the heavy chain variable region; Chothia and Lesk (1987) J. Mol. Biol. 196: 901-917, herein incorporated by reference. Unless otherwise specified, the terms "complementarity determining region" and "CDR" as used herein, include the residues that encompass IMGT, Kabat and Chothia definitions.

As used herein, the term "framework" refers to the residues of the variable region other than the CDR residues as defined herein. There are four separate framework sub-regions that make up the framework: FR1, FR2, FR3, and FR4.

The term "T cell receptor" or "T cell antigen receptor" refers to the antigen/MHC binding heterodimeric protein product of a vertebrate, e.g. mammalian, TCR gene complex, including the human TCR α, β, γ and δ chains. For example, the complete sequence of the human β TCR locus has been sequenced, as published by Rowen et al. (1996) Science 272(5269):1755-1762; the human α TCR locus has been sequenced and resequenced, for example see Mackelprang et al. (2006) Hum Genet. 119(3):255-66; see a general analysis of the T-cell receptor variable gene segment families in Arden Immunogenetics. 1995; 42(6):455-500; each of which is herein specifically incorporated by reference for the sequence information provided and referenced in the publication.

As used herein, "antigen" refers to any substance that, when introduced into a body, e.g., of a patient or subject, can stimulate an immune response, such as the production of an antibody or T cell receptor that recognizes the antigen. Antigens include molecules such as nucleic acids, lipids, ribonucleoprotein complexes, protein complexes, proteins, polypeptides, peptides and naturally occurring or synthetic modifications of such molecules against which an immune response involving T and/or B lymphocytes can be generated. With regard to autoimmune disease, the antigens herein are often referred to as autoantigens. With regard to allergic disease the antigens herein are often referred to as allergens. Autoantigens are any molecule produced by the organism that can be the target of an immunologic response, including peptides, polypeptides, and proteins encoded within the genome of the organism and post-translationally-generated modifications of these peptides, polypeptides, and proteins. Such molecules also include carbohydrates, lipids and other molecules produced by the organism. Antigens of interest also include vaccine antigens, which include, without limitation, pathogen antigens, cancer associated antigens, allergens, and the like.

As used herein, the term vaccine refers to a formulation comprising an antigen that is administered in a dose and regimen sufficient to produce an immune response to the antigen, usually a long-term term response, and frequently a long-term immunoglobulin response. A vaccine formulation is comprised of the antigen of interest, and frequently includes an adjuvant. Antigens include microbes, e.g. bacteria, viruses, protozoans, etc.; tumor antigens; and the like. Examples of vaccines include killed organisms, e.g. influenza, cholera, polio, rabies, hepatitis A, etc.; attenuated organisms, e.g. measles, mumps, rubella, BCG, etc.; toxins, e.g. tetanus, diphtheria, etc.; protein subunits, e.g. hepatitis B, human papillomavirus, hemagglutinin and neuraminidase of influenza, etc.; conjugates of coat proteins, e.g. H. influenzae B, etc.; DNA vaccines; and the like. Many vaccines have a schedule for primary and booster immunizations, although others are delivered as a single dose.

The time to response is very consistent for a given vaccine formulation, i.e. the time to generate detectable clonal populations will generally not vary by more than 10-20% between individuals; and will generally be consistent across vaccine formulations, i.e. the time to generate detectable clonal populations will not vary by more than 30-40% between individuals, as the response time is based on the kinetic of the underlying immune cell interactions. Factors that may alter the timing to response may include prior exposure to the antigen, dose, the presence of adjuvant, etc. Vaccines of a similar dose and adjuvant are expected to be very consistent in response time. For human use, adjuvants in the US are generally aluminum phosphate, aluminum hydroxide, or squalene. Other adjuvants include Freund's complete or incomplete adjuvant, virosomes, phosphate adjuvants, GS21, MF59, etc.

Allergens include immunogenic compounds that cause an enhanced Th2-type T cell response and IgE B cell response in a susceptible individual, also referred to as atopy, including asthma associated allergens. Allergens of interest include antigens found in food, such as strawberries, peanuts, milk proteins, egg whites, etc. Other allergens of interest include various airborne antigens, such as grass pollens, animal danders, house mite feces, etc. Molecularly cloned allergens include *Dermatophagoides pteryonyssinus* (Der P1); LoI pI-V from rye grass pollen; a number of insect venoms, including venom from jumper ant *Myrmecia pilosula; Apis mellifera* bee venom phospholipase A2 ($PLA_2$ and antigen 5S; phospholipases from the yellow jacket *Vespula maculifrons* and white faced hornet *Dolichovespula maculata*; a large number of pollen proteins, including birch pollen, ragweed pollen, Parol (the major allergen of *Parietaria officinalis*) and the cross-reactive allergen Parjl (from *Parietaria judaica*), and other atmospheric pollens including *Olea europaea, Artemisia* sp., gramineae, etc. Other allergens of interest are those responsible for allergic dermatitis caused by blood sucking arthropods, e.g. Diptera, including mosquitoes (*Anopheles* sp., *Aedes* sp., *Culiseta* sp., *Culex* sp.); flies (*Phlebotomus* sp., *Culicoides* sp.) particularly black flies, deer flies and biting midges; ticks (*Dermacenter* sp., *Ornithodoros* sp., *Otobius* sp.); fleas, e.g. the order Siphonaptera, including the genera *Xenopsylla, Pulex* and *Ctenocephalides felis felis*. The specific allergen may be a polysaccharide, fatty acid moiety, protein, etc.

Tumor-suppressor genes, or more precisely, the proteins for which they code, either have a dampening or repressive effect on the regulation of the cell cycle or promote apoptosis, and sometimes do both. The functions of tumor-suppressor proteins may include genes that are involved cell cycle continuation, coupling of cell cycle to DNA damage, involvement in cell adhesion, DNA repair proteins, etc. Specific examples include without limitation retinoblastoma protein (pRb); p53 tumor-suppressor protein; PTEN; APC, CD95, ST5, ST7, and ST14; HNPCC, MEN1 and BRCA.

Oncogenes are tumor-inducing agents, and are often, although not necessarily, proteins involved in signal transduction and execution of mitogenic signals. Examples include, without limitation, RAS, WNT, MYC, ERK, TRK, epidermal growth factor receptor (EGFR), platelet-derived growth factor receptor (PDGFR), vascular endothelial growth factor receptor (VEGFR), HER2/neu Src-family, Syk-ZAP-70 family, BTK family of tyrosine kinases, Abl. Somatic mutations to oncogenes may include sequence alterations that cause a change in the protein structure, causing an increase in protein (enzyme) activity; a loss of regulation, an increase of protein expression, an increase of protein or mRNA stability, gene duplication, a chromosome translocation, and the like.

As used herein, the terms "subject", "patient", "individual" refer to any animal, usually a mammal, e.g. mouse, rat, dog, horse, monkey, and preferably a human.

Sample, as used herein, refers to a composition, often a physiological composition, e.g. a blood sample, lymph node sample, synovial fluid sample, CSF fluid, tumor biopsy sample, etc. from an individual that contains a cell population comprising genetic sequences that have, or are suspected of having, sequence diversity at a locus of interest. By diverse, it is meant that at least 2, at least 4, at least 8, at least 16, at least 32, at least 64, at least 128, at least 264, at least about $10^4$ distinct sequences are represented at the locus of interest. Sequence diversity may include loci having at least about $10^5$ distinct sequences; at least about $10^6$ distinct sequences; at least about $10^7$ distinct sequences or more. While not all such sequences may be expected to be present in a given sample, samples of interest generally provide at least a portion of the locus diversity, comprising cells representing more than 2, 4, 8, 10, $10^2$, $10^3$, $10^4$, or more different sequences for a combinatorial antigen receptor of interest, where usually each cell comprises a distinct sequence.

Suitable cells for analysis include, without limitation, various hematopoietic cells, particularly including lymphocytes, tumor cells, etc. Lymphocytes expressing immunoglobulin include pre-B cells, B-cells, e.g. memory B cells, and plasma cells. Lymphocytes expressing T cell receptors include thymocytes, NK cells, pre-T cells and T cells, where many subsets of T cells are known in the art, e.g. Th1, Th2, Th17, CTL, T reg, etc.

Samples can include biopsies, or other clinical specimens containing cells. Some samples comprise cancer cells, such as carcinomas, melanomas, sarcomas, lymphomas, myelomas, leukemias, and the like.

Samples can be separated by centrifugation, elutriation, density gradient separation, apheresis, affinity selection, panning, FACS, centrifugation with Hypaque, etc. prior to analysis. For analysis of lymphocytes, often a mononuclear fraction (PBMC) comprising lymphocytes, monocytes, etc. is used.

A sample for use in the methods described herein may be one that is collected from a person with a malignancy or hyperproliferative condition, including lymphomas, leukemias, and plasmacytomas. A lymphoma is a solid neoplasm of lymphocyte origin, and is most often found in the lymphoid tissue. Thus, for example, a biopsy from a lymph node, e.g. a tonsil, containing such a lymphoma would constitute a suitable biopsy. Samples may be obtained from a patient at one or a plurality of time points in the progression of disease and/or treatment of the disease.

B lineage malignancies of interest include, without limitation, multiple myeloma; acute lymphocytic leukemia (ALL); chronic lymphocytic leukemia (CLL); diffuse large B cell lymphoma; mucosa-associated lymphatic tissue lymphoma (MALT); small cell lymphocytic lymphoma; mantle cell lymphoma (MCL); Burkitt lymphoma; mediastinal large B cell lymphoma; Waldenström macroglobulinemia; nodal marginal zone B cell lymphoma (NMZL); splenic marginal zone lymphoma (SMZL); intravascular large B-cell lymphoma; primary effusion lymphoma; lymphomatoid granulomatosis, etc. Non-malignant B cell hyperproliferative conditions include monoclonal B cell lymphocytosis (MBL).

T lineage malignancies of interest include, without limitation, precursor T-cell lymphoblastic lymphoma; T-cell prolymphocytic leukemia; T-cell granular lymphocytic leukemia; aggressive NK cell leukemia; adult T-cell lymphoma/leukemia (HTLV 1-positive); extranodal NK/T-cell lymphoma; enteropathy-type T-cell lymphoma; hepatosplenic γδ T-cell lymphoma; subcutaneous panniculitis-like T-cell lymphoma; mycosis fungoides/Sezary syndrome; anaplastic large cell lymphoma, T/null cell; peripheral T-cell lymphoma; angioimmunoblastic T-cell lymphoma; chronic lymphocytic leukemia (CLL); acute lymphocytic leukemia (ALL); prolymphocytic leukemia; hairy cell leukemia.

Inflammatory conditions are of interest for analysis by the methods of the invention, and include a number of diseases having an infectious or autoimmune component.

Neurological inflammatory conditions are of interest, e.g. Alzheimer's Disease, Parkinson's Disease, Lou Gehrig's Disease, etc. and demyelinating diseases, such as multiple sclerosis, chronic inflammatory demyelinating polyneuropathy, etc. as well as inflammatory conditions such as rheumatoid arthritis. Systemic lupus erythematosus (SLE) is an autoimmune disease characterized by polyclonal B cell activation, which results in a variety of anti-protein and non-protein autoantibodies (see Kotzin et al. (1996) Cell 85:303-306 for a review of the disease). These autoantibodies form immune complexes that deposit in multiple organ systems, causing tissue damage. An autoimmune component may be ascribed to atherosclerosis, where candidate autoantigens include Hsp60, oxidized LDL, and 2-Glycoprotein I (2GPI).

Conditions associated with immunodeficiency are also of interest for analysis, including congenital and acquired immunodeficiency syndromes.

As used herein, the term "a genetic sample' refers to a portion of biological material containing mRNA or DNA from an individual, which portion of material is extracted, subjected to aliquoting to generate replicates, amplification and sequencing. The term an "aliquot" refers to a sub-fraction of a sample that is subjected to amplification and sequencing, i.e. a replicate. As previously discussed, the methods of the invention include at least 2 aliquots, or replicates, and may include at least 3, 4, 5, 6, 8, 10 or more aliquots.

As used herein a "read" is a single observation of DNA sequence from one amplification reaction, i.e. one aliquot from a sample. A "sequence" is derived from one or more reads, and corresponds to a single allele at a locus of interest. The set of sequences obtained from a single aliquot may be conveniently grouped for analysis Clonal expansion, as used herein, refers to the proliferation of a cell having a specific combinatorial antigen receptor sequence, which sequence may be productively rearranged and expressed, for example where the proliferation is in response to antigenic stimulation. In other situations, e.g. with transformed or otherwise aberrantly hyperproliferative cells, the combinatorial antigen receptor sequence may not be expressed and may not be productively rearranged.

The term "clone" refers to a population of cells from an individual that have a shared allelic sequence, for example a mutation in an oncogene, a combination of germline V, D, and J regions, and junctional nucleotides, etc. Clonal combinatorial antigen receptors typically have identical germline regions and substantially identical junctional nucleotides, e.g. differing by not more than 1, not more than 2, not more than 3 nucleotides. These features are assigned by sequence comparison and alignment routines.

The term "coincident" is used herein to refer to a single sequence that is identified in two or more aliquots, or replicate samples. It may be noted that sequences appearing more than once in a single aliquot are not considered to be coincident, as the duplication can result from amplification of a single starting template.

Amplification refers to the process by which DNA templates are increased in number through multiple rounds of replication. Conveniently, polymerase chain reaction (PCR) is the method of amplification, but such is not required, and other methods, such as loop-mediated isothermal amplification (LIA); ligation detection reaction (LDR); ligase chain reaction (LCR); nucleic acid sequence based amplification (NASBA); multiple displacement amplification (MDA); C-probes in combination with rolling circle amplification; and the like may find use. See, for example, Kozlowski et al. (2008) Electrophoresis. 29(23):4627-36; Monis et al. (2006) Infect Genet Evol. 6(1):2-12; Zhang et al. (2006) Clin Chim Acta. 363(1-2):61-70; Cao (2004) Trends Biotechnol. 22(1):38-44; Schweitzer and Kingsmore (2001) Curr Opin Biotechnol. 12(1):21-7; Lisby (1999) Mol Biotechnol. 12(1):75-99.

As known in the art, amplification reactions can be performed in a number of configurations, e.g. liquid phase, solid phase, emulsion, gel format, etc.

It is preferable to utilize a high fidelity polymerase in the amplification reaction to preserve sequence fidelity, typically a polymerase having an intact proof-reading function, e.g. Pfx50™ DNA Polymerase; Pfu polymerase, Vent polymerase, Phusion High-Fidelity DNA Polymerase; and the like.

Amplification by PCR is performed with at least two primers. For the methods of the invention, a set of primers is used that is sufficient to amplify all or a defined portion of the variable sequences at the locus of interest, which locus may include any or all of the afore-mentioned IgH and TCR loci. Exemplary IgH primers are provided in the examples.

Primer sets usually amplify at least 50% of the known rearrangements at the locus of interest, at least 75%, at least 85%, at least 90%, at least 95%, or more. Primers may further comprise nucleotides useful in subsequent sequencing, e.g. pyrosequencing. Such sequences are readily designed by commercially available software programs or companies (e.g. see Biotage). Amplification primers may optionally include a barcode sequence, to aid in the identification of clones (see Parameswaran et al. (2007) Nucleic Acids Research 35(19):e30, herein specifically incorporated by reference).

Sequencing platforms include, but are not limited to those commercialized by: 454/Roche Lifesciences including but not limited to the methods and apparatus described in Margulies et al., Nature (2005) 437:376-380 (2005); and U.S. Pat. Nos. 7,244,559; 7,335,762; 7,211,390; 7,244,567; 7,264,929; 7,323,305; Helicos BioSciences Corporation (Cambridge, Mass.) as described in U.S. application Ser. No. 11/167,046, and U.S. Pat. Nos. 7,501,245; 7,491,498; 7,276,720; and in U.S. Patent Application Publication Nos. US20090061439; US20080087826; US20060286566; US20060024711; US20060024678; US20080213770; and US20080103058; Applied Biosystems (e.g. SOLiD sequencing); Dover Systems (e.g., Polonator G.007 sequencing); Illumina as described U.S. Pat. Nos. 5,750,341; 6,306,597; and 5,969,119; and Pacific Biosciences as described in U.S. Pat. Nos. 7,462,452; 7,476,504; 7,405,281; 7,170,050; 7,462,468; 7,476,503; 7,315,019; 7,302,146; 7,313,308; and US Application Publication Nos. US20090029385; US20090068655; US20090024331; and US20080206764. All references are herein incorporated by reference. Such methods and apparatuses are provided here by way of example and are not intended to be limiting.

The term "isolated" when used in relation to a nucleic acid, as in "an isolated oligonucleotide" or "isolated polynucleotide" refers to a nucleic acid sequence that is identified and separated from at least one contaminant nucleic acid with which it is ordinarily associated (e.g. host cell proteins).

As used herein, the terms "portion" when used in reference to a nucleotide sequence (as in "a portion of a given nucleotide sequence") refers to fragments of that sequence. The fragments may range in size from ten nucleotides to the entire nucleotide sequence minus one nucleotide (e.g., 10 nucleotides, 20, 30, 40, 50, 100, 200, etc.).

As used herein, the term "portion" when in reference to an amino acid sequence (as in "a portion of a given amino acid sequence") refers to fragments of that sequence. The fragments may range in size from six amino acids to the entire amino acid sequence minus one amino acid (e.g., 6 amino acids, 10, 20, 30, 40, 75, 200, etc.)

As used herein, the terms "treat," "treatment," "treating," and the like, refer to obtaining a desired pharmacologic and/or physiologic effect. The effect may be prophylactic in terms of completely or partially preventing a disease or symptom thereof and/or may be therapeutic in terms of a partial or complete cure for a disease and/or adverse affect attributable to the disease. "Treatment," as used herein, covers any treatment of a disease in a mammal, particularly in a human, and includes: (a) preventing the disease from occurring in a subject which may be predisposed to the disease but has not yet been diagnosed as having it; (b) inhibiting the disease, i.e., arresting its development; and (c) relieving the disease, e.g., causing regression of the disease, e.g., to completely or partially remove symptoms of the disease.

"Suitable conditions" shall have a meaning dependent on the context in which this term is used. That is, when used in connection with an antibody, the term shall mean conditions that permit an antibody to bind to its corresponding antigen. When this term is used in connection with nucleic acid hybridization, the term shall mean conditions that permit a nucleic acid of at least 15 nucleotides in length to hybridize to a nucleic acid having a sequence complementary thereto. When used in connection with contacting an agent to a cell, this term shall mean conditions that permit an agent capable of doing so to enter a cell and perform its intended function. In one embodiment, the term "suitable conditions" as used herein means physiological conditions.

Before the present active agents and methods are described, it is to be understood that this invention is not limited to the particular methodology, products, apparatus and factors described, as such methods, apparatus and formulations may, of course, vary. It is also to be understood that the terminology used herein is for the purpose of describing particular embodiments only, and is not intended to limit the scope of the present invention which will be limited only by appended claims.

It must be noted that as used herein and in the appended claims, the singular forms "a," "and," and "the" include plural referents unless the context clearly dictates otherwise. Thus, for example, reference to "a drug candidate" refers to one or mixtures of such candidates, and reference to "the method" includes reference to equivalent steps and methods known to those skilled in the art, and so forth.

Unless defined otherwise, all technical and scientific terms used herein have the same meaning as commonly understood by one of ordinary skill in the art to which this invention belongs. All publications mentioned herein are incorporated herein by reference for the purpose of describing and disclosing devices, formulations and methodologies which are described in the publication and which might be used in connection with the presently described invention.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges may independently be included in the smaller ranges is also encompassed within the invention, subject to any specifically excluded limit in the stated range. Where the stated range includes one or both of the limits, ranges excluding either both of those included limits are also included in the invention.

In the following description, numerous specific details are set forth to provide a more thorough understanding of the present invention. However, it will be apparent to one of skill in the art that the present invention may be practiced without one or more of these specific details. In other instances, well-known features and procedures well known to those skilled in the art have not been described in order to avoid obscuring the invention.

Generally, conventional methods of protein synthesis, recombinant cell culture and protein isolation, and recombinant DNA techniques within the skill of the art are employed in the present invention. Such techniques are explained fully in the literature, see, e.g., Maniatis, Fritsch & Sambrook, Molecular Cloning: A Laboratory Manual (1982); Sambrook, Russell and Sambrook, Molecular Cloning: A Laboratory Manual (2001); Harlow, Lane and Harlow, Using Antibodies: A Laboratory Manual: Portable Protocol NO. I, Cold Spring Harbor Laboratory (1998); and Harlow and Lane, Antibodies: A Laboratory Manual, Cold Spring Harbor Laboratory; (1988) Protein Methods (Bollag et al., John Wiley & Sons 1996); Nonviral Vectors for Gene Therapy (Wagner et al. eds., Academic Press 1999); Viral Vectors (Kaplift & Loewy eds., Academic Press 1995); Immunology Methods Manual (I. Lefkovits ed., Academic Press 1997); and Cell and Tissue Culture: Laboratory Procedures in Biotechnology (Doyle & Griffiths, John Wiley & Sons 1998). Reagents, cloning vectors, and kits for genetic manipulation referred to in this disclosure are available from commercial vendors such as BioRad, Stratagene, Invitrogen, Sigma-Aldrich, and ClonTech.

DETAILED DESCRIPTION OF THE EMBODIMENTS

Methods are provided for the detection and analysis of clonality in a cell population, where the cells in the population are diverse with respect to genetic sequences at a locus of interest. Exemplary loci of interest are immunoglobulin and T cell antigen receptor genetic sequences, including without limitation each of IgH, IgLλ, IgLκ, TCRα, TCRβ, TCRγ, TCRδ, wherein genetic recombination events act to create an extensive repertoire of different sequences.

In the methods of the invention, a sample comprising a complex cell population is obtained from an individual, particularly an individual that is, or that will be, subject to clonal expansion of a cell population. Samples of interest may include samples obtained from patients having a hyperproliferative condition, for example involving lymphocytes, e.g. lymphomas, leukemias, myelomas and benign lymphoproliferative conditions. Such individuals may be tested at one or a plurality of time points, including, without limitation, at the time of diagnosis, prior to, during and/or after cytoreductive treatment; and at various timepoints to monitor disease progression. Samples of interest also include individuals before and/or after specific antigenic stimulation, e.g. following vaccination, where vaccines include cancer antigens, pathogen antigens, allergens, autoantigens for tolerization. Antigenic stimulation may also be monitored before and/or after infection, e.g. to monitor epidemic or pandemic situations. Samples of interest also include individuals before and/or after transplantation of an allogeneic tissue. Samples of interest also include individuals suspected of having an autoimmune or inflammatory disease. Such individuals may be tested at one or a plurality of time points, including, without limitation, at the time of diagnosis, prior to, during and/or after cytoreductive treatment; and at various timepoints to monitor disease progression.

Patient samples include a variety of bodily fluids in which cells are present, e.g. blood and derivatives thereof, CSF; synovial fluid, tumor biopsy samples, spleen, lymph nodes, bone marrow, cord blood, etc. Samples may be obtained at one or more suitable time points, depending on the needs of the specific analysis. As described above, patient samples of interest may comprise complex cell populations, and the desired cell population may further be subjected to selection or sorting by various methods.

DNA is obtained from the cell sample. In some embodiments, genomic DNA is utilized, which is readily extracted from cells using conventional methods known in the art. It will further be understood by one of skill in the art that a lymphocyte may comprise two distinct rearranged alleles at a locus of interest, although generally only one allele is productively rearranged. In other embodiments, mRNA is obtained from the cells and converted to cDNA for amplification purposes using conventional methods. It will be understood by those of skill in the art that determination of clonality based on mRNA samples will require that aliquots be obtained prior to extraction of RNA from the cells, as one cell may comprise multiple copies of mRNA corresponding to a sequence of interest.

An important feature of the methods of the invention is the analysis of replicate samples, where replicates are frequently aliquots of cells or DNA from a single sample. Replicates may also be two cell samples obtained from an individual. Replicates are obtained prior to amplification of the DNA, as the amplification reaction has the potential to generate coincidence by duplication of the initial template sequence.

The DNA replicates are amplified by any convenient methods and sequenced, as previously described. Generally at least about 10, $10^2$, $10^3$ or more reads are obtained for each replicate sample, where a preferred read includes the variable sequence at the locus of interest. The sequences thus obtained are compared and a determination is made of coincident sequences across replicates, where coincident sequences are defined as those that share germline segments, e.g. V, D, J, as appropriate for the receptor being analyzed, and that share junctional nucleotide sequences. A variety of algorithms can be used to analyze the sequence data obtained using this method. The presence of coincident sequences across replicates is indicative of clonal expansion of a cell.

Clonally expanded cell populations are detectable by the presence of coincident sequences in distinct amplicon pools, e.g. in at least 2 replicates, in at least 3 replicates, usually in at least 4 replicates, in at least five replicates, or more.

The minimum expected number of binary sequence coincidences is achieved under the condition of equal representation of each sequence type (any preferential representation of one or more sequence types for a given value of total repertoire number would only increase the coincidence frequency). For example, in analysis of immunoglobulin loci, where ("IgHR", the total number of distinct IgH sequences present in the peripheral blood of an individual), the minimal expected coincidence number (for example, for time point 1) is given by the following formula: $(½)*\Sigma_{i=1 \; to \; 6} (S_i * \Sigma_{(j=1 \; to \; 6; j \neq i)} \{1-[1-(1/\text{IgHR})]^{Sj}\})$ where S1 ... S6 are the numbers of distinct sequences determined for the six independent amplicon pools prepared from that time point. Starting with an arbitrary sequence in one amplicon pool, (1/IgHR) is the probability that any single determined sequence in another pool would match that sequence, 1−(1/IgHR) is the probability that any single determined sequence in another pool would not match that sequence, and [1−(1/IgHR)] Sj is the probability that no determined sequence from an amplicon pool with Sj determined sequences would match that sequence. The value $[1(1/\text{IgHR})] \; S^j$, summed for every element in the sequence set, yields a value that is twice the expected number of coincidences (because this sum counts each binary coincidence once for each participating sequence and hence twice in total). The formula above represents this sum. Similar calculations can be used for greater than binary sequence coincidence.

In some preferred embodiments, the methods of the invention are used in determining the efficacy of a therapy for treatment of a hyperproliferative or autoimmune disease, or for efficacy of vaccination, either at an individual level, or in the analysis of a group of patients, e.g. in a clinical trial format. Such embodiments typically involve the comparison of two time points for a patient or group of patients. The patient status is expected to differ between the two time points as the result of a therapeutic agent, therapeutic regimen, or other intervention to a patient undergoing treatment.

Examples of formats for such embodiments may include, without limitation, testing the effect of a therapy or vaccination at two or more time points, where a first time point is a diagnosed but untreated patient; and a second or additional time point(s) is a patient treated with a candidate therapeutic agent or regimen. An additional time point may include a patient vaccinated with a candidate agent or regimen, and challenged with the antigen, e.g. by community exposure to an infectious agent, ex vivo antigen challenge, skin test, etc.

In another format, a first time point is a diagnosed patient in disease remission, e.g. as ascertained by current clinical criteria, as a result of a candidate therapeutic agent or regimen. A second or additional time point(s) is a patient treated with a candidate therapeutic agent or regime.

In such clinical trial formats, each set of time points may correspond to a single patient, to a patient group, e.g. a cohort group, or to a mixture of individual and group data. Additional control data may also be included in such clinical trial formats, e.g. a placebo group, a disease-free group, and the like, as are known in the art. Formats of interest include crossover studies, randomized, double-blind, placebo-controlled, parallel group trial is also capable of testing drug efficacy, and the like. See, for example, Clinical Trials: A Methodologic Perspective Second Edition, S. Piantadosi, Wiley-Interscience; 2005, ISBN-13: 978-0471727811; and Design and Analysis of Clinical Trials: Concepts and Methodologies, S. Chow and J. Liu, Wiley-Interscience; 2003; ISBN-13: 978-0471249856, each herein specifically incorporated by reference. Specific clinical trials of interest include analysis of therapeutic agents for the treatment of hyperproliferative conditions involving lymphocytes, analysis of immunosuppressive therapies, including antigen-specific immunotherapies; analysis of vaccine responses, and the like In some embodiments, a blinded crossover clinical trial format is utilized. In another embodiments a randomized, double-blind, placebo-controlled, parallel group trial is used to test drug efficacy.

In other embodiments, a clinical trial format is utilized to test the efficacy of a vaccine, for example by determining the percent of vaccinated individuals that are serological responders following vaccination, e.g. following a single dose of vaccine, following a booster, etc. The methods of the invention allow determination of which individuals are responder within a short, defined time period, for example within less than about 10 days, less than about 9 days, less than about 8 days, including within 7 days following immunization. The ability to assess the efficacy of the vaccine in such a short time frame provides substantial advantages over the prior art, which can require 21 days or more to determine serological responsiveness. In one embodiment, a cohort of individuals, e.g. a mammal or avian, including without limitation humans, dogs, cats, horses, cows, sheep, pigs, chickens, ducks, and the like, are vaccinated with a test vaccine formulation, usually in combination with a randomized control group immunized with the formulation in the absence of antigen. At a defined period of from about 7 to about 10 days, a sample, e.g. a blood sample, is drawn from the individuals, and analyzed for the presence of clonal B cell populations. The presence of such clonal populations is indicative that the individual is serologically response to the vaccine antigen. As discussed above, the data may be normalized by dividing the total number of coincident sequences detected between replicates of a sample by the total number of possible pairwise comparisons between sequences in different replicates from that sample.

Also provided are databases of sequence analyses relating to a treatment or condition of interest. Such databases will typically comprise analysis profiles of various individuals following a clinical protocol of interest etc., where such profiles are further described below.

The profiles and databases thereof may be provided in a variety of media to facilitate their use. "Media" refers to a manufacture that contains the expression profile information of the present invention. The databases of the present invention can be recorded on computer readable media, e.g. any medium that can be read and accessed directly by a computer. Such media include, but are not limited to: magnetic storage media, such as floppy discs, hard disc storage medium, and magnetic tape; optical storage media such as CD-ROM; electrical storage media such as RAM and ROM; and hybrids of these categories such as magnetic/optical storage media. One of skill in the art can readily appreciate how any of the presently known computer readable mediums can be used to create a manufacture comprising a recording of the present database information. "Recorded" refers to a process for storing information on computer readable medium, using any such methods as known in the art. Any convenient data storage structure may be chosen, based on the means used to access the stored information. A variety of data processor programs and formats can be used for storage, e.g. word processing text file, database format, etc.

As used herein, "a computer-based system" refers to the hardware means, software means, and data storage means used to analyze the information of the present invention. The minimum hardware of the computer-based systems of the present invention comprises a central processing unit (CPU), input means, output means, and data storage means. A skilled artisan can readily appreciate that any one of the currently available computer-based system are suitable for use in the present invention. The data storage means may comprise any manufacture comprising a recording of the present information as described above, or a memory access means that can access such a manufacture.

A variety of structural formats for the input and output means can be used to input and output the information in the computer-based systems of the present invention. Such presentation provides a skilled artisan with a ranking of similarities and identifies the degree of similarity contained in the test expression profile.

The methods of the invention find use in a centralized setting, e.g. the analysis of patient samples in a clinical laboratory. Such assays may conveniently utilize one or more of the primer sets provided herein. Such assays may include an analysis of the clonality present in a sample, e.g. the presence of clonal changes in cancer cells, the presence of residual disease in a cancer patient, the presence of clonal lymphocytes specific for an antigen of interest, including vaccine antigens, and the like.

Also provided are reagents and kits thereof for practicing one or more of the above-described methods. The subject reagents and kits thereof may vary greatly. Reagents of interest include reagents specifically designed for use in production of the above described analysis. Kits may include amplification primers, including without limitation one or more of the sets of primers identified herein, reagents amplification and sequence, and such containers as are required for sample collection.

The kits may further include a software package for statistical analysis of the sequences. In addition to the above components, the subject kits will further include instructions for practicing the subject methods. These instructions may be present in the subject kits in a variety of forms, one or more of which may be present in the kit. One form in which these instructions may be present is as printed information on a suitable medium or substrate, e.g., a piece or pieces of paper on which the information is printed, in the packaging of the kit, in a package insert, etc. Yet another means would be a computer readable medium, e.g., diskette, CD, etc., on which the information has been recorded. Yet another means that may be present is a website address which may be used via the internet to access the information at a removed site. Any convenient means may be present in the kits.

The following examples are put forth so as to provide those of ordinary skill in the art with a complete disclosure and description of how to make and use the present invention, and are not intended to limit the scope of the invention or to represent that the experiments below are all or the only experiments performed. Efforts have been made to ensure accuracy with respect to numbers used (e.g., amounts, temperature, and the like), but some experimental errors and deviations may be present. Unless indicated otherwise, parts are parts by weight, molecular weight is weight average molecular weight, temperature is in degrees Centigrade, and pressure is at or near atmospheric.

EXPERIMENTAL

Example 1

Using a bar-coding strategy to allow pooling of multiple libraries of rearranged IgH V-D-J gene loci from many human blood samples, high-throughput pyrosequencing was performed to characterize the B cell populations in a series of human clinical specimens. Deep sequencing of immune receptor gene populations offered specific and detailed molecular characterization as well as high sensitivity for detecting sequences of interest and to transform understanding of the human immune system while aiding in diagnosis and tracking of lymphoid malignancies.

Results

Bar-Coded High-Throughput Pyrosequencing of Rearranged IgH Loci.

We amplified rearranged IgH loci in human blood samples with BIOMED-2 nucleic acid primers adapted for high-throughput DNA pyrosequencing. A unique 6-, 7-, or 10-nucleotide sequence "bar code" in the primers used for a particular sample allowed pooling and bulk sequencing of many libraries together and subsequent sorting of sequences from each sample (FIG. 1). Patient specimens in our initial two replicate experiments included peripheral blood of three healthy individuals, with experimental replicates of one individual's blood sample at each of two different time points 14 months apart; tissue specimens from patients with lymphomas; and peripheral blood from patients with chronic lymphocytic leukemia. We also studied samples generated by serial 10-fold dilutions of a chronic lymphocytic leukemia peripheral blood specimen into a healthy control peripheral blood sample to assess the sensitivity of the sequencing approach for detecting small numbers of clonal B cells among a background B cell population (Table 1). From all specimens pooled for experiment 1, we obtained 299,846 different IgH rearrangement sequences, whereas experiment 2 yielded 207,043 sequences. All sequence reads used for further analysis were full-length IgH amplicons extending from the V gene segment FR2 framework region primer to the J primer region.

TABLE 1

| No. | Description | Sample type | Clonality assay result |
|---|---|---|---|
| 1 | Healthy donor 1, time 0 | Blood | Negative |
| 2 | Healthy donor 1, time 0 | Blood | Negative |
| 3 | Healthy donor 1, time 14 months | Blood | Negative |
| 4 | Healthy donor 1, time 14 months | Blood | Negative |
| 5 | Patient 1; CLL/SLL time 0 | Blood | Positive |
| 6 | Patient 1; CLL/SLL time 3 months | Blood | Positive |
| 7 | Patient 2; FL | Lymph node | Positive |
| 8 | Patient 3; FL and SLL in lymph node | Lymph node | Positive |
| 9 | Patient 4; CLL/SLL | Blood | Oligoclonal |
| 10 | Patient 5; PTLD, marrow infiltrate | Bone marrow | Positive |
| 11 | Patient 5; PTLD, liver DLBCL | Liver | Positive |
| 12 | Healthy donor 2 | Blood | Negative |
| 13 | Patient 6; CLL | Blood | Positive |
| 14 | Healthy donor 3 | Blood | Negative |
| 15 | Patient 6 CLL diluted 1:10 | Blood | Positive |
| 16 | Patient 6 CLL diluted 1:100 | Blood | Negative |
| 17 | Patient 6 CLL diluted 1:1000 | Blood | Negative |
| 18 | Patient 6 CLL diluted 1:10,000 | Blood | Negative |
| 19 | Patient 6 CLL diluted 1:100,000 | Blood | Negative |

Patient specimens for IgH sequencing.
The clonality assay results are those obtained with standard PCR amplification and capillary electrophoresis of product amplicons.
Blood, peripheral blood mononuclear cells;
Lymph node, formalin-fixed, paraffin-embedded lymph node tissue;
Liver, formalin-fixed, paraffin-embedded liver tissue;
CLL/SLL, chronic lymphocytic leukemia/small lymphocytic lymphoma;
FL, follicular lymphoma;
PTLD, posttransplant lymphoproliferative disease;
DLBCL, diffuse large B cell lymphoma.

Figure 2:
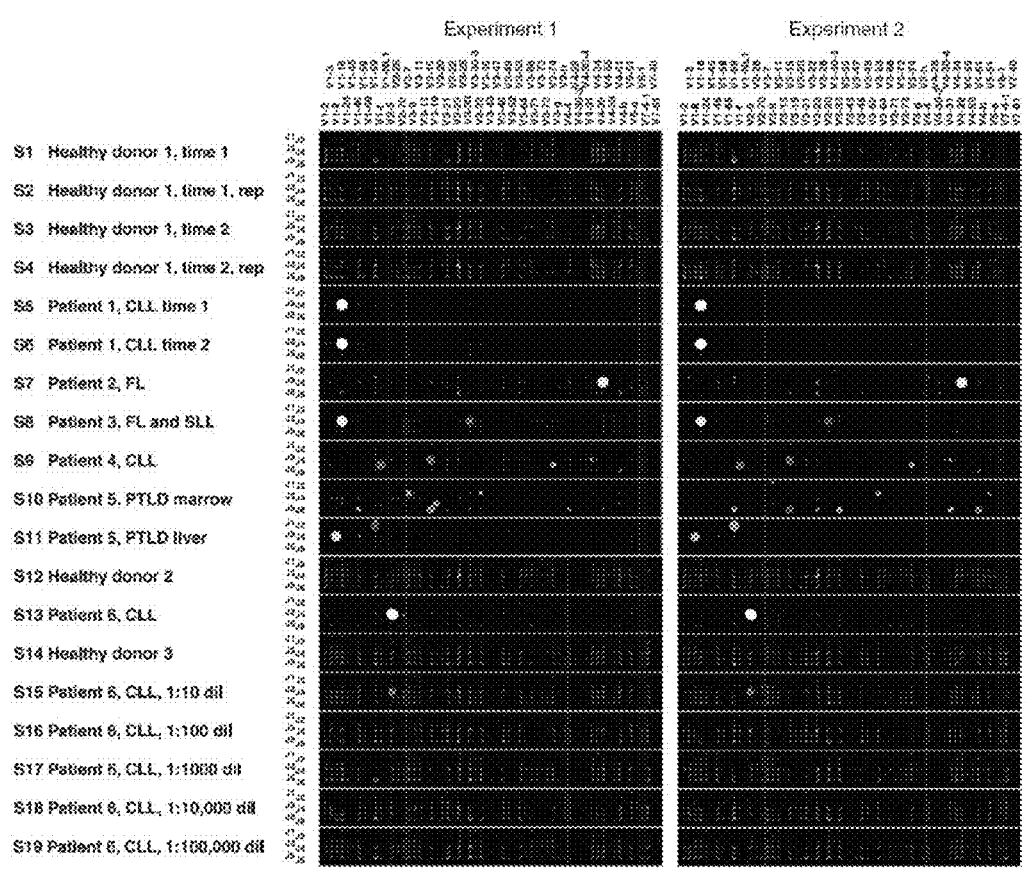
FIG. 2. IgH V and J gene segment usage in healthy peripheral blood, oligoclonal or indeterminate specimens, and lymphoid malignancy specimens. Bar-coded IgH rearrangement libraries were PCR amplified from genomic DNA of human specimens, pooled, and characterized by high-throughput pyrosequencing. Experiments 1 and 2 were independent experimental replicates beginning with different aliquots of the template DNA from each specimen. Each wide row represents the IgH sequences identified in a single sample. Samples (S1 to S19) are labeled at the far left. The x axis (across the top of the panels) indicates the V gene segment used in the receptor, and the y axis (the column at the left of the panels) within each wide row represents the J gene segments used. The size and color of the circle at a given point indicates what proportion of all sequences in the sample used that particular combination of V and J gene segments. Sequences in which V, D, or J segments or junctions could not be unambiguously assigned were filtered before generation of these plots. rep, replicate sequence pool PCR amplified from an independent aliquot of template DNA; CLL, chronic lymphocytic leukemia; FL, follicular lymphoma; SLL, small lymphocytic lymphoma; PTLD, posttransplant lymphoproliferative disorder; dil, dilution.

An overview of the IgH amplicon sequences in the data sets from experiments 1 and 2 is shown in FIG. 2, with each point in the two dimensional grid for each sample indicating the V gene segment and the J gene segment used by a particular IgH V-D-J rearrangement. The size and color warmth of the circle at each point indicates what proportion of all sequences in the sample had the indicated V and J gene segment usage. Healthy peripheral blood lymphocyte populations showed a diverse use of different V and J gene segments, whereas samples that contained clonal IgH populations corresponding to lymphomas or chronic lymphocytic leukemia specimens were readily identified. Plots of the data showing the V, D, and J segment usage are shown in FIG. 4.

Evaluation of Clonal Malignancies.

Human cancers are clonal proliferations of cells that have sustained mutational damage, leading to dysregulated proliferation, survival, and response to the extracellular environment. Molecular clonality testing of IgH receptor and TCR γ loci, accomplished with a PCR and capillary electrophoresis, is a helpful adjunct to morphological and immunophenotypic evaluation of suspected B or T cell malignancies.

Blood or bone marrow samples from some patients give indeterminate or oligoclonal patterns of reactivity for a variety of reasons: Few lymphocytes may be present, there may be genuine oligoclonal lymphocyte populations, or clonal lymphocytes may have separately detected rearrangements from two chromosomes. We compared the results from DNA sequencing of the products of independent PCR replicates for such samples. One such difficult case is represented by the bone marrow and liver specimens from patient 5 in Table 1. The patient had undergone liver transplantation and subsequently developed a large B cell lymphoma in the liver as a manifestation of post-transplant lymphoproliferative disorder, a condition in which immunosuppression leads to B or T cell lymphomas that are typically associated with Epstein-Barr virus infection (FIG. 2). The patient's bone marrow showed small lymphoid aggregates that were shown to contain B cells on morphological and immunohistochemical stain evaluation. Capillary electrophoresis sizing of V-D-J rearrangements in the bone marrow sample gave support for a clonal population, but it was unclear whether this population represented involvement of the patient's bone marrow by the lymphoma seen in the liver. The sequencing data resolved this uncertainty, showing no relation between the liver lymphoma clone associated with IGHV1-8*01-IGHD2-8*01-IGHJ4*02 and the bone marrow B cells. Instead, a separate clonal B cell population that used gene segments IGHV3-15*04-IGHD3-9*01-IGHJ6*02 was present in the bone marrow. Patients with posttransplant lymphoproliferative disorder can develop multiple independent malignant clones, making the extra information provided by sequencing analysis of replicate PCR products particularly helpful. The other V-D-J rearrangements detected in the patient's bone marrow differed between the two replicate experiments, indicating the presence of small numbers of non-clonal B cells in the specimen.

Another diagnostically challenging case, the chronic lymphocytic leukemia of patient 4, showed an oligoclonal pattern by standard PCR and capillary electrophoresis analysis. A consistent pattern was seen with deep sequencing of the sample. Finally, the two distinct V-D-J rearrangements in a lymph node from patient 3 indicated that there were two separate clonal B cell populations in the specimen, a conclusion supported by morphological and immunophenotypic evidence of two different B cell lymphomas (follicular lymphoma and small lymphocytic lymphoma) in the tissue.

Minimal Residual Disease Testing by Sequencing.

Figure 3:
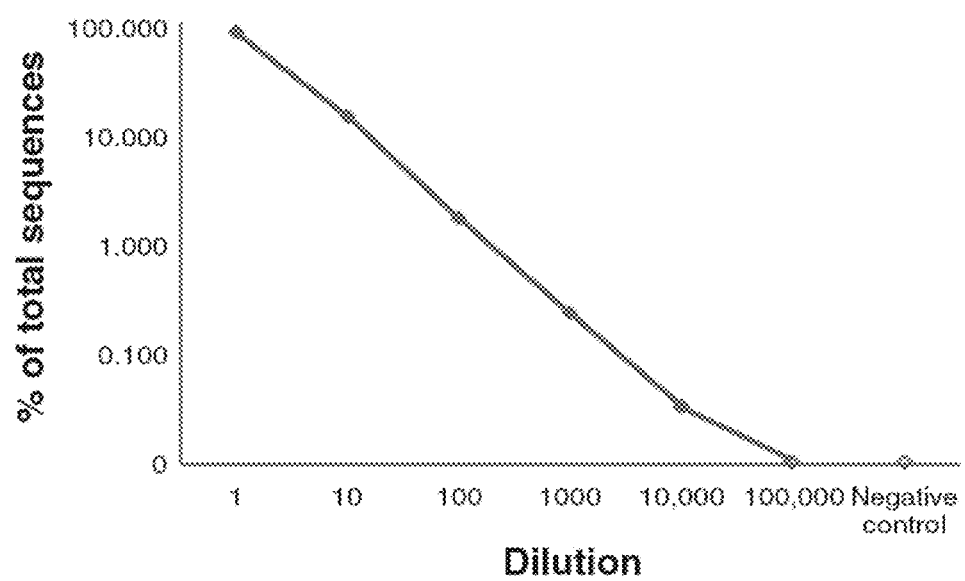
FIG. 3. Titration of a chronic lymphocytic leukemia clonal sample into healthy peripheral blood. Pooled bar-coded IgH library sequencing was carried out on a series of 10-fold dilutions of a chronic lymphocytic leukemia blood sample (sample 13) into a healthy control blood sample (sample 14) to evaluate the sensitivity and linearity of high-throughput sequencing for detection of a known clonal sequence. The percentage of sequences matching the chronic lymphocytic leukemia clone in each diluted specimen is plotted on a log scale, with zero indicating that no sequences were detected. The counts of clonal sequences in each sample were as follows: CLL sample, 7805 clonal of 8612 total; healthy blood control, 0 clonal of 7518 total; 1:10 dilution, 2095 clonal of 13,717 total; 1:100 dilution, 156 clonal of 8674 total; 1:1000 dilution, 23 clonal of 9471 total; 1:10,000 dilution, 3 clonal of 8895 total; 1:100,000 dilution, 0 clonal of 6940 total. The negative control is the healthy donor blood sample used for diluting the clonal CLL sample. A second experiment measuring fewer sequences from independent PCR amplifications from the same samples detected the following number of clonal sequences in each sample: CLL sample, 422 clonal of 566 total; healthy blood control, 0 clonal of 270 total; 1:10 dilution, 189 clonal of 665 total; 1:100 dilution, 11 clonal of 230 total; 1:1000 dilution, 0 clonal of 344 total; 1:10,000 dilution, 0 clonal of 329 total; 1:100,000 dilution, 0 clonal of 208 total.
Figures 1, 4A:
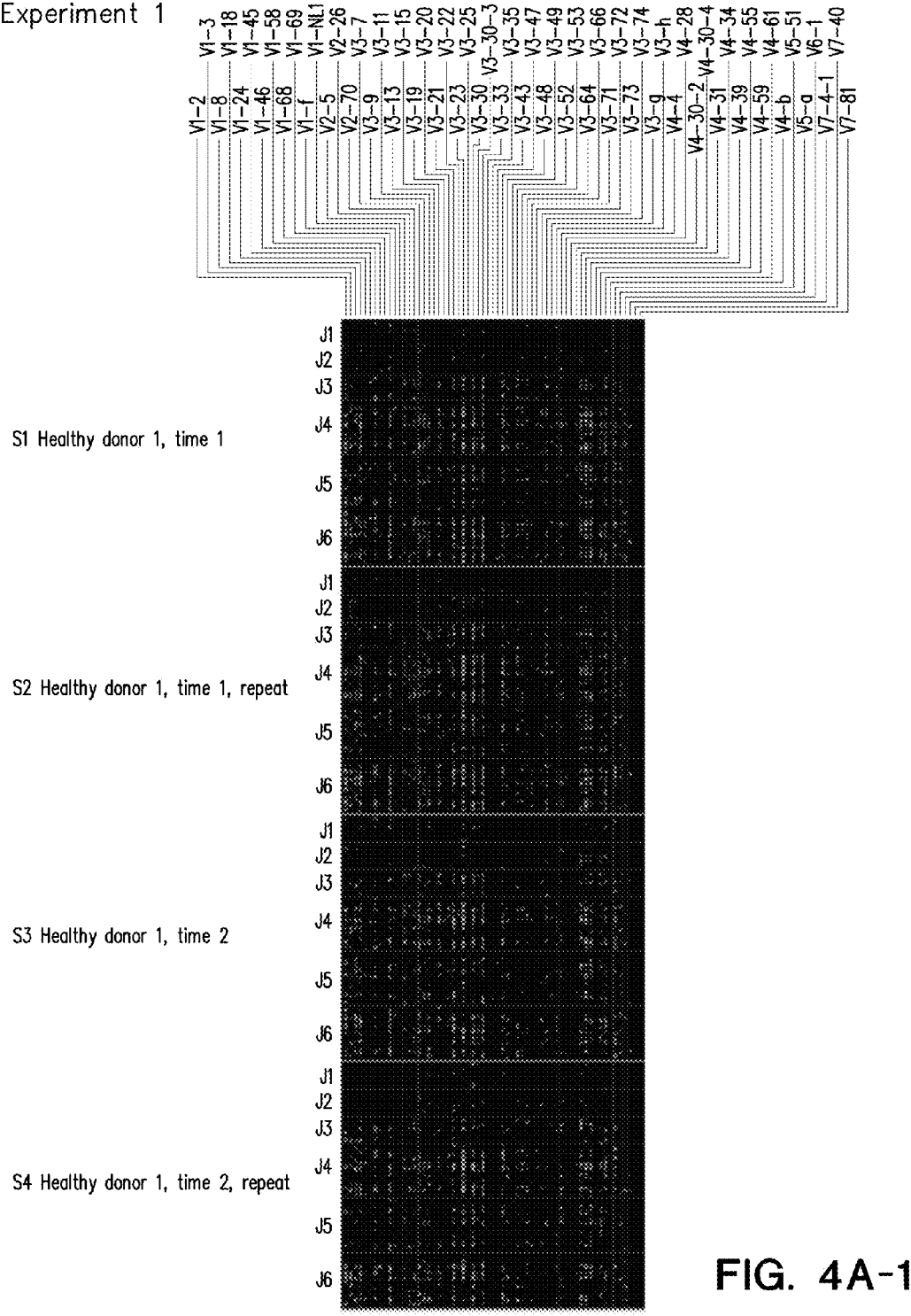
FIG. 4A-4E. V-D-J plots of healthy peripheral blood and lymphoid malignancies. Each box represents the IgH sequences identified in a sample. The x-axis indicates the V gene segment used in the receptor, the large rows on the y-axis indicate the J segment used, and the rows within the wide rows represent the D gene segment used. The size and color-warmth of the circle at a given point shows the proportion of all sequences in the sample used that combination of V, D and J gene segments. The D and J segment rows are scaled according to the number of distinct segments present in each sample.
Figures 2, 4A:
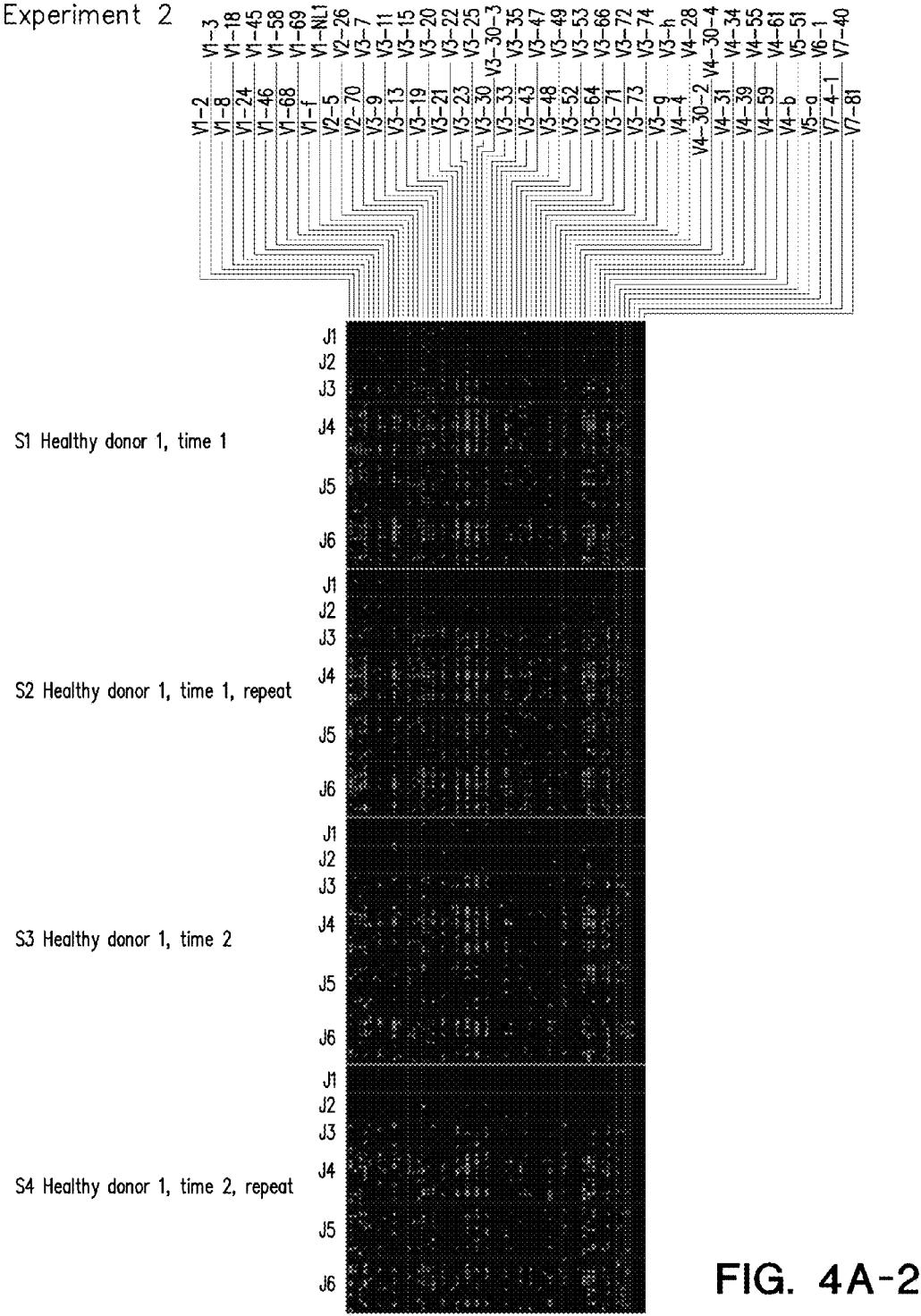
Figures 1, 4B:
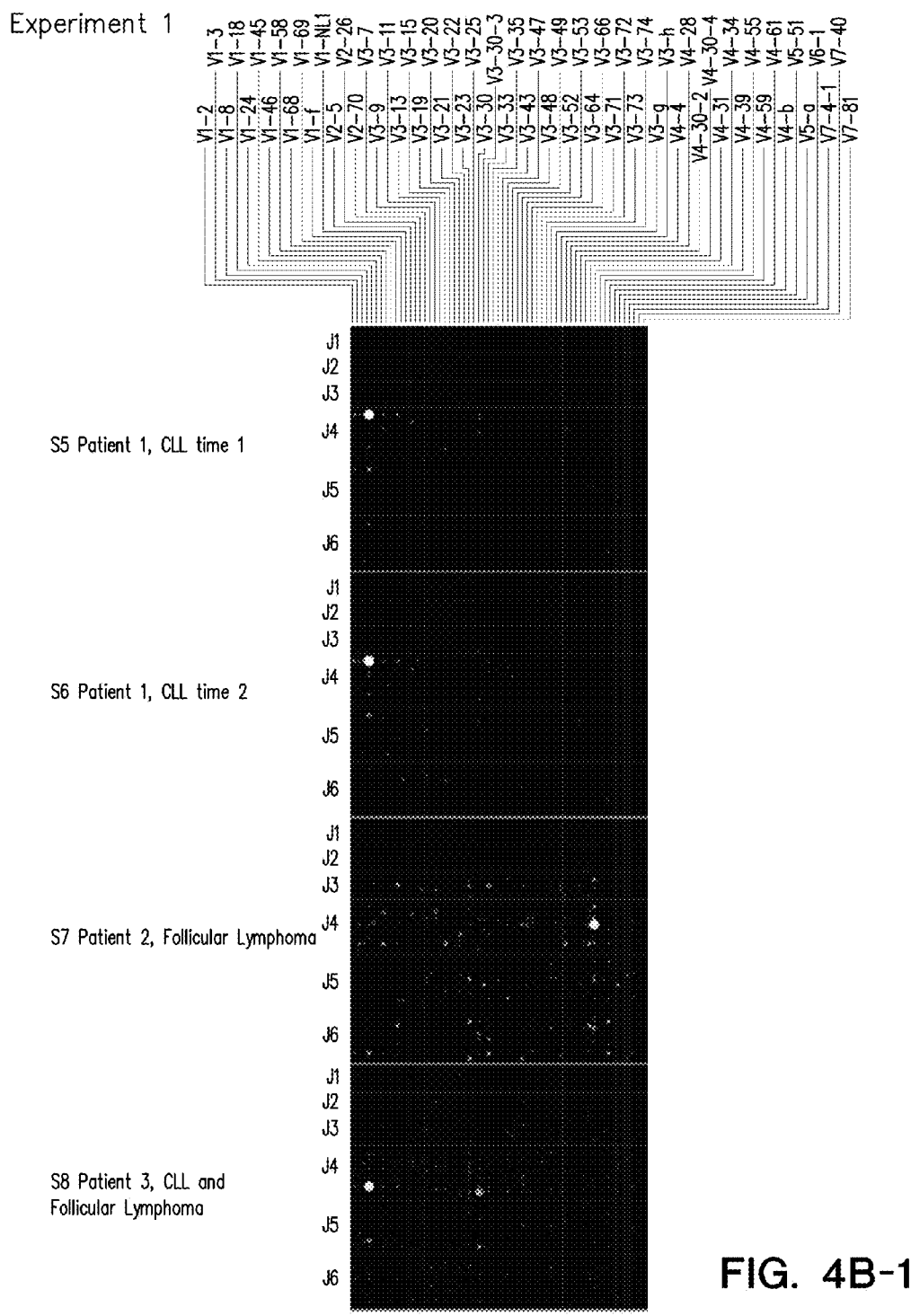
Figures 2, 4B:
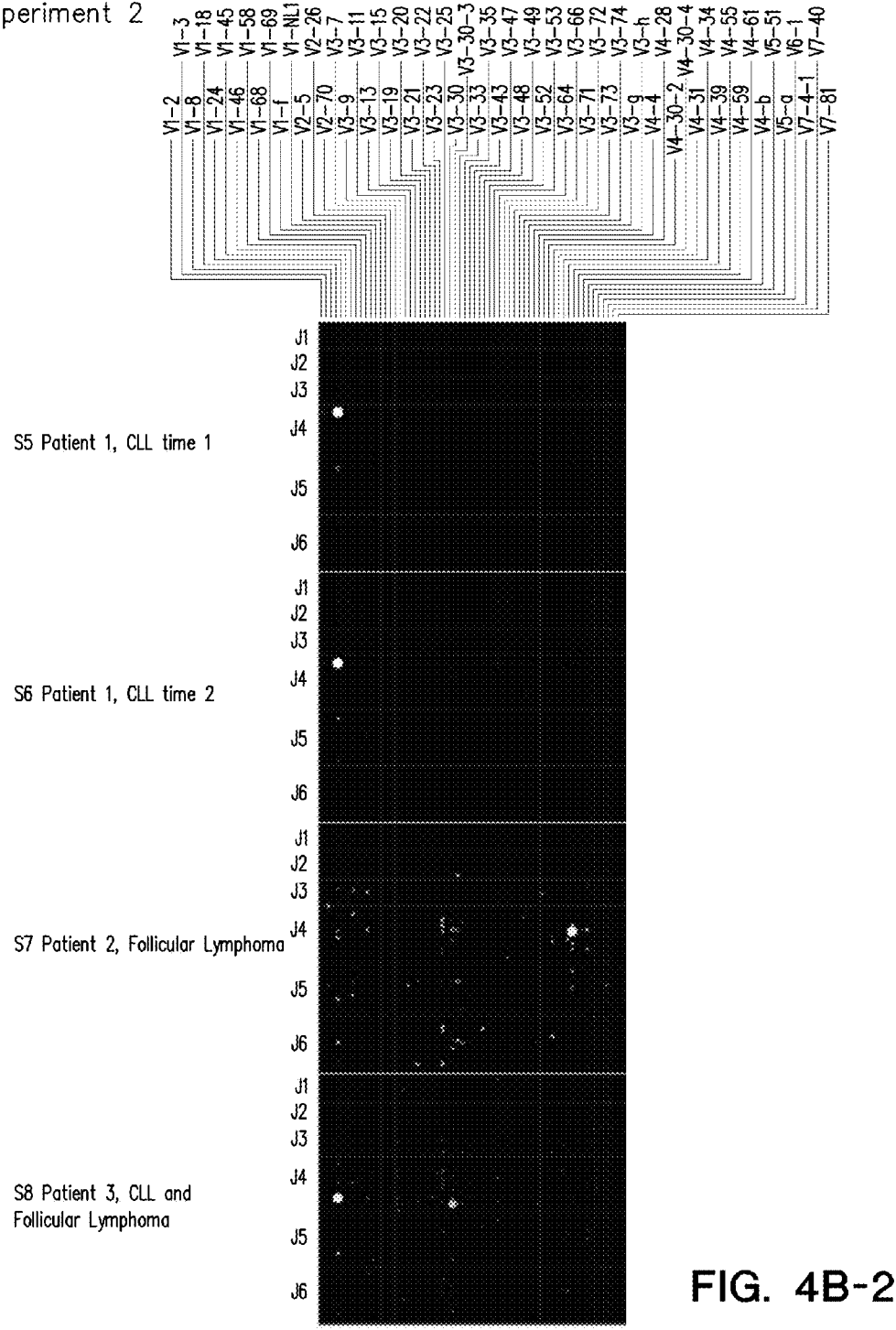
Figures 1, 4C:
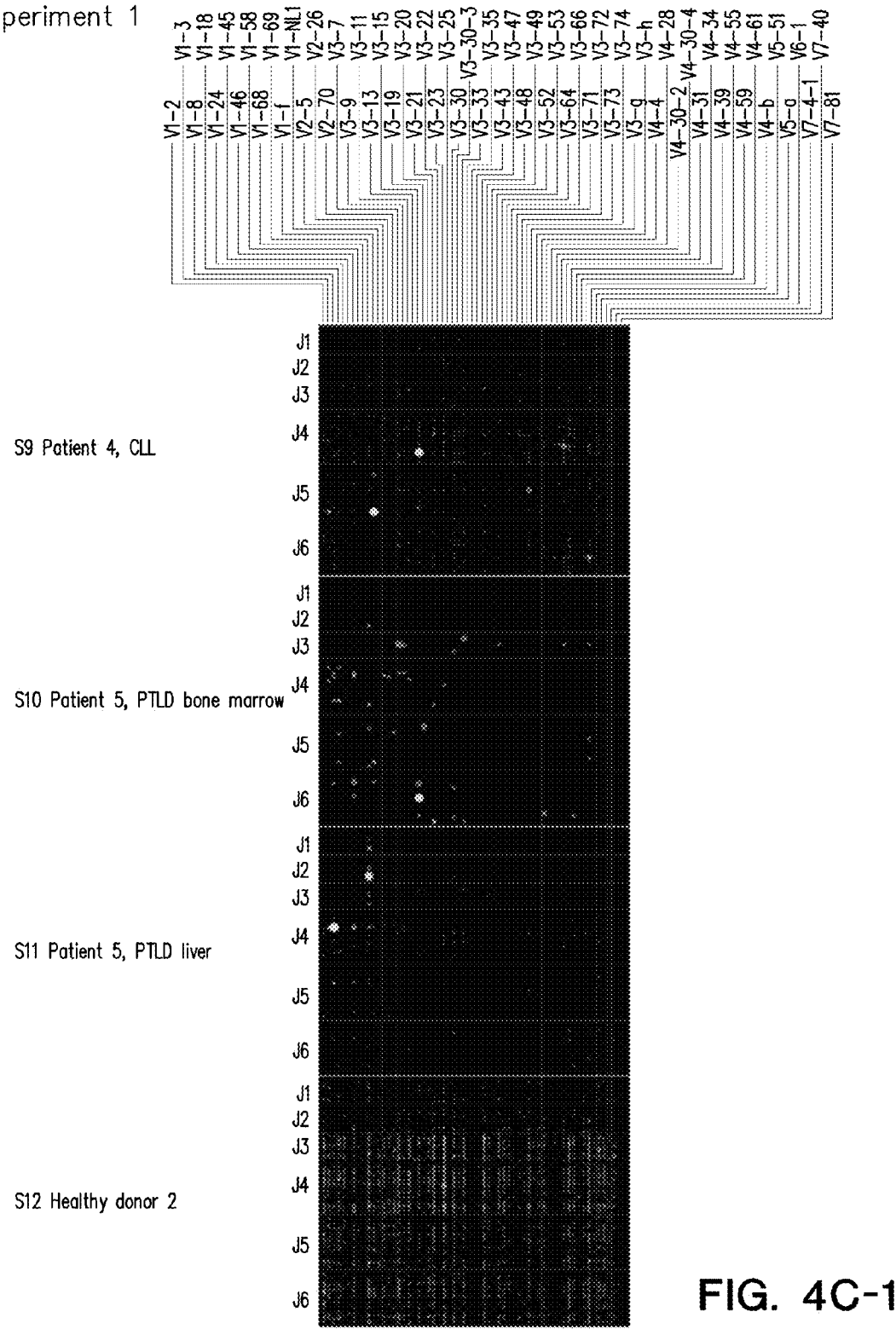
Figures 2, 4C:
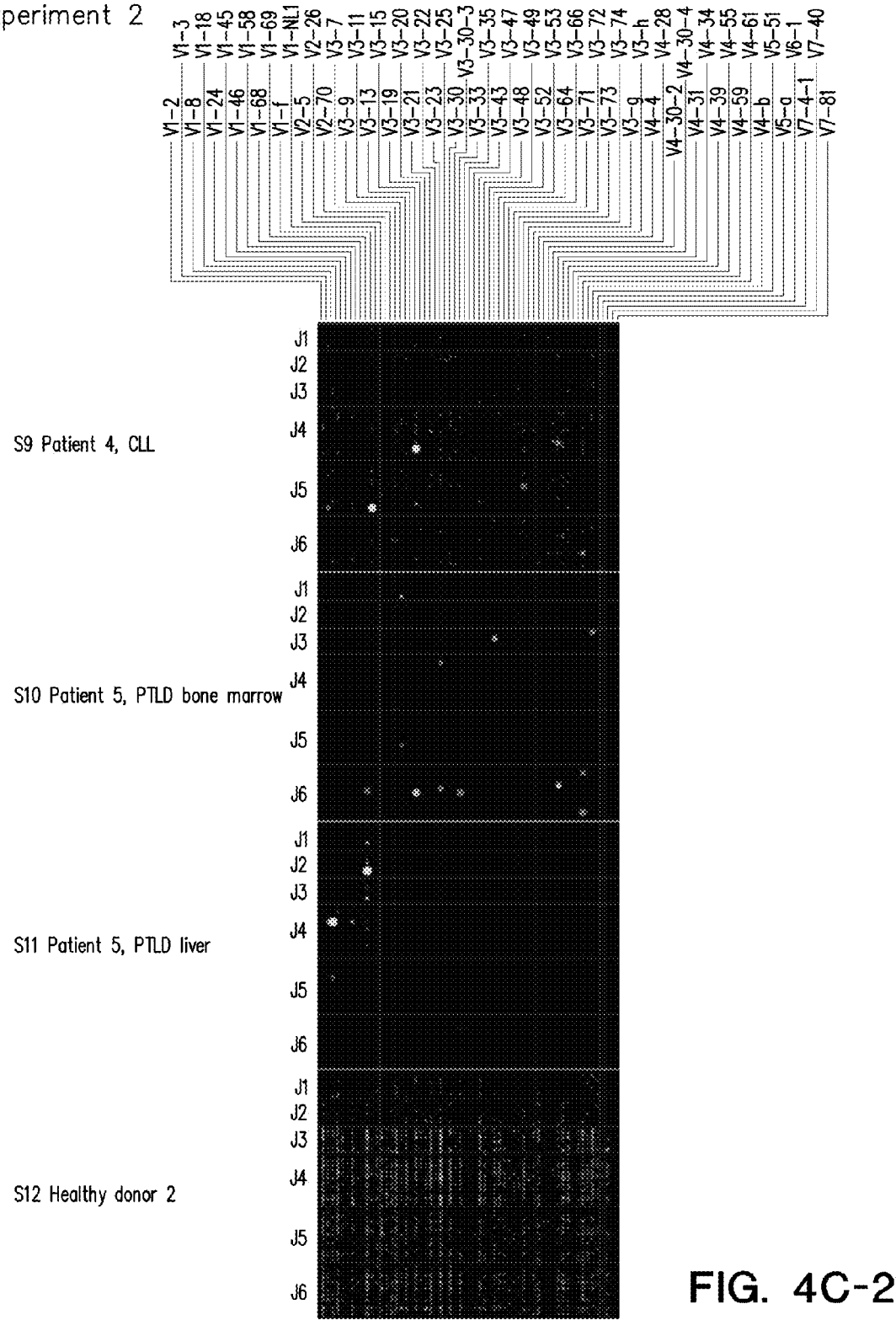
Figures 1, 4D:
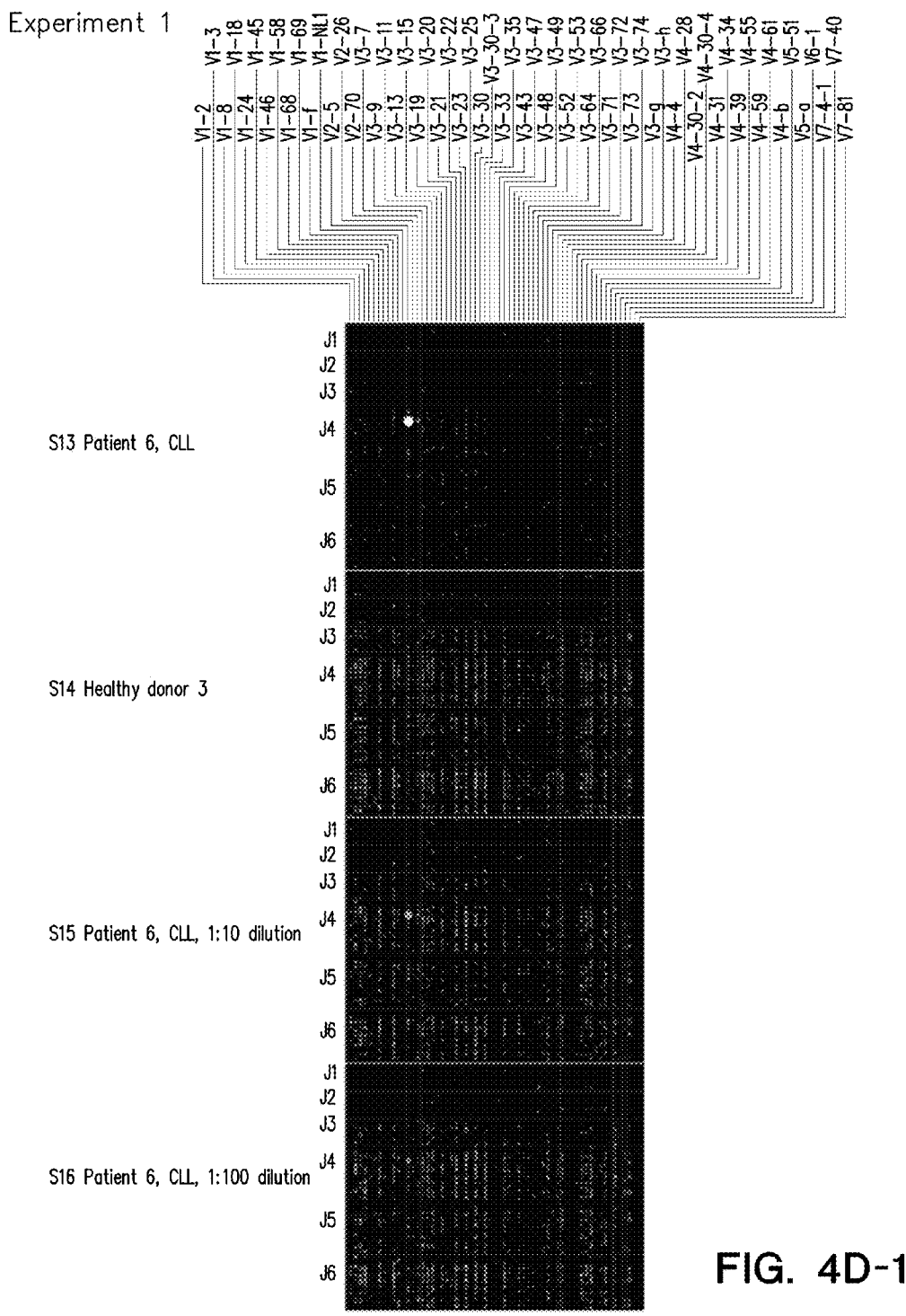
Figures 2, 4D:
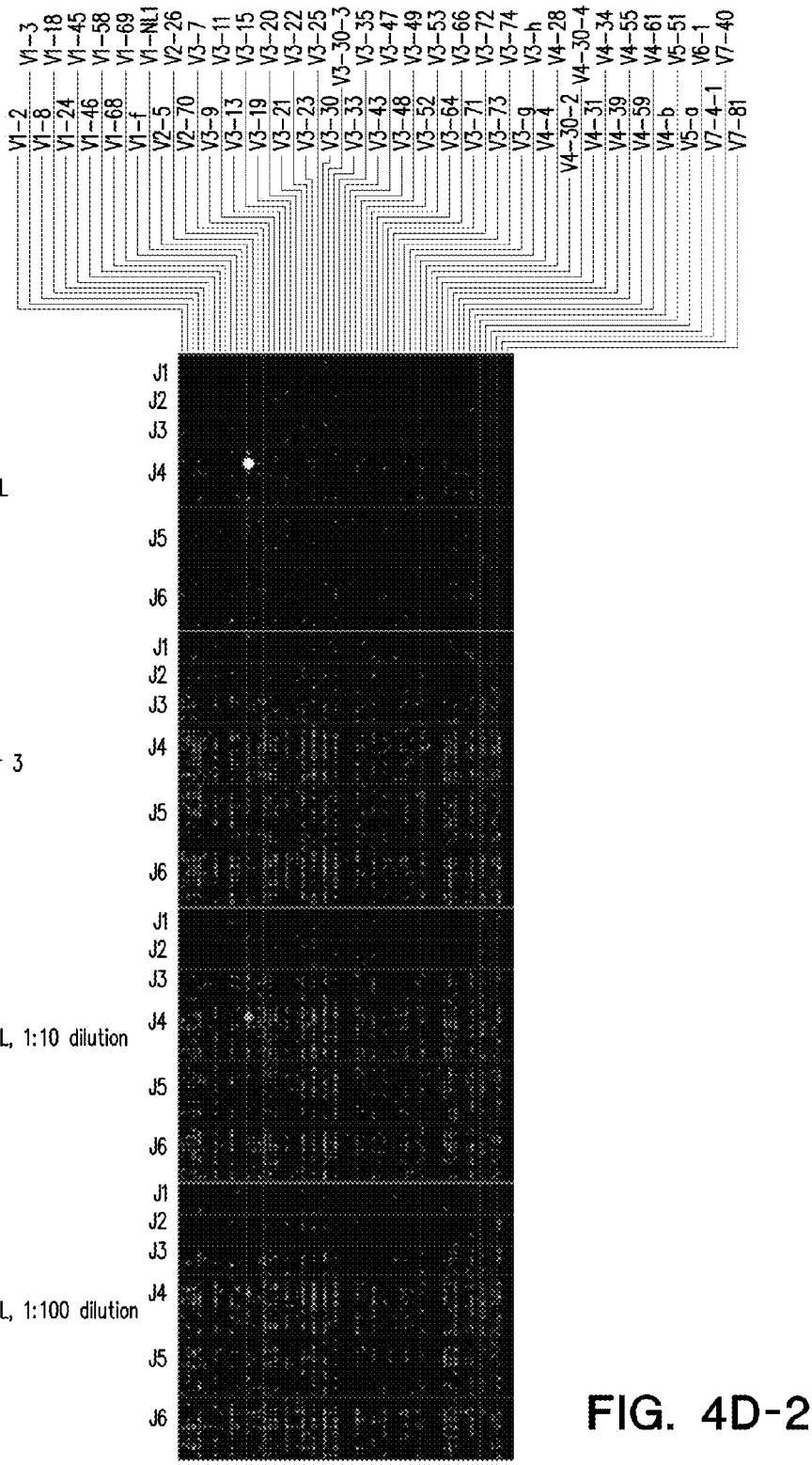
Figures 1, 4E:
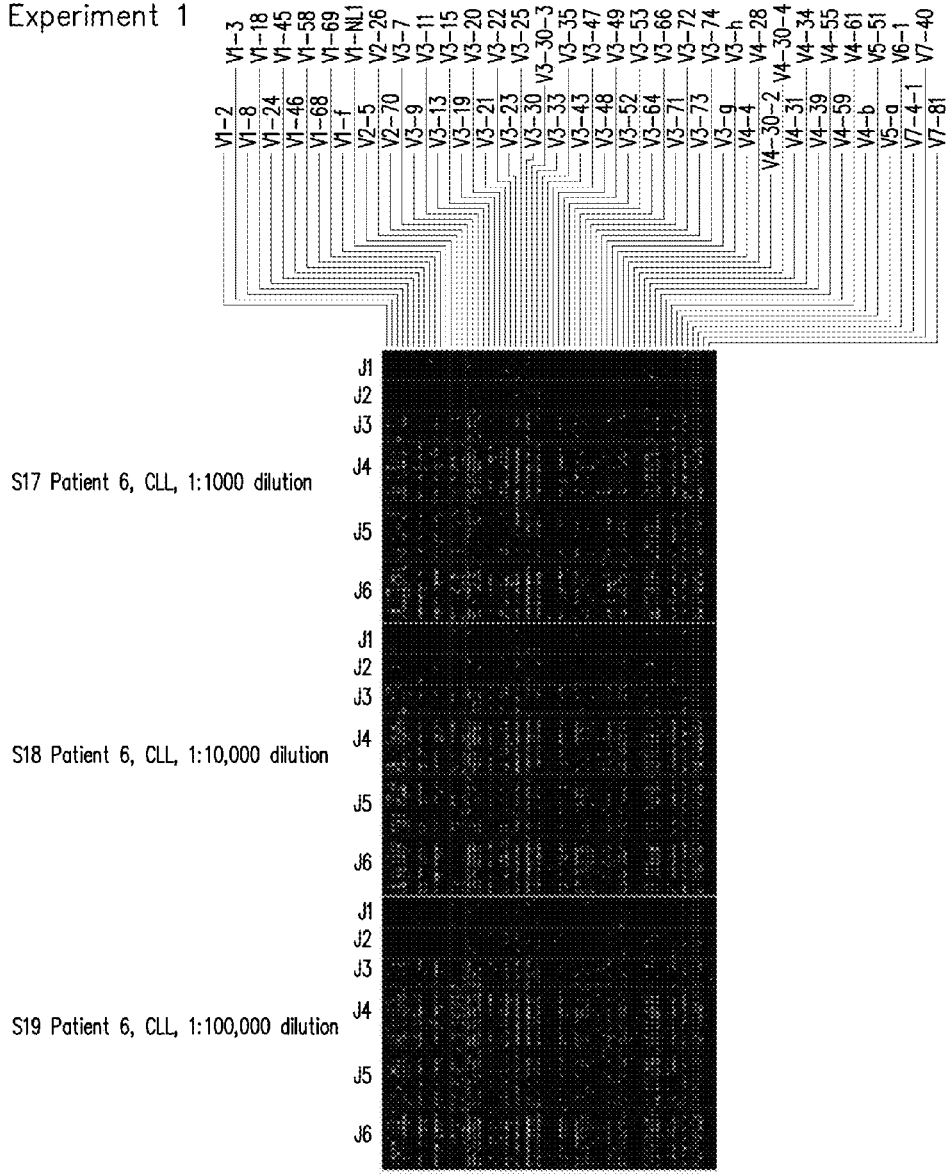
Figures 2, 4E:
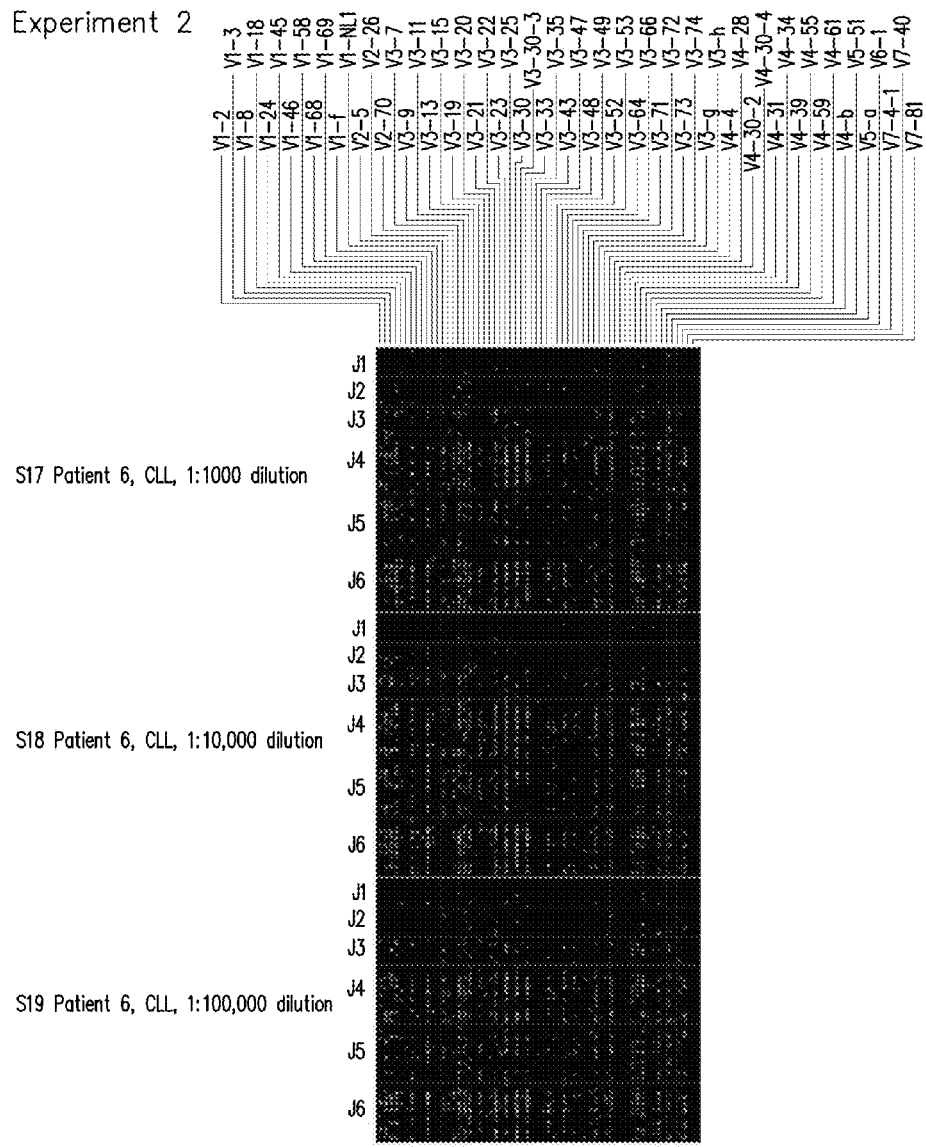
Figure 5:
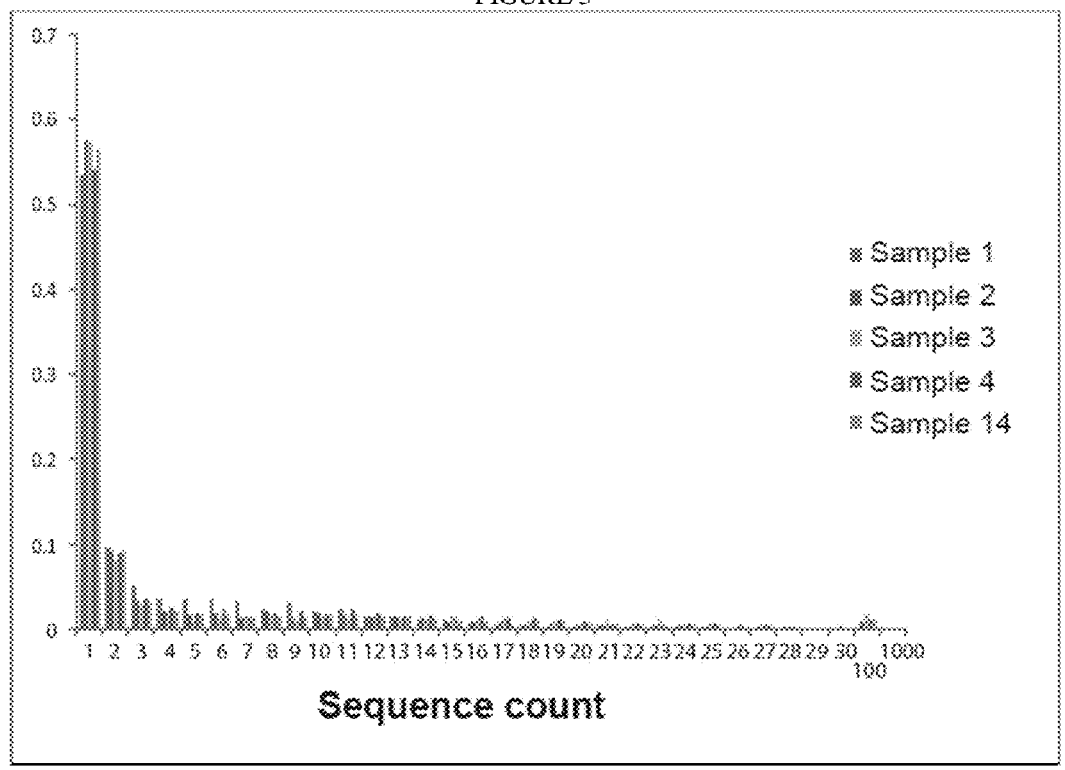
FIG. 5. Sequence complexity of healthy donor blood specimens. The histograms indicate the copy number distribution of distinct sequences in each sample that shared the same V, D and J gene segments as well as V-D and D-J junctions. As judged by comparisons between replicates of the same sample, most of the multi-copy sequences in individual replicates of normal control peripheral blood specimens are the result of PCR amplification, rather than true amplified clones. Further, these data suggest that the multi-copy sequences within a replicate do not appear to reflect a systematic bias in amplification of sequences using a particular V, D or J segment, but rather a stochastic event, perhaps in the earliest rounds of the PCR reaction.
Figure 6:
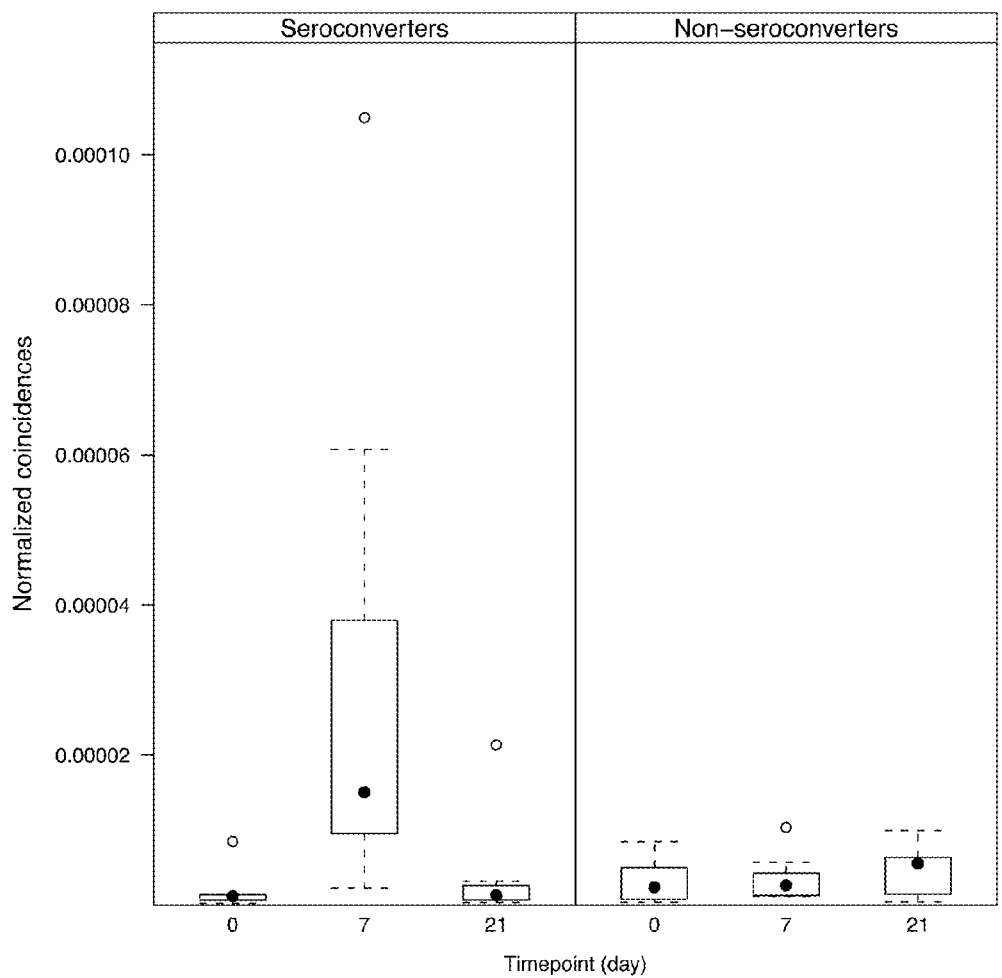
FIG. 6. Coincident sequence counts at day 7 post-vaccination are elevated in seroconverters compared to non-seroconverters. Normalized coincident sequence counts were determined for each sample as indicated in the Materials and Methods section. Seroconverting subjects show increased normalized coincident sequence counts at day 7 post-vaccination, while non-seroconverting subjects show no significant change. Box-and-whisker plots are shown. The dark dot is the median for each group, the edges of the box mark the $25^{th}$ and $75^{th}$ percentile, and the empty dots are outliers.
Figure 7:
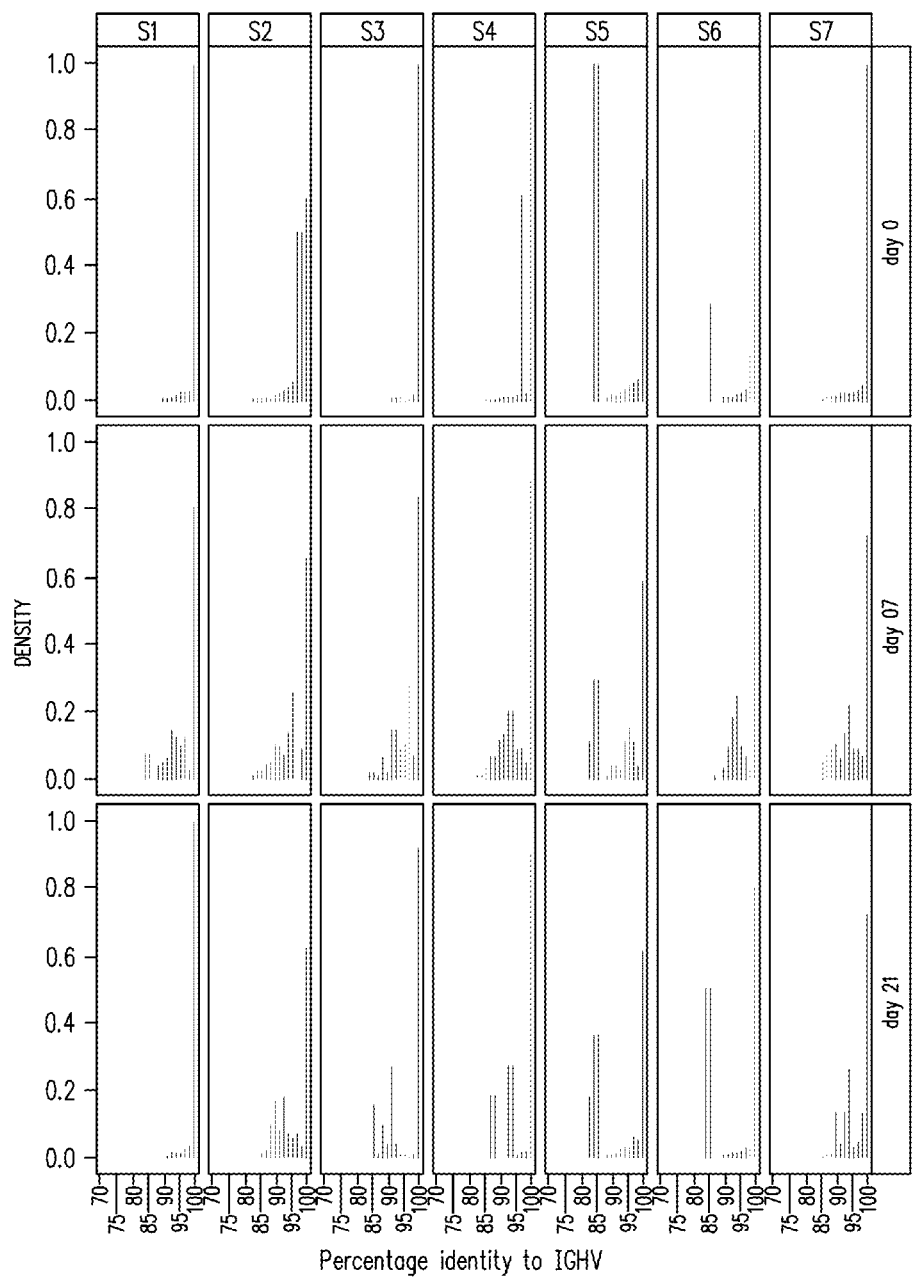
FIG. 7. Change in hypermutation levels in coincident sequences following vaccination correlates with seroconversion. Columns S1-S7 display data from individual seroconverter subjects, while columns NS1-NS7 display data from individual non-seroconverter subjects. The histograms show the distribution of levels of hypermutation (measured as percent sequence match to germline IgHV gene segment, so that more heavily hypermutated sequences are displayed toward the left) in coincident sequences (dark bars), total IgH sequences (white bars) in individual seroconverter and non-seroconverter subjects. Areas of overlap in the histograms for coincident sequences and total IgH are indicated with grey. The seroconverters show increased levels of hypermutation in coincident sequences at day 7 post-vaccination.
Figure 7:
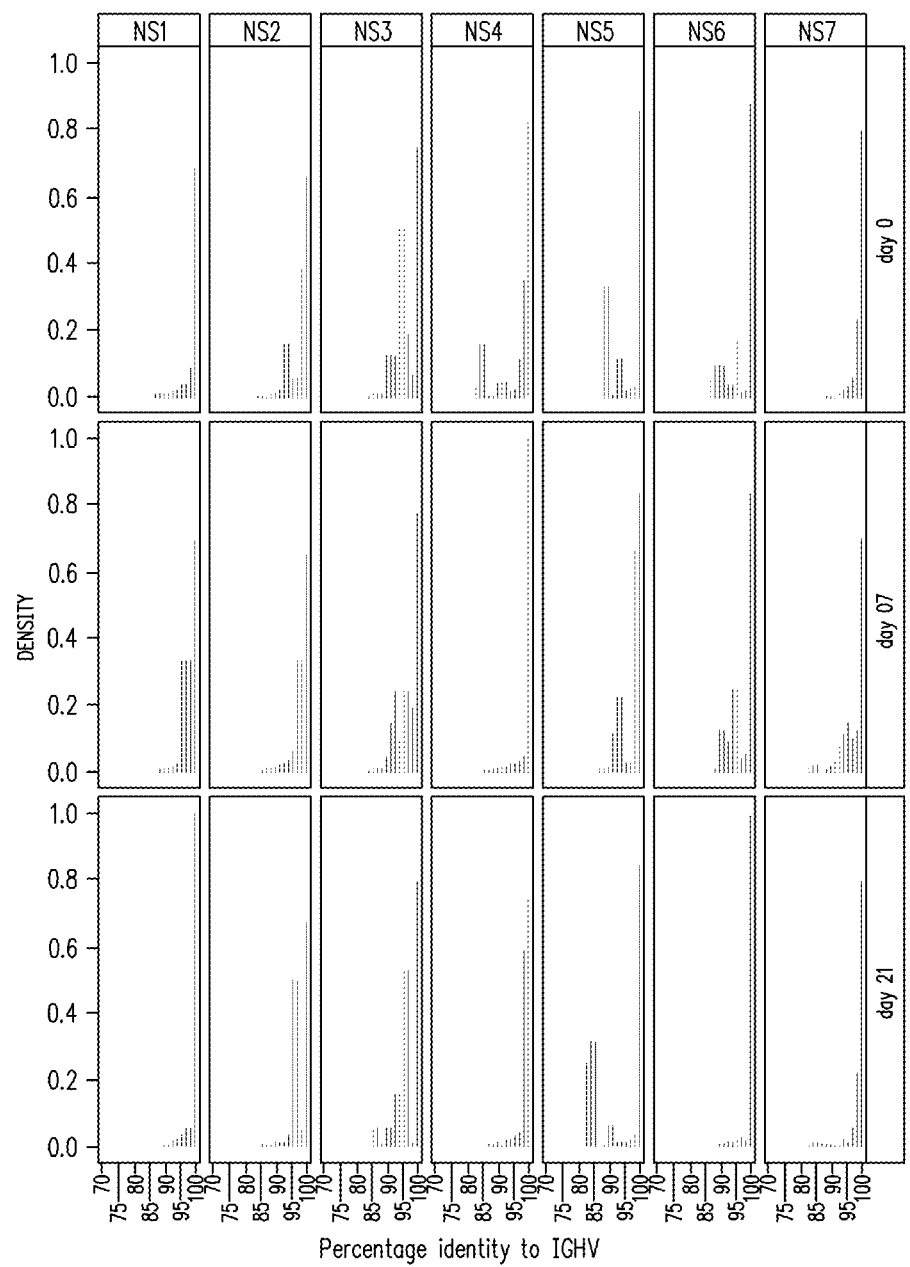

To evaluate the sensitivity of deep sequencing for detection of a clonal lymphoid population in a background of polyclonal cells, we performed serial 10-fold dilutions of a known clonal chronic lymphocytic leukemia blood sample into normal peripheral blood. The percentage of clonal sequences detected at each dilution is shown in FIG. 3 for experiment 2, demonstrating detection down to a 1:10,000 dilution. This represents detection of 0.5 cells per microliter of blood when between 7500 and 14,000 sequences are measured per sample of DNA template derived from ~10 ml of blood.

We next evaluated clinical specimens from patients with chronic lymphocytic leukemia who had undergone total lymphoid irradiation and anti-thymocyte globulin therapy followed by human leukocyte antigen-identical allogeneic peripheral blood progenitor cell transplantation and compared the results of deep sequencing analysis to results from patient- and clone-specific real-time PCR assays (Table 2). In these experiments, the patients with chronic lymphocytic leukemia were different from the patients tested in our initial experiments described in Table 1, and the minimal residual disease (MRD) sequencing was performed in a separate instrument run. Realtime PCR assay results were reported as confidently positive if at least 100 copies per microgram of template DNA were detected. Table 2 demonstrates that all specimens showed agreement between the high throughput sequencing data and real-time PCR assay, although for the lowest confidently positive real-time PCR result for chronic lymphocytic leukemia patient A the clone was detected in only one of the two high throughput sequencing sample replicates.

TABLE 2

| Patient | Specimen | Clone copies* | Total sequences | % | Clone copies† | Total sequences | % | RT-PCR (copies/μg) |
|---|---|---|---|---|---|---|---|---|
| CLL A sample 1 | Diagnostic lymph node | 7,227 | 11,190 | 64.6 | 5,745 | 8,935 | 64.3 | >100,000 |
| CLL A sample 2 | Blood | 0 | 341 | 0.0 | 0 | 670 | 0.0 | 10 |
| CLL A sample 3 | Blood | 38 | 1,477 | 2.6 | 60 | 3,350 | 1.8 | 1,485 |
| CLL A sample 4 | Blood | 0 | 588 | 0.0 | 0 | 1,657 | 0.0 | 91 |
| CLL A sample 5 | Blood | 0 | 430 | 0.0 | 0 | 491 | 0.0 | 37 |
| CLL A sample 6 | Bone marrow | 0 | 1,471 | 0.0 | 21 | 2,991 | 0.7 | 314 |
| CLL B sample 1 | Diagnostic bone marrow | 2,461 | 4,363 | 56.4 | 1,964 | 3,581 | 54.8 | >100,000 |
| CLL B sample 2 | Bone marrow | 1,080 | 1,974 | 54.7 | 1,656 | 3,002 | 55.2 | 5,496 |
| CLL B sample 3 | Blood | 0 | 162 | 0.0 | 0 | 208 | 0.0 | 24 |
| CLL B sample 4 | Blood | 0 | 114 | 0.0 | 0 | 117 | 0.0 | 10 |
| CLL B sample 5 | Bone marrow | 188 | 493 | 38.1 | 343 | 1,127 | 30.4 | 944 |
| Unrelated CLL | Blood | 0 | 5,326 | 0.0 | 0 | 7,673 | 0.0 | |
| Normal control | Tonsil | 0 | 14,007 | 0.0 | 0 | 5,167 | 0.0 | |

*First replicate.
†Second replicate.
Comparison of high-throughput sequencing with real-time PCR MRD monitoring assays. For each patient specimen, IgH rearrangements were amplified from 200 ng of genomic DNA of the indicated specimen types with bar-coded primers adapted for 454 pyrosequencing. The IgH rearrangement libraries were pooled and sequenced. The number of clonal sequences (matching the initial diagnostic specimen clone) and the total number of sequences obtained are listed. Data from pyrosequencing were compared to the results of custom quantitative real-time PCR assays designed to amplify the patient's malignant clonal sequence. The RT-PCR results were considered positive if >100 copies per microgram of template DNA were detected.

Peripheral Blood B Cell Repertoire in Healthy Subjects.

To identify potentially expanded B cell clones within healthy peripheral blood, we looked for independent occurrences of "coincident" IgH sequences (identical V, D, and J segments and identical V-D and D-J junction sequences) in independent pools from the same individual. Such coincidences could have resulted from clonally related cells; indeed, clonal relations are likely for a majority of these coincidences, given both the diversity of the potential repertoire of IgH rearrangements and the absence of rearrangements found in this individual from comparable sequence samples from different individuals. We note that any population with a limited IgH rearrangement repertoire would be expected to show large numbers of such coincidences. Instead, we observed only small numbers of coincident sequences in our data. From six independent amplification pools derived from the blood of a single individual at one time point, we observed only 19 potential coincidences from a total of 10,921 distinct IgH rearrangements sequenced. Seven independent amplification pools from a second time point (14 months later) gave comparable results (25 potential coincidences from a total of 7450 distinct rearrangements sequenced) (Table 3).

TABLE 3

| | T1r2 | T1r3 | T1r4 | T1r5 | T1r6 | T2r1 | T2r2 | T2r3 | T2r4 | T2r5 | T2r6 | T2r7 |
|---|---|---|---|---|---|---|---|---|---|---|---|---|
| T1r1 | 2 | 2 | 1 | 1 | 1 | 2 | 1 | 2 | 0 | 2 | 2 | 1 |
| T1r2 | | 1 | 1 | 0 | 4 | 3 | 0 | 0 | 1 | 0 | 1 | 0 |
| T1r3 | | | 0 | 2 | 0 | 0 | 0 | 1 | 0 | 0 | 1 | 0 |
| T1r4 | | | | 1 | 2 | 0 | 0 | 1 | 1 | 0 | 3 | 1 |
| T1r5 | | | | | 1 | 1 | 0 | 0 | 1 | 0 | 2 | 2 |
| T1r6 | | | | | | 0 | 0 | 0 | 0 | 0 | 2 | 1 |
| T2r1 | | | | | | | 0 | 1 | 1 | 1 | 1 | 1 |
| T2r2 | | | | | | | | 0 | 2 | 2 | 0 | 1 |
| T2r3 | | | | | | | | | 1 | 2 | 0 | 2 |
| T2r4 | | | | | | | | | | 2 | 0 | 2 |
| T2r5 | | | | | | | | | | | 1 | 0 |
| T2r6 | | | | | | | | | | | | 5 |

Coincident sequences in a healthy donor's peripheral blood at two time points. IgH rearrangements from peripheral blood mononuclear cells of a healthy blood donor were PCR amplified in multiple independent replicate PCR reactions and sequenced. The table shows the number of identical sequences detected in more than one replicate (termed coincident sequences). Blood samples from two time points separated by 14 months were analyzed. Sequences from different replicates were considered to be coincident sequences if they shared the same V, D, and J segment usage as well as the same V-D and D-J junctional nucleotide sequences. T1, initial time point; T2, second time point 14 months later; r1 through r7, replicates 1 through 7.

It is noteworthy that we see only slightly fewer coincidences when comparing aliquots between the two time points (0.76 coincidences per sample comparison versus 1.22 for comparisons within the same time point). Although the difference is statistically significant (P<0.05, Fisher's exact one-tailed test), the modest ratio between intratemporal and intertemporal coincidence levels indicates a considerable degree of persistence in the clonal populations in this individual.

The numbers of coincident sequences observed when comparing sequence data from any two aliquots provide strong evidence for substantial diversity in the IgH repertoire. Minimal estimates obtained with approaches similar to the "birthday problem" in probability theory yield a lower bound of ~2 million different IgH rearrangements in these samples. The analysis leading to this lower bound estimate does not yield an upper bound on repertoire; in particular, it is not possible from these data to rule out a category of IgH rearrangements that are very diverse but present in single- or low-copy number in ~2×10$^9$ B cells in peripheral blood. Thus, the true complexity of the blood IgH repertoire could certainly be much greater than 2×10$^6$. In addition to the total complexity of the IgH pool, it is of interest to evaluate the degree to which clonal cell populations above a certain size are present in normal peripheral blood. No sequence was identified in more than 2 of the 13 sequence sets from independent amplicon pools (Table 3).

Using a similar analysis to that described above, we can derive an upper bound for the most abundant IgH rearrangements. For the healthy individual examined in these experiments, this analysis yields a maximum contribution to the sequence pool of 1 of 1000 for any individual clone (P<0.01) in this individual. Within these experimental estimates of the lower bound of the IgH repertoire size, and the upper bound of the largest clone size, a variety of combinations of clonally expanded populations of different sizes could give rise to our observed data. Estimation of the upper limit of the IgH repertoire would require much more extensive sequencing to evaluate the extent of single-copy or very small clonal expansions of B cells and would require characterization of a significant fraction of the blood volume of a healthy donor, which presents ethical concerns. It should be noted that this analysis of the blood does not exclude the possibility that other tissues may contain B cells that are clonally related to circulating cells and does not address the exchange of B cells between the blood and other hematolymphoid compartments of the body.

Diversity of Clonal B Cell Expansions in Healthy Subjects of Various Ages.

We extended our analysis of healthy human patients to an additional 23 subjects ranging in age from 19 to 79 years by sequencing sixfold replicate samples of peripheral blood IgHs from each individual. We detected considerable interindividual variation in the number of expanded lymphocyte clones and expanded clone sizes (Table 4). Using an analysis similar to that performed for the healthy donor in Table 3, we calculated the minimum IgH repertoire size and the largest clone size for these additional subjects. Our data confirm that at least 15 of the 23 additional normal human samples had IgH pools of >1,000,000 different rearrangements. Although the additional eight individuals may have comparable diversity, the lower bound estimates were somewhat lower, relative to the other 15 subjects, because of the greater numbers of weakly amplified clones detected and the lower total yield of sequences from these samples. For a majority of the healthy samples, no sequence appeared in more than two of six sequenced DNA aliquots; for these individuals, this places an upper limit of 0.1% to 0.3% of the measured B cell repertoire that could be dedicated to any single clone, similar to the results from the individual in Table 3. Two of the apparently healthy blood donors in our sample set had expanded B cell clones that were large enough to be detected in all six sequencing replicates. The size of these larger clones can be estimated by the expanded clonal sequence's proportion of total sequences obtained from these patients: For the 54-year-old patient, this value was 0.15%, whereas for the 68-year-old patient the value was 1.5% of the total sequences.

TABLE 4

| | | Coincidences | | | | | |
|---|---|---|---|---|---|---|---|
| Age | Total sequences | 2 | 3 | 4 | 5 | 6 | Minimum diversity |
| 19 | 19,368 | 22 | 0 | 0 | 0 | 0 | 2,136,616 |
| 20 | 12,598 | 61 | 0 | 2 | 0 | 0 | 704,883 |

TABLE 4-continued

| Age | Total sequences | Coincidences | | | | | Minimum diversity |
|---|---|---|---|---|---|---|---|
| | | 2 | 3 | 4 | 5 | 6 | |
| 23 | 6,964 | 11 | 0 | 0 | 0 | 0 | 1,133,759 |
| 25 | 6,522 | 10 | 0 | 0 | 0 | 0 | 1,328,380 |
| 31 | 4,086 | 10 | 1 | 1 | 0 | 0 | 474,366 |
| 32 | 6,112 | 9 | 0 | 0 | 0 | 0 | 1,328,380 |
| 35 | 5,358 | 4 | 0 | 0 | 0 | 0 | 1,860,053 |
| 37 | 5,253 | 4 | 1 | 1 | 0 | 0 | 1,973,903 |
| 38 | 2,173 | 18 | 2 | 1 | 0 | 0 | 70,876 |
| 42 | 4,094 | 11 | 0 | 0 | 0 | 0 | 381,515 |
| 44 | 2,249 | 3 | 0 | 0 | 0 | 0 | 438,241 |
| 45 | 6,781 | 65 | 2 | 2 | 0 | 0 | 325,619 |
| 45 | 7,697 | 12 | 0 | 0 | 0 | 0 | 1,409,687 |
| 50 | 6,841 | 6 | 1 | 0 | 0 | 0 | 1,718,401 |
| 54 | 10,822 | 13 | 1 | 0 | 0 | 1 | 3,369,228 |
| 55 | 3,426 | 7 | 0 | 0 | 0 | 0 | 513,469 |
| 60 | 5,173 | 8 | 3 | 0 | 0 | 0 | 704,883 |
| 61 | 5,092 | 1 | 0 | 0 | 0 | 0 | 6,349,446 |
| 68 | 7,028 | 11 | 1 | 2 | 0 | 1 | 1,897,254 |
| 70 | 5,552 | 10 | 0 | 0 | 0 | 0 | 1,276,797 |
| 75 | 7,064 | 5 | 0 | 1 | 0 | 0 | 3,303,164 |
| 78 | 5,895 | 4 | 0 | 0 | 0 | 0 | 3,051,613 |
| 79 | 7,127 | 11 | 0 | 0 | 0 | 0 | 1,587,537 |

Coincident IgH sequences in peripheral blood of healthy donors of various ages. Peripheral blood samples from 23 healthy donors of ages ranging from 19 to 79 years were analyzed by deep sequencing IgH rearrangements in six replicates from each sample. The number of distinct sequences detected in more than one replicate (termed coincident sequences) from each individual is tabulated below. Sequences from different replicates were considered to be coincident sequences if they shared the same V, D, and J segment usage as well as the same V-D and D-J junctional nucleotide sequences. Calculation of the minimum IgH repertoire diversity in each patient, as indicated by the number of coincident sequences detected, is described in the methods.

These data demonstrate that detection of clonal populations that make up >0.1% of the total B cell population is readily possible with the small blood samples used for this work (<0.1 ml of blood was sufficient for the multiple replicates from these specimens). Further, these results suggest that searches for persistent premalignant or pathological clonal populations at the 0.1% level might be facilitated in certain cases by the limited set of amplified candidates in the normal repertoire.

Deep sequencing data sets of this kind enables explicit detection of preferentially rearranged or selected combinations of V, D, or J segments in IgHs in specific populations. Using the healthy control specimens in our current data sets, we have seen evidence of preferential pairwise segment associations for at least three combinations (D2-2 with J6, D3-22 with J3, and D3-3 with J6) across the group of individuals. Overrepresentation of these D-J combinations (that is, a frequency of the D-J combination that is greater than the products of the D and J frequencies) was observed in 122 of 138, 113 of 138, and 119 of 138 sequenced aliquots, respectively. With a false discovery rate of $<10^{-7}$ (no examples of overrepresentation in this number of aliquots were found in $10^7$ randomly shuffled data sets), these were the most consistent nonrandom associations seen with the data set. We interpret these results as reflecting nonrandom character in rearrangement or selection in this specific population of individuals (Stanford's blood donor pool in a fixed time frame). One could expect different specific nonrandom characters in other populations with distinct histories of community immune response and genetic compositions.

Modern DNA sequencing methods open a new window of investigation into the complex gene rearrangements necessary for human lymphocyte function. Our results using multiplexed bar-coded IgH sequencing of multiple replicate samples of blood from 24 healthy subjects represent the most extensive characterization to date of human B cell populations. For a majority of the healthy individuals, our results were sufficient to place a lower limit of 1,000,000 on the number of distinct IgH rearrangements in circulating lymphocytes and an upper bound of 0.1% to 0.3% of total B cells on the representation of any single clone within the repertoire. A small number of individual amplified clones with greater representation were observed in healthy individuals in our sample set, with the largest clonal populations (seen in patients aged 54 and 68 years) accounting for 0.15% to 1.5% of total sequences of the observed sequence space from circulating B cells. These larger expanded clones may be the result of physiological responses to environmental antigens or pathogens; alternatively, these could represent the precursors to lymphoid malignancies, such as chronic lymphocytic leukemia, which have a strong association with advanced patient age. Recent and older literature describing monoclonal B cell lymphocytosis (MBL) using multiparameter flow cytometry assays to detect B cells with aberrant surface protein expression has indicated that between 5% and 12% of adults have these atypical B cell populations, and essentially all patients who develop chronic lymphocytic leukemia can be shown to have had preceding MBL. An important caveat is that most patients who show MBL do not go on to develop chronic lymphocytic leukemia.

High-throughput immune receptor sequencing provides an unprecedented degree of sensitivity and specificity in tracking monoclonal B cell expansions and enables detection of clonal B cell populations that do not show aberrant cell surface marker expression. Deep sequencing of IgH rearrangements simplifies the assessment of overt populations of suspected malignant B cells in clinical samples and shows success in MRD testing after treatment of leukemia patients. A substantial advantage of the MRD detection approach used here is that all patient samples can be analyzed with a single uniform assay rather than having to tailor individual real-time PCR assays to each patient's clonal malignant sequence and to validate these assays individually as unique clinical tests, an expensive and laborious process likely to limit the accessibility of MRD testing. Having a sequence-based assay that can detect variants from the original malignant clonal sequences present at diagnosis is an advantage in screening for disease relapse. Recent microarray-based data from studies of acute lymphoblastic leukemias suggest that genomic copy number changes may occur relatively frequently at immune receptor loci between initial diagnostic specimens and relapse specimens. For the most sensitive detection of residual disease and clonal variants in a variety of B cell neoplasms, particularly those such as follicular lymphoma that have ongoing hypermutation of rearranged IgH gene loci, one may use several different primer sets (for example, making use of all three framework regions of the IgH V genes) to avoid false-negative results that arise from mutations at primer-binding sites.

The deep sequencing approach of the present invention to lymphocyte population analysis provides insights into autoimmune and infectious diseases, medical manipulations of the immune system such as vaccination, and harmful outcomes of current therapies such as graft versus host disease after stem cell transplantation. Immune receptor sequencing in medical scenarios that involve lymphoid malignancies or immune-mediated diseases are broadly useful for gathering diagnostic, prognostic, and disease-monitoring information.

Materials and Methods

Specimens

Specimens of human peripheral blood and tissues were obtained under Institutional Review Board approved protocols at our institution (Stanford University). Samples for testing for minimal residual disease in chronic lymphocytic leukemia patients were initial diagnostic specimens from lymph node or bone marrow, and blood or bone marrow specimens taken at various time-points after chemotherapy and allogeneic stem cell transplantation. Anonymized healthy control samples from adults of various ages were obtained from blood donors. Subjects gave informed consent for blood donation and were determined to be healthy via evaluation of their suitability to act as blood donors, including screening for malignant or infectious disease history, pregnancy, current infections, travel history, and recent vaccination with live attenuated viral vaccines. Healthy donor samples were also tested and found to be negative for serologic and/or nucleic acid-based evidence of infection by hepatitis B virus, hepatitis C virus, human immunodeficiency virus types 1 and 2, West Nile virus, *Treponema pallidum*, and *Trypanosoma cruzi*. Additional screening to rule out donors with allergic disorders was conducted by measuring total plasma IgE. Donors were included as healthy controls if their total IgE levels were below 25 IU/mL.

DNA Template Preparation

Peripheral blood mononuclear cells were isolated by centrifugation of diluted blood layered over Hypaque 1077 (Sigma-Aldrich, St. Louis, Mo.). The peripheral blood of a healthy adult typically contains between 200-500 B cells per microliter. Twenty-micron sections of formalin-fixed and paraffin-embedded tissue samples were extracted with xylenes, washed with ethanol, and subjected to proteinase K digestion prior to DNA purification. Column purification (Qiagen, Valencia, Calif.) or magnetic bead-based isolation (Magnapure, Roche Diagnostics Corporation, Indianapolis, Ind.) was used to purify the DNA templates.

PCR Primer Design

The BIOMED-2 consortium has developed a clinically validated set of DNA primers for immune receptor amplification, including 7 sequences that anneal to framework region 2 (FR2) of IgH V gene segment family members and a common IgH J sequence. The initial evaluation of patient samples in this study was done by capillary electrophoresis of BIOMED-2 amplicons. For sequencing experiments, these primers were augmented with additional sequence elements at the 5' ends to permit emulsion PCR, amplicon capture, and pyrosequencing. A 6-, 7- or 10-nucleotide unique sequence "barcode" was also added to identify the sample from which particular amplicon products are derived. Barcodes were designed to differ from each other at 2 or more nucleotide positions and to not contain polynucleotide repeats. High-fidelity "ultramer" synthesis chemistry was used for all primers (Integrated DNA Technologies, Coralville, Iowa).

PCR Amplifications and Sequencing Sample Preparation

PCR amplifications were performed using 100 or 200 ng of template genomic DNA, 10 pg of each primer, and 0.5 µL of AmpliTaq Gold enzyme (Applied Biosystems, Foster City, Calif.) per 50-µL reaction. Initial PCR amplification used the following program: (95° C. for 10 min); 35 cycles of (95° C. for 30 s, 58° C. for 45 s, 72° C. for 45 s); (72° C. for 10 min). To minimize the incidence of heteroduplexes in the final sample, 10 µL of the PCR products were amplified for 2 additional cycles in fresh PCR mix. The length of the PCR products obtained using the FR2 primer set in these experiments was 250-300 base pairs. Amplicons were pooled in equal amounts and purified by 1.5% agarose gel electrophoresis and gel extraction, with dissolution of the gel slice at room temperature in lysis buffer prior to column purification (Qiagen, Valencia, Calif.). For each specimen used for Experiments 1 and 2, a single PCR amplification was performed, with the exception of healthy donor 1, where 6 replicate amplifications were performed from the sample obtained at time point 1, and 7 replicate amplifications were performed from the sample collected at time point 2. For the minimal residual disease specimens described in Table 2, 2 independent PCR amplifications were performed. For the additional healthy control subjects described in Table 4, 6 independent PCR amplifications were performed and pooled for sequencing.

High-Throughput Pyrosequencing

The total DNA concentration in amplicon library pools was quantified with the PicoGreen fluorescence assay (Invitrogen, Carlsbad, Calif.). Sequencing data presented in this paper are derived from 4 independent experiments performed on the 454 GS-FLX instrument (454 Life Sciences, a Roche Company, Branford, Conn.). Two of the runs were performed using Standard chemistry and the remaining two runs were performed using Titanium chemistry, with long-range amplicon pyrosequencing beginning from the "B" primer in the manufacturer's protocol. The two Titanium sequencing runs also contained sequences for experiments and samples apart from those discussed in this study.

Sequence Data Analysis

Sequences from each input specimen were sorted based on recognition of a perfect match of the sample barcode, as well as a perfect match to the first 3 bases of the IgH J common primer. Sequences without perfect match barcodes were not considered further. Alignment of rearranged IgH sequences to germ line V, D and J segments and determination of V-D and D-J junctions were performed using the IgBLAST algorithm (National Center for Biotechnology Information). Sequences that contained single base pair insertions or deletions in the V or J gene segments were filtered from the data set, based on the known error properties of pyrosequencing. One 454 Standard FLX-derived data set (Experiment 1) in which two additional PCR cycles were performed on the pooled sample library before sequencing showed some evidence of trace cross-contamination of highly abundant sequences from malignant specimens in other samples, but this artifact was absent from a complete replicate experiment in which PCR of the pooled libraries was not performed (Experiment 2). Some apparently artifactual non-Ig sequences were present in the sequenced samples and were filtered prior to analysis.

Clonality Calculations

"Coincident sequences" are defined as those with identity in V, D, and J segment usage, and in V-D and D-J junctional bases. Clonally expanded cell populations should be detectable by the presence of coincident sequences in distinct amplicon pools. We drew no conclusion from sequences repeatedly observed within a single amplicon pool, as such "intra-pool" identities can conceivably result from amplification of a single initial molecule during PCR. Our initial calculations of diversity in a healthy B cell repertoire were predominantly derived from 13 replicate samples from a healthy individual: Six independent amplicon pools from an initial time point and seven independent amplicon pools from a time point taken 14 months later. Inter-pool coincident sequences were rare in our data, accounting for a total of 19 sequences in the six pools from time point 1 and 25 sequences from the seven pools from time point 2 (these were from a total of 10,921 and 7450 distinct sequences determined for the two time points, respectively). We did not identify any sequences that were present in 3 or more amplicon pools in this initial subject. A lower bound for the blood B cell IgH repertoire ("IgHR", the total number of distinct IgH sequences present in the peripheral blood of an individual) can be calculated from these data based on the minimum expected number of coincidences that would have been generated by various values of IgHR. The minimum expected number of binary sequence coincidences is achieved under the condition of equal representation of each sequence type (any preferential representation of one or more sequence types for a given value of IgHR would only increase the coincidence frequency).

The minimal expected coincidence number (for example, for time point 1) is given by the following formula: $(1/2)*\Sigma i=1$ to $6(Si*\Sigma(j=1$ to $6; j\neq 1)\{1-[1-(1/IgHR)]Sj\})$ where S1 ... S6 are the numbers of distinct sequences determined for the six independent amplicon pools prepared from that time point. Starting with an arbitrary sequence in one amplicon pool, (1/IgHR) is the probability that any single determined sequence in another pool would match that sequence, $1-(1/IgHR)$ is the probability that any single determined sequence in another pool would not match that sequence, and $[1-(1/IgHR)]$ Sj is the probability that no determined sequence from an amplicon pool with Sj determined sequences would match that sequence. The value $[1(1/IgHR)]$ Sj, summed for every element in the sequence set, yields a value that is twice the expected number of coincidences (because this sum counts each binary coincidence once for each participating sequence and hence twice in total). The formula above represents this sum. A related probabilistic calculation is that of the largest clonal expansion that could be present in the blood without being detected in more than 2 amplicon pools.

In our analysis of the 13 independent amplicon pools from the two distinct time points for blood samples from healthy donor 1, the lack of any sequence detected in three or more pools gives an upper bound on the maximum clone size. As a sample calculation, if 10% of sequences derived from an individual were from a single clone, then an arbitrary group of 1000 independent sequences could only avoid this sequence if each independent sequence were from the other 90% of available rearrangements. For 1000 sequences, this probability is $(0.9)1000$ or $1.7\times 10^{-46}$; under these circumstances it is virtually certain that at least three (and in fact all six) of the amplicon pools would contain the 10% clone. Taking into account the slightly different numbers of sequences from the amplified clones, our data yield a conclusion that a clone making up $>1/1000$ of the sequenced repertoire (or approximately 2 million cells) would have a >99% chance of being recovered in at least three different amplicon pools at the first time point (see Clonality and Diversity Calculations for detailed computation). These calculations were repeated for the additional 23 healthy subjects described in Table 4; for the two subjects in which larger clones were detected in all 6 replicate sequencing samples, an estimation of clone size was obtained by dividing the number of sequence reads from the amplified clone by the total number of sequence reads for that individual.

Analysis of V, D, and J Segment Combination Frequencies

Nonrandom representation of pairs of V, D or J segments in the healthy control IgH sequence data sets was assessed by comparing the frequency of pairwise combinations of segments to the product of the individual segment frequencies. Combinations of segments that showed consistent under- or over-representation in large numbers of independent samples were considered as candidates for nonrandom association. The three most significant over-represented combinations in our data set were validated using a false discovery test with 10 million randomly shuffled versions of the experimental dataset.

PCR-Based CLL Minimal Residual Disease Tests

Quantitative real-time PCR monitoring of minimal residual disease was performed using patient allele-specific oligonucleotides as previously described. When consensus probes were unsuitable, probes specific for the clonal third complementarity region were designed. Minimal residual disease assays were performed on the ABI 7900 (Applied Biosystems).

TABLE 5

Sub-table 5a: Primer sequences for IgH from Boyd et al., Science Translational Medicine, 2010

| Sample | Primer Name | Sequence (5' to 3') |
|---|---|---|
| All | 454VH1-FR2 | GCCTCCCTCGCGCCATCAGCTGGGTGCGACAGGCCCCTGGACAA (SEQ ID NO: 1) |
| All | 454VH2-FR2 | GCCTCCCTCGCGCCATCAGTGGATCCGTCAGCCCCCAGGGAAGG (SEQ ID NO: 2) |
| All | 454VH3-FR2 | GCCTCCCTCGCGCCATCAGGGTCCGCCAGGCTCCAGGGAA (SEQ ID NO: 3) |
| All | 454VH4-FR2 | GCCTCCCTCGCGCCATCAGTGGATCCGCCAGCCCCCAGGGAAGG (SEQ ID NO: 4) |
| All | 454VH5-FR2 | GCCTCCCTCGCGCCATCAGGGGTGCGCCAGATGCCCGGGAAAGG (SEQ ID NO: 5) |
| All | 454VH6-FR2 | GCCTCCCTCGCGCCATCAGTGGATCAGGCAGTCCCCATCGAGAG (SEQ ID NO: 6) |
| All | 454VH7-FR2 | GCCTCCCTCGCGCCATCAGTTGGGTGCGACAGGCCCCTGGACAA (SEQ ID NO: 7) |
| 1 | IgHJ6mer_barcode_1 | GCCTTGCCAGCCCGCTCAG-TTACCT-CTTACCTGAGGAGACGGTGACC (SEQ ID NO: 8) |
| 2 | IgHJ6mer_barcode_2 | GCCTTGCCAGCCCGCTCAG-TTACCG-CTTACCTGAGGAGACGGTGACC (SEQ ID NO: 9) |
| 3 | IgHJ6mer_barcode_3 | GCCTTGCCAGCCCGCTCAG-TTAAGT-CTTACCTGAGGAGACGGTGACC (SEQ ID NO: 10) |
| 4 | IgHJ6mer_barcode_4 | GCCTTGCCAGCCCGCTCAG-TTAGTT-CTTACCTGAGGAGACGGTGACC (SEQ ID NO: 11) |
| 5 | IgHJ6mer_barcode_5 | GCCTTGCCAGCCCGCTCAG-TTAACC-CTTACCTGAGGAGACGGTGACC (SEQ ID NO: 12) |

TABLE 5-continued

Sub-table 5a: Primer sequences for IgH from Boyd et al.,
Science Translational Medicine, 2010

| Sample | Primer Name | Sequence (5' to 3') |
|---|---|---|
| 6 | IgHJ6mer_barcode_6 | GCCTTGCCAGCCCGCTCAG-TTCCGG-CTTACCTGAGGAGACGGTGACC (SEQ ID NO: 13) |
| 7 | IgHJ6mer_barcode_9 | GCCTTGCCAGCCCGCTCAG-TACGTT-CTTACCTGAGGAGACGGTGACC (SEQ ID NO: 14) |
| 8 | IgHJ6mer_barcode_10 | GCCTTGCCAGCCCCTCCAG-TAACGG-CTTACCTGAGGAGACGGTGACC (SEQ ID NO: 15) |
| 9 | IgHJ6mer_barcode_11 | GCCTTGCCAGCCCGCTCAG-TAAGGT-CTTACCTGAGGAGACGGTGACC (SEQ ID NO: 16) |
| 10 | IgHJ6mer_barcode_12 | GCCTTGCCAGCCCGCTCAG-TAACTT-CTTACCTGAGGAGACGGTGACC (SEQ ID NO: 17) |
| 11 | IgHJ6mer_barcode_13 | GCCTTGCCAGCCCGCTCAG-TCCGGT-CTTACCTGAGGAGACGGTGACC (SEQ ID NO: 18) |
| 12 | IgHJ6mer_barcode_16 | GCCTTGCCAGCCCGCTCAG-AACCTT-CTTACCTGAGGAGACGGTGACC (SEQ ID NO: 19) |
| 13 | IgHJ7mer_barcode_1 | GCCTTGCCAGCCCGCTCAG-ATTCCAG-CTTACCTGAGGAGACGGTGACC (SEQ ID NO: 20) |
| 14 | IgHJ7mer_barcode_2 | GCCTTGCCAGCCCGCTCAG-ATCCAAG-CTTACCTGAGGAGACGGTGACC (SEQ ID NO: 21) |
| 15 | IgHJ7mer_barcode_3 | GCCTTGCCAGCCCGCTCAG-ATCAAGG-CTTACCTGAGGAGACGGTGACC (SEQ ID NO: 22) |
| 16 | IgHJ7mer_barcode_4 | GCCTTGCCAGCCCGCTCAG-ATTCAGG-CTTACCTGAGGAGACGGTGACC (SEQ ID NO: 23) |
| 17 | IgHJ7mer_barcode_5 | GCCTTGCCAGCCCGCTCAG-CTTCCAG-CTTACCTGAGGAGACGGTGACC (SEQ ID NO: 24) |
| 18 | IgHJ7mer_barcode_6 | GCCTTGCCAGCCCGCTCAG-CTCCAAG-CTTACCTGAGGAGACGGTGACC (SEQ ID NO: 25) |
| 19 | IgHJ7mer_barcode_7 | GCCTTGCCAGCCCGCTCAG-CTCAAGG-CTTACCTGAGGAGACGGTGACC (SEQ ID NO: 26) |
| (Experiment 2) 20 | 454IgHJ6mer_barcode_17 | GCCTTGCCAGCCCGCTCAG-AAGGTT-CTTACCTGAGGAGACGGTGACC (SEQ ID NO: 27) |
| (Experiment 2) 21 | 454IgHJ6mer_barcode_18 | GCCTTGCCAGCCCGCTCAG-AACGGT-CTTACCTGAGGAGACGGTGACC (SEQ ID NO: 28) |
| (Experiment 2) 22 | 454IgHJ6mer_barcode_19 | GCCTTGCCAGCCCGCTCAG-CCGGTT-CTTACCTGAGGAGACGGTGACC (SEQ ID NO: 29) |
| (Experiment 2) 23 | 454IgHJ6mer_barcode_20 | GCCTTGCCAGCCCGCTCAG-TAAACC-CTTACCTGAGGAGACGGTGACC (SEQ ID NO: 30) |
| (Experiment 2) 24 | 454IgHJ7mer_barcode_8 | GCCTTGCCAGCCCGCTCAG-CTTCAGG-CTTACCTGAGGAGACGGTGACC (SEQ ID NO: 31) |
| (Experiment 2) 25 | 454IgHJ7mer_barcode_9 | GCCTTGCCAGCCCGCTCAG-TTTCCAG-CTTACCTGAGGAGACGGTGACC (SEQ ID NO: 32) |
| (Experiment 2) 26 | 454IgHJ7mer_barcode_10 | GCCTTGCCAGCCCGCTCAG-TTCCAAG-CTTACCTGAGGAGACGGTGACC (SEQ ID NO: 33) |
| (Experiment 2) 27 | 454IgHJ7mer_barcode_11 | GCCTTGCCAGCCCGCTCAG-TTCAAGG-CTTACCTGAGGAGACGGTGACC (SEQ ID NO: 34) |
| (Experiment 2) 28 | 454IgHJ7mer_barcode_12 | GCCTTGCCAGCCCGCTCAG-TTTCAGG-CTTACCTGAGGAGACGGTGACC (SEQ ID NO: 35) |
| Vprimerset1 | 454VH1-FR2-set1 | GCCTCCCTCGCGCCATCCGACTCAGCCTTCCTAAGCTGGGTGCGACAGGCCCCTGGACAA (SEQ ID NO: 36) |
| Vprimerset1 | 454VH2-FR2-set1 | GCCTCCCTCGCGCCATCCGACTCAGCCTTCCTAAGTGGATCCGTCAGCCCCAGGGAAGG (SEQ ID NO: 37) |

TABLE 5-continued

Sub-table 5a: Primer sequences for IgH from Boyd et al.,
Science Translational Medicine, 2010

| Sample | Primer Name | Sequence (5' to 3') |
|---|---|---|
| Vprimerset1 | 454VH3-FR2-set1 | GCCTCCCTCGCGCCATCCGACTCAGCCTTCCTAAGGGTCCGCCAGGCTCCAGGGAA (SEQ ID NO: 38) |
| Vprimerset1 | 454VH4-FR2-set1 | GCCTCCCTCGCGCCATCCGACTCAGCCTTCCTAAGTGGATCCGCCAGCCCCAGGGAAGG (SEQ ID NO: 39) |
| Vprimerset1 | 454VH5-FR2-set1 | GCCTCCCTCGCGCCATCCGACTCAGCCTTCCTAAGGGGTGCGCCAGATGCCCGGGAAGG (SEQ ID NO: 40) |
| Vprimerset1 | 454VH6-FR2-set1 | GCCTCCCTCGCGCCATCCGACTCAGCCTTCCTAAGTGGATCAGGCAGTCCCCATCGAGAG (SEQ ID NO: 41) |
| Vprimerset1 | 454VH7-FR2-set1 | GCCTCCCTCGCGCCATCCGACTCAGCCTTCCTAAGTTGGGTGCGACAGGCCCCTGGACAA (SEQ ID NO: 42) |
| Vprimerset2 | 454VH1-FR2-set2 | GCCTCCCTCGCGCCATCCGACTCAGAGCTCCTAAGCTGGGTGCGACAGGCCCCTGGACAA (SEQ ID NO: 43) |
| Vprimerset2 | 454VH2-FR2-set2 | GCCTCCCTCGCGCCATCCGACTCAGAGCTCCTAAGTGGATCCGTCAGCCCCAGGGAAGG (SEQ ID NO: 44) |
| Vprimerset2 | 454VH3-FR2-set2 | GCCTCCCTCGCGCCATCCGACTCAGAGCTCCTAAGGGTCCGCCAGGCTCCAGGGAA (SEQ ID NO: 45) |
| Vprimerset2 | 454VH4-FR2-set2 | GCCTCCCTCGCGCCATCCGACTCAGAGCTCCTAAGTGGATCCGCCAGCCCCAGGGAAGG (SEQ ID NO: 46) |
| Vprimerset2 | 454VH5-FR2-set2 | GCCTCCCTCGCGCCATCCGACTCAGAGCTCTTAAGGGGTGCGCCAGATGCCCGGGAAGG (SEQ ID NO: 47) |
| Vprimerset2 | 454VH6-FR2-set2 | GCCTCCCTCGCGCCATCCGACTCAGAGCTCCTAAGTGGATCAGGCAGTCCCCATCGAGAG (SEQ ID NO: 48) |
| Vprimerset2 | 454VH7-FR2-set2 | GCCTCCCTCGCGCCATCCGACTCAGAGCTCCTAAGTTGGGTGCGACAGGCCCCTGGACAA (SEQ ID NO: 49) |
| Vprimerset3 | 454VH1-FR2-set3 | GCCTCCCTCGCGCCATCCGACTCAGACGTCCTAAGCTGGGTGCGACAGGCCCCTGGACAA (SEQ ID NO: 50) |
| Vprimerset3 | 454VH2-FR2-set3 | GCCTCCCTCGCGCCATCCGACTCAGACGTCCTAAGTGGATCCGTCAGCCCCAGGGAAGG (SEQ ID NO: 51) |
| Vprimerset3 | 454VH3-FR2-set3 | GCCTCCCTCGCGCCATCCGACTCAGACGTCCTAAGGGTCCGCCAGGCTCCAGGGAA (SEQ ID NO:52) |
| Vprimerset3 | 454VH4-FR2-set3 | GCCTCCCTCGCGCCATCCGACTCAGACGTCCTAAGTGGATCCGCCAGCCCCAGGGAAGG (SEQ ID NO: 53) |
| Vprimerset3 | 454VH5-FR2-set3 | GCCTCCCTCGCGCCATCCGACTCAGACGTCCTAAGGGGTGCGCCAGATGCCCGGGAAGG (SEQ ID NO: 54) |
| Vprimerset3 | 454VH6-FR2-set3 | GCCTCCCTCGCGCCATCCGACTCAGACGTCCTAAGTGGATCAGGCAGTCCCCATCGAGAG (SEQ ID NO: 55) |
| Vprimerset3 | 454VH7-FR2-set3 | GCCTCCCTCGCGCCATCCGACTCAGACGTCCTAAGTTGGGTGCGACAGGCCCCTGGACAA (SEQ ID NO: 56) |
| CLLAsample1 | 454IgHJ-10mer-54 | GCCTTGCCAGCCCGCGCAGTCTCAG-TGTCCAATAA-CTTACCTGAGGAGACGGTGACC (SEQ ID NO: 57) |
| CLLAsample2 | 454IgHJ-10mer-55 | GCCTTGCCAGCCCGCGCAGTCTCAG-CGGCCAATAA-CTTACCTGAGGAGACGGTGACC (SEQ ID NO: 58) |
| CLLAsample3 | 454IgHJ-10mer-56 | GCCTTGCCAGCCCGCGCAGTCTCAG-CAACCAATAA-CTTACCTGAGGAGACGGTGACC (SEQ ID NO: 59) |
| CLLAsample4 | 454IgHJ-10mer-57 | GCCTTGCCAGCCCGCGCAGTCTCAG-CCTCCAATAA-CTTACCTGAGGAGACGGTGACC (SEQ ID NO: 60) |
| CLLAsample5 | 454IgHJ-10mer-58 | GCCTTGCCAGCCCGCGCAGTCTCAG-ATTCCAATAA-CTTACCYGAGGAGACGGTGACC (SEQ ID NO: 61) |
| CLLAsample6 | 454IgHJ-10mer-59 | GCCTTGCCAGCCCGCGCAGTCTCAG-ACGCCAATAA-CTTACCTGAGGAGACGGTGACC (SEQ ID NO: 62) |

TABLE 5-continued

Sub-table 5a: Primer sequences for IgH from Boyd et al., Science Translational Medicine, 2010

| Sample | Primer Name | Sequence (5' to 3') |
|---|---|---|
| CLLBsample1 | 454IgHJ-10mer-62 | GCCTTGCCAGCCCGCGCAGTCTCAG-TGTCCGGCAA-CTTACCTGAGGAGACGGTGACC (SEQ ID NO: 63) |
| CLLBsample2 | 454IgHJ-10mer-63 | GCCTTGCCAGCCCGCGCAGTCTCAG-CGGCCGGCAA-CTTACCTGAGGAGACGGTGACC (SEQ ID NO: 64) |
| CLLBsample3 | 454IgHJ-10mer-64 | GCCTTGCCAGCCCGCGCAGTCTCAG-CAACCGGCAA-CTTACCTGAGGAGACGGTGACC (SEQ ID NO: 65) |
| CLLBsample4 | 454IgHJ-10mer-65 | GCCTTGCCAGCCCGCGCAGTCTCAG-CCTCCGGCAA-CTTACCTGAGGAGACGGTGACC (SEQ ID NO: 66) |
| CLLBsample5 | 454IgHJ-10mer-66 | GCCTTGCCAGCCCGCGCAGTCTCAG-ATTCCGGCAA-CTTACCTGAGGAGACGGTGACC (SEQ ID NO: 67) |
| Unrelated CLL | 454IgHJ-10mer-61 | GCCTTGCCAGCCCGCGCAGTCTCAG-TTACCGGCAA-CTTACCTGAGGAGACGGTGACC (SEQ ID NO: 68) |
| Tonsil | 454IgHJ-10mer-67 | GCCTTGCCAGCCCGCGCAGTCTCAG-ACGCCGGCAA-CTTACCTGAGGAGACGGTGACC (SEQ ID NO: 69) |
| Vprimerset4 | 454VH1-FR2-set4 | GCCTCCCTCGCGCCATCCGACTCAGTAGTGCCAGGCTGGGTGCGACAGGCCCCTGGACAA (SEQ ID NO: 70) |
| Vprimerset4 | 454VH2-FR2-set4 | GCCTCCCTCGCGCCATCCGACTCAGTAGTGCCAGGTGGATCCGTCAGCCCCAGGGAAGG (SEQ ID NO: 71) |
| Vprimerset4 | 454VH3-FR2-set4 | GCCTCCCTCGCGCCATCCGACTCAGTAGTGCCAGGGGTCCGCCAGGCTCCAGGGAA (SEQ ID NO: 72) |
| Vprimerset4 | 454VH4-FR2-set4 | GCCTCCCTCGCGCCATCCGACTCAGTAGTGCCAGGTGGATCCGCCAGCCCCAGGGAAGG (SEQ ID NO: 73) |
| Vprimerset4 | 454VH5-FR2-set4 | GCCTCCCTCGCGCCATCCGACTCAGTAGTGCCAGGGGTGCGCCAGATGCCCGGGAAAGG (SEQ ID NO: 74) |
| Vprimerset4 | 454VH6-FR2-set4 | GCCTCCCTCGCGCCATCCGACTCAGTAGTGCCAGGTGGATCAGGCAGTCCCCATCGAGAG (SEQ ID NO: 75) |
| Vprimerset4 | 454VH7-FR2-set4 | GCCTCCCTCGCGCCATCCGACTCAGTAGTGCCAGGTTGGGTGCGACAGGCCCCTGGACAA (SEQ ID NO: 76) |
| Vprimerset5 | 454VH1-FR2-set5 | GCCTCCCTCGCGCCATCCGACTCAGTGTTGCCAGGCTGGGTGCGACAGGCCCCTGGACAA (SEQ ID NO: 77) |
| Vprimerset5 | 454VH2-FR2-set5 | GCCTCCCTCGCGCCATCCGACTCAGTGTTGCCAGGTGGATCCGTCAGCCCCAGGGAAGG (SEQ ID NO: 78) |
| Vprimerset5 | 454VH3-FR2-set5 | GCCTCCCTCGCGCCATCCGACTCAGTGTTGCCAGGGGTCCGCCAGGCTCCAGGAA (SEQ ID NO: 79) |
| Vprimerset5 | 454VH4-FR2-set5 | GCCTCCCTCGCGCCATCCGACTCAGTGTTGCCAGGTGGATCCGCCAGCCCCAGGGAAGG (SEQ ID NO: 80) |
| Vprimerset5 | 454VH5-FR2-set5 | GCCTCCCTCGCGCCATCCGACTCAGTGTTGCCAGGGGTGCGCCAGATGCCCGGGAAAGG (SEQ ID NO: 81) |
| Vprimerset5 | 454VH6-FR2-set5 | GCCTCCCTCGCGCCATCCGACTCAGTGTTGCCAGGTGGATCAGGCAGTCCCCATCGAGAG (SEQ ID NO: 82) |
| Vprimerset5 | 454VH7-FR2-set5 | GCCTCCCTCGCGCCATCCGACTCAGTGTTGCCAGGTTGGGTGCGACAGGCCCCTGGACAA (SEQ ID NO: 83) |
| Vprimerset6 | 454VH1-FR2-set6 | GCCTCCCTCGCGCCATCCGACTCAGCGGTGCCAGGCTGGGTGCGACAGGCCCCTGGACAA (SEQ ID NO: 84) |
| Vprimerset6 | 454VH2-FR2-set6 | GCCTCCCTCGCGCCATCCGACTCAGCGGTGCCAGGTGGATCCGTCAGCCCCAGGGAAGG (SEQ ID NO: 85) |
| Vprimerset6 | 454VH3-FR2-set6 | GCCTCCCTCGCGCCATCCGACTCAGCGGTGCCAGGGGTCCGCCAGGCTCCAGGAA (SEQ ID NO: 86) |
| Vprimerset6 | 454VH4-FR2-set6 | GCCTCCCTCGCGCCATCCGACTCAGCGGTGCCAGGTGGATCCGCCAGCCCCAGGGAAGG (SEQ ID NO: 87) |

TABLE 5-continued

Sub-table 5a: Primer sequences for IgH from Boyd et al.,
Science Translational Medicine, 2010

| Sample | Primer Name | Sequence (5' to 3') |
|---|---|---|
| Vprimerset6 | 454VH5-FR2-set6 | GCCTCCCTCGCGCCATCCGACTCAGCGGTGCCAGGGGTGCGCCAGATGCCCGGGAAGG (SEQ ID NO: 88) |
| Vprimerset6 | 454VH6-FR2-set6 | GCCTCCCTCGCGCCATCCGACTCAGCGGTGCCAGGTGGATCAGGCAGTCCCCATCGAGAG (SEQ ID NO: 89) |
| Vprimerset6 | 454VH7-FR2-set6 | GCCTCCCTCGCGCCATCCGACTCAGCGGTGCCAGGTTGGGTGCGACAGGCCCCTGGACAA (SEQ ID NO: 90) |
| Vprimerset7 | 454VH1-FR2-set7 | GCCTCCCTCGCGCCATCCGACTCAGCAATGCCAGGCTGGGTGCGACAGGCCCCTGGACAA (SEQ ID NO: 91) |
| Vprimerset7 | 454VH2-FR2-set7 | GCCTCCCTCGCGCCATCCGACTCAGCAATGCCAGGTGGATCCGTCAGCCCCAGGGAAGG (SEQ ID NO: 92) |
| Vprimerset7 | 454VH3-FR2-set7 | GCCTCCCTCGCGCCATCCGACTCAGCAATGCCAGGGGTCCGCCAGGCTCCAGGGAA (SEQ ID NO: 93) |
| Vprimerset7 | 454VH4-FR2-set7 | GCCTCCCTCGCGCCATCCGACTCAGCAATGCCAGGTGGATCCGCCAGCCCCAGGGAAGG (SEQ ID NO: 94) |
| Vprimerset7 | 454VH5-FR2-set7 | GCCTCCCTCGCGCCATCCGACTCAGCAATGCCAGGGGTGCGCCAGATGCCCGGGAAGG (SEQ ID NO: 95) |
| Vprimerset7 | 454VH6-FR2-set7 | GCCTCCCTCGCGCCATCCGACTCAGCAATGCCAGGTGGATCAGGCAGTCCCCATCGAGAG (SEQ ID NO: 96) |
| Vprimerset7 | 454VH7-FR2-set7 | GCCTCCCTCGCGCCATCCGACTCAGCAATGCCAGGTTGGGTGCGACAGGCCCCTGGACAA (SEQ ID NO: 97) |
| Vprimerset8 | 454VH1-FR1-set1 | GCCTCCCTCGCGCCATCCGACTCAGTTATGCCAGGGGCCTCAGTGAAGGTCTCCTGCAAG (SEQ ID NO: 98) |
| Vprimerset8 | 454VH2-FR1-set1 | GCCTCCCTCGCGCCATCCGACTCAGTTATGCCAGGGTCTGGTCCTACGCTGGTGAAACCC (SEQ ID NO: 99) |
| Vprimerset8 | 454VH3-FR1-set1 | GCCTCCCTCGCGCCATCCGACTCAGTTATGCCAGGCTGGGGGTCCCTGAGACTCTCCTG (SEQ ID NO: 100) |
| Vprimerset8 | 454VH4-FR1-set1 | GCCTCCCTCGCGCCATCCGACTCAGTTATGCCAGGCTTCGGAGACCCTCTCCCTCACCTG (SEQ ID NO: 101) |
| Vprimerset8 | 454VH5-FR1-set1 | GCCTCCCTCGCGCCATCCGACTCAGTTATGCCAGGCGGGAGTCTCTGAAGATCTCCTGT (SEQ ID NO: 102) |
| Vprimerset8 | 454VH6-FR1-set1 | GCCTCCCTCGCGCCATCCGACTCAGTTATGCCAGGTCGCAGACCCTCTCACTCACCTGTG (SEQ ID NO: 103) |
| Vprimerset9 | 454VH1-FR1-set2 | GCCTCCCTCGCGCCATCCGACTCAGTCCTGCCAGGGGCCTCAGTGAAGGTCTCCTGCAAG (SEQ ID NO: 104) |
| Vprimerset9 | 454VH2-FR1-set2 | GCCTCCCTCGCGCCATCCGACTCAGTCCTGCCAGGGTCTGGTCCTACGCTGGTGAAACCC (SEQ ID NO: 105) |
| Vprimerset9 | 454VH3-FR1-set2 | GCCTCCCTCGCGCCATCCGACTCAGTCCTGCCAGGCTGGGGGTCCCTGAGACTCTCCTG (SEQ ID NO: 106) |
| Vprimerset9 | 454VH4-FR1-set2 | GCCTCCCTCGCGCCATCCGACTCAGTCCTGCCAGGCTTCGGAGACCCTGTCCCTCACCTG (SEQ ID NO: 107) |
| Vprimerset9 | 454VH5-FR1-set2 | GCCTCCCTCGCGCCATCCGACTCAGTCCTGCCAGGCGGGAGTCTCTGAAGATCTCCTGT (SEQ ID NO: 108) |
| Vprimerset9 | 454VH6-FR1-set2 | GCCTCCCTCGCGCCATCCGACTCAGTCCTGCCAGGTCGCAGACCCTCTCACTCACCTGTG (SEQ ID NO: 109) |
| 19 | 454IgHJ-10mer-41 | GCCTTGCCAGCCCGCGCAGTCTCAGATTCAATAAGCTTACCTGAGGAGACGGTGACC (SEQ ID NO: 110) |
| 20 | 454IgHJ-10mer-43 | GCCTTGCCAGCCCGCGCAGTCTCAGTAGCAATTCGCTTACCTGAGGAGACGGTGACC (SEQ ID NO: 111) |
| 23 | 454IgHJ-10mer-45 | GCCTTGCCAGCCCGCGCAGTCTCAGTGTCAATTCGCTTACCTGAGGAGACGGTGACC (SEQ ID NO: 112) |

TABLE 5-continued

Sub-table 5a: Primer sequences for IgH from Boyd et al., Science Translational Medicine, 2010

| Sample | Primer Name | Sequence (5' to 3') |
|---|---|---|
| 25 | 454IgHJ-10mer-46 | GCCTTGCCAGCCCGCGCAGTCTCAGCGGCAATTCGCTTACCTGAGGAGACGGTGACC (SEQ ID NO: 113) |
| 31 | 454IgHJ-10mer-47 | GCCTTGCCAGCCCGCGCAGTCTCAGCAACAATTCGCTTACCTGAGGAGACGGTGACC (SEQ ID NO: 114) |
| 32 | 454IgHJ-10mer-48 | GCCTTGCCAGCCCGCGCAGTCTCAGCCTCAATTCGCTTACCTGAGGAGACGGTGACC (SEQ ID NO: 115) |
| 35 | 454IgHJ-10mer-49 | GCCTTGCCAGCCCGCGCAGTCTCAGAGCCAATTCGCTTACCTGAGGAGACGGTGACC (SEQ ID NO: 116) |
| 37 | 454IgHJ-10mer-50 | GCCTTGCCAGCCCGCGCAGTCTCAGATTCAATTCGCTTACCTGAGGAGACGGTGACC (SEQ ID NO: 117) |
| 38 | 454IgHJ-10mer-51 | GCCTTGCCAGCCCGCGCAGTCTCAGACGCAATTCGCTTACCTGAGGAGACGGTGACC (SEQ ID NO: 118) |
| 42 | 454IgHJ-10mer-52 | GCCTTGCCAGCCCGCGCAGTCTCAGTAGCCAATAACTTACCTGAGGAGACGGTGACC (SEQ ID NO: 119) |
| 44 | 454IgHJ-10mer-53 | GCCTTGCCAGCCCGCGCAGTCTCAGTTACCAATAACTTACCTGAGGAGACGGTGACC (SEQ ID NO: 120) |
| 45a | 454IgHJ-10mer-54 | GCCTTGCCAGCCCGCGCAGTCTCAGTGTCCAATAACTTACCTGAGGAGACGGTGACC (SEQ ID NO: 121) |
| 45b | 454IgHJ-10mer-55 | GCCTTGCCAGCCCGCGCAGTCTCAGCGGCCAATAACTTACCTGAGGAGACGGTGACC (SEQ ID NO: 122) |
| 50 | 454IgHJ-10mer-57 | GCCTTGCCAGCCCGCGCAGTCTCAGCCTCCAATAACTTACCTGAGGAGACGGTGACC (SEQ ID NO: 123) |
| 54 | 454IgHJ-10mer-59 | GCCTTGCCAGCCCGCGCAGTCTCAGACGCCAATAACTTACCTGAGGAGACGGTGACC (SEQ ID NO: 124) |
| 55 | 454IgHJ-10mer-60 | GCCTTGCCAGCCCGCGCAGTCTCAGTAGCCGGCAACTTACCTGAGGAGACGGTGACC (SEQ ID NO: 125) |
| 60 | 454IgHJ-10mer-61 | GCCTTGCCAGCCCGCGCAGTCTCAGTTACCGGCAACTTACCTGAGGAGACGGTGACC (SEQ ID NO: 126) |
| 61 | 454IgHJ-10mer-62 | GCCTTGCCAGCCCGCGCAGTCTCAGTGTCCGGCAACTTACCTGAGGAGACGGTGACC (SEQ ID NO: 127) |
| 68 | 454IgHJ-10mer-64 | GCCTTGCCAGCCCGCGCAGTCTCAGCAACCGGCAACTTACCTGAGGAGACGGTGACC (SEQ ID NO: 128) |
| 70 | 454IgHJ-10mer-65 | GCCTTGCCAGCCCGCGCAGTCTCAGCCTCCGGCAACTTACCTGAGGAGACGGTGACC (SEQ ID NO: 129) |
| 75 | 454IgHJ-10mer-66 | GCCTTGCCAGCCCGCGCAGTCTCAGATTCCGGCAACTTACCTGAGGAGACGGTGACC (SEQ ID NO: 130) |
| 78 | 454IgHJ-10mer-67 | GCCTTGCCAGCCCGCGCAGTCTCAGACGCCGGCAACTTACCTGAGGAGACGGTGACC (SEQ ID NO: 131) |
| 79 | 454IgHJ-10mer-68 | GCCTTGCCAGCCCGCGCAGTCTCAGTAGCCGCAGGCTTACCTGAGGAGACGGTGACC (SEQ ID NO: 132) |

Sub-TABLE 5b

10-Base Barcodes for Use in Primers for Multiplexed PCR of IGH, IGK, IGL, TCRA, TCRB, TCRG and TCRD, or Other Gene Loci

| Barcode# | Barcode | |
|---|---|---|
| 1 | TAGAAGCAAG | (SEQ ID NO: 133) |
| 2 | TGTAAGCAAG | (SEQ ID NO: 134) |
| 3 | CGGAAGCAAG | (SEQ ID NO: 135) |
| 4 | CCTAAGCAAG | (SEQ ID NO: 136) |

Sub-TABLE 5b-continued

10-Base Barcodes for Use in Primers for Multiplexed PCR of IGH, IGK, IGL, TCRA, TCRB, TCRG and TCRD, or Other Gene Loci

| Barcode# | Barcode | |
|---|---|---|
| 5 | AGCAAGCAAG | (SEQ ID NO: 137) |
| 6 | ATTAAGCAAG | (SEQ ID NO: 138) |
| 7 | ACGAAGCAAG | (SEQ ID NO: 139) |
| 8 | TAGAGGCAGG | (SEQ ID NO: 140) |
| 9 | TTAAGGCAGG | (SEQ ID NO: 141) |
| 10 | TGTAGGCAGG | (SEQ ID NO: 142) |
| 11 | CGGAGGCAGG | (SEQ ID NO: 143) |
| 12 | CCTAGGCAGG | (SEQ ID NO: 144) |
| 13 | AGCAGGCAGG | (SEQ ID NO: 145) |
| 14 | ATTAGGCAGG | (SEQ ID NO: 146) |
| 15 | ACGAGGCAGG | (SEQ ID NO: 147) |
| 16 | TAGCATTAGG | (SEQ ID NO: 148) |
| 17 | TTACATTAGG | (SEQ ID NO: 149) |
| 18 | TGTCATTAGG | (SEQ ID NO: 150) |
| 19 | CGGCATTAGG | (SEQ ID NO: 151) |
| 20 | CAACATTAGG | (SEQ ID NO: 152) |
| 21 | CCTCATTAGG | (SEQ ID NO: 153) |
| 22 | AGCCATTAGG | (SEQ ID NO: 154) |
| 23 | ATTCATTAGG | (SEQ ID NO: 155) |
| 24 | ACGCATTAGG | (SEQ ID NO: 156) |
| 25 | TAGCATTCCA | (SEQ ID NO: 157) |
| 26 | TTACATTCCA | (SEQ ID NO: 158) |
| 27 | TGTCATTCCA | (SEQ ID NO: 159) |
| 28 | CGGCATTCCA | (SEQ ID NO: 160) |
| 29 | CAACATTCCA | (SEQ ID NO: 161) |
| 30 | CCTCATTCCA | (SEQ ID NO: 162) |
| 31 | AGCCATTCCA | (SEQ ID NO: 163) |
| 32 | ATTCATTCCA | (SEQ ID NO: 164) |
| 33 | ACGCATTCCA | (SEQ ID NO: 165) |
| 34 | TAGCAATAAG | (SEQ ID NO: 166) |
| 35 | TTACAATAAG | (SEQ ID NO: 167) |
| 36 | TGTCAATAAG | (SEQ ID NO: 168) |
| 37 | CGGCAATAAG | (SEQ ID NO: 169) |
| 38 | CAACAATAAG | (SEQ ID NO: 170) |
| 39 | CCTCAATAAG | (SEQ ID NO: 171) |
| 40 | AGCCAATAAG | (SEQ ID NO: 172) |
| 41 | ATTCAATAAG | (SEQ ID NO: 173) |
| 42 | ACGCAATAAG | (SEQ ID NO: 174) |
| 43 | TAGCAATTCG | (SEQ ID NO: 175) |
| 44 | TTACAATTCG | (SEQ ID NO: 176) |
| 45 | TGTCAATTCG | (SEQ ID NO: 177) |
| 46 | CGGCAATTCG | (SEQ ID NO: 178) |
| 47 | CAACAATTCG | (SEQ ID NO: 179) |
| 48 | CCTCAATTCG | (SEQ ID NO: 180) |
| 49 | AGCCAATTCG | (SEQ ID NO: 181) |
| 50 | ATTCAATTCG | (SEQ ID NO: 182) |
| 51 | ACGCAATTCG | (SEQ ID NO: 183) |
| 52 | TAGCCAATAA | (SEQ ID NO: 184) |
| 53 | TTACCAATAA | (SEQ ID NO: 185) |
| 54 | TGTCCAATAA | (SEQ ID NO: 186) |
| 55 | CGGCCAATAA | (SEQ ID NO: 187) |
| 56 | CAACCAATAA | (SEQ ID NO: 188) |
| 57 | CCTCCAATAA | (SEQ ID NO: 189) |
| 58 | ATTCCAATAA | (SEQ ID NO: 190) |
| 59 | ACGCCAATAA | (SEQ ID NO: 191) |
| 60 | TAGCCGGCAA | (SEQ ID NO: 192) |
| 61 | TTACCGGCAA | (SEQ ID NO: 193) |
| 62 | TGTCCGGCAA | (SEQ ID NO: 194) |
| 63 | CGGCCGGCAA | (SEQ ID NO: 195) |
| 64 | CAACCGGCAA | (SEQ ID NO: 196) |
| 65 | CCTCCGGCAA | (SEQ ID NO: 197) |
| 66 | ATTCCGGCAA | (SEQ ID NO: 198) |
| 67 | ACGCCGGCAA | (SEQ ID NO: 199) |
| 68 | TAGCCGCAGG | (SEQ ID NO: 200) |
| 69 | TTACCGCAGG | (SEQ ID NO: 201) |
| 70 | TGTCCGCAGG | (SEQ ID NO: 202) |
| 71 | CGGCCGCAGG | (SEQ ID NO: 203) |
| 72 | CAACCGCAGG | (SEQ ID NO: 204) |
| 73 | CCTCCGCAGG | (SEQ ID NO: 205) |
| 74 | ATTCCGCAGG | (SEQ ID NO: 206) |
| 75 | ACGCCGCAGG | (SEQ ID NO: 207) |
| 76 | TAGCCGTTAG | (SEQ ID NO: 208) |
| 77 | TTACCGTTAG | (SEQ ID NO: 209) |
| 78 | TGTCCGTTAG | (SEQ ID NO: 210) |

Sub-TABLE 5b-continued

10-Base Barcodes for Use in Primers for Multiplexed PCR of IGH, IGK, IGL, TCRA, TCRB, TCRG and TCRD, or Other Gene Loci

| Barcode# | Barcode | |
|---|---|---|
| 79 | CGGCCGTTAG | (SEQ ID NO: 211) |
| 80 | CAACCGTTAG | (SEQ ID NO: 212) |
| 81 | CCTCCGTTAG | (SEQ ID NO: 213) |
| 82 | ATTCCGTTAG | (SEQ ID NO: 214) |
| 83 | ACGCCGTTAG | (SEQ ID NO: 215) |
| 84 | TAGCGGTAAG | (SEQ ID NO: 216) |
| 85 | TTACGGTAAG | (SEQ ID NO: 217) |
| 86 | TGTCGGTAAG | (SEQ ID NO: 218) |
| 87 | CGGCGGTAAG | (SEQ ID NO: 219) |
| 88 | CAACGGTAAG | (SEQ ID NO: 220) |
| 89 | CCTCGGTAAG | (SEQ ID NO: 221) |
| 90 | AGCCGGTAAG | (SEQ ID NO: 222) |
| 91 | ATTCGGTAAG | (SEQ ID NO: 223) |
| 92 | ACGCGGTAAG | (SEQ ID NO: 224) |
| 93 | TAGTAGGCGG | (SEQ ID NO: 225) |
| 94 | TTATAGGCGG | (SEQ ID NO: 226) |
| 95 | TCCTAGGCGG | (SEQ ID NO: 227) |
| 96 | TGTTAGGCGG | (SEQ ID NO: 228) |
| 97 | CGGTAGGCGG | (SEQ ID NO: 229) |
| 98 | CAATAGGCGG | (SEQ ID NO: 230) |
| 99 | CCTTAGGCGG | (SEQ ID NO: 231) |
| 100 | AGCTAGGCGG | (SEQ ID NO: 232) |
| 101 | ACGTAGGCGG | (SEQ ID NO: 233) |
| 102 | TAGTAATAGG | (SEQ ID NO: 234) |
| 103 | TTATAATAGG | (SEQ ID NO: 235) |
| 104 | TCCTAATAGG | (SEQ ID NO: 236) |
| 105 | TGTTAATAGG | (SEQ ID NO: 237) |
| 106 | CGGTAATAGG | (SEQ ID NO: 238) |
| 107 | CAATAATAGG | (SEQ ID NO: 239) |
| 108 | CCTTAATAGG | (SEQ ID NO: 240) |
| 109 | AGCTAATAGG | (SEQ ID NO: 241) |
| 110 | ACGTAATAGG | (SEQ ID NO: 242) |
| 111 | TAGTAACCAA | (SEQ ID NO: 243) |
| 112 | TTATAACCAA | (SEQ ID NO: 244) |
| 113 | TCCTAACCAA | (SEQ ID NO: 245) |
| 114 | TGTTAACCAA | (SEQ ID NO: 246) |
| 115 | CGGTAACCAA | (SEQ ID NO: 247) |
| 116 | CAATAACCAA | (SEQ ID NO: 248) |
| 117 | CCTTAACCAA | (SEQ ID NO: 249) |
| 118 | AGCTAACCAA | (SEQ ID NO: 250) |
| 119 | ACGTAACCAA | (SEQ ID NO: 251) |
| 120 | TAGTCCGTAA | (SEQ ID NO: 252) |
| 121 | TTATCCGTAA | (SEQ ID NO: 253) |
| 122 | TCCTCCGTAA | (SEQ ID NO: 254) |
| 123 | TGTTCCGTAA | (SEQ ID NO: 255) |
| 124 | CGGTCCGTAA | (SEQ ID NO: 256) |
| 125 | CAATCCGTAA | (SEQ ID NO: 257) |
| 126 | CCTTCCGTAA | (SEQ ID NO: 258) |
| 127 | AGCTCCGTAA | (SEQ ID NO: 259) |
| 128 | ACGTCCGTAA | (SEQ ID NO: 260) |
| 129 | TAGTGGCAAG | (SEQ ID NO: 261) |
| 130 | TTATGGCAAG | (SEQ ID NO: 262) |
| 131 | TCCTGGCAAG | (SEQ ID NO: 263) |
| 132 | TGTTGGCAAG | (SEQ ID NO: 264) |
| 133 | CGGTGGCAAG | (SEQ ID NO: 265) |
| 134 | CAATGGCAAG | (SEQ ID NO: 266) |
| 135 | CCTTGGCAAG | (SEQ ID NO: 267) |
| 136 | AGCTGGCAAG | (SEQ ID NO: 268) |
| 137 | ACGTGGCAAG | (SEQ ID NO: 269) |
| 138 | TAGTCCGGTG | (SEQ ID NO: 270) |
| 139 | TTATCCGGTG | (SEQ ID NO: 271) |
| 140 | TCCTCCGGTG | (SEQ ID NO: 272) |
| 141 | TGTTCCGGTG | (SEQ ID NO: 273) |
| 142 | CGGTCCGGTG | (SEQ ID NO: 274) |
| 143 | CAATCCGGTG | (SEQ ID NO: 275) |
| 144 | CCTTCCGGTG | (SEQ ID NO: 276) |
| 145 | AGCTCCGGTG | (SEQ ID NO: 277) |
| 146 | ACGTCCGGTG | (SEQ ID NO: 278) |
| 147 | TAGTCCTAAG | (SEQ ID NO: 279) |
| 148 | TTATCCTAAG | (SEQ ID NO: 280) |
| 149 | TCCTCCTAAG | (SEQ ID NO: 281) |
| 150 | TGTTCCTAAG | (SEQ ID NO: 282) |
| 151 | CGGTCCTAAG | (SEQ ID NO: 283) |
| 152 | CAATCCTAAG | (SEQ ID NO: 284) |

Sub-TABLE 5b-continued

10-Base Barcodes for Use in Primers for Multiplexed PCR of IGH, IGK, IGL, TCRA, TCRB, TCRG and TCRD, or Other Gene Loci

| Barcode# | Barcode | |
|---|---|---|
| 153 | CCTTCCTAAG | (SEQ ID NO: 285) |
| 154 | AGCTCCTAAG | (SEQ ID NO: 286) |
| 155 | ACGTCCTAAG | (SEQ ID NO: 287) |
| 156 | TAGTGCCAGG | (SEQ ID NO: 288) |
| 157 | TTATGCCAGG | (SEQ ID NO: 289) |
| 158 | TCCTGCCAGG | (SEQ ID NO: 290) |
| 159 | TGTTGCCAGG | (SEQ ID NO: 291) |
| 160 | CGGTGCCAGG | (SEQ ID NO: 292) |
| 161 | CAATGCCAGG | (SEQ ID NO: 293) |
| 162 | CCTTGCCAGG | (SEQ ID NO: 294) |
| 163 | AGCTGCCAGG | (SEQ ID NO: 295) |
| 164 | ACGTGCCAGG | (SEQ ID NO: 296) |
| 165 | TAGTTATTCG | (SEQ ID NO: 297) |
| 166 | TTATTATTCG | (SEQ ID NO: 298) |
| 167 | TCCTTATTCG | (SEQ ID NO: 299) |
| 168 | CGGTTATTCG | (SEQ ID NO: 300) |
| 169 | CAATTATTCG | (SEQ ID NO: 301) |
| 170 | AGCTTATTCG | (SEQ ID NO: 302) |
| 171 | ACGTTATTCG | (SEQ ID NO: 303) |
| 172 | TAGTTAATCC | (SEQ ID NO: 304) |
| 173 | TTATTAATCC | (SEQ ID NO: 305) |
| 174 | TCCTTAATCC | (SEQ ID NO: 306) |
| 175 | CGGTTAATCC | (SEQ ID NO: 307) |
| 176 | CAATTAATCC | (SEQ ID NO: 308) |
| 177 | AGCTTAATCC | (SEQ ID NO: 309) |
| 178 | ACGTTAATCC | (SEQ ID NO: 310) |
| 179 | TAGTTCGGAA | (SEQ ID NO: 311) |
| 180 | TTATTCGGAA | (SEQ ID NO: 312) |
| 181 | TCCTTCGGAA | (SEQ ID NO: 313) |
| 182 | CGGTTCGGAA | (SEQ ID NO: 314) |
| 183 | CAATTCGGAA | (SEQ ID NO: 315) |
| 184 | AGCTTCGGAA | (SEQ ID NO: 316) |
| 185 | ACGTTCGGAA | (SEQ ID NO: 317) |
| 186 | TAGTTGTTAA | (SEQ ID NO: 318) |
| 187 | TTATTGTTAA | (SEQ ID NO: 319) |
| 188 | TCCTTGTTAA | (SEQ ID NO: 320) |
| 189 | CGGTTGTTAA | (SEQ ID NO: 321) |
| 190 | CAATTGTTAA | (SEQ ID NO: 322) |
| 191 | AGCTTGTTAA | (SEQ ID NO: 323) |
| 192 | ACGTTGTTAA | (SEQ ID NO: 324) |
| 193 | TAGTTAACAG | (SEQ ID NO: 325) |
| 194 | TTATTAACAG | (SEQ ID NO: 326) |
| 195 | TCCTTAACAG | (SEQ ID NO: 327) |
| 196 | CGGTTAACAG | (SEQ ID NO: 328) |
| 197 | CAATTAACAG | (SEQ ID NO: 329) |
| 198 | AGCTTAACAG | (SEQ ID NO: 330) |
| 199 | ACGTTAACAG | (SEQ ID NO: 331) |
| 200 | CTCCATTAGG | (SEQ ID NO: 332) |
| 201 | CTCCATTCCA | (SEQ ID NO: 333) |
| 202 | CTCCAATAAG | (SEQ ID NO: 334) |
| 203 | CTCCAATTCG | (SEQ ID NO: 335) |
| 204 | CTCCGGTAAG | (SEQ ID NO: 336) |

Sequencing primers have the general design:

5' [sequencing instrument primer sequence][barcode][gene-specific primer sequence] 3'

For clarity, the primer tables listed below contain only nucleotide sequence of the gene-specific region, which will be understood by one of skill in the art to be linked to an appropriate barcode (for example as described in the table above); and linked to a sequencing instrument primer sequence. For example, an exemplary 454 sequencing instrument primers would be the CGTATCGCCTCCCTCGCGCCATCAG (SEQ ID NO:337) (454 Titanium A) sequence for the V primer side, and the CTATGCGCCTTGCCAGCCCGCTCAG (SEQ ID NO:338 (454 Titanium B) sequence for the J primer side.

However, other sequencing instrument primers may be used as appropriate for the platform.

Sub-TABLE 5c

Additional Primers for IGH

| IGH_V_primer primer_name | IGH_V_region_sequences IGH_V_region | |
|---|---|---|
| VH1-FR2 | [SEQUENCING INSTRUMENT PRIMER][barcode]CTGGGTGCGACAGGCCCCTGGACAA | (SEQ ID NO: 339) |
| VH2-FR2 | [SEQUENCING INSTRUMENT PRIMER][barcode]TGGATCCGTCAGCCCCCAGGGAAGG | (SEQ ID NO: 340) |
| VH3-FR2 | [SEQUENCING INSTRUMENT PRIMER][barcode]GGTCCGCCAGGCTCCAGGGAA | (SEQ ID NO: 341) |
| VH4-FR2 | [SEQUENCING INSTRUMENT PRIMER][barcode]TGGATCCGCCAGCCCCCAGGGAAGG | (SEQ ID NO: 342) |
| VH5-FR2 | [SEQUENCING INSTRUMENT PRIMER][barcode]GGGTGCGCCAGATGCCCGGGAAAGG | (SEQ ID NO: 343) |
| VH6-FR2 | [SEQUENCING INSTRUMENT PRIMER][barcode]TGGATCAGGCAGTCCCCATCGAGAG | (SEQ ID NO: 344) |
| VH7-FR2 | [SEQUENCING INSTRUMENT PRIMER][barcode]TTGGGTGCGACAGGCCCCTGGACAA | (SEQ ID NO: 345) |
| VH1-FR1 | [SEQUENCING INSTRUMENT PRIMER][barcode]GGCCTCAGTGAAGGTCTCCTGCAAG | (SEQ ID NO: 346) |
| VH2-FR1 | [SEQUENCING INSTRUMENT PRIMER][barcode]GTCTGGTCCTACGCTGGTGAAACCC | (SEQ ID NO: 347) |
| VH3-FR1 | [SEQUENCING INSTRUMENT PRIMER][barcode]CTGGGGGGTCCCTGAGACTCTCCTG | (SEQ ID NO: 348) |
| VH4-FR1 | [SEQUENCING INSTRUMENT PRIMER][barcode]CTTCGGAGACCCTGTCCCTCACCTG | (SEQ ID NO: 349) |
| VH5-FR1 | [SEQUENCING INSTRUMENT PRIMER][barcode]CGGGGAGTCTCTGAAGATCTCCTGT | (SEQ ID NO: 350) |
| VH6-FR1 | [SEQUENCING INSTRUMENT PRIMER][barcode]TCGCAGACCCTCTCACTCACCTGTG | (SEQ ID NO: 351) |
| IGH_J_primer formula primer_name | IGH_J_region_sequences IGH_J_region | |
| JH | [SEQUENCING INSTRUMENT PRIMER][barcode]CTTACCTGAGGAGACGGTGACC | (SEQ ID NO: 352) |

Sub-TABLE 5d

Primers for Amplifying IGH Isotype Forms

| Ig_isotype constant_ region_primers primer_name | ig_isotype_sequence | |
|---|---|---|
| IgG | [SEQUENCING INSTRUMENT PRIMER][barcode]TTCGGGGAAGTAGTCCTTGA | (SEQ ID NO: 353) |
| IgM | [SEQUENCING INSTRUMENT PRIMER][barcode]GGGAATTCTCACAGGAGACG | (SEQ ID NO: 354) |
| IgD | [SEQUENCING INSTRUMENT PRIMER][barcode]CCCTGATATGATGGGGAACA | (SEQ ID NO: 355) |
| IgA | [SEQUENCING INSTRUMENT PRIMER][barcode]GAAGACCTTGGGGCTGGT | (SEQ ID NO: 356) |
| IgE | [SEQUENCING INSTRUMENT PRIMER][barcode]GAAGACGGATGGGCTCTGT | (SEQ ID NO: 357) |

Sub-TABLE 5e

Primers for Ig Kappa Light Chain

| Primer name | Gene Target | Titanium sequence A or B(incl TCAG key)/Barcode/Gene segment (5'>3') | |
|---|---|---|---|
| AF-JDM-1 | VK1f | [SEQUENCING INSTRUMENT PRIMER][BAR CODE] TCTGCATCTGTAGGAGACAGAGTCA | (SEQ ID NO: 358) |
| AF-JDM-2 | VK2f | [SEQUENCING INSTRUMENT PRIMER][BAR CODE] GGCCTCCATCTCCTGCAGGTCTAGTC | (SEQ ID NO: 359) |
| AF-JDM-3 | VK3f | [SEQUENCING INSTRUMENT PRIMER][BAR CODE] ACCCTCTCCTGCAGGGCCAGTCAG | (SEQ ID NO: 360) |
| AF-JDM-4 | VK4 | [SEQUENCING INSTRUMENT PRIMER][BAR CODE] CAACTGCAAGTCCAGCCAGAGTGTTTT | (SEQ ID NO: 361) |
| AF-JDM-5 | VK5 | [SEQUENCING INSTRUMENT PRIMER][BAR CODE] CCTGCAAAGCCAGCCAAGACATTGAT | (SEQ ID NO: 362) |
| AF-JDM-6 | VK6 | [SEQUENCING INSTRUMENT PRIMER][BAR CODE] AGGAGAAAGTCACCATCACCTGCC | (SEQ ID NO: 363) |
| AF-JDM-7 | VK7 | [SEQUENCING INSTRUMENT PRIMER][BAR CODE] GCCACCATCACCTGCAGAGCCAGTG | (SEQ ID NO: 364) |
| AF-JDM-8 | VK1f | [SEQUENCING INSTRUMENT PRIMER][BAR CODE] TCTGCATCTGTAGGAGACAGAGTCA | (SEQ ID NO: 365) |
| AF-JDM-9 | VK2f | [SEQUENCING INSTRUMENT PRIMER][BAR CODE] GGCCTCCATCTCCTGCAGGTCTAGTC | (SEQ ID NO: 366) |
| AF-JDM-10 | VK3f | [SEQUENCING INSTRUMENT PRIMER][BAR CODE] ACCCTCTCCTGCAGGGCCAGTCAG | (SEQ ID NO: 367) |
| AF-JDM-11 | VK4 | [SEQUENCING INSTRUMENT PRIMER][BAR CODE] CAACTGCAAGTCCAGCCAGAGTGTTTT | (SEQ ID NO: 368) |
| AF-JDM-12 | VK5 | [SEQUENCING INSTRUMENT PRIMER][BAR CODE] CCTGCAAAGCCAGCCAAGACATTGAT | (SEQ ID NO: 369) |
| AF-JDM-13 | VK6 | [SEQUENCING INSTRUMENT PRIMER][BAR CODE] AGGAGAAAGTCACCATCACCTGCC | (SEQ ID NO: 370) |
| AF-JDM-14 | VK7 | [SEQUENCING INSTRUMENT PRIMER][BAR CODE] GCCACCATCACCTGCAGAGCCAGTG | (SEQ ID NO: 371) |
| AF-JDM-15 | JK1-4 | [SEQUENCING INSTRUMENT PRIMER][BAR CODE] GATCTCCACCTTGGTCCC | (SEQ ID NO: 372) |
| AF-JDM-16 | JK5 | [SEQUENCING INSTRUMENT PRIMER][BAR CODE] AATCTCCAGTCGTGTCCC | (SEQ ID NO: 373) |
| AF-JDM-17 | JK1-4 | [SEQUENCING INSTRUMENT PRIMER][BAR CODE] GATCTCCACCTTGGTCCC | (SEQ ID NO: 374) |
| AF-JDM-18 | JK5 | [SEQUENCING INSTRUMENT PRIMER][BAR CODE] AATCTCCAGTCGTGTCCC | (SEQ ID NO: 375) |
| AF-JDM-19 | JK1-4 | [SEQUENCING INSTRUMENT PRIMER][BAR CODE] GATCTCCACCTTGGTCCC | (SEQ ID NO: 376) |
| AF-JDM-20 | JK5 | [SEQUENCING INSTRUMENT PRIMER][BAR CODE] AATCTCCAGTCGTGTCCC | (SEQ ID NO: 377) |
| AF-JDM-21 | JK1-4 | [SEQUENCING INSTRUMENT PRIMER][BAR CODE] GATCTCCACCTTGGTCCC | (SEQ ID NO: 378) |
| AF-JDM-22 | JK5 | [SEQUENCING INSTRUMENT PRIMER][BAR CODE] AATCTCCAGTCGTGTCCC | (SEQ ID NO: 379) |
| AF-JDM-23 | JK1-4 | [SEQUENCING INSTRUMENT PRIMER][BAR CODE] GATCTCCACCTTGGTCCC | (SEQ ID NO: 380) |
| AF-JDM-24 | JK5 | [SEQUENCING INSTRUMENT PRIMER][BAR CODE] AATCTCCAGTCGTGTCCC | (SEQ ID NO: 381) |

Sub-TABLE 5f

Primers for Ig Lambda Light Chain

| Primer Name | Gene Segment Target | Titanium sequence A or B(incl TCAG key)/Barcode/Gene segment (5'>3') | |
|---|---|---|---|
| AF-JDM-25 VL1-1 | VL1 | [SEQUENCING INSTRUMENT PRIMER][BARCODE]CAGGGCAGAGGGTCACCATCTC | (SEQ ID NO: 382) |
| AF-JDM-26 VL2-1 | VL2 | [SEQUENCING INSTRUMENT PRIMER][BARCODE]TCCTGCACTGGAACCAGCAGTG | (SEQ ID NO: 383) |
| AF-JDM-27 VL3-1 | VL3 | [SEQUENCING INSTRUMENT PRIMER][BARCODE]GTACCAGCAGAAGCCAGGCCAG | (SEQ ID NO: 384) |
| AF-JDM-28 VL4/9-1 | VL4/9 | [SEQUENCING INSTRUMENT PRIMER][BARCODE]CCTCGGTCAAGCTCACCTGCAC | (SEQ ID NO: 385) |
| AF-JDM-29 VL5/11-1 | VL5/11 | [SEQUENCING INSTRUMENT PRIMER][BARCODE]GCATCAGCCAGACTCACCTGCA | (SEQ ID NO: 386) |
| AF-JDM-30 VL6-1 | VL6 | [SEQUENCING INSTRUMENT PRIMER][BARCODE]CGGTAACCATCTCCTGCACCCG | (SEQ ID NO: 387) |
| AF-JDM-31 VL7-1 | VL7 | [SEQUENCING INSTRUMENT PRIMER][BARCODE]CCAGGAGGGACAGTCACTCTCACC | (SEQ ID NO: 388) |
| AF-JDM-32 VL8-1 | VL8 | [SEQUENCING INSTRUMENT PRIMER][BARCODE]CCTGGAGGGACAGTCACACTCACT | (SEQ ID NO: 389) |
| AF-JDM-33 VL10-1 | VL10 | [SEQUENCING INSTRUMENT PRIMER][BARCODE]CCGCCACACTCACCTGCACTGG | (SEQ ID NO: 390) |
| AF-JDM-34 JL1_3-1 | JL1/2/3 | [SEQUENCING INSTRUMENT PRIMER][BARCODE]CTAGGACGGTGAGCTTGGTCCC | (SEQ ID NO: 391) |
| AF-JDM-35 JL4-1 | JL4 | [SEQUENCING INSTRUMENT PRIMER][BARCODE]CTAAAATGATCAGCTGGGTTCCTCCAC | (SEQ ID NO: 392) |
| AF-JDM-36 JL5-1 | JL5 | [SEQUENCING INSTRUMENT PRIMER][BARCODE]ACGGTCAGCTCGGTCCCCTCAC | (SEQ ID NO: 393) |
| AF-JDM-37 JL6-1 | JL6 | [SEQUENCING INSTRUMENT PRIMER][BARCODE]GACGGTCACCTTGGTGCCACTG | (SEQ ID NO: 394) |
| AF-JDM-38 JL7-1 | JL7 | [SEQUENCING INSTRUMENT PRIMER][BARCODE]AGGACGGTCAGCTGGGTGCCTC | (SEQ ID NO: 395) |
| AF-JDM-39 JL1_3-2 | JL1/2/3 | [SEQUENCING INSTRUMENT PRIMER][BARCODE]CTAGGACGGTGAGCTTGGTCCC | (SEQ ID NO: 396) |
| AF-JDM-40 JL4-2 | JL4 | [SEQUENCING INSTRUMENT PRIMER][BARCODE]CTAAAATGATCAGCTGGGTTCCTCCAC | (SEQ ID NO: 397) |
| AF-JDM-41 JL5-2 | JL5 | [SEQUENCING INSTRUMENT PRIMER][BARCODE]ACGGTCAGCTCGGTCCCCTCAC | (SEQ ID NO: 398) |
| AF-JDM-42 JL6-2 | JL6 | [SEQUENCING INSTRUMENT PRIMER][BARCODE]GACGGTCACCTTGGTGCCACTG | (SEQ ID NO: 399) |
| AF-JDM-43 JL7-2 | JL7 | [SEQUENCING INSTRUMENT PRIMER][BARCODE]AGGACGGTCAGCTGGGTGCCTC | (SEQ ID NO: 400) |
| AF-JDM-44 JL1_3-3 | JL1/2/3 | [SEQUENCING INSTRUMENT PRIMER][BARCODE]CTAGGACGGTGAGCTTGGTCCC | (SEQ ID NO: 401) |
| AF-JDM-45 JL4-3 | JL4 | [SEQUENCING INSTRUMENT PRIMER][BARCODE]CTAAAATGATCAGCTGGGTTCCTCCAC | (SEQ ID NO: 402) |
| AF-JDM-46 JL5-3 | JL5 | [SEQUENCING INSTRUMENT PRIMER][BARCODE]ACGGTCAGCTCGGTCCCCTCAC | (SEQ ID NO: 403) |
| AF-JDM-47 JL6-3 | JL6 | [SEQUENCING INSTRUMENT PRIMER][BARCODE]GACGGTCACCTTGGTGCCACTG | (SEQ ID NO: 404) |
| AF-JDM-48 JL7-3 | JL7 | [SEQUENCING INSTRUMENT PRIMER][BARCODE]AGGACGGTCAGCTGGGTGCCTC | (SEQ ID NO: 405) |

Sub-TABLE 5f-continued

Primers for Ig Lambda Light Chain

| Primer Name | Gene Segment Target | Titanium sequence A or B(incl TCAG key)/Barcode/Gene segment (5'>3') | |
|---|---|---|---|
| AF-JDM-54 VL1b-1 | VL1b | [SEQUENCING INSTRUMENT PRIMER][BARCODE]TGGTACCAGCAGCTCCCAGGAA | (SEQ ID NO: 406) |

Sub-TABLE 5g

Primers for TCRA

| TCR_alpha_V_primer name primer_name | sequencing primer + barcode + TCR_alpha_V_region_sequences | |
|---|---|---|
| TCR_alpha_V1_1 | [SEQUENCING INSTRUMENT PRIMER][barcode] GGCGGAGCACCCACATTTCTTTC | (SEQ ID NO: 407) |
| TCR_alpha_V1_2 | [SEQUENCING INSTRUMENT PRIMER][barcode] GCTGGCGAAGCACCCACATTTC | (SEQ ID NO: 408) |
| TCR_alpha_V2 | [SEQUENCING INSTRUMENT PRIMER][barcode] CCGGGATGTGCACCAAGACTC | (SEQ ID NO: 409) |
| TCR_alpha_V3 | [SEQUENCING INSTRUMENT PRIMER][barcode] CAATACCCCAACCGAGGCCTC | (SEQ ID NO: 410) |
| TCR_alpha_V4 | [SEQUENCING INSTRUMENT PRIMER][barcode] GTTTCCCAGCCAAGGACCACG | (SEQ ID NO: 411) |
| TCR_alpha_V5 | [SEQUENCING INSTRUMENT PRIMER][barcode] GGTATAAGCAAGAACCTGGAGCAGG | (SEQ ID NO: 412) |
| TCR_alpha_V6 | [SEQUENCING INSTRUMENT PRIMER][barcode] CAGTGGTACCGACAAGATCCAGG | (SEQ ID NO: 413) |
| TCR_alpha_V7 | [SEQUENCING INSTRUMENT PRIMER][barcode] GCAGTGGTACAGGCAAAATACAGG | (SEQ ID NO: 414) |
| TCR_alpha_V8_1 | [SEQUENCING INSTRUMENT PRIMER][barcode] CCTTATCTCTTCTGGTATGTCCAGTC | (SEQ ID NO: 415) |
| TCR_alpha_V8_2 | [SEQUENCING INSTRUMENT PRIMER][barcode] CCTTATCTCTTCTGGTATGTGCAGTC | (SEQ ID NO: 416) |
| TCR_alpha_V9 | [SEQUENCING INSTRUMENT PRIMER][barcode] GGTCTACAGCTCCTCCTGAAAGC | (SEQ ID NO: 417) |
| TCR_alpha_V10 | [SEQUENCING INSTRUMENT PRIMER][barcode] GAGGTCCTGTTTCCCTGACAATCATG | (SEQ ID NO: 418) |
| TCR_alpha_V11 | [SEQUENCING INSTRUMENT PRIMER][barcode] GCAGGATCCGGGGAGAAGAC | (SEQ ID NO: 419) |
| TCR_alpha_V12_1 | [SEQUENCING INSTRUMENT PRIMER][barcode] GTTGATAATGTRCATATACTCCAATGGTG | (SEQ ID NO: 420) |
| TCR_alpha_V12_2 | [SEQUENCING INSTRUMENT PRIMER][barcode] CCTGAGTTGCTGATGTACACATAC | (SEQ ID NO: 421) |
| TCR_alpha_V12_3 | [SEQUENCING INSTRUMENT PRIMER][barcode] CTGGTACAGACAGGATTGCAGG | (SEQ ID NO: 422) |
| TCR_alpha_V13_1 | [SEQUENCING INSTRUMENT PRIMER][barcode] CTACTTCCCTTGGTATAAGCAAGAAC | (SEQ ID NO: 423) |
| TCR_alpha_V13_2 | [SEQUENCING INSTRUMENT PRIMER][barcode] GGTCCTCAATTCATTATAGACATTCGTTC | (SEQ ID NO: 424) |
| TCR_alpha_V14 | [SEQUENCING INSTRUMENT PRIMER][barcode] GGTACAAGCAGCCCAGCAGTGG | (SEQ ID NO: 425) |
| TCR_alpha_V16 | [SEQUENCING INSTRUMENT PRIMER][barcode] CAGTACTCCAGACAACGCCTCC | (SEQ ID NO: 426) |

Sub-TABLE 5g-continued

Primers for TCRA

| | | |
|---|---|---|
| TCR_alpha_V17 | [SEQUENCING INSTRUMENT PRIMER][barcode] CAGGTAGAGGCCTTGTCCACC | (SEQ ID NO: 427) |
| TCR_alpha_V18 | [SEQUENCING INSTRUMENT PRIMER][barcode] GCCTGAGCTCCTCCTGAAAAGTTC | (SEQ ID NO: 428) |
| TCR_alpha_V19 | [SEQUENCING INSTRUMENT PRIMER][barcode] GTACAAGCAACCACCAAGTGGAG | (SEQ ID NO: 429) |
| TCR_alpha_V20 | [SEQUENCING INSTRUMENT PRIMER][barcode] CTGGTATAGGCAAGATCCTGGGAAAG | (SEQ ID NO: 430) |
| TCR_alpha_V21 | [SEQUENCING INSTRUMENT PRIMER][barcode] CTCCAGTGGTTTAGGCAGGACC | (SEQ ID NO: 431) |
| TCR_alpha_V22 | [SEQUENCING INSTRUMENT PRIMER][barcode] CCTTGGGGACAGCTCATCAACC | (SEQ ID NO: 432) |
| TCR_alpha_V23 | [SEQUENCING INSTRUMENT PRIMER][barcode] GATAGCCATACGTCCAGATGTGAGTG | (SEQ ID NO: 433) |
| TCR_alpha_V24 | [SEQUENCING INSTRUMENT PRIMER][barcode] CAGCACCAATTTCACCTGCAGC | (SEQ ID NO: 434) |
| TCR_alpha_V25 | [SEQUENCING INSTRUMENT PRIMER][barcode] GTATAAGCAAAGGCCTGGTGGACATC | (SEQ ID NO: 435) |
| TCR_alpha_V26_1 | [SEQUENCING INSTRUMENT PRIMER][barcode] ATTGGTATCGACAGATTCACTCCCAGG | (SEQ ID NO: 436) |
| TCR_alpha_V26_2 | [SEQUENCING INSTRUMENT PRIMER][barcode] GGTATCGACAGCTICCCTCC | (SEQ ID NO: 437) |
| TCR_alpha_V27 | [SEQUENCING INSTRUMENT PRIMER][barcode] GAGCCTGGGGAAGGTCCTG | (SEQ ID NO: 438) |
| TCR_alpha_V29 | [SEQUENCING INSTRUMENT PRIMER][barcode] GAAGGTCCTACATTCCTGATATCTATAAG | (SEQ ID NO: 439) |
| TCR_alpha_V30 | [SEQUENCING INSTRUMENT PRIMER][barcode] GGCAGAAGCATGGTGAAGCACC | (SEQ ID NO: 440) |
| TCR_alpha_V34 | [SEQUENCING INSTRUMENT PRIMER][barcode] CTGGTATAAGCAAAAGTATGGTGAAGG | (SEQ ID NO: 441) |
| TCR_alpha_V35 | [SEQUENCING INSTRUMENT PRIMER][barcode] GGCTGGCTATGGTACAAGCAGG | (SEQ ID NO: 442) |
| TCR_alpha_V36 | [SEQUENCING INSTRUMENT PRIMER][barcode] GCTCCCACATTTCTATTTATGCTAACTTC | (SEQ ID NO: 443) |
| TCR_alpha_V38 | [SEQUENCING INSTRUMENT PRIMER][barcode] CCAGCAGGCAGATGATTCTCG | (SEQ ID NO: 444) |
| TCR_alpha_V39 | [SEQUENCING INSTRUMENT PRIMER][barcode] TATTGGTACAGGCAGGATCCTGG | (SEQ ID NO: 445) |
| TCR_alpha_V40 | [SEQUENCING INSTRUMENT PRIMER][barcode] CCTTTTCTGGTATGTGGAATACCC | (SEQ ID NO: 446) |
| TCR_alpha_V41 | [SEQUENCING INSTRUMENT PRIMER][barcode] GTGCCTTACACTGGCTGCAACAG | (SEQ ID NO: 447) |

| TCR_alpha_constant primer name | TCR_alpha_constant region_sequences | |
|---|---|---|
| TCR-constant primer1 | [SEQUENCING INSTRUMENT PRIMER][barcode] AATAGGCAGACAGACTTGTCACTGG | (SEQ ID NO: 448) |
| TCR-constant primer2 | [SEQUENCING INSTRUMENT PRIMER][barcode] TTGAGAATCAAAATCGGTGAATAGG | (SEQ ID NO: 449) |
| TCR-constant primer3 | [SEQUENCING INSTRUMENT PRIMER][barcode] TCAAAATCGGTGAATAGGCA | (SEQ ID NO: 450) |

Sub-TABLE 5g-continued

Primers for TCRA

| | | |
|---|---|---|
| TCR-constant primer4 | [SEQUENCING INSTRUMENT PRIMER][barcode] TCTCAGCTGGT ACACGGCAG | (SEQ ID NO: 451) |

Sub-TABLE 5h

Primers for TCRB

Gene specific sequence

| TRBV primer name | | |
|---|---|---|
| TRBV1_BD | AATCACTTCACACCTGAATGCC | (SEQ ID NO: 452) |
| TRBV10_BD1 | GCTGAGGCTGATCCATTACTCATATG | (SEQ ID NO: 453) |
| TRBV10_BD2 | CTGAGGCTGATCTATTACTCAGC | (SEQ ID NO: 454) |
| TRBV10_BD3 | CTGAGGCTAATCCATTACTCATATG | (SEQ ID NO: 455) |
| TRBV11_BD1 | CAGATCCTGGGACAGGGC | (SEQ ID NO: 456) |
| TRBV11_BD2 | CCTTTACTGGTACCTGCAGAACTTG | (SEQ ID NO: 457) |
| TRBV11_BD3 | CCTTTACTGGTACCGGCAGAAC | (SEQ ID NO: 458) |
| TRBV12_BD1 | CTCTGGTACAGACAGACCTTTGTG | (SEQ ID NO: 459) |
| TRBV12_BD2 | GAGATACCTTCGTGCAGGGAC | (SEQ ID NO: 460) |
| TRBV12_BD3 | CTGGTACAGACAGACCATGATGC | (SEQ ID NO: 461) |
| TRBV13_BD1 | GACACTGTCTACTGGTACCAGCAG | (SEQ ID NO: 462) |
| TRBV14_BD | GATAATCTTTATTGGTATCGACGTGTT | (SEQ ID NO: 463) |
| TRBV15_BD | AACGTCATGTACTGGTACCAGCAG | (SEQ ID NO: 464) |
| TRBV16_BD | GATGAAACAGGTATGCCCAAGG | (SEQ ID NO: 465) |
| TRBV17_BD | GTTCACTGGTACCGACAGAATCTGA | (SEQ ID NO: 466) |
| TRBV18_BD | AGTCATGTTTACTGGTATCGGCAG | (SEQ ID NO: 467) |
| TRBV19_BD | GATGCCATGTACTGGTACCGAC | (SEQ ID NO: 468) |
| TRBV2_BD | CTCAGAGAAGTCTGAAATATTCGATGATC | (SEQ ID NO: 469) |
| TRBV20_BD | GCCACAACTATGTTTTGGTATCGTC | (SEQ ID NO: 470) |
| TRBV21_BD | GCTGGAAGAAGAGCTCAAGTTT | (SEQ ID NO: 471) |
| TRBV21_BD | GCTGGAAGAAGAGCTCAAGTTT | (SEQ ID NO: 472) |
| TRBV23_BD | GAACAAGTTCTTCAAGAAACGGAG | (SEQ ID NO: 473) |
| TRBV23_BD2 | GAACAAGTTCTTCAAGAAATGGAG | (SEQ ID NO: 474) |
| TRBV24_BD1 | GAATGTACTGGTATCGACAAGACC | (SEQ ID NO: 475) |
| TRBV25_BD | CAAGATCCAGGAATGGAACTACAC | (SEQ ID NO: 476) |
| TRBV26_BD1 | GTTACAATGTACTGGTATCGACAGGA | (SEQ ID NO: 477) |
| TRBV26_BD2 | GTTGCAATGTACTGGTATCGACAGAAC | (SEQ ID NO: 478) |
| TRBV27_BD | GAGTATATGTCCTGGTATCGACAAG | (SEQ ID NO: 479) |
| TRBV28_BD | GTATCGACAAGACCCAGGTCTG | (SEQ ID NO: 480) |
| TRBV29_BD1 | GACAGAGCCTGACACTGAT | (SEQ ID NO: 481) |
| TRBV29_BD2 | CTGGACAGAGCGTGACACTGAT | (SEQ ID NO: 482) |

Sub-TABLE 5h-continued

Primers for TCRB

Gene specific sequence

| | | |
|---|---|---|
| TRBV3_BD1 | GATACTATGTATTGGTATAAACAGG | (SEQ ID NO: 483) |
| TRBV3_BD2 | GGAGCCAATTTTAAATGAAACAGTTCCA | (SEQ ID NO: 484) |
| TRBV30_BD | GCCTCCAGCTGCTCTTCTAC | (SEQ ID NO: 485) |
| TRBV4_BD1 | GGTACAAGCAGAAAGCTAAGAAGC | (SEQ ID NO: 486) |
| TRBV5_BD1 | GTGTATCCTGGTACCAACAG | (SEQ ID NO: 487) |
| TRBV5_BD2 | TGTGTCCTGGTACCAACAGG | (SEQ ID NO: 488) |
| TRBV5_BD3 | ACCAGTGTGTCCTCGTACCAAC | (SEQ ID NO: 489) |
| TRBV5_BD4 | GGTACCAACAGGCCCTGG | (SEQ ID NO: 490) |
| TRBV6_BD1 | GTATCGACAAGACCCAGGCA | (SEQ ID NO: 491) |
| TRBV6_BD2 | CTGGTATAGACAAGATCTAGGACTG | (SEQ ID NO: 492) |
| TRBV7_BD1 | ATTGGTACCGACAGAGCCTGG | (SEQ ID NO: 493) |
| TRBV7_BD2 | TGCCCTTTACTGGTACCGACA | (SEQ ID NO: 494) |
| TRBV7_BD3 | GATGCTCAACGAGACAAATCAGGGC | (SEQ ID NO: 495) |
| TRBV7_BD4 | GTATCCCTTTATTGGTACCGACAGG | (SEQ ID NO: 496) |
| TRBV7_BD5 | GGTATCAACAGGCCCTGG | (SEQ ID NO: 497) |
| TRBV7_BD6 | GGTACCAACAGGCCCTCGG | (SEQ ID NO: 498) |
| TRBV7_BD7 | CCAGAGTTTCTGACTTACTTCCAGA | (SEQ ID NO: 499) |
| TRBV9_BD | CTCTCTGTGTACTGGTACC | (SEQ ID NO: 500) |
| TRBJ primer name | | |
| TRBJ1-1 | CAACTGTGAGTCTGGTGCCTT | (SEQ ID NO: 501) |
| TRBJ1-2 | CTACAACGGTTAACCTGGTCC | (SEQ ID NO: 502) |
| TRBJ1-3 | CCTACAACAGTGAGCCAACTT | (SEQ ID NO: 503) |
| TRBJ1-4 | CAAGACAGAGAGCTGGGTTC | (SEQ ID NO: 504) |
| TRBJ1-5 | CTAGGATGGAGAGTCGAGTC | (SEQ ID NO: 505) |
| TRBJ1-6 | CTGTCACAGTGAGCCTGGTC | (SEQ ID NO: 506) |
| TRBJ2-1 | CTGGCCCGAAGAACTGCT | (SEQ ID NO: 507) |
| TRBJ2-2 | TCAGCCTAGAGCCTTCTCCA | (SEQ ID NO: 508) |
| TRBJ2-3 | GTGCCTGGGCCAAAATACTG | (SEQ ID NO: 509) |
| TRBJ2-4 | GGCGCCGAAGTACTGAATGTT | (SEQ ID NO: 510) |
| TRBJ2-5 | CCTGGCCCGAAGTACTGG | (SEQ ID NO: 511) |
| TRBJ2-6 | GTCAGCCTGCTGCCGGC | (SEQ ID NO: 512) |
| TRBJ2-7 | GTGACCGTGAGCCTGGT | (SEQ ID NO: 513) |
| TCRB-constant | [sequencing instrument primer][barcode] tctgatggctcaaacacagc | (SEQ ID NO: 514) |

Sub-TABLE 5i

| Primers for TCRG | | |
|---|---|---|
| TCRg V_primer name | | |
| primer_name | TCR_g_V_region_sequences | |
| Vg1f | [SEQUENCING INSTRUMENT PRIMER][barcode]GGAAGGCCCCACAGCRTCTT | (SEQ ID NO: 515) |
| Vg10 | [SEQUENCING INSTRUMENT PRIMER][barcode]AGCATGGGTAAGACAAGCAA | (SEQ ID NO: 516) |
| Vg9 | [SEQUENCING INSTRUMENT PRIMER][barcode]CGGCACTGTCAGAAAGGAATC | (SEQ ID NO: 517) |
| Vg11 | [SEQUENCING INSTRUMENT PRIMER][barcode]CTTCCACTTCCACTTTGAA | (SEQ ID NO: 518) |
| TCRg_J_primer name | | |
| primer_name | TCRg_J_region TCRg_J_region | |
| J1.1/2.1 | [sequencing primer][barcode] TTACCAGGCGAAGTTACTATGAGC | (SEQ ID NO: 519) |
| J1.3/2.3 | [sequencing primer][barcode] GTGTTGTTCCACTGCCAAAGAG | (SEQ ID NO: 520) |

V_D_J_VDjunc_DJjunc

Healthy donor 1, First time-point

| | | |
|---|---|---|
| IGHV1-18*01_IGHD2-21*02_IGHJ4*02_AAGGGC_GGCG | | (SEQ ID NO: 521) |
| IGHV3-21*02_IGHD3-22*01_IGHJ4*02_CCCCCCAGTAGGG_CGC | | (SEQ ID NO: 522) |
| IGHV5-a*03_IGHD3-22*01_IGHJ4*02_GGGGGTGC_CCTA | | (SEQ ID NO: 523) |
| IGHV5-a*03_IGHD4-17*01_IGHJ6*02_CGGA_CGTGCGGGG | | (SEQ ID NO: 524) |
| IGHV3-23*04_IGHD3-22*01_IGHJ6*02_TGGGGATACTGACAC_TGGAGTCCCCCCG | | (SEQ ID NO: 525) |
| IGHV2-70*01_IGHD3-22*01_IGHJ3*02_GTT_CCGACCGGGG | | (SEQ ID NO: 526) |
| IGHV3-21*02_IGHD3-9*01_IGHJ6*02_GGTCCCCTCTGGGA_GGGGCCAGG | | (SEQ ID NO: 527) |
| IGHV3-23*04_IGHD6-19*01_IGHJ5*02_GTTTCCTAAT_CGAAT | | (SEQ ID NO: 528) |
| IGHV2-5*08_IGHD3-22*01_IGHJ5*02_CGGCGCG_CG | | (SEQ ID NO: 529) |
| IGHV3-15*02_IGHD1-26*01_IGHJ3*02_TCTGTGG_CCG | | (SEQ ID NO: 530) |
| IGHV3-15*02_IGHD2-2*03_IGHJ6*02_CCCGTATGC_CTG | | (SEQ ID NO: 531) |
| IGHV1-2*03_IGHD2-2*03_IGHJ4*02_TCGGGTCC_CGTACGGCCCCTTCCGAT | | (SEQ ID NO: 532) |
| IGHV3-23*04_IGHD3-3*01_IGHJ6*02_CTTAGAAC_GACA | | (SEQ ID NO: 533) |
| IGHV6-1*02_IGHD3-3*01_IGHJ5*02_NO-BASES | | |
| IGHV1-69*13_IGHD5-12*01_IGHJ6*02_TGCCAGTA_NO-BASES | | (SEQ ID NO: 534) |
| IGHV1-69*09_IGHD2-2*03_IGHJ5*02_GGCCCCACG_NO_BASES | | (SEQ ID NO: 535) |
| IGHV3-11*03_IGHD1-26*01_IGHJ6*02_CGGCACTTGA_NO_BASES | | (SEQ ID NO: 536) |
| IGHV3-7*01_IGHD5-24*01_IGHJ4*03_NO-BASES_NO_BASES | | |
| IGHV3-21*02_IGHD1-26*01_IGHJ4*02_TCCGC_NO-BASES | | (SEQ ID NO: 537) |

Healthy donor 1, Second time-point

| | | |
|---|---|---|
| IGHV3-21*02_IGHD6-19*01_IGHJ6*02_TGAGGA_GCCG | | (SEQ ID NO: 538) |
| IGHV3-53*01_IGHD6-19*01_IGHJ4*02_AAGGGG_C | | (SEQ ID NO: 539) |
| IGHV3-48*01_IGHD2-2*01_IGHJ5*02_TGTGG_GCGAACCC | | (SEQ ID NO: 540) |
| IGHV3-23*04_IGHD6-19*01_IGHJ4*02_TGACATT_TAG | | (SEQ ID NO: 541) |

Sub-TABLE 5i-continued

Primers for TCRG

| | |
|---|---|
| IGHV3-23*04_IGHD2-15*01_IGHJ6*02_AGGTCT_CCATCCGGGTC | (SEQ ID NO: 542) |
| IGHV3-23*04_IGHD3-3*01_IGHJ5*02_CCCC_TGGGG | (SEQ ID NO: 543) |
| IGHV1-69*13_IGHD3-16*02_IGHJ5*02_CAGA_TTAC | (SEQ ID NO: 544) |
| IGHV3-15*02_IGHD3-10*02_IGHJ4*02_TCTAGAGACCGTGGCA_CCCA | (SEQ ID NO: 545) |
| IGHV1-45*03_IGHD3-22*01_IGHJ5*02_TGTTCGCAACTG_TG | (SEQ ID NO: 546) |
| IGHV4-31*03_IGHD1-26*01_IGHJ4*02_TCGA_CCCG | (SEQ ID NO: 547) |
| IGHV1-18*01_IGHD2-15*01_IGHJ6*02_GCTCCCTGTAGAATTT_CGTCCCGAAACCGAT | (SEQ ID NO: 548) |
| IGHV1-69*13_IGHD4-23*01_IGHJ1*01_TCAC_CCT | (SEQ ID NO: 549) |
| IGHV4-61*08_IGHD2-15*01_IGHJ6*02_TGATCGCCGCCGATA_TTTCTCCGGCA | (SEQ ID NO: 550) |
| IGHV3-30*17_IGHD1-7*01_IGHJ5*02_TCGGGAGGACGGACGGGG_TATAGGT | (SEQ ID NO: 551) |
| IGHV4-39*01_IGHD6-13*01_IGHJ4*02_TGTTGACCGGG_ACCGTGA | (SEQ ID NO: 552) |
| IGHV1-2*04_IGHD2-2*03_IGHJ6*02_GGCGG_TGGGG | (SEQ ID NO: 553) |
| IGHV3-33*01_IGHD4-17*01_IGHJ5*02_TCGA_TCGGG | (SEQ ID NO: 554) |
| IGHV1-46*03_IGHD1-26*01_IGHJ1*01_GG_CGAGGCC | (SEQ ID NO: 555) |
| IGHV4-61*08_IGHD3-10*01_IGHJ4*02_GAGCACGG_C | (SEQ ID NO: 556) |
| IGHV3-30*19_IGHD3-10*01_IGHJ4*02_TGTTACAA_CCCCATTACC | (SEQ ID NO: 557) |
| IGHV3-33*01_IGHD2-8*01_IGHJ6*02_GAGAGG_NO-BASES | (SEQ ID NO: 558) |
| IGHV1-2*03_IGHD2-2*01_IGHJ3*02_CAGTACGGGGGACCCT_NO-BASES | (SEQ ID NO: 559) |
| IGHV3-30*02_IGHD3-10*01_IGHJ4*02_CCTCTCACCA_NO-BASES | (SEQ ID NO: 560) |
| IGHV4-61*08_IGHD6-13*01_IGHJ2P*01_CAC . . . GAC_NO-BASES | (SEQ ID NO: 561) |
| IGHV3-74*03_IGHD1-26*01_IGHJ6*02_GGCCGGTAGTGTCA_NO-BASES | (SEQ ID NO: 562) |

In replicates from both time-points

| | |
|---|---|
| IGHV4-31*03_IGHD3-10*02_IGHJ6*02_GGACAGC_CCGCC | (SEQ ID NO: 563) |
| IGHV4-39*01_IGHD2-2*03_IGHJ5*02_TCTTCCGTTGTGGCTCCA_TCA | (SEQ ID NO: 564) |
| IGHV1-69*13_IGHD3-3*01_IGHJ6*02_CGTTCGCCC_AC | (SEQ ID NO: 565) |
| IGHV3-7*01_IGHD2-2*03_IGHJ6*02_TGAG_AAGAGGTC | (SEQ ID NO: 566) |
| IGHV3-9*01_IGHD1-26*01_IGHJ5*02_GATACCTATTGGGGT_CGGGGCGTTC | (SEQ ID NO: 567) |
| IGHV1-69*13_IGHD3-10*01_IGHJ4*02_CTAGAATCCTT_GG | (SEQ ID NO: 568) |
| IGHV4-39*05_IGHD6-19*01_IGHJ1*01_TGGGGTAACC_AGGTACCCGGGG | (SEQ ID NO: 569) |
| IGHV1-8*01_IGHD2-2*03_IGHJ6*02_GGGAATAG_CCCCCCC | (SEQ ID NO: 570) |
| IGHV4-39*01_IGHD5-5*01_IGHJ6*02_TGTAGCCC_GGGGTTTCG | (SEQ ID NO: 571) |
| IGHV3-23*04_IGHD6-19*01_IGHJ5*02_GCTCAGGG_GGGTTAGG | (SEQ ID NO: 572) |
| IGHV4-31*03_IGHD1-26*01_IGHJ2*01_CGCCCGGG_TGA | (SEQ ID NO: 573) |
| IGHV3-72*01_IGHD1-7*01_IGHJ4*02_TTAAGT_CCGAATC | (SEQ ID NO: 574) |
| IGHV4-61*08_IGHD5-12*01_IGHJ6*02_GGGGC_C | (SEQ ID NO: 575) |
| IGHV4-61*08_IGHD3-10*01_IGHJ6*02_TAGTGGGCTG_CAC | (SEQ ID NO: 576) |
| IGHV2-70*01_IGHD3-22*01_IGHJ6*02_GTCC_CCCTTGGG | (SEQ ID NO: 577) |
| IGHV4-39*01_IGHD3-10*01_IGHJ6*02_GTCCCCAACCCC_GCCC | (SEQ ID NO: 578) |

Sub-TABLE 5i-continued

Primers for TCRG

| | |
|---|---|
| IGHV3-21*02_IGHD2-15*01_IGHJ6*02_TCA_CCA | (SEQ ID NO: 579) |
| IGHV4-31*03_IGHD1-26*01_IGHJ4*02_CTCCCCGCAAGA_GGGCGCCTTCAAGGAA | (SEQ ID NO: 580) |
| IGHV6-1*02_IGHD2-8*01_IGHJ6*02_CCCAAGCAA_ATTTCTCCGA | (SEQ ID NO: 581) |
| IGHV3-21*02_IGHD6-6*01_IGHJ6*02_TG_TTTCT | (SEQ ID NO: 582) |
| IGHV3-21*02_IGHD2-15*01_IGHJ4*02_CCATAGG_GCG | (SEQ ID NO: 583) |
| IGHV1-46*02_IGHD3-3*02_IGHJ5*02_TTCGAGTGGTAAA_TGGG | (SEQ ID NO: 584) |
| IGHV1-46*02_IGHD3-22*01_IGHJ4*02_GGGTTCCTCG_NO-BASES | (SEQ ID NO: 585) |
| IGHV3-h*01_IGHD2-15*01_IGHJ6*04_C_NO-BASES | (SEQ ID NO: 586) |
| IGHV4-61*08_IGHD3-3*01_IGHJ6*02_NO-BASES_GAGCTTCGTATCTCCC | (SEQ ID NO: 587) |
| IGHV3-7*01_IGHD6-13*01_IGHJ4*02_CTG_NO-BASES | (SEQ ID NO: 588) |
| IGHV3-21*02_IGHD3-16*02_IGHJ4*02_AGGGTCGGG_NO-BASES | (SEQ ID NO: 589) |
| IGHV3-48*02_IGHD2-8*01_IGHJ6*02_GCCCTA_NO-BASES | (SEQ ID NO: 590) |
| IGHV3-21*02_IGHD3-22*01_IGHJ4*02_NO-BASES_AAC | (SEQ ID NO: 591) |
| IGHV3-21*02_IGHD5-24*01_IGHJ5*02_NO-BASES_TCCCT | (SEQ ID NO: 592) |
| IGHV4-34*02_IGHD3-9*01_IGHJ5*02_CTCTCGGTTCAGGGGAGG_NO-BASES | (SEQ ID NO: 593) |
| IGHV4-61*08_IGHD5-24*01_IGHJ2*01_GGGCCTAC_NO-BASES | (SEQ ID NO: 594) |

Detailed Description of Clonality and Diversity Calculations i.

Introduction to this section: In what follows, we describe three calculations related to diversity and clonality in the immune response. The repertoire of immune rearrangements consists of a remarkable diversity of potential receptors that can be encoded. For the immunoglobulin heavy chain, the product of 27 D regions*6 J regions*>50 V regions*two junctions [which can have any sequence and variable length, hence millions of possible sequences] yields a virtually limitless set of possibilities. We use this information to categorize each sequence. This assignment also yields a grouping of individual sequences in terms of their origins. Several points should be made in advance about the calculations to be described. 1. Each yields a lower bound as to the diversity in the populations of cells present in the B cell repertoire. Upper bounds cannot simply be estimated, as we cannot rule out the possibility of very large numbers of rare clones (e.g., single-cell clones) that would contribute rather modestly to the total number of cells but substantially to the diversity of specificities. The lower bounds derived from this analysis are nonetheless remarkable and are of considerable interest in understanding the immune repertoire and immune responses. 2. For several of the calculations, we begin with a very restrictive (and likely unrealistic) assumption that a subset of individual rearrangements are represented in equal numbers in a population; we calculate frequencies based on this assumptions, and then show that the result provides an lower bound for a "real world" situation in which individual rearrangements are represented at different frequencies in the population. 3. There is a PCR-based redundancy in the amplicon pools. That is, there are many cases in which a single sequence has been captured in the PCR reaction that gave rise to a given amplicon pool, with several amplified products from the same original template molecule sequenced. This is highly evident in looking at the complex normal samples in that the number of coincidences between samples (identical sequence assignments that occur in more than one aliquot) is much fewer than the number of coincidences within each sample. We also see a high number of coincident sequences (data not shown) in duplicate runs of sequence from the same amplification reaction in different 454 sequencing runs. Thus much of the sequence redundancy in the individual aliquots is due to simple "oversampling" of the sequence pool. ii.

For the purposes of complexity estimates, we define a number of terms that refer to groups of sequences either in the biological repertoire or in the experimental dataset.

Estimates of upper bound for amplified clonal populations: For any given clone (which we'll arbitrarily designate "Clone1") in a given individual (who we'll arbitrarily designate "Individual1"), a key value is the number of times that clone is represented in the total blood of the individual. The number of total rearranged rIgH-DNA segments in Individual1 with the Clone1 rearrangement is designated Individual1.Incidence(Clone1). We can also define a total number of rearranged IgH DNA segments as Individual1.Incidence(AllClones). The relative incidence of Clone1 in the population is then given by Individual1.Incidence(Clone1)/Individual1.Incidence(AllClones) We will abbreviate this with the value f1, or long-form Individual1.Fraction(Clone1). So far, f1 is a property of the individual and the clone and not an experimental value. We can reasonably assume that for each rIgH-DNA included in an Aliquot, there is a probability f1 that that rIgH-DNA corresponds to Clone1. The segment then needs to jump through two hoops before we sequence it. First it has to be captured using the V- and J-segment specific primers during the initial amplification reaction, so that it starts amplifying, second it needs to be present in the pool of sequences that are actually utilized for emulsion PCR and sequencing in the 454 instrument protocol. It is conceivable for any given sequence that either of these processes is highly inefficient (or unusually efficient), so that Clone1 would be under-represented or over-represented in the pool of determined sequences. We use the adjusted value fa to indicate the value f adjusted to account for sequence-specific differences in capture and/or amplification. Thus fa is the fraction of sequences (in a large sample set) that would be available and sequence-ready following a requirement for initial capture and amplification. Each Aliquot's data set derives from a sample subset with a certain number of cells, each represented a variable number of times in the sequence data from that Aliquot. Of the clones present in the original sample and not represented in the data obtained from a specific Aliquot's dataset, a fraction will have been lost due to not being in the Aliquot (due to a finite size of the aliquot), a fraction will be absent due to not having been captured in the initial PCR amplification reaction, and a fraction will be present in the amplified mixture of sequences from the aliquot but not been fortunate enough to attach to a bead that was actually sequenced. For an exemplary Aliquot ("Aliquot1") and an exemplary clone ("Clone1"), fa1 is the probability that any individual independently-derived read that is present in Aliquot1's dataset would have come from Clone1. The number of opportunities to choose an instance of Clone1 in the sample will be the number of independently-derived sequences present in the Aliquot1 dataset (which we'll call "S1"). For a blood sample containing an extensive diversity of B cells (i.e. cases in which coincidences between independent aliquots of the same blood sample are a small fraction of the total sequence diversity, a condition met by all of the healthy samples in our dataset), S1 is very close to the number of unique Clone identities (which we'll call "U1") represented in the aliquot's DNA sequence read dataset. For samples with greater redundancy (e.g. for future analysis of samples from individuals undergoing concerted immune responses), there is some potential under-estimation of S1 due to the possibility that more than one sequence from an individual clone was independently captured and is represented in a given Aliquot's dataset. That this effect is extremely small in our normal samples is evident in that the numbers of coincidences between samples is very small relative to the total number of unique sequences in each sample. The correction value in the case where there were a more substantial number of coincidences would be S1=U1/(1−frco) where frco is the fraction of sequenced rIgH-DNAs that are co-detected in an equivalent but independent aliquot of the same DNA. Although a precise value for frco is not easily calculated from the data, a rough estimate and hard upper bound can be experimentally determined as the fraction of sequence Reads that are shared between independent and equivalent aliquots. Given the observed coincidence frequencies, we again stress that the adjustment for our normal samples (on S1 values that are in the hundreds and thousands and coincidence values generally in the single digits) is negligible. At this point, we can describe the probability of an arrangement of positive and negative results for detection of a particular clonal sequence within n different aliquots based on S1, S2 . . . Sn and fa. As an example, the probability that S1 and S2 would be positive for Clone1 but S3, S4, and S5 would be negative would be $(1-(1-f)^{S1})*(1-(1-f)^{S1})*((1-f)^{S3})*((1-f)^{S4})*((1-f)^{S5})$. This is just one way that we can get a situation where there are two positive and three negative aliquots. To get a more complete picture, we can take all subsets P of the set 1 . . . n which contain up to two members and calculate $$\sum_P \left\{ \prod_{i \in P}^{(i)} (1-(1-fa)^{Si})_{j \in P}^{(j)} - fa \right)^{Sj} \right\}.$$

Plugging the values of Si in for the six independent replicates of the first time point on the normal blood sample, we get an estimate of how frequently a clone Clone1 of frequency f would have appeared in at least three of the individual aliquots. Reassuringly, this value is near 100% for a value of fa that is near 1, and 0% if fa is vanishingly small. At fa=1/1040, this value crosses 99%. This says we'd have had a >99% chance of having 3 or more aliquots positive for any clone whose occurrence in the detected B cell repertoire was >1/1040. This would correspond to any clone consisting of more than approximately 2,000,000 B cells in a total blood B cell population of $2\times10^9$ cells.

Estimating a lower bound for Ig-rearrangement diversity in each sequenced aliquot Next we calculate the minimum numbers of individual sequences that were captured and amplified in the sequenced libraries. Here we start with the assumption of a set of sequences that are present in the amplified pool, each with a distinct probability of being recruited in the emulsion PCR for 454 sequencing. Some of these sequences may be (and in this case certainly are) represented at higher levels than others in the 454 sequencing pool. For this calculation, we are interested in what number of sequences are present in this pool at levels comparable to those that are captured for sequencing in the incidence=1 class but which were "unlucky" in not getting picked. The distribution of frequencies for individual classes of sequence can be thought of as a sum of Poisson distributions for different probabilities of inclusion. We can then use P[1] and P[2] to get a lower bound for P[0], using the fact that any variation in values of the probability of capture fa between different groups of clones will actually increase the frequency of P[0] relative to what would be predicted from the simple Poisson model. To make our lower bound estimate of the P[0] class, we use the facts $P[0]=\exp(-fa*Si)$ $P[1]=(fa*Si)*\exp(-fa*Si)$ $P[2]=(fa*Si)^2*\exp(-fa*Si)/2$ So $P[0]=P[1]*(P[1]/P[2]*2)$ It should be stressed that this leads us to a lower limit on P[0], since any variation, particularly at the low end in fa will yield a class of clones with lower inclusion frequency that could be quite large. When these calculations are performed on the real data from the canonical healthy human sample, we obtain the following numbers:

Table of Calculated Sequence Incidences in PCR Amplicon Pools

Table of Calculated Sequence Incidences in PCR Amplicon Pools

| | Total | S01 | S02 | S03 | S04 | S24 | S25 | S26 | S27 | S28 | S29 | S30 | S31 | S32 |
|---|---|---|---|---|---|---|---|---|---|---|---|---|---|---|
| Distinct Sequences | 18315 | 2116 | 2264 | 1234 | 1088 | 1687 | 1558 | 1151 | 1088 | 1529 | 1786 | 827 | 914 | 1173 |
| 1 Hit Sequences | na | 923 | 966 | 504 | 402 | 687 | 612 | 456 | 435 | 628 | 713 | 334 | 324 | 485 |
| 2_Hit_Sequences | na | 215 | 297 | 118 | 160 | 183 | 201 | 101 | 92 | 172 | 226 | 120 | 105 | 93 |
| Est. 0_Hit_Seq (lower bound) | na | 1981 | 1571 | 1076 | 505 | 1290 | 932 | 1029 | 1028 | 1146 | 1125 | 465 | 500 | 1265 |
| Est. total distinct Seq (incl 0_hit) | na | 4097 | 3835 | 2310 | 1593 | 2977 | 2490 | 2180 | 2116 | 2675 | 2911 | 1292 | 1414 | 2438 |
| Actual measured sequences | na | 7845 | 7292 | 5411 | 3878 | 6435 | 5032 | 4958 | 5951 | 5303 | 5999 | 2383 | 3769 | 6625 |

Samples S01, S02, S24, S25, S28, and S29 are from time point 1 while S03, S04, S26, S27, S30, S31, and S32 are from time point 2. Note that the total estimated available complexities of the pools used for 454 sequencing are in the range of 2490-4097 for time point 1 of this healthy human sample. The number of B cells added to these amplifications was estimated at 2750. This argues strongly against a large number of B cells with poorly captured, non-amplifiable, or non-sequencable rearrangements. Note also that there is an uncertainty in these calculations as to what fraction of B cells have one versus two amplifiable rearrangements. We observe in-frame stop codons in approximately 20% of the sequences from our dataset (data not shown), suggesting that non-productive rearrangements are likely to be only a modest fraction of the total sequence space. From this analysis, it is clear that a substantial fraction of functional rearrangements can be amplified in this protocol. v. Estimating a lower bound for Ig-rearrangement diversity in an individual following sequencing of several aliquots. Next we calculate a minimal diversity for the sequence space being explored in an individual for whom we have sequences from several aliquots. Start in this case with the assumption that there are a large number of micro-clones each with a frequency fa in the population. For any instance of a unique sequence in a set, the probability of that sequence showing up in any given instance in another set is fa. The probability of showing up in another specific aliquot (j) is $1-(1-fa)^{Sj}$. So the number of expected coincidences from this sequence is $\Sigma_{j \neq i}(1-(1-fa)^{Sj})$. The total number of expected coincidences from all of the sequences in Aliquot (i) is then $Si*\Sigma_{j \neq i}(1-(1-fa)^{Sj})$. The total number of coincidences between sequences in different aliquots is then expected to be $\Sigma_i(Si*\Sigma_{j \neq i}(1-(1-fa)^{Sj}))/2$ (divided by two since we've counted each coincidence twice). Note that we operate on real observed sequences P[1], P[2], . . . , not on the P[0] class above since we have no way to estimate coincidences that involve the P[0] class.

If the distribution of frequencies fa were to be non-uniform (i.e. not the same for every clone), the complexity could potentially be larger than the minimum estimates here, not smaller. The argument for this is reasonably intuitive: a non-uniform distribution of frequencies will serve to increase the frequency of coincidences for a given base of complexity. Thus the coincidences may all frequently come from a class of clones that are over-represented relative to the bulk of (relatively rare clones). We note that the above complexity estimates were based on a situation where there were binary coincidences (sequences that were present in two aliquots) but no higher order coincidences (sequences present in more than two aliquots). Where higher order coincidences are present, the reflect evidence for amplified clones (see above) but not necessarily the complexity of the IgHDNA population as a whole. Fortunately it is possible to provide an upper bound on complexity in which only true binary coincidences are considered. The following calculation allows this. The number of expected true binary coincidences from a given sequence is $\Sigma_{j \neq i}[(1-(1-fa)^{Sj})*\Pi_{k \neq (i \, or \, j)}(1-fa)^{Sk}]$. The total number of expected coincidences from all of the sequences in Aliquot (i) is then $Si*\Sigma_{j \neq i}[(1-(1-fa)^{Sj})*\Pi_{k \neq (i \, or \, j)}(1-fa)^{Sk}]$. The total number of coincidences between sequences in different aliquots is then expected to be $\Sigma_i\{Si*\Sigma_{j \neq i}[(1-(1-fa)^{Sj})*\Pi_{k \neq (i \, or \, j)}(1-fa)^{Sk}]\}/2$.

Example 2

Analysis of Vaccination Responses by Immune Receptor Sequencing Materials and Methods Specimens.

De-identified specimens of genomic DNA from human peripheral blood mononuclear cells were obtained under Institutional Review Board approved protocols at our institution (Stanford University). Subjects were recruited at Duke University and provided informed consent, and the Duke University Institutional Review Board approved the protocols for all studies. Subjects were given trivalent inactivated seasonal influenza vaccine. Blood was drawn from immunized subjects on day 0 before vaccination and on days 7 and 21 after challenge.

Serological measurements. Subjects were classified as influenza vaccine 'seroconverters' or 'non-seroconverters' based on measurements of pre-vaccination and day 21 post-vaccination plasma antibody titers in hemagglutination inhibition assays (Cottey et al. Influenza virus. Curr Protoc Immunol Chapter 19, Unit 19 11 (2001)). 'Seroconverters' were those whose titer increased 4-fold above pre-vaccination baseline, or increased from undetectable at baseline to at least 1:40. Influenza stocks were grown in embryonated eggs and were titered for hemagglutination units on turkey red blood cells. To perform HAI assays, serial dilutions in PBS of plasma or transfected cell supernatants were placed into 96-well plates and were mixed with an equal volume of washed turkey red blood cells (0.5%) and incubated at room temperature for 30 min before hemagglutination was read directly from the wells.

DNA Template Preparation. Peripheral blood mononuclear cells were isolated by centrifugation of diluted whole blood over Hypaque 1077 (Sigma-Aldrich). Column purification (Qiagen, Valencia, Calif.) was used to isolate genomic DNA template.

PCR amplifications and sequencing sample preparation. PCR amplifications were performed using 100 ng of template genomic DNA for each of 6 replicate PCR amplifications for each sample. 10 pg of each primer, and 0.5 µL of AmpliTaq Gold enzyme (Applied Biosystems, Foster City, Calif.) per 50 µL reaction were used. Primers are shown in Table 6. Initial PCR amplification used the following program: (95° C. for 10 minutes); 35 cycles of (95° C. for 30 seconds, 58° C. for 45 seconds, 72° C. for 90 seconds); (72° C. for 10 minutes). 10 µL of the products were amplified for 2 additional cycles in fresh PCR mix to minimize heteroduplexes in the final product (Boyd, S. D., et al. *Sci Transl Med* 1, 12ra23). Amplicons from the various replicate PCR reactions for all samples were pooled in equal amounts and purified by 1.5% agarose gel electrophoresis and gel extraction, with dissolution of the gel slice at room temperature in lysis buffer prior to column purification (Qiagen, Valencia, Calif.).

High-throughput pyrosequencing. Amplicon library pools were quantitated by real-time PCR (Roche, Conn.) or PicoGreen fluorescence assay (Invitrogen, Carlsbad, Calif.), (Parameswaran et al. (2007) *Nucleic Acids Res* 35, e130). Sequencing was performed on the 454 instrument using Titanium chemistry, with long-range amplicon pyrosequencing beginning from the "B" primer in the manufacturer's protocol (Roche, Conn.).

Sequence data analysis. Sequences from each input specimen were sorted based on recognition of a perfect match of the sample barcode and the IgHJ common primer, while individual replicate libraries from each sample were identified by a perfect match to the V primer barcode and IgHV segment primers. Alignment of rearranged IgH sequences to germline V, D and J segments, and determination of V-D junctions and D-J junctions was performed using the IgBLAST algorithm (NCBI) and the iHMMune-align algorithm (Gaeta et aL (2007) *Bioinformatics* 23, 1580-1587). Sequences containing single base-pair insertions or deletions in the V or J gene segments were filtered from the dataset, based on the known error properties of pyrosequencing (Huse et al. (2007) *Genome Biol* 8, R143; Margulies et al. (2005) *Nature* 437, 376-380; Johnson et al. (2006) *Genome Res* 16, 1505-1516). Artifactual non-IgH sequences in the data were filtered out prior to further analysis.

Detection of 'Coincident Sequences' Providing Evidence for Amplified B Cell Clones.

"Coincident sequences," (those with identity in V, D, and J segment usage, and in V-D and D-J junctional bases) were detected as previously described (van Dongen et al. (2003) *Leukemia* 17, 2257-2317) by being identified in IgH amplicons sequence libraries from independent PCR replicates from an individual, and provide evidence of clonally expanded B cell populations. Sequences repeatedly observed within a single amplicon pool were not taken in isolation as evidence of an expanded B cell clone, as such "intra-pool" multi-copy sequences could be the result of amplification of a single initial molecule during PCR. In comparing the total number of 'coincident sequences' between samples or individuals, the total number of copies of a sequence within a replicate PCR library were included.

Normalization of 'Coincident Sequence' Counts.

To normalize the counts of 'coincident sequences' detected in samples that had been sequenced to different depths (i.e., where more total sequences had been obtained from the replicate amplification pools of one sample compared to another), the total number of coincident sequences detected between the PCR replicate libraries of a sample was divided by the total number of possible pairwise comparisons between sequences in different PCR replicate library data sets from that sample.

Results

Prediction of Seroconversion Status by Measurement of Normalized Coincident Sequence Counts Following Vaccination.

Evidence of expanded B cell clones in the blood following vaccination is provided by detection of coincident IgH VDJ sequences. Normalized counts of these coincident sequences using the approach described in the Materials and Methods reveal a diagnostic characteristic at day 7 post-vaccination of increased normalized coincident sequence counts in individuals who demonstrate vaccine-specific seroconversion (adequate increase of neutralizing anti-viral titers) at day 21 post-vaccination. There was a significant difference in the day 7 coincident sequence counts between the two groups ($p=0.03$, Mann-Whitney test) prior to normalization.

Change of hypermutation level of IgH V segments in coincident sequences at day 7 post-vaccination correlates with seroconversion. B cell clones in the blood (as assessed by detection of coincident sequences) following vaccination show consistently higher levels of hypermutation of IgH V segments compared to pre-vaccination samples in subjects who demonstrate vaccine-specific seroconversion (adequate increase of neutralizing anti-viral titers) at day 21 post-vaccination. Hypermutation levels are counted by comparing V segments in rearranged V(D)J to germline V segment sequences. The sequences set forth in Table 6 generally include a sequencing instrument primer, as indicated, linked to a barcode and a gene specific primer.

TABLE 6

Primers used for multiplexed and barcoded PCR amplification of IGH rearrangements.

| Primer Name | Sequence (5' to 3') | |
|---|---|---|
| Jhcons10mer-1 | [SEQUENCING INSTRUMENT PRIMER] TAGAAGCAAGCTTACCTGAGGAGACGGTGACC | (SEQ ID NO: 595) |
| Jhcons10mer-2 | [SEQUENCING INSTRUMENT PRIMER] TGTAAGCAAGCTTACCTGAGGAGACGGTGACC | (SEQ ID NO: 596) |
| Jhcons10mer-3 | [SEQUENCING INSTRUMENT PRIMER] CGGAAGCAAGCTTACCTGAGGAGACGGTGACC | (SEQ ID NO: 597) |
| Jhcons10mer-4 | [SEQUENCING INSTRUMENT PRIMER] CCTAAGCAAGCTTACCTGAGGAGACGGTGACC | (SEQ ID NO: 598) |
| Jhcons10mer-5 | [SEQUENCING INSTRUMENT PRIMER] AGCAAGCAAGCTTACCTGAGGAGACGGTGACC | (SEQ ID NO: 599) |

TABLE 6-continued

Primers used for multiplexed and barcoded PCR amplification of IGH rearrangements.

| Primer Name | Sequence (5' to 3') | |
|---|---|---|
| Jhcons10mer-6 | [SEQUENCING INSTRUMENT PRIMER] ATTAAGCAAGCTTACCTGAGGAGACGGTGACC | (SEQ ID NO: 600) |
| Jhcons10mer-7 | [SEQUENCING INSTRUMENT PRIMER] ACGAAGCAAGCTTACCTGAGGAGACGGTGACC | (SEQ ID NO: 601) |
| Jhcons10mer-8 | [SEQUENCING INSTRUMENT PRIMER] TAGAGGCAGGCTTACCTGAGGAGACGGTGACC | (SEQ ID NO: 602) |
| Jhcons10mer-9 | [SEQUENCING INSTRUMENT PRIMER] TTAAGGCAGGCTTACCTGAGGAGACGGTGACC | (SEQ ID NO: 603) |
| Jhcons10mer-10 | [SEQUENCING INSTRUMENT PRIMER] TGTAGGCAGGCTTACCTGAGGAGACGGTGACC | (SEQ ID NO: 604) |
| Jhcons10mer-11 | [SEQUENCING INSTRUMENT PRIMER] CGGAGGCAGGCTTACCTGAGGAGACGGTGACC | (SEQ ID NO: 605) |
| Jhcons10mer-12 | [SEQUENCING INSTRUMENT PRIMER] CCTAGGCAGGCTTACCTGAGGAGACGGTGACC | (SEQ ID NO: 606) |
| Jhcons10mer-13 | [SEQUENCING INSTRUMENT PRIMER] AGCAGGCAGGCTTACCTGAGGAGACGGTGACC | (SEQ ID NO: 607) |
| Jhcons10mer-14 | [SEQUENCING INSTRUMENT PRIMER] ATTAGGCAGGCTTACCTGAGGAGACGGTGACC | (SEQ ID NO: 608) |
| Jhcons10mer-15 | [SEQUENCING INSTRUMENT PRIMER] ACGAGGCAGGCTTACCTGAGGAGACGGTGACC | (SEQ ID NO: 609) |
| Jhcons10mer-16 | [SEQUENCING INSTRUMENT PRIMER] TAGCATTAGGCTTACCTGAGGAGACGGTGACC | (SEQ ID NO: 610) |
| Jhcons10mer-17 | [SEQUENCING INSTRUMENT PRIMER] TTACATTAGGCTTACCTGAGGAGACGGTGACC | (SEQ ID NO: 611) |
| Jhcons10mer-18 | [SEQUENCING INSTRUMENT PRIMER] TGTCATTAGGCTTACCTGAGGAGACGGTGACC | (SEQ ID NO: 612) |
| Jhcons10mer-19 | [SEQUENCING INSTRUMENT PRIMER] CGGCATTAGGCTTACCTGAGGAGACGGTGACC | (SEQ ID NO: 613) |
| Jhcons10mer-20 | [SEQUENCING INSTRUMENT PRIMER] CAACATTAGGCTTACCTGAGGAGACGGTGACC | (SEQ ID NO: 614) |
| Jhcons10mer-21 | [SEQUENCING INSTRUMENT PRIMER] CCTCATTAGGCTTACCTGAGGAGACGGTGACC | (SEQ ID NO: 615) |
| Jhcons10mer-22 | [SEQUENCING INSTRUMENT PRIMER] AGCCATTAGGCTTACCTGAGGAGACGGTGACC | (SEQ ID NO: 616) |
| Jhcons10mer-23 | [SEQUENCING INSTRUMENT PRIMER] ATTCATTAGGCTTACCTGAGGAGACGGTGACC | (SEQ ID NO: 617) |
| Jhcons10mer-24 | [SEQUENCING INSTRUMENT PRIMER] ACGCATTAGGCTTACCTGAGGAGACGGTGACC | (SEQ ID NO: 618) |
| Jhcons10mer-25 | [SEQUENCING INSTRUMENT PRIMER] TAGCATTCCACTTACCTGAGGAGACGGTGACC | (SEQ ID NO: 619) |
| Jhcons10mer-26 | [SEQUENCING INSTRUMENT PRIMER] TTACATTCCACTTACCTGAGGAGACGGTGACC | (SEQ ID NO: 620) |
| Jhcons10mer-27 | [SEQUENCING INSTRUMENT PRIMER] TGTCATTCCACTTACCTGAGGAGACGGTGACC | (SEQ ID NO: 621) |
| Jhcons10mer-28 | [SEQUENCING INSTRUMENT PRIMER] CGGCATTCCACTTACCTGAGGAGACGGTGACC | (SEQ ID NO: 622) |
| Jhcons10mer-29 | [SEQUENCING INSTRUMENT PRIMER] CAACATTCCACTTACCTGAGGAGACGGTGACC | (SEQ ID NO: 623) |
| Jhcons10mer-30 | [SEQUENCING INSTRUMENT PRIMER] CCTCATTCCACTTACCTGAGGAGACGGTGACC | (SEQ ID NO: 624) |

TABLE 6-continued

Primers used for multiplexed and barcoded PCR amplification of IGH rearrangements.

| Primer Name | Sequence (5' to 3') | |
|---|---|---|
| Jhcons10mer-31 | [SEQUENCING INSTRUMENT PRIMER]<br>AGCCATTCCACTTACCTGAGGAGACGGTGACC | (SEQ ID NO: 625) |
| Jhcons10mer-32 | [SEQUENCING INSTRUMENT PRIMER]<br>ATTCATTCCACTTACCTGAGGAGACGGTGACC | (SEQ ID NO: 626) |
| Jhcons10mer-33 | [SEQUENCING INSTRUMENT PRIMER]<br>ACGCATTCCACTTACCTGAGGAGACGGTGACC | (SEQ ID NO: 627) |
| Jhcons10mer-34 | [SEQUENCING INSTRUMENT PRIMER]<br>TAGCAATAAGCTTACCTGAGGAGACGGTGACC | (SEQ ID NO: 628) |
| Jhcons10mer-35 | [SEQUENCING INSTRUMENT PRIMER]<br>TTACAATAAGCTTACCTGAGGAGACGGTGACC | (SEQ ID NO: 629) |
| Jhcons10mer-36 | [SEQUENCING INSTRUMENT PRIMER]<br>TGTCAATAAGCTTACCTGAGGAGACGGTGACC | (SEQ ID NO: 630) |
| Jhcons10mer-37 | [SEQUENCING INSTRUMENT PRIMER]<br>CGGCAATAAGCTTACCTGAGGAGACGGTGACC | (SEQ ID NO: 631) |
| Jhcons10mer-38 | [SEQUENCING INSTRUMENT PRIMER]<br>CAACAATAAGCTTACCTGAGGAGACGGTGACC | (SEQ ID NO: 632) |
| Jhcons10mer-39 | [SEQUENCING INSTRUMENT PRIMER]<br>CCTCAATAAGCTTACCTGAGGAGACGGTGACC | (SEQ ID NO: 633) |
| Jhcons10mer-40 | [SEQUENCING INSTRUMENT PRIMER]<br>AGCCAATAAGCTTACCTGAGGAGACGGTGACC | (SEQ ID NO: 634) |
| Jhcons10mer-41 | [SEQUENCING INSTRUMENT PRIMER]<br>ATTCAATAAGCTTACCTGAGGAGACGGTGACC | (SEQ ID NO: 635) |
| Jhcons10mer-42 | [SEQUENCING INSTRUMENT PRIMER]<br>ACGCAATAAGCTTACCTGAGGAGACGGTGACC | (SEQ ID NO: 636) |
| Jhcons10mer-43 | [SEQUENCING INSTRUMENT PRIMER]<br>TAGCAATTCGCTTACCTGAGGAGACGGTGACC | (SEQ ID NO: 637) |
| Jhcons10mer-44 | [SEQUENCING INSTRUMENT PRIMER]<br>TTACAATTCGCTTACCTGAGGAGACGGTGACC | (SEQ ID NO: 638) |
| Jhcons10mer-45 | [SEQUENCING INSTRUMENT PRIMER]<br>TGTCAATTCGCTTACCTGAGGAGACGGTGACC | (SEQ ID NO: 639) |
| Jhcons10mer-46 | [SEQUENCING INSTRUMENT PRIMER]<br>CGGCAATTCGCTTACCTGAGGAGACGGTGACC | (SEQ ID NO: 640) |
| Jhcons10mer-47 | [SEQUENCING INSTRUMENT PRIMER]<br>CAACAATTCGCTTACCTGAGGAGACGGTGACC | (SEQ ID NO: 641) |
| Jhcons10mer-48 | [SEQUENCING INSTRUMENT PRIMER]<br>CCTCAATTCGCTTACCTGAGGAGACGGTGACC | (SEQ ID NO: 642) |
| Jhcons10mer-49 | [SEQUENCING INSTRUMENT PRIMER]<br>AGCCAATTCGCTTACCTGAGGAGACGGTGACC | (SEQ ID NO: 643) |
| Jhcons10mer-50 | [SEQUENCING INSTRUMENT PRIMER]<br>ATTCAATTCGCTTACCTGAGGAGACGGTGACC | (SEQ ID NO: 644) |
| Jhcons10mer-51 | [SEQUENCING INSTRUMENT PRIMER]<br>ACGCAATTCGCTTACCTGAGGAGACGGTGACC | (SEQ ID NO: 645) |
| Jhcons10mer-52 | [SEQUENCING INSTRUMENT PRIMER]<br>TAGCCAATAACTTACCTGAGGAGACGGTGACC | (SEQ ID NO: 646) |
| Jhcons10mer-53 | [SEQUENCING INSTRUMENT PRIMER]<br>TTACCAATAACTTACCTGAGGAGACGGTGACC | (SEQ ID NO: 647) |
| Jhcons10mer-54 | [SEQUENCING INSTRUMENT PRIMER]<br>TGTCCAATAACTTACCTGAGGAGACGGTGACC | (SEQ ID NO: 648) |
| Jhcons10mer-55 | [SEQUENCING INSTRUMENT PRIMER]<br>CGGCCAATAACTTACCTGAGGAGACGGTGACC | (SEQ ID NO: 649) |

TABLE 6-continued

Primers used for multiplexed and barcoded PCR amplification of IGH rearrangements.

| Primer Name | Sequence (5' to 3') | |
|---|---|---|
| Jhcons10mer-56 | [SEQUENCING INSTRUMENT PRIMER]<br>CAACCAATAACTTACCTGAGGAGACGGTGACC | (SEQ ID NO: 650) |
| Jhcons10mer-57 | [SEQUENCING INSTRUMENT PRIMER]<br>CCTCCAATAACTTACCTGAGGAGACGGTGACC | (SEQ ID NO: 651) |
| Jhcons10mer-58 | [SEQUENCING INSTRUMENT PRIMER]<br>ATTCCAATAACTTACCTGAGGAGACGGTGACC | (SEQ ID NO: 652) |
| Jhcons10mer-59 | [SEQUENCING INSTRUMENT PRIMER]<br>ACGCCAATAACTTACCTGAGGAGACGGTGACC | (SEQ ID NO: 653) |
| Jhcons10mer-60 | [SEQUENCING INSTRUMENT PRIMER]<br>TAGCCGGCAACTTACCTGAGGAGACGGTGACC | (SEQ ID NO: 654) |
| Jhcons10mer-61 | [SEQUENCING INSTRUMENT PRIMER]<br>TTACCGGCAACTTACCTGAGGAGACGGTGACC | (SEQ ID NO: 655) |
| Jhcons10mer-62 | [SEQUENCING INSTRUMENT PRIMER]<br>TGTCCGGCAACTTACCTGAGGAGACGGTGACC | (SEQ ID NO: 656) |
| Jhcons10mer-63 | [SEQUENCING INSTRUMENT PRIMER]<br>CGGCCGGCAACTTACCTGAGGAGACGGTGACC | (SEQ ID NO: 657) |
| Jhcons10mer-64 | [SEQUENCING INSTRUMENT PRIMER]<br>CAACCGGCAACTTACCTGAGGAGACGGTGACC | (SEQ ID NO: 658) |
| Jhcons10mer-65 | [SEQUENCING INSTRUMENT PRIMER]<br>CCTCCGGCAACTTACCTGAGGAGACGGTGACC | (SEQ ID NO: 659) |
| Jhcons10mer-66 | [SEQUENCING INSTRUMENT PRIMER]<br>ATTCCGGCAACTTACCTGAGGAGACGGTGACC | (SEQ ID NO: 660) |
| Jhcons10mer-67 | [SEQUENCING INSTRUMENT PRIMER]<br>ACGCCGGCAACTTACCTGAGGAGACGGTGACC | (SEQ ID NO: 661) |
| Jhcons10mer-68 | [SEQUENCING INSTRUMENT PRIMER]<br>TAGCCGCAGGCTTACCTGAGGAGACGGTGACC | (SEQ ID NO: 662) |
| Jhcons10mer-69 | [SEQUENCING INSTRUMENT PRIMER]<br>TTACCGCAGGCTTACCTGAGGAGACGGTGACC | (SEQ ID NO: 663) |
| Jhcons10mer-70 | [SEQUENCING INSTRUMENT PRIMER]<br>TGTCCGCAGGCTTACCTGAGGAGACGGTGACC | (SEQ ID NO: 664) |
| Jhcons10mer-71 | [SEQUENCING INSTRUMENT PRIMER]<br>CGGCCGCAGGCTTACCTGAGGAGACGGTGACC | (SEQ ID NO: 665) |
| Jhcons10mer-72 | [SEQUENCING INSTRUMENT PRIMER]<br>CAACCGCAGGCTTACCTGAGGAGACGGTGACC | (SEQ ID NO: 666) |
| Jhcons10mer-73 | [SEQUENCING INSTRUMENT PRIMER]<br>CCTCCGCAGGCTTACCTGAGGAGACGGTGACC | (SEQ ID NO: 667) |
| Jhcons10mer-74 | [SEQUENCING INSTRUMENT PRIMER]<br>ATTCCGCAGGCTTACCTGAGGAGACGGTGACC | (SEQ ID NO: 668) |
| Jhcons10mer-75 | [SEQUENCING INSTRUMENT PRIMER]<br>ACGCCGCAGGCTTACCTGAGGAGACGGTGACC | (SEQ ID NO: 669) |
| Jhcons10mer-76 | [SEQUENCING INSTRUMENT PRIMER]<br>TAGCCGTTAGCTTACCTGAGGAGACGGTGACC | (SEQ ID NO: 670) |
| Jhcons10mer-77 | [SEQUENCING INSTRUMENT PRIMER]<br>TTACCGTTAGCTTACCTGAGGAGACGGTGACC | (SEQ ID NO: 671) |
| Jhcons10mer-78 | [SEQUENCING INSTRUMENT PRIMER]<br>TGTCCGTTAGCTTACCTGAGGAGACGGTGACC | (SEQ ID NO: 672) |
| Jhcons10mer-79 | [SEQUENCING INSTRUMENT PRIMER]<br>CGGCCGTTAGCTTACCTGAGGAGACGGTGACC | (SEQ ID NO: 673) |
| Jhcons10mer-80 | [SEQUENCING INSTRUMENT PRIMER]<br>CAACCGTTAGCTTACCTGAGGAGACGGTGACC | (SEQ ID NO: 674) |

TABLE 6-continued

Primers used for multiplexed and barcoded PCR amplification of IGH rearrangements.

| Primer Name | Sequence (5' to 3') | |
|---|---|---|
| Jhcons10mer-81 | [SEQUENCING INSTRUMENT PRIMER]<br>CCTCCGTTAGCTTACCTGAGGAGACGGTGACC | (SEQ ID NO: 675) |
| Jhcons10mer-82 | [SEQUENCING INSTRUMENT PRIMER]<br>ATTCCGTTAGCTTACCTGAGGAGACGGTGACC | (SEQ ID NO: 676) |
| Jhcons10mer-83 | [SEQUENCING INSTRUMENT PRIMER]<br>ACGCCGTTAGCTTACCTGAGGAGACGGTGACC | (SEQ ID NO: 677) |
| Jhcons10mer-84 | [SEQUENCING INSTRUMENT PRIMER]<br>TAGCGGTAAGCTTACCTGAGGAGACGGTGACC | (SEQ ID NO: 678) |
| Jhcons10mer-85 | [SEQUENCING INSTRUMENT PRIMER]<br>TTACGGTAAGCTTACCTGAGGAGACGGTGACC | (SEQ ID NO: 679) |
| Jhcons10mer-86 | [SEQUENCING INSTRUMENT PRIMER]<br>TGTCGGTAAGCTTACCTGAGGAGACGGTGACC | (SEQ ID NO: 680) |
| Jhcons10mer-87 | [SEQUENCING INSTRUMENT PRIMER]<br>CGGCGGTAAGCTTACCTGAGGAGACGGTGACC | (SEQ ID NO: 681) |
| Jhcons10mer-88 | [SEQUENCING INSTRUMENT PRIMER]<br>CAACGGTAAGCTTACCTGAGGAGACGGTGACC | (SEQ ID NO: 682) |
| Jhcons10mer-89 | [SEQUENCING INSTRUMENT PRIMER]<br>CCTCGGTAAGCTTACCTGAGGAGACGGTGACC | (SEQ ID NO: 683) |
| Jhcons10mer-90 | [SEQUENCING INSTRUMENT PRIMER]<br>AGCCGGTAAGCTTACCTGAGGAGACGGTGACC | (SEQ ID NO: 684) |
| Jhcons10mer-91 | [SEQUENCING INSTRUMENT PRIMER]<br>ATTCGGTAAGCTTACCTGAGGAGACGGTGACC | (SEQ ID NO: 685) |
| Jhcons10mer-92 | [SEQUENCING INSTRUMENT PRIMER]<br>ACGCGGTAAGCTTACCTGAGGAGACGGTGACC | (SEQ ID NO: 686) |
| Jhcons10mer-93 | [SEQUENCING INSTRUMENT PRIMER]<br>TAGTAGGCGGCTTACCTGAGGAGACGGTGACC | (SEQ ID NO: 687) |
| Jhcons10mer-94 | [SEQUENCING INSTRUMENT PRIMER]<br>TTATAGGCGGCTTACCTGAGGAGACGGTGACC | (SEQ ID NO: 688) |
| Jhcons10mer-95 | [SEQUENCING INSTRUMENT PRIMER]<br>TCCTAGGCGGCTTACCTGAGGAGACGGTGACC | (SEQ ID NO: 689) |
| Jhcons10mer-96 | [SEQUENCING INSTRUMENT PRIMER]<br>TGTTAGGCGGCTTACCTGAGGAGACGGTGACC | (SEQ ID NO: 690) |
| Jhcons10mer-97 | [SEQUENCING INSTRUMENT PRIMER]<br>CGGTAGGCGGCTTACCTGAGGAGACGGTGACC | (SEQ ID NO: 691) |
| Jhcons10mer-98 | [SEQUENCING INSTRUMENT PRIMER]<br>CAATAGGCGGCTTACCTGAGGAGACGGTGACC | (SEQ ID NO: 692) |
| Jhcons10mer-99 | [SEQUENCING INSTRUMENT PRIMER]<br>CCTTAGGCGGCTTACCTGAGGAGACGGTGACC | (SEQ ID NO: 693) |
| Jhcons10mer-100 | [SEQUENCING INSTRUMENT PRIMER]<br>AGCTAGGCGGCTTACCTGAGGAGACGGTGACC | (SEQ ID NO: 694) |
| Jhcons10mer-101 | [SEQUENCING INSTRUMENT PRIMER]<br>ACGTAGGCGGCTTACCTGAGGAGACGGTGACC | (SEQ ID NO: 695) |
| Jhcons10mer-102 | [SEQUENCING INSTRUMENT PRIMER]<br>TAGTAATAGGCTTACCTGAGGAGACGGTGACC | (SEQ ID NO: 696) |
| Jhcons10mer-103 | [SEQUENCING INSTRUMENT PRIMER]<br>TTATAATAGGCTTACCTGAGGAGACGGTGACC | (SEQ ID NO: 697) |
| Jhcons10mer-104 | [SEQUENCING INSTRUMENT PRIMER]<br>TCCTAATAGGCTTACCTGAGGAGACGGTGACC | (SEQ ID NO: 698) |
| Jhcons10mer-105 | [SEQUENCING INSTRUMENT PRIMER]<br>TGTTAATAGGCTTACCTGAGGAGACGGTGACC | (SEQ ID NO: 699) |

TABLE 6-continued

Primers used for multiplexed and barcoded PCR amplification of IGH rearrangements.

| Primer Name | Sequence (5' to 3') | |
|---|---|---|
| Jhcons10mer-106 | [SEQUENCING INSTRUMENT PRIMER]<br>CGGTAATAGGCTTACCTGAGGAGACGGTGACC | (SEQ ID NO: 700) |
| Jhcons10mer-107 | [SEQUENCING INSTRUMENT PRIMER]<br>CAATAATAGGCTTACCTGAGGAGACGGTGACC | (SEQ ID NO: 701) |
| Jhcons10mer-108 | [SEQUENCING INSTRUMENT PRIMER]<br>CCTTAATAGGCTTACCTGAGGAGACGGTGACC | (SEQ ID NO: 702) |
| Jhcons10mer-109 | [SEQUENCING INSTRUMENT PRIMER]<br>AGCTAATAGGCTTACCTGAGGAGACGGTGACC | (SEQ ID NO: 703) |
| Jhcons10mer-110 | [SEQUENCING INSTRUMENT PRIMER]<br>ACGTAATAGGCTTACCTGAGGAGACGGTGACC | (SEQ ID NO: 704) |
| Jhcons10mer-111 | [SEQUENCING INSTRUMENT PRIMER]<br>TAGTAACCAACTTACCTGAGGAGACGGTGACC | (SEQ ID NO: 705) |
| Jhcons10mer-112 | [SEQUENCING INSTRUMENT PRIMER]<br>TTATAACCAACTTACCTGAGGAGACGGTGACC | (SEQ ID NO: 706) |
| Jhcons10mer-113 | [SEQUENCING INSTRUMENT PRIMER]<br>TCCTAACCAACTTACCTGAGGAGACGGTGACC | (SEQ ID NO: 707) |
| Jhcons10mer-114 | [SEQUENCING INSTRUMENT PRIMER]<br>TGTTAACCAACTTACCTGAGGAGACGGTGACC | (SEQ ID NO: 708) |
| Jhcons10mer-115 | [SEQUENCING INSTRUMENT PRIMER]<br>CGGTAACCAACTTACCTGAGGAGACGGTGACC | (SEQ ID NO: 709) |
| Jhcons10mer-116 | [SEQUENCING INSTRUMENT PRIMER]<br>CAATAACCAACTTACCTGAGGAGACGGTGACC | (SEQ ID NO: 710) |
| Jhcons10mer-117 | [SEQUENCING INSTRUMENT PRIMER]<br>CCTTAACCAACTTACCTGAGGAGACGGTGACC | (SEQ ID NO: 711) |
| Jhcons10mer-118 | [SEQUENCING INSTRUMENT PRIMER]<br>AGCTAACCAACTTACCTGAGGAGACGGTGACC | (SEQ ID NO: 712) |
| Jhcons10mer-119 | [SEQUENCING INSTRUMENT PRIMER]<br>ACGTAACCAACTTACCTGAGGAGACGGTGACC | (SEQ ID NO: 713) |
| Jhcons10mer-120 | [SEQUENCING INSTRUMENT PRIMER]<br>TAGTCCGTAACTTACCTGAGGAGACGGTGACC | (SEQ ID NO: 714) |
| Jhcons10mer-121 | [SEQUENCING INSTRUMENT PRIMER]<br>TTATCCGTAACTTACCTGAGGAGACGGTGACC | (SEQ ID NO: 715) |
| Jhcons10mer-122 | [SEQUENCING INSTRUMENT PRIMER]<br>TCCTCCGTAACTTACCTGAGGAGACGGTGACC | (SEQ ID NO: 716) |
| Jhcons10mer-123 | [SEQUENCING INSTRUMENT PRIMER]<br>TGTTCCGTAACTTACCTGAGGAGACGGTGACC | (SEQ ID NO: 717) |
| Jhcons10mer-124 | [SEQUENCING INSTRUMENT PRIMER]<br>CGGTCCGTAACTTACCTGAGGAGACGGTGACC | (SEQ ID NO: 718) |
| Jhcons10mer-125 | [SEQUENCING INSTRUMENT PRIMER]<br>CAATCCGTAACTTACCTGAGGAGACGGTGACC | (SEQ ID NO: 719) |
| Jhcons10mer-126 | [SEQUENCING INSTRUMENT PRIMER]<br>CCTTCCGTAACTTACCTGAGGAGACGGTGACC | (SEQ ID NO: 720) |
| Jhcons10mer-127 | [SEQUENCING INSTRUMENT PRIMER]<br>AGCTCCGTAACTTACCTGAGGAGACGGTGACC | (SEQ ID NO: 721) |
| Jhcons10mer-128 | [SEQUENCING INSTRUMENT PRIMER]<br>ACGTCCGTAACTTACCTGAGGAGACGGTGACC | (SEQ ID NO: 722) |
| Jhcons10mer-129 | [SEQUENCING INSTRUMENT PRIMER]<br>TAGTGGCAAGCTTACCTGAGGAGACGGTGACC | (SEQ ID NO: 723) |
| Jhcons10mer-130 | [SEQUENCING INSTRUMENT PRIMER]<br>TTATGGCAAGCTTACCTGAGGAGACGGTGACC | (SEQ ID NO: 724) |

TABLE 6-continued

Primers used for multiplexed and barcoded PCR amplification of IGH rearrangements.

| Primer Name | Sequence (5' to 3') | |
|---|---|---|
| Jhcons10mer-131 | [SEQUENCING INSTRUMENT PRIMER]<br>TCCTGGCAAGCTTACCTGAGGAGACGGTGACC | (SEQ ID NO: 725) |
| Jhcons10mer-132 | [SEQUENCING INSTRUMENT PRIMER]<br>TGTTGGCAAGCTTACCTGAGGAGACGGTGACC | (SEQ ID NO: 726) |
| Jhcons10mer-133 | [SEQUENCING INSTRUMENT PRIMER]<br>CGGTGGCAAGCTTACCTGAGGAGACGGTGACC | (SEQ ID NO: 727) |
| Jhcons10mer-134 | [SEQUENCING INSTRUMENT PRIMER]<br>CAATGGCAAGCTTACCTGAGGAGACGGTGACC | (SEQ ID NO: 728) |
| Jhcons10mer-135 | [SEQUENCING INSTRUMENT PRIMER]<br>CCTTGGCAAGCTTACCTGAGGAGACGGTGACC | (SEQ ID NO: 729) |
| Jhcons10mer-136 | [SEQUENCING INSTRUMENT PRIMER]<br>AGCTGGCAAGCTTACCTGAGGAGACGGTGACC | (SEQ ID NO: 730) |
| Jhcons10mer-137 | [SEQUENCING INSTRUMENT PRIMER]<br>ACGTGGCAAGCTTACCTGAGGAGACGGTGACC | (SEQ ID NO: 731) |
| Jhcons10mer-138 | [SEQUENCING INSTRUMENT PRIMER]<br>TAGTCCGGTGCTTACCTGAGGAGACGGTGACC | (SEQ ID NO: 732) |
| Jhcons10mer-139 | [SEQUENCING INSTRUMENT PRIMER]<br>TTATCCGGTGCTTACCTGAGGAGACGGTGACC | (SEQ ID NO: 733) |
| Jhcons10mer-140 | [SEQUENCING INSTRUMENT PRIMER]<br>TCCTCCGGTGCTTACCTGAGGAGACGGTGACC | (SEQ ID NO: 734) |
| Jhcons10mer-141 | [SEQUENCING INSTRUMENT PRIMER]<br>TGTTCCGGTGCTTACCTGAGGAGACGGTGACC | (SEQ ID NO: 735) |
| Jhcons10mer-142 | [SEQUENCING INSTRUMENT PRIMER]<br>CGGTCCGGTGCTTACCTGAGGAGACGGTGACC | (SEQ ID NO: 736) |
| Jhcons10mer-143 | [SEQUENCING INSTRUMENT PRIMER]<br>CAATCCGGTGCTTACCTGAGGAGACGGTGACC | (SEQ ID NO: 737) |
| Jhcons10mer-144 | [SEQUENCING INSTRUMENT PRIMER]<br>CCTTCCGGTGCTTACCTGAGGAGACGGTGACC | (SEQ ID NO: 738) |
| Jhcons10mer-145 | [SEQUENCING INSTRUMENT PRIMER]<br>AGCTCCGGTGCTTACCTGAGGAGACGGTGACC | (SEQ ID NO: 739) |
| Jhcons10mer-146 | [SEQUENCING INSTRUMENT PRIMER]<br>ACGTCCGGTGCTTACCTGAGGAGACGGTGACC | (SEQ ID NO: 740) |
| Jhcons10mer-147 | [SEQUENCING INSTRUMENT PRIMER]<br>TAGTCCTAAGCTTACCTGAGGAGACGGTGACC | (SEQ ID NO: 741) |
| Jhcons10mer-148 | [SEQUENCING INSTRUMENT PRIMER]<br>TTATCCTAAGCTTACCTGAGGAGACGGTGACC | (SEQ ID NO: 742) |
| Jhcons10mer-149 | [SEQUENCING INSTRUMENT PRIMER]<br>TCCTCCTAAGCTTACCTGAGGAGACGGTGACC | (SEQ ID NO: 743) |
| Jhcons10mer-150 | [SEQUENCING INSTRUMENT PRIMER]<br>TGTTCCTAAGCTTACCTGAGGAGACGGTGACC | (SEQ ID NO: 744) |
| Jhcons10mer-151 | [SEQUENCING INSTRUMENT PRIMER]<br>CGGTCCTAAGCTTACCTGAGGAGACGGTGACC | (SEQ ID NO: 745) |
| Jhcons10mer-152 | [SEQUENCING INSTRUMENT PRIMER]<br>CAATCCTAAGCTTACCTGAGGAGACGGTGACC | (SEQ ID NO: 746) |
| Jhcons10mer-165 | [SEQUENCING INSTRUMENT PRIMER]<br>TAGTTATTCGCTTACCTGAGGAGACGGTGACC | (SEQ ID NO: 747) |
| Jhcons10mer-166 | [SEQUENCING INSTRUMENT PRIMER]<br>TTATTATTCGCTTACCTGAGGAGACGGTGACC | (SEQ ID NO: 748) |
| Jhcons10mer-167 | [SEQUENCING INSTRUMENT PRIMER]<br>TCCTTATTCGCTTACCTGAGGAGACGGTGACC | (SEQ ID NO: 749) |

TABLE 6-continued

Primers used for multiplexed and barcoded PCR amplification of IGH rearrangements.

| Primer Name | Sequence (5' to 3') | |
|---|---|---|
| Jhcons10mer-168 | [SEQUENCING INSTRUMENT PRIMER]<br>CGGTTATTCGCTTACCTGAGGAGACGGTGACC | (SEQ ID NO: 750) |
| Jhcons10mer-169 | [SEQUENCING INSTRUMENT PRIMER]<br>CAATTATTCGCTTACCTGAGGAGACGGTGACC | (SEQ ID NO: 751) |
| Jhcons10mer-170 | [SEQUENCING INSTRUMENT PRIMER]<br>AGCTTATTCGCTTACCTGAGGAGACGGTGACC | (SEQ ID NO: 752) |
| Jhcons10mer-171 | [SEQUENCING INSTRUMENT PRIMER]<br>ACGTTATTCGCTTACCTGAGGAGACGGTGACC | (SEQ ID NO: 753) |
| Jhcons10mer-172 | [SEQUENCING INSTRUMENT PRIMER]<br>TAGTTAATCCCTTACCTGAGGAGACGGTGACC | (SEQ ID NO: 754) |
| Jhcons10mer-173 | [SEQUENCING INSTRUMENT PRIMER]<br>TTATTAATCCCTTACCTGAGGAGACGGTGACC | (SEQ ID NO: 755) |
| Jhcons10mer-174 | [SEQUENCING INSTRUMENT PRIMER]<br>TCCTTAATCCCTTACCTGAGGAGACGGTGACC | (SEQ ID NO: 756) |
| Jhcons10mer-175 | [SEQUENCING INSTRUMENT PRIMER]<br>CGGTTAATCCCTTACCTGAGGAGACGGTGACC | (SEQ ID NO: 757) |
| Jhcons10mer-176 | [SEQUENCING INSTRUMENT PRIMER]<br>CAATTAATCCCTTACCTGAGGAGACGGTGACC | (SEQ ID NO: 758) |
| VH2-FR2_10mer-1 | [SEQUENCING INSTRUMENT PRIMER]<br>CCTTCCTAAGTGGATCCGTCAGCCCCCAGGGAAGG | (SEQ ID NO: 759) |
| VH3-FR2_10mer-1 | [SEQUENCING INSTRUMENT PRIMER]<br>CCTTCCTAAGGGTCCGCCAGGCTCCAGGGAA | (SEQ ID NO: 760) |
| VH4-FR2_10mer-1 | [SEQUENCING INSTRUMENT PRIMER]<br>CCTTCCTAAGTGGATCCGCCAGCCCCCAGGGAAGG | (SEQ ID NO: 761) |
| VH5-FR2_10mer-1 | [SEQUENCING INSTRUMENT PRIMER]<br>CCTTCCTAAGGGGTGCGCCAGATGCCCGGGAAGG | (SEQ ID NO: 762) |
| VH6-FR2_10mer-1 | [SEQUENCING INSTRUMENT PRIMER]<br>CCTTCCTAAGTGGATCAGGCAGTCCCCATCGAGAG | (SEQ ID NO: 763) |
| VH7-FR2_10mer-1 | [SEQUENCING INSTRUMENT PRIMER]<br>CCTTCCTAAGTTGGGTGCGACAGGCCCTGGACAA | (SEQ ID NO: 764) |
| VH1-FR2_10mer-2 | [SEQUENCING INSTRUMENT PRIMER]<br>AGCTCCTAAGCTGGGTGCGACAGGCCCTGGACAA | (SEQ ID NO: 765) |
| VH2-FR2_10mer-2 | [SEQUENCING INSTRUMENT PRIMER]<br>AGCTCCTAAGTGGATCCGTCAGCCCCCAGGGAAGG | (SEQ ID NO: 766) |
| VH3-FR2_10mer-2 | [SEQUENCING INSTRUMENT PRIMER]<br>AGCTCCTAAGGGTCCGCCAGGCTCCAGGGAA | (SEQ ID NO: 767 |
| VH4-FR2_10mer-2 | [SEQUENCING INSTRUMENT PRIMER]<br>AGCTCCTAAGTGGATCCGCCAGCCCCCAGGGAAGG | (SEQ ID NO: 768) |
| VH5-FR2_10mer-2 | [SEQUENCING INSTRUMENT PRIMER]<br>AGCTCCTAAGGGGTGCGCCAGATGCCCGGGAAGG | (SEQ ID NO: 769) |
| VH6-FR2_10mer-2 | [SEQUENCING INSTRUMENT PRIMER]<br>AGCTCCTAAGTGGATCAGGCAGTCCCCATCGAGAG | (SEQ ID NO: 770) |
| VH7-FR2_10mer-2 | [SEQUENCING INSTRUMENT PRIMER]<br>AGCTCCTAAGTTGGGTGCGACAGGCCCTGGACAA | (SEQ ID NO: 771) |
| VH1-FR2_10mer-3 | [SEQUENCING INSTRUMENT PRIMER]<br>ACGTCCTAAGCTGGGTGCGACAGGCCCTGGACAA | (SEQ ID NO: 772) |
| VH2-FR2_10mer-3 | [SEQUENCING INSTRUMENT PRIMER]<br>ACGTCCTAAGTGGATCCGTCAGCCCCCAGGGAAGG | (SEQ ID NO: 773) |
| VH3-FR2_10mer-3 | [SEQUENCING INSTRUMENT PRIMER]<br>ACGTCCTAAGGGTCCGCCAGGCTCCAGGGAA | (SEQ ID NO: 774) |

TABLE 6-continued

Primers used for multiplexed and barcoded PCR amplification of IGH rearrangements.

| Primer Name | Sequence (5' to 3') |
|---|---|
| VH4-FR2_10mer-3 | [SEQUENCING INSTRUMENT PRIMER] (SEQ ID NO: 775) ACGTCCTAAGTGGATCCGCCAGCCCCCAGGGAAGG |
| VH5-FR2_10mer-3 | [SEQUENCING INSTRUMENT PRIMER] (SEQ ID NO: 776) ACGTCCTAAGGGGTGCGCCAGATGCCCGGGAAAGG |
| VH6-FR2_10mer-3 | [SEQUENCING INSTRUMENT PRIMER] (SEQ ID NO: 777) ACGTCCTAAGTGGATCAGGCAGTCCCCATCGAGAG |
| VH7-FR2_10mer-3 | [SEQUENCING INSTRUMENT PRIMER] (SEQ ID NO: 778) ACGTCCTAAGTTGGGTGCGACAGGCCCTGGACAA |
| VH1-FR2_10mer-4 | [SEQUENCING INSTRUMENT PRIMER] (SEQ ID NO: 779) TAGTGCCAGGCTGGGTGCGACAGGCCCTGGACAA |
| VH2-FR2_10mer-4 | [SEQUENCING INSTRUMENT PRIMER] (SEQ ID NO: 780) TAGTGCCAGGTGGATCCGTCAGCCCCCAGGGAAGG |
| VH3-FR2_10mer-4 | [SEQUENCING INSTRUMENT PRIMER] (SEQ ID NO: 781) TAGTGCCAGGGGTCCGCCAGGCTCCAGGGAA |
| VH4-FR2_10mer-4 | [SEQUENCING INSTRUMENT PRIMER] (SEQ ID NO: 782) TAGTGCCAGGTGGATCCGCCAGCCCCCAGGGAAGG |
| VH5-FR2_10mer-4 | [SEQUENCING INSTRUMENT PRIMER] (SEQ ID NO: 783) TAGTGCCAGGGGGTGCGCCAGATGCCCGGGAAAGG |
| VH6-FR2_10mer-4 | [SEQUENCING INSTRUMENT PRIMER] (SEQ ID NO: 784) TAGTGCCAGGTGGATCAGGCAGTCCCCATCGAGAG |
| VH7-FR2_10mer-4 | [SEQUENCING INSTRUMENT PRIMER] (SEQ ID NO: 785) TAGTGCCAGGTTGGGTGCGACAGGCCCTGGACAA |
| VH1-FR2_10mer-5 | [SEQUENCING INSTRUMENT PRIMER] (SEQ ID NO: 786) TGTTGCCAGGCTGGGTGCGACAGGCCCTGGACAA |
| VH2-FR2_10mer-5 | [SEQUENCING INSTRUMENT PRIMER] (SEQ ID NO: 787) TGTTGCCAGGTGGATCCGTCAGCCCCCAGGGAAGG |
| VH3-FR2_10mer-5 | [SEQUENCING INSTRUMENT PRIMER] (SEQ ID NO: 788) TGTTGCCAGGGGTCCGCCAGGCTCCAGGGAA |
| VH4-FR2_10mer-5 | [SEQUENCING INSTRUMENT PRIMER] (SEQ ID NO: 789) TGTTGCCAGGTGGATCCGCCAGCCCCCAGGGAAGG |
| VH5-FR2_10mer-5 | [SEQUENCING INSTRUMENT PRIMER] (SEQ ID NO: 790) TGTTGCCAGGGGGTGCGCCAGATGCCCGGGAAAGG |
| VH6-FR2_10mer-5 | [SEQUENCING INSTRUMENT PRIMER] (SEQ ID NO: 791) TGTTGCCAGGTGGATCAGGCAGTCCCCATCGAGAG |
| VH7-FR2_10mer-5 | [SEQUENCING INSTRUMENT PRIMER] (SEQ ID NO: 792) TGTTGCCAGGTTGGGTGCGACAGGCCCTGGACAA |
| VH1-FR2_10mer-6 | [SEQUENCING INSTRUMENT PRIMER] (SEQ ID NO: 793) CGGTGCCAGGCTGGGTGCGACAGGCCCTGGACAA |
| VH2-FR2_10mer-6 | [SEQUENCING INSTRUMENT PRIMER] (SEQ ID NO: 794) CGGTGCCAGGTGGATCCGTCAGCCCCCAGGGAAGG |
| VH3-FR2_10mer-6 | [SEQUENCING INSTRUMENT PRIMER] (SEQ ID NO: 795) CGGTGCCAGGGGTCCGCCAGGCTCCAGGGAA |
| VH4-FR2_10mer-6 | [SEQUENCING INSTRUMENT PRIMER] (SEQ ID NO: 796) CGGTGCCAGGTGGATCCGCCAGCCCCCAGGGAAGG |
| VH5-FR2_10mer-6 | [SEQUENCING INSTRUMENT PRIMER] (SEQ ID NO: 797) CGGTGCCAGGGGGTGCGCCAGATGCCCGGGAAAGG |
| VH6-FR2_10mer-6 | [SEQUENCING INSTRUMENT PRIMER] (SEQ ID NO: 798) CGGTGCCAGGTGGATCAGGCAGTCCCCATCGAGAG |
| VH7-FR2_10mer-6 | [SEQUENCING INSTRUMENT PRIMER] (SEQ ID NO: 799) CGGTGCCAGGTTGGGTGCGACAGGCCCTGGACAA |

TABLE 6-continued

Primers used for multiplexed and barcoded PCR amplification of IGH rearrangements.

| Primer Name | Sequence (5' to 3') |
|---|---|
| VH1-FR2_10mer-7 | [SEQUENCING INSTRUMENT PRIMER] (SEQ ID NO: 800) CAATGCCAGGCTGGGTGCGACAGGCCCCTGGACAA |
| VH2-FR2_10mer-7 | [SEQUENCING INSTRUMENT PRIMER] (SEQ ID NO: 801) CAATGCCAGGTGGATCCGTCAGCCCCCAGGGAAGG |
| VH3-FR2_10mer-7 | [SEQUENCING INSTRUMENT PRIMER] (SEQ ID NO: 802) CAATGCCAGGGGTCCGCCAGGCTCCAGGGAA |
| VH4-FR2_10mer-7 | [SEQUENCING INSTRUMENT PRIMER] (SEQ ID NO: 803) CAATGCCAGGTGGATCCGCCAGCCCCCAGGGAAGG |
| VH5-FR2_10mer-7 | [SEQUENCING INSTRUMENT PRIMER] (SEQ ID NO: 804) CAATGCCAGGGGGTGCGCCAGATGCCCGGGAAGG |
| VH6-FR2_10mer-7 | [SEQUENCING INSTRUMENT PRIMER] (SEQ ID NO: 805) CAATGCCAGGTGGATCAGGCAGTCCCCATCGAGAG |
| VH7-FR2_10mer-7 | [SEQUENCING INSTRUMENT PRIMER] (SEQ ID NO: 806) CAATGCCAGGTTGGGTGCGACAGGCCCCTGGACAA |
| VH1-FR2_10mer-8 | [SEQUENCING INSTRUMENT PRIMER] (SEQ ID NO: 808) CTCCGGTAAGCTGGGTGCGACAGGCCCCTGGACAA |
| VH2-FR2_10mer-8 | [SEQUENCING INSTRUMENT PRIMER] (SEQ ID NO: 809) CTCCGGTAAGTGGATCCGTCAGCCCCCAGGGAAGG |
| VH3-FR2_10mer-8 | [SEQUENCING INSTRUMENT PRIMER] (SEQ ID NO: 809) CTCCGGTAAGGGTCCGCCAGGCTCCAGGGAA |
| VH4-FR2_10mer-8 | [SEQUENCING INSTRUMENT PRIMER] (SEQ ID NO: 810) CTCCGGTAAGTGGATCCGCCAGCCCCCAGGGAAGG |
| VH5-FR2_10mer-8 | [SEQUENCING INSTRUMENT PRIMER] (SEQ ID NO: 811) CTCCGGTAAGGGGTGCGCCAGATGCCCGGGAAGG |
| VH6-FR2_10mer-8 | [SEQUENCING INSTRUMENT PRIMER] (SEQ ID NO: 812) CTCCGGTAAGTGGATCAGGCAGTCCCCATCGAGAG |
| VH7-FR2_10mer-8 | [SEQUENCING INSTRUMENT PRIMER] (SEQ ID NO: 813) CTCCGGTAAGTTGGGTGCGACAGGCCCCTGGACAA |
| VH1-FR2_10mer-9 | [SEQUENCING INSTRUMENT PRIMER] (SEQ ID NO: 814) CAATTCGGAACTGGGTGCGACAGGCCCCTGGACAA |
| VH2-FR2_10mer-9 | [SEQUENCING INSTRUMENT PRIMER] (SEQ ID NO: 815) CAATTCGGAATGGATCCGTCAGCCCCCAGGGAAGG |
| VH3-FR2_10mer-9 | [SEQUENCING INSTRUMENT PRIMER] (SEQ ID NO: 816) CAATTCGGAAGGTCCGCCAGGCTCCAGGGAA |
| VH4-FR2_10mer-9 | [SEQUENCING INSTRUMENT PRIMER] (SEQ ID NO: 817) CAATTCGGAATGGATCCGCCAGCCCCCAGGGAAGG |
| VH5-FR2_10mer-9 | [SEQUENCING INSTRUMENT PRIMER] (SEQ ID NO: 818) CAATTCGGAAGGGTGCGCCAGATGCCCGGGAAGG |
| VH6-FR2_10mer-9 | [SEQUENCING INSTRUMENT PRIMER] (SEQ ID NO: 819) CAATTCGGAATGGATCAGGCAGTCCCCATCGAGAG |
| VH7-FR2_10mer-9 | [SEQUENCING INSTRUMENT PRIMER] (SEQ ID NO: 820) CAATTCGGAATTGGGTGCGACAGGCCCCTGGACAA |
| VH1-FR2_10mer-10 | [SEQUENCING INSTRUMENT PRIMER] (SEQ ID NO: 821) ACGTTAATCCCTGGGTGCGACAGGCCCCTGGACAA |
| VH2-FR2_10mer-10 | [SEQUENCING INSTRUMENT PRIMER] (SEQ ID NO: 822) ACGTTAATCCTGGATCCGTCAGCCCCCAGGGAAGG |
| VH3-FR2_10mer-10 | [SEQUENCING INSTRUMENT PRIMER] (SEQ ID NO: 823) ACGTTAATCCGGTCCGCCAGGCTCCAGGGAA |
| VH4-FR2_10mer-10 | [SEQUENCING INSTRUMENT PRIMER] (SEQ ID NO: 824) ACGTTAATCCTGGATCCGCCAGCCCCCAGGGAAGG |

TABLE 6-continued

Primers used for multiplexed and barcoded PCR amplification of IGH rearrangements.

| Primer Name | Sequence (5' to 3') |
|---|---|
| VH5-FR2_10mer-10 | [SEQUENCING INSTRUMENT PRIMER] (SEQ ID NO: 825) ACGTTAATCCGGGTGCGCCAGATGCCCGGGAAAGG |
| VH6-FR2_10mer-10 | [SEQUENCING INSTRUMENT PRIMER] (SEQ ID NO: 826) ACGTTAATCCTGGATCAGGCAGTCCCCATCGAGAG |
| VH7-FR2_10mer-10 | [SEQUENCING INSTRUMENT PRIMER] (SEQ ID NO: 827) ACGTTAATCCTTGGGTGCGACAGGCCCCTGGACAA |
| VH1-FR2_10mer-11 | [SEQUENCING INSTRUMENT PRIMER] (SEQ ID NO: 828) TAGTTCGGAACTGGGTGCGACAGGCCCCTGGACAA |
| VH2-FR2_10mer-11 | [SEQUENCING INSTRUMENT PRIMER] (SEQ ID NO: 829) TAGTTCGGAATGGATCCGTCAGCCCCCAGGGAAGG |
| VH3-FR2_10mer-11 | [SEQUENCING INSTRUMENT PRIMER] (SEQ ID NO: 830) TAGTTCGGAAGGTCCGCCAGGCTCCAGGGAA |
| VH4-FR2_10mer-11 | [SEQUENCING INSTRUMENT PRIMER] (SEQ ID NO: 831) TAGTTCGGAATGGATCCGCCAGCCCCCAGGGAAGG |
| VH5-FR2_10mer-11 | [SEQUENCING INSTRUMENT PRIMER] (SEQ ID NO: 832) TAGTTCGGAAGGGTGCGCCAGATGCCCGGGAAAGG |
| VH6-FR2_10mer-11 | [SEQUENCING INSTRUMENT PRIMER] (SEQ ID NO: 833) TAGTTCGGAATGGATCAGGCAGTCCCCATCGAGAG |
| VH7-FR2_10mer-11 | [SEQUENCING INSTRUMENT PRIMER] (SEQ ID NO: 834) TAGTTCGGAATTGGGTGCGACAGGCCCCTGGACAA |
| VH1-FR2_10mer-12 | [SEQUENCING INSTRUMENT PRIMER] (SEQ ID NO: 835) TTATTCGGAACTGGGTGCGACAGGCCCCTGGACAA |
| VH2-FR2_10mer-12 | [SEQUENCING INSTRUMENT PRIMER] (SEQ ID NO: 836) TTATTCGGAATGGATCCGTCAGCCCCCAGGGAAGG |
| VH3-FR2_10mer-12 | [SEQUENCING INSTRUMENT PRIMER] (SEQ ID NO: 837) TTATTCGGAAGGTCCGCCAGGCTCCAGGGAA |
| VH4-FR2_10mer-12 | [SEQUENCING INSTRUMENT PRIMER] (SEQ ID NO: 838) TTATTCGGAATGGATCCGCCAGCCCCCAGGGAAGG |
| VH5-FR2_10mer-12 | [SEQUENCING INSTRUMENT PRIMER] (SEQ ID NO: 839) TTATTCGGAAGGGTGCGCCAGATGCCCGGGAAAGG |
| VH6-FR2_10mer-12 | [SEQUENCING INSTRUMENT PRIMER] (SEQ ID NO: 840) TTATTCGGAATGGATCAGGCAGTCCCCATCGAGAG |
| VH7-FR2_10mer-12 | [SEQUENCING INSTRUMENT PRIMER] (SEQ ID NO: 841) TTATTCGGAATTGGGTGCGACAGGCCCCTGGACAA |
| VH1-FR1_10mer-1 | [SEQUENCING INSTRUMENT PRIMER] (SEQ ID NO: 842) TTATGCCAGGGGCCTCAGTGAAGGTCTCCTGCAAG |
| VH2-FR1_10mer-1 | [SEQUENCING INSTRUMENT PRIMER] (SEQ ID NO: 843) TTATGCCAGGGTCTGGTCCTACGCTGGTGAAACCC |
| VH3-FR1_10mer-1 | [SEQUENCING INSTRUMENT PRIMER] (SEQ ID NO: 844) TTATGCCAGGCTGGGGGGTCCCTGAGACTCTCCTG |
| VH4-FR1_10mer-1 | [SEQUENCING INSTRUMENT PRIMER] (SEQ ID NO: 845) TTATGCCAGGCTTCGGAGACCCTGTCCCTCACCTG |
| VH5-FR1_10mer-1 | [SEQUENCING INSTRUMENT PRIMER] (SEQ ID NO: 846) TTATGCCAGGCGGGAGTCTCTGAAGATCTCCTGT |
| VH6-FR1_10mer-1 | [SEQUENCING INSTRUMENT PRIMER] (SEQ ID NO: 847) TTATGCCAGGTCGCAGACCCTCTCACTCACCTGTG |
| VH1-FR1_10mer-2 | [SEQUENCING INSTRUMENT PRIMER] (SEQ ID NO: 848) TCCTGCCAGGGGCCTCAGTGAAGGTCTCCTGCAAG |
| VH2-FR1_10mer-2 | [SEQUENCING INSTRUMENT PRIMER] (SEQ ID NO: 849) TCCTGCCAGGGTCTGGTCCTACGCTGGTGAAACCC |

TABLE 6-continued

Primers used for multiplexed and barcoded PCR amplification of IGH rearrangements.

| Primer Name | Sequence (5' to 3') | |
|---|---|---|
| VH3-FR1_10mer-2 | [SEQUENCING INSTRUMENT PRIMER]<br>TCCTGCCAGGCTGGGGGGTCCCTGAGACTCTCCTG | (SEQ ID NO: 850) |
| VH4-FR1_10mer-2 | [SEQUENCING INSTRUMENT PRIMER]<br>TCCTGCCAGGCTTCGGAGACCCTGTCCCTCACCTG | (SEQ ID NO: 851) |
| VH5-FR1_10mer-2 | [SEQUENCING INSTRUMENT PRIMER]<br>TCCTGCCAGGCGGGGAGTCTCTGAAGATCTCCTGT | (SEQ ID NO: 852) |
| VH6-FR1_10mer-2 | [SEQUENCING INSTRUMENT PRIMER]<br>TCCTGCCAGGTCGCAGACCCTCTCACTCACCTGTG | (SEQ ID NO: 853) |
| VH1-FR1_10mer-3 | [SEQUENCING INSTRUMENT PRIMER]<br>CCTTGCCAGGGGCCTCAGTGAAGGTCTCCTGCAAG | (SEQ ID NO: 854) |
| VH2-FR1_10mer-3 | [SEQUENCING INSTRUMENT PRIMER]<br>CCTTGCCAGGGTCTGGTCCTACGCTGGTGAAACCC | (SEQ ID NO: 855) |
| VH3-FR1_10mer-3 | [SEQUENCING INSTRUMENT PRIMER]<br>CCTTGCCAGGCTGGGGGGTCCCTGAGACTCTCCTG | (SEQ ID NO: 856) |
| VH4-FR1_10mer-3 | [SEQUENCING INSTRUMENT PRIMER]<br>CCTTGCCAGGCTTCGGAGACCCTGTCCCTCACCTG | (SEQ ID NO: 857) |
| VH5-FR1_10mer-3 | [SEQUENCING INSTRUMENT PRIMER]<br>CCTTGCCAGGCGGGGAGTCTCTGAAGATCTCCTGT | (SEQ ID NO: 858) |
| VH6-FR1_10mer-3 | [SEQUENCING INSTRUMENT PRIMER]<br>CCTTGCCAGGTCGCAGACCCTCTCACTCACCTGTG | (SEQ ID NO: 859) |
| VH1-FR1_10mer-4 | [SEQUENCING INSTRUMENT PRIMER]<br>AGCTTAATCCGGCCTCAGTGAAGGTCTCCTGCAAG | (SEQ ID NO: 860) |
| VH2-FR1_10mer-4 | [SEQUENCING INSTRUMENT PRIMER]<br>AGCTTAATCCGTCTGGTCCTACGCTGGTGAAACCC | (SEQ ID NO: 861) |
| VH3-FR1_10mer-4 | [SEQUENCING INSTRUMENT PRIMER]<br>AGCTTAATCCCTGGGGGGTCCCTGAGACTCTCCTG | (SEQ ID NO: 862) |
| VH4-FR1_10mer-4 | [SEQUENCING INSTRUMENT PRIMER]<br>AGCTTAATCCCTTCGGAGACCCTGTCCCTCACCTG | (SEQ ID NO: 863) |
| VH5-FR1_10mer-4 | [SEQUENCING INSTRUMENT PRIMER]<br>AGCTTAATCCCGGGGAGTCTCTGAAGATCTCCTGT | (SEQ ID NO: 864) |
| VH6-FR1_10mer-4 | [SEQUENCING INSTRUMENT PRIMER]<br>AGCTTAATCCTCGCAGACCCTCTCACTCACCTGTG | (SEQ ID NO: 865) |
| VH1-FR1_10mer-5 | [SEQUENCING INSTRUMENT PRIMER]<br>CTCCATTAGGGGCCTCAGTGAAGGTCTCCTGCAAG | (SEQ ID NO: 866) |
| VH2-FR1_10mer-5 | [SEQUENCING INSTRUMENT PRIMER]<br>CTCCATTAGGGTCTGGTCCTACGCTGGTGAAACCC | (SEQ ID NO: 867) |
| VH3-FR1_10mer-5 | [SEQUENCING INSTRUMENT PRIMER]<br>CTCCATTAGGCTGGGGGGTCCCTGAGACTCTCCTG | (SEQ ID NO: 868) |
| VH4-FR1_10mer-5 | [SEQUENCING INSTRUMENT PRIMER]<br>CTCCATTAGGCTTCGGAGACCCTGTCCCTCACCTG | (SEQ ID NO: 869) |
| VH5-FR1_10mer-5 | [SEQUENCING INSTRUMENT PRIMER]<br>CTCCATTAGGCGGGGAGTCTCTGAAGATCTCCTGT | (SEQ ID NO: 870) |
| VH6-FR1_10mer-5 | [SEQUENCING INSTRUMENT PRIMER]<br>CTCCATTAGGTCGCAGACCCTCTCACTCACCTGTG | (SEQ ID NO: 871) |
| VH1-FR1_10mer-6 | [SEQUENCING INSTRUMENT PRIMER]<br>CTCCATTCCAGGCCTCAGTGAAGGTCTCCTGCAAG | (SEQ ID NO: 872) |
| VH2-FR1_10mer-6 | [SEQUENCING INSTRUMENT PRIMER]<br>CTCCATTCCAGTCTGGTCCTACGCTGGTGAAACCC | (SEQ ID NO: 873) |
| VH3-FR1_10mer-6 | [SEQUENCING INSTRUMENT PRIMER]<br>CTCCATTCCACTGGGGGGTCCCTGAGACTCTCCTG | (SEQ ID NO: 874) |

TABLE 6-continued

Primers used for multiplexed and barcoded PCR amplification of IGH rearrangements.

| Primer Name | Sequence (5' to 3') |
|---|---|
| VH4-FR1_10mer-6 | [SEQUENCING INSTRUMENT PRIMER] (SEQ ID NO: 875)<br>CTCCATTCCACTTCGGAGACCCTGTCCCTCACCTG |
| VH5-FR1_10mer-6 | [SEQUENCING INSTRUMENT PRIMER] (SEQ ID NO: 876)<br>CTCCATTCCACGGGGAGTCTCTGAAGATCTCCTGT |
| VH6-FR1_10mer-6 | [SEQUENCING INSTRUMENT PRIMER] (SEQ ID NO: 877)<br>CTCCATTCCATCGCAGACCCTCTCACTCACCTGTG |
| VH1-FR1_10mer-7 | [SEQUENCING INSTRUMENT PRIMER] (SEQ ID NO: 878)<br>CTCCAATAAGGGCCTCAGTGAAGGTCTCCTGCAAG |
| VH2-FR1_10mer-7 | [SEQUENCING INSTRUMENT PRIMER] (SEQ ID NO: 879)<br>CTCCAATAAGGTCTGGTCCTACGCTGGTGAAACCC |
| VH3-FR1_10mer-7 | [SEQUENCING INSTRUMENT PRIMER] (SEQ ID NO: 880)<br>CTCCAATAAGCTGGGGGTCCCTGAGACTCTCCTG |
| VH4-FR1_10mer-7 | [SEQUENCING INSTRUMENT PRIMER] (SEQ ID NO: 881)<br>CTCCAATAAGCTTCGGAGACCCTGTCCCTCACCTG |
| VH5-FR1_10mer-7 | [SEQUENCING INSTRUMENT PRIMER] (SEQ ID NO: 882)<br>CTCCAATAAGCGGGGAGTCTCTGAAGATCTCCTGT |
| VH6-FR1_10mer-7 | [SEQUENCING INSTRUMENT PRIMER] (SEQ ID NO: 883)<br>CTCCAATAAGTCGCAGACCCTCTCACTCACCTGTG |
| VH1-FR1_10mer-8 | [SEQUENCING INSTRUMENT PRIMER] (SEQ ID NO: 884)<br>CTCCAATTCGGGCCTCAGTGAAGGTCTCCTGCAAG |
| VH2-FR1_10mer-8 | [SEQUENCING INSTRUMENT PRIMER] (SEQ ID NO: 885)<br>CTCCAATTCGGTCTGGTCCTACGCTGGTGAAACCC |
| VH3-FR1_10mer-8 | [SEQUENCING INSTRUMENT PRIMER] (SEQ ID NO: 886)<br>CTCCAATTCGCTGGGGGTCCCTGAGACTCTCCTG |
| VH4-FR1_10mer-8 | [SEQUENCING INSTRUMENT PRIMER] (SEQ ID NO: 887)<br>CTCCAATTCGCTTCGGAGACCCTGTCCCTCACCTG |
| VH5-FR1_10mer-8 | [SEQUENCING INSTRUMENT PRIMER] (SEQ ID NO: 888)<br>CTCCAATTCGCGGGGAGTCTCTGAAGATCTCCTGT |
| VH6-FR1_10mer-8 | [SEQUENCING INSTRUMENT PRIMER] (SEQ ID NO: 889)<br>CTCCAATTCGTCGCAGACCCTCTCACTCACCTGTG |
| VH1-FR1_10mer-9 | [SEQUENCING INSTRUMENT PRIMER] (SEQ ID NO: 890)<br>CGGTTCGGAAGGCCTCAGTGAAGGTCTCCTGCAAG |
| VH2-FR1_10mer-9 | [SEQUENCING INSTRUMENT PRIMER] (SEQ ID NO: 891)<br>CGGTTCGGAAGTCTGGTCCTACGCTGGTGAAACCC |
| VH3-FR1_10mer-9 | [SEQUENCING INSTRUMENT PRIMER] (SEQ ID NO: 892)<br>TCCTTCGGAACTGGGGGGTCCCTGAGACTCTCCTG |
| VH4-FR1_10mer-9 | [SEQUENCING INSTRUMENT PRIMER] (SEQ ID NO: 893)<br>TCCTTCGGAACTTCGGAGACCCTGTCCCTCACCTG |
| VH5-FR1_10mer-9 | [SEQUENCING INSTRUMENT PRIMER] (SEQ ID NO: 894)<br>TCCTTCGGAACGGGGAGTCTCTGAAGATCTCCTGT |
| VH6-FR1_10mer-9 | [SEQUENCING INSTRUMENT PRIMER] (SEQ ID NO: 895)<br>TCCTTCGGAATCGCAGACCCTCTCACTCACCTGTG |
| VH1-FR1_10mer-10 | [SEQUENCING INSTRUMENT PRIMER] (SEQ ID NO: 896)<br>TCCTTCGGAAGGCCTCAGTGAAGGTCTCCTGCAAG |
| VH2-FR1_10mer-10 | [SEQUENCING INSTRUMENT PRIMER] (SEQ ID NO: 897)<br>TCCTTCGGAAGTCTGGTCCTACGCTGGTGAAACCC |
| VH3-FR1_10mer-10 | [SEQUENCING INSTRUMENT PRIMER] (SEQ ID NO: 898)<br>TCCTTCGGAACTGGGGGGTCCCTGAGACTCTCCTG |
| VH4-FR1_10mer-10 | [SEQUENCING INSTRUMENT PRIMER] (SEQ ID NO: 899)<br>TCCTTCGGAACTTCGGAGACCCTGTCCCTCACCTG |

TABLE 6-continued

Primers used for multiplexed and barcoded PCR amplification of IGH rearrangements.

| Primer Name | Sequence (5' to 3') |
| --- | --- |
| VH5-FR1_10mer-10 [SEQUENCING INSTRUMENT PRIMER] (SEQ ID NO: 900) TCCTTCGGAACGGGGAGTCTCTGAAGATCTCCTGT | |
| VH6-FR1_10mer-10 [SEQUENCING INSTRUMENT PRIMER] (SEQ ID NO: 901) TCCTTCGGAATCGCAGACCCTCTCACTCACCTGTG | |

What is claimed is:

1. A method of determining the clonal expansion of B cells in response of an individual to a vaccine, the method comprising:
    obtaining a cell sample comprising B cells from said individual in a short defined time period following immunization with said vaccine;
    dividing said cell sample comprising B cells, or genomic DNA derived therefrom, into at least two distinct pools;
    amplifying genomic DNA sequences at an immunoglobulin heavy chain locus in said at least two distinct pools with a primer set that amplifies at least 50% of the known rearrangements at the locus;
    sequencing at least $10^3$ reads of the amplified genomic DNA at the locus of interest from said at least two distinct pools;
    comparing sequences from said amplified genomic DNA to detect the presence of sequences that are coincident in said at least two distinct pools of nucleic acid;
    wherein the presence of coincident sequences is indicative of clonal expansion and responsiveness to said vaccine.

2. A method of determining the clonal expansion of B cells in response of an individual to a vaccine, the method comprising:
    obtaining a cell sample comprising B cells from said individual in a short defined time period following immunization with said vaccine wherein said short defined time period is less than about 14 days;
    dividing said cell sample comprising B cells, or genomic DNA derived therefrom, into at least two distinct pools;
    amplifying genomic DNA sequences at an immunoglobulin heavy chain locus in said at least two distinct pools with a primer set that amplifies at least 75% of the known rearrangements at the locus;
    sequencing at least $10^3$ reads of the amplified genomic DNA at the locus of interest from said at least two distinct pools;
    comparing sequences from said amplified genomic DNA to detect the presence of sequences that are coincident in said at least two distinct pools of nucleic acid;
    wherein the presence of coincident sequences is indicative of clonal expansion and responsiveness to said vaccine.

3. The method of claim 2 in which the sequences are selected by amplification using oligonucleotide primers set forth in Table 6 with homology to specific regions of the genome.

4. The method of claim 2, wherein the short defined time period is less than about 7 days.

* * * * *